US012745901B2

(12) United States Patent
Sagiv et al.

(10) Patent No.: US 12,745,901 B2
(45) Date of Patent: Sep. 29, 2026

(54) SYSTEMS AND METHODS FOR DETECTING FAILURE IN PLASMA TREATMENT

(71) Applicant: PLASMATICA LTD., Moshav Bnei Atarot (IL)

(72) Inventors: Adam Sagiv, Moshav Bnei Atarot (IL); Amnon Lam, Kibutz Givat Oz (IL)

(73) Assignee: PLASMATICA LTD., Salit (IL)

( * ) Notice: Subject to any disclaimer, the term of this patent is extended or adjusted under 35 U.S.C. 154(b) by 75 days.

(21) Appl. No.: 18/784,291

(22) Filed: Jul. 25, 2024

(65) Prior Publication Data

US 2024/0374127 A1 Nov. 14, 2024

Related U.S. Application Data

(63) Continuation of application No. 18/491,630, filed on Oct. 20, 2023, now Pat. No. 12,070,193, which is a (Continued)

(30) Foreign Application Priority Data

Dec. 7, 2021 (IL) .......................................... 288770

(51) Int. Cl.

| | |
|---|---|
| ***A61B 1/12*** | (2006.01) |
| ***A61B 90/70*** | (2016.01) |
| ***H05H 1/24*** | (2006.01) |

(52) U.S. Cl.

CPC .............. *A61B 1/127* (2013.01); *A61B 90/70* (2016.02); *H05H 1/2406* (2013.01); *A61B 2090/701* (2016.02)

(58) Field of Classification Search

None

See application file for complete search history.

(56) References Cited

U.S. PATENT DOCUMENTS 3,925,178 A 12/1975 Gesser et al.
4,055,378 A 10/1977 Feneberg et al.
(Continued)

FOREIGN PATENT DOCUMENTS

CA 3035491 A1 3/2017
CA 3216142 A1 * 10/2022 ........... H05H 1/2406
(Continued)

OTHER PUBLICATIONS

International Preliminary Report on Patentability in International Application No. PCT/IL2018/050304, report completed May 8, 2019 (15 pages).

(Continued)

*Primary Examiner* — Srinivas Sathiraju

(74) *Attorney, Agent, or Firm* — FINNEGAN, HENDERSON, FARABOW, GARRETT & DUNNER L.L.P.

(57) ABSTRACT

Systems, devices, methods, and computer readable media for generating plasma for treating objects may be provided. Embodiments include a housing; a plasma-generation zone within the housing configured to enable accommodation of an object; circuitry for supplying energy to carry out a plasma treatment for increasing hydrophilicity of the object to a desired level; at least one sensor configured to measure at least one plasma-activation parameter during the plasma treatment; and at least one processor configured to: determine, based on the at least one plasma-activation parameter, that the plasma treatment is below a threshold for increasing the hydrophilicity of the object to the desired level; and output a notification indicating plasma treatment failure.

20 Claims, 33 Drawing Sheets

Related U.S. Application Data continuation of application No. PCT/IB2022/000240, filed on Apr. 22, 2022.

(60) Provisional application No. 63/178,024, filed on Apr. 22, 2021.

(56) References Cited

U.S. PATENT DOCUMENTS

| | | | | |
|---|---|---|---|---|
| 4,122,942 | A | 10/1978 | Wolfson | |
| 4,143,949 | A | 3/1979 | Chen | |
| 4,214,014 | A | 7/1980 | Höfer et al. | |
| 4,312,575 | A | 1/1982 | Peyman et al. | |
| 4,632,844 | A | 12/1986 | Yanagihara et al. | |
| 4,643,876 | A | 2/1987 | Jacobs et al. | |
| 4,827,870 | A * | 5/1989 | Lee | G02B 5/287 427/255.6 |
| 5,009,920 | A * | 4/1991 | Lee | C23C 16/509 427/166 |
| 6,855,329 | B1 | 2/2005 | Shakesheff et al. | |
| 7,078,074 | B2 * | 7/2006 | Matsuzawa | B05D 1/62 427/166 |
| 7,931,584 | B2 | 4/2011 | Akagi et al. | |
| 7,985,188 | B2 * | 7/2011 | Felts | C23C 16/54 427/527 |
| 8,047,215 | B1 | 11/2011 | Sasaki | |
| 8,168,130 | B2 | 5/2012 | Sato et al. | |
| 8,328,982 | B1 * | 12/2012 | Babayan | H05H 1/2406 156/345.43 |
| 8,349,125 | B2 | 1/2013 | Vane et al. | |
| 8,409,077 | B2 | 4/2013 | Orihara et al. | |
| 8,475,451 | B2 | 7/2013 | Cho | |
| 8,501,106 | B2 | 8/2013 | Sato et al. | |
| 8,618,435 | B2 * | 12/2013 | Bohori | B23K 9/013 219/121.36 |
| 8,663,625 | B2 | 3/2014 | Stroock et al. | |
| 8,696,983 | B2 | 4/2014 | Hayashi et al. | |
| 9,072,443 | B2 | 7/2015 | Hashido et al. | |
| 9,248,207 | B1 | 2/2016 | Heyoung | |
| 10,413,168 | B2 * | 9/2019 | Sagiv | H01J 37/32 |
| 10,596,287 | B2 | 3/2020 | Dang et al. | |
| 10,755,901 | B2 * | 8/2020 | Chambers | H01J 37/32559 |
| 10,820,402 | B2 * | 10/2020 | Lam | H05H 1/2406 |
| 10,827,601 | B1 * | 11/2020 | Williams | H05H 1/24 |
| 10,857,372 | B2 * | 12/2020 | Zuidervaart | H05H 1/2406 |
| 10,923,331 | B1 * | 2/2021 | Williams | H01J 37/32568 |
| 11,243,393 | B2 * | 2/2022 | Lam | H05H 1/2406 |
| 11,246,480 | B2 * | 2/2022 | Sagiv | A61B 1/127 |
| 11,533,801 | B2 * | 12/2022 | Boughton | H01J 37/321 |
| 11,715,321 | B2 * | 8/2023 | Hiemstra | G06F 3/0436 345/174 |
| 11,896,203 | B2 * | 2/2024 | Sagiv | A61B 1/127 |
| 11,896,204 | B2 * | 2/2024 | Sagiv | A61B 1/127 |
| 11,974,728 | B2 | 5/2024 | Sagiv et al. | |
| 12,070,193 | B2 * | 8/2024 | Sagiv | H05H 1/2406 |
| 12,262,877 | B2 * | 4/2025 | Sagiv | A61B 1/127 |
| 2002/0053353 | A1 | 5/2002 | Kawata et al. | |
| 2004/0037736 | A1 | 2/2004 | Perruchot et al. | |
| 2004/0084146 | A1 | 5/2004 | Sekiya | |
| 2005/0045589 | A1 | 3/2005 | Rastogi et al. | |
| 2006/0252986 | A1 | 11/2006 | Akagi et al. | |
| 2007/0078245 | A1 * | 4/2007 | Hoffman | G02B 1/043 526/279 |
| 2008/0002146 | A1 | 1/2008 | Stachowski et al. | |
| 2008/0243032 | A1 | 10/2008 | Hindelang et al. | |
| 2010/0094090 | A1 * | 4/2010 | Mejia | A61B 1/0014 600/156 |
| 2010/0249503 | A1 * | 9/2010 | Yazawa | A61B 1/041 600/109 |
| 2010/0286479 | A1 * | 11/2010 | Ashida | A61M 25/10184 600/116 |
| 2010/0292537 | A1 * | 11/2010 | Ashida | A61B 1/018 600/116 |
| 2011/0283477 | A1 * | 11/2011 | Ashpis | H10F 19/00 15/405 |
| 2011/0301412 | A1 | 12/2011 | Cho | |
| 2013/0137928 | A1 | 5/2013 | Karasawa et al. | |
| 2014/0290700 | A1 | 10/2014 | Langford | |
| 2014/0371528 | A1 | 12/2014 | Yen et al. | |
| 2015/0005582 | A1 | 1/2015 | Poll et al. | |
| 2015/0035918 | A1 | 2/2015 | Matsumoto et al. | |
| 2015/0209461 | A1 | 7/2015 | Itarashiki et al. | |
| 2015/0380681 | A1 * | 12/2015 | Furukawa | H10K 50/854 257/40 |
| 2016/0068960 | A1 | 3/2016 | Jung et al. | |
| 2016/0331437 | A1 | 11/2016 | Holbeche et al. | |
| 2018/0138022 | A1 | 5/2018 | Lam et al. | |
| 2018/0221610 | A1 * | 8/2018 | Larson | H04N 7/183 |
| 2018/0305019 | A1 * | 10/2018 | Hubschwerlen | B64C 21/02 |
| 2019/0021584 | A1 * | 1/2019 | Sagiv | A61B 1/253 |
| 2019/0365215 | A1 * | 12/2019 | Sagiv | A61B 1/127 |
| 2020/0023997 | A1 * | 1/2020 | Lowe | G08G 5/54 |
| 2020/0077505 | A1 * | 3/2020 | Lam | H05H 1/2406 |
| 2020/0118674 | A1 * | 4/2020 | Le | A61B 1/121 |
| 2020/0196912 | A1 * | 6/2020 | Ariyama | A61B 5/117 |
| 2021/0023250 | A1 | 1/2021 | Golkowski et al. | |
| 2021/0041690 | A1 * | 2/2021 | Lam | G02B 27/0006 |
| 2022/0125291 | A1 * | 4/2022 | Sagiv | A61B 1/127 |
| 2022/0203014 | A1 * | 6/2022 | Shuler | A61M 1/90 |
| 2022/0240770 | A1 * | 8/2022 | Sagiv | A61B 1/127 |
| 2022/0257105 | A1 * | 8/2022 | Sagiv | A61B 1/127 |
| 2022/0366719 | A1 * | 11/2022 | Hiemstra | G06F 3/0436 |
| 2023/0351797 | A1 * | 11/2023 | Hiemstra | G06F 3/0436 |
| 2024/0049958 | A1 * | 2/2024 | Sagiv | A61B 90/70 |
| 2024/0138664 | A1 * | 5/2024 | Sagiv | A61B 1/127 |
| 2024/0374127 | A1 * | 11/2024 | Sagiv | A61B 90/70 |

FOREIGN PATENT DOCUMENTS

| | | | | |
|---|---|---|---|---|
| CN | 102006831 | A | 4/2011 | |
| CN | 102512702 | A | 6/2012 | |
| CN | 103585650 | A | 2/2014 | |
| CN | 104661422 | A | 5/2015 | |
| CN | 204618406 | U | 9/2015 | |
| CN | 108135463 | B | 8/2020 | |
| CN | 111789568 | A | 10/2020 | |
| EP | 0302419 | A2 | 2/1989 | |
| EP | 1110557 | A2 | 6/2001 | |
| EP | 1867683 | A1 | 12/2007 | |
| EP | 1889562 | A1 | 2/2008 | |
| EP | 2115499 | A0 | 11/2009 | |
| EP | 3346901 | B1 | 7/2020 | |
| EP | 3813495 | A1 | 4/2021 | |
| GB | 2286200 | A | 8/1995 | |
| IL | 279819 | B | 10/2021 | |
| IL | 288770 | B1 | 6/2023 | |
| JP | H0337030 | A | 2/1991 | |
| JP | H06218279 | A | 8/1994 | |
| JP | H1043128 | A | 2/1998 | |
| JP | 2002-110397 | A | 4/2002 | |
| JP | 2003-207601 | A | 7/2003 | |
| JP | 2003-210556 | A | 7/2003 | |
| JP | 2006-021027 | A | 1/2006 | |
| JP | 2006-087514 | A | 4/2006 | |
| JP | 2006-095173 | A | 4/2006 | |
| JP | 2009-512467 | A | 3/2009 | |
| JP | 2018-531767 | A | 11/2018 | |
| JP | 6678744 | B2 | 4/2020 | |
| JP | 2020-114396 | A | 7/2020 | |
| JP | 6973818 | B2 | 12/2021 | |
| JP | 2022-009584 | A | 1/2022 | |
| JP | 7084079 | B2 | 6/2022 | |
| JP | 2022-105703 | A | 7/2022 | |
| KR | 2018-0054669 | A | 5/2018 | |
| WO | WO 95/04609 | | 2/1995 | |
| WO | WO 2006/129472 | A1 | 7/2006 | |
| WO | WO 2007/032172 | A1 | 3/2007 | |
| WO | WO 2009/020105 | A1 | 2/2009 | |
| WO | WO-2017042806 | A1 * | 3/2017 | A61B 1/127 |
| WO | WO 2017/153898 | A1 | 11/2017 | |

(56) References Cited

FOREIGN PATENT DOCUMENTS

WO WO 2018/167792 A1 9/2018
WO WO-2022224040 A2 * 10/2022 ........... H05H 1/2406

OTHER PUBLICATIONS

International Search Report and Written Opinion of the International Searching Authority in International Application No. PCT/IB2022/000240, mailed by the Israel Patent Office on Jan. 16, 2023 (19 pages).

International Search Report and Written Opinion of the International Searching Authority in International Application No. PCT/IL2016/050990, mailed by the Israel Patent Office on Jan. 3, 2017 (7 pages).

International Search Report and Written Opinion of the International Searching Authority in International Application No. PCT/IL2018/050304, mailed by the Israel Patent Office on Jul. 19, 2018 (12 pages).

Search Report from the Israel Patent Office (ILPO) for Application No. 288770, dated Apr. 4, 2022 (2 pages).

* cited by examiner

SYSTEMS AND METHODS FOR DETECTING FAILURE IN PLASMA TREATMENT

CROSS-REFERENCE TO RELATED APPLICATIONS

This application is a continuation of U.S. application Ser. No. 18/491,630, filed Oct. 20, 2023, which is a continuation of International Application PCT/IB2022/000240, filed Apr. 22, 2022, which claims the benefit of priority of U.S. Provisional Patent Application No. 63/178,024, filed Apr. 22, 2021, and Israel Patent Application No. 288770, filed Dec. 7, 2021, each of which is hereby incorporated by reference in its entirety.

TECHNICAL FIELD

The disclosure, in some embodiments, relates to the field of viewing instruments, and more particularly, to techniques for improving the effectiveness of viewing instruments by reducing an accumulation of condensation.

BACKGROUND

Medical scopes are widely used in medical procedures, particularly in minimally invasive surgical procedures. Such scopes generally fall into two categories-endoscopes and laparoscopes, both of which are used to visualize internal areas of the body. Endoscopes are commonly used to obtain a visual of the interior of a hollow organ or cavity such as a digestive tract. Laparoscopes are commonly inserted through small incisions in a patient's skin. As a shorthand, both are often referred to as endoscopes. By way of example only, endoscopes can be used to perform arthroscopy, bronchoscopy, colonoscopy, cystoscopy, enterostomy, hysteroscopy, laparoscopy, laryngoscopy, mediastinoscopy, sigmoidoscopy, esophagogastroduodenoscopy, and ureteroscopy. The medical scopes used to perform these procedures have optics at one end (e.g., a lens) as discussed below.

Endoscopes often include a distal end configured to be inserted into a patient's body, and a proximal end configured to remain outside the patient's body during the procedure. Typically, the distal end includes a viewport such as a lens or a window or a bare end of an optical fiber or even a mirror (such as a dentist mirror, for example). Through the viewport, the scope enables collecting an image of the surroundings of the viewport, e.g., using a light-sensitive device such as a CCD. The viewport may be aimed to collect light from in front of the device (namely from a region coinciding with the longitudinal axis of the device), or the viewport may be slanted in an angle relative to the longitudinal axis or may be facing perpendicular to the longitudinal axis of the device (as is demonstrated for example in colonoscopies). The proximal end often includes or is connected to a control portion configured to be operated by a medical practitioner (e.g., a handle), possibly including user interface components such as switches, navigating sticks, touch screens, and touch pads.

Laparoscopes often include a rod or shaft capable of a rigid or relatively rigid position and having a viewport, sometimes including an objective lens, at the distal end, and an eyepiece and/or an integrated visual display at the proximal end. The scope may also be connected to a remote visual display device or a video camera to record surgical procedures.

In a laparoscopic procedure, the patient's abdominal or pelvic cavity is accessed through one or two or more relatively small incisions (typically between about 3 mm and about 15 mm) and a laparoscope may be inserted through one of the incisions to allow the practitioner a view of the target internal organs for surgery. The abdomen is typically inflated with a gas using an insufflator—carbon dioxide is usually used for insufflation—to distend the abdominal space by elevating the abdominal wall above the internal organs and thereby create a sufficient working and viewing space for the surgeon.

The local environment within a patient's abdominal space is generally humid and warm compared to the endoscope or laparoscope which is being inserted. Consequently, the viewport of the laparoscope tends to blur, e.g., due to fog, that is to say due to condensation of vapor on the viewport, or, for example, due to accumulation of droplets, e.g., blood droplets originating from surgical activity during the procedure. A similar phenomenon may occur with non-laparoscopic endoscopes. When such fogging occurs, the surgeon's view is inhibited, requiring the surgeon in some instances to remove the scope from the body in order to wipe the lens.

SUMMARY

Embodiments consistent with the present disclosure provide systems and methods generally relating to plasma treatments for prevention of fogging on optical surfaces. The disclosed systems and methods may be implemented using a combination of conventional hardware and software as well as specialized hardware and software, such as a machine constructed and/or programmed specifically for performing functions associated with the disclosed method steps. Consistent with other disclosed embodiments, non-transitory computer readable storage media may store program instructions, which are executable by at least one processing device and perform any of the steps and/or methods described herein.

Consistent with disclosed embodiments, systems, devices, methods, and computer readable media for treating objects with plasma are disclosed. For example, a plasma generation device for treating objects is disclosed. The embodiments may include a housing; a plasma-generation zone within the housing configured to enable accommodation of an object; circuitry for supplying energy to carry out a plasma treatment for increasing hydrophilicity of the object to a desired level; at least one sensor configured to measure at least one plasma-activation parameter during the plasma treatment; and at least one processor configured to determine, based on the at least one plasma-activation parameter, that the plasma treatment is below a threshold for increasing the hydrophilicity of the object to the desired level, and output a notification indicating of plasma treatment failure.

Consistent with disclosed embodiments, systems, devices, methods, and computer readable media for treating elongated tools with plasma are disclosed. The embodiments may include a housing; a bore within the housing, the bore having an open end on a surface of the housing for insertion of the elongated tool therein; at least one vacuum pump for causing a vacuum in at least a portion of the bore; an insertion detector for determining when the elongated tool is inserted within the bore; a vacuum sensor associated with the housing for determining an extent of negative pressure in the at least a portion of the bore; a plasma generator for generating plasma within the bore; and at least one processor configured to: receive an insertion signal from the insertion detector indicating that the elongated tool is within the bore;

in response to the insertion signal, activate the at least one vacuum pump to generate a negative pressure in the at least a portion of the bore; receive a signal from the vacuum sensor and determine therefrom that a negative pressure in the at least a portion of the bore is sufficient for plasma generation; and activate the plasma generator after the determination is made that negative pressure in the at least a portion of bore is sufficient for plasma generation, thereby exposing a distal end region of the elongated tool to plasma.

Consistent with disclosed embodiments, systems, devices, methods, and computer readable media for inhibiting condensation distortion on optical elements are disclosed. For example, a device for inhibiting condensation distortion on an optical element of a medical instrument configured for insertion into a body cavity is disclosed. The embodiments may include a housing; a cavity within the housing, the cavity being sized to removably retain at least a portion of the medical instrument therein, wherein the portion includes the optical element; a plasma activation zone within the cavity and arranged such that when the at least a portion of the medical instrument is retained within the cavity, the optical element is located within the plasma activation zone; a plasma generator configured to be activated to cause formation of a plasma cloud in the plasma activation zone in a vicinity of the optical element; and a controller configured to activate the plasma generator for a time period sufficient to cause the optical element to become hydrophilic prior to insertion into the body cavity.

Consistent with disclosed embodiments, systems, devices, methods, and computer readable media for inhibiting condensation distortion on optical elements are disclosed. The embodiments may include a housing; a chamber within the housing; electrical circuitry in the housing; a plasma activation region associated with the chamber and being configured to retain the optical element in a manner exposing an optical surface of the optical element thereof to the plasma activation region, wherein the plasma-activation region is configured to contain gas on a first side of a dielectric barrier and the electrical circuitry is configured to form an electrical connection with a first electrode located on the first side of the dielectric barrier; a second electrode connected to the electrical circuitry, and being located on a second side of the dielectric barrier, opposite the plasma activation region; and at least one processor configured to: control electricity flow through the circuitry to cause an electric field associated with a voltage drop between the first electrode and a second electrode to thereby generate plasma within the plasma-activation region; and maintain the generated plasma in the plasma-generating region for time period sufficient to cause the optical surface to become hydrophilic.

Consistent with disclosed embodiments, systems, devices, methods, and computer readable media for generating plasma for treating objects are disclosed. For example, a plasma generator for treating objects is disclosed. The embodiments may include a housing; a plasma generation zone within the housing configured to enable accommodation of an object; a plasma generator for enabling formation of plasma within the plasma generation zone; a plurality of vacuum pumps within the housing, each pump having a vacuum inlet; a plurality of conduits within the housing connecting the plurality of vacuum pumps in series, such that when activated, the series of pumps cause a vacuum within the plasma generation zone; and at least one processor configured to simultaneously operate the plurality of vacuum pumps while the object is in a region of the plasma generation zone.

Some disclosed embodiments involve systems and methods for inhibiting condensation distortion on an optical element of a medical instrument configured for insertion into a body cavity. The optical element of the medical instrument may be treated to cause at least one surface of the optical element to become super-hydrophilic. Once treated, the medical instrument, with the super-hydrophilic optical element, is inserted into the body cavity and exposed to moisture, such that the moisture forms a film barrier on the at least one surface of the optical element to thereby inhibit condensation distortion.

Consistent with some disclosed embodiments, systems, devices, methods, and computer readable media for treating equipment of differing dimensions in a vacuum environment are disclosed. These embodiments may include an enclosure having a channel for receiving elongated tools of varying diameters, the enclosure being divided into a vacuum chamber region and a non-vacuum region. These embodiments may also include an annular seal disposed between the vacuum chamber region and the non-vacuum region, the annular seal being formed of a flexible material and configured to form a vacuum seal against a wall of a first tool when the first tool is inserted therein and against a wall of a second tool when the second tool is inserted therein, wherein the first tool has a diameter at least one and a half times greater than a diameter of the second tool.

Some embodiments may include inserting during a first treatment session, a first removable enclosure into a housing, the first removable enclosure being divided into a vacuum chamber region and a non-vacuum region separated by a first annular seal configured to adjust to varying tool sizes; inserting during the first treatment session, a first elongated tool into the first removable enclosure, the first elongated tool having a first region of a first dimension; sealing, upon insertion of the first elongated tool, the first region of the first dimension with the first annular seal; maintaining the first elongated tool in the first enclosure during an establishment of at least a partial vacuum in the vacuum chamber region; and extracting the first elongated tool from the first enclosure. These embodiments may also include inserting during a second treatment session, a second removable enclosure into the housing, the second removable enclosure being divided into a second vacuum chamber region and a second non-vacuum region separated by a second annular seal corresponding in configuration to the first annular seal; inserting during the second treatment session, a second elongated tool into the second removable enclosure, the second elongated tool having a second region of a second dimension differing from the first dimension; sealing, upon insertion of the second elongated tool, the second region of the second dimension with the second annular seal; maintaining the second elongated tool in the second enclosure during an establishment of at least a partial vacuum in the second vacuum chamber region; and extracting the second elongated tool from the second enclosure. Some disclosed embodiments may also involve maintaining during a second treatment session, the first removable enclosure within the housing; inserting during the second treatment session, a second elongated tool into the first removable enclosure, the second elongated tool having a second region of a second dimension differing from the first dimension; sealing, upon insertion of the second elongated tool, the second region of the second dimension with the first annular seal; maintaining the second elongated tool in the first enclosure during an establishment of at least a partial vacuum in the vacuum chamber region; and extracting the second elongated tool from the first enclosure.

Some disclosed embodiments include an apparatus for preparing a medical device for a medical procedure. The medical device may have a distal segment configured to be inserted into a patient's body, the distal segment having an optical member having an optical surface. Some disclosed apparatuses include an operational unit, an adapter configured to be detached from the operational unit, and at least one electrode which may be included in the operational unit or in the adapter or (where there are more than one electrode) both. The operational unit may include an EM power source and a housing having a slot configured to receive the adapter in the slot. The operational unit may also include an adapter identifier, configured to receive an identification signal from a corresponding transponder, and a controller functionally associated with the adapter identifier. The adapter may include a hollow cylinder extending between an opening and a distal end of the hollow cylinder, wherein the opening is dimensioned to allow insertion of the distal segment into the hollow cylinder. The adapter may also include a seal positioned in the hollow cylinder and defining a distal portion of the hollow cylinder between the seal and the distal end of the hollow cylinder. The seal is dimensioned to sealingly fit an external circumference of the distal segment when the distal segment is inserted into the hollow cylinder. The adapter may also include a transponder, being configured to transmit the identification signal identifying the adapter or a position thereof relative to the adapter identifier, when the adapter is in the slot. The apparatus is configured, when the distal segment is in the hollow cylinder of the adapter, the adapter is in the slot and the adapter identifier receives the identification signal from the transponder, to apply a plasma-generating EM field in the distal portion of the hollow cylinder by the at least one electrode, the electrode receiving EM power from the power source.

According to some embodiments, the adapter includes a hollow cylinder extending between an opening dimensioned and configured to receive the distal segment of the medical device and a distal end of the hollow cylinder. The adapter may also include a seal positioned in the hollow cylinder and defining a distal portion of the hollow cylinder between the seal and the distal end of the hollow cylinder, the seal dimensioned to sealingly fit an external circumference of the distal segment when the distal segment is inserted into the hollow cylinder. The adapter may also include a transponder configured to transmit an identification signal identifying the adapter when the adapter is in the slot. In some embodiments, the transponder stores information identifying the adapter. In some embodiments, the transponder is configured to transmit the identification signal in response to a coded signal, thereby identifying the adapter.

According to some embodiments, a seal in the adaptor is dimensioned to sealingly fit distal segments having external circumferences in a range between a first circumference L and a second circumference greater than 1.5 L. The adapter may also include an electrical feedthrough electrically connecting an external contact outside of the hollow cylinder to an electrical conductor inside the hollow cylinder in the distal portion thereof.

Some disclosed embodiments involve a method of preparing at least a first medical device and a second medical device for a medical procedure carried out on a single patient. Each such medical device has a distal segment including an optical member. The circumference of the distal segment of one of the first and second medical devices is L and the circumference of the distal segment of the other medical device is greater than 1.2 L. Some disclosed methods include providing a plasma chamber having at least one electrode electrically associable with a power source and configured for applying in the plasma chamber a plasma generating EM field. The plasma chamber may also have an opening and a seal dimensioned and configured to receive the distal segment of each of the first and second medical devices in the opening. An associated method may also include inserting the distal segment of the first medical device into the plasma chamber through the opening so that the seal and the distal end together seal the opening. Such a method may also include supplying EM power from the power source to the at least one electrode, thereby applying a plasma generating EM field and generating plasma in the vicinity of the optical member. The method may further include repeating the steps of inserting the distal segment and supplying EM power for the second medical device.

Consistent with some disclosed embodiments, an adaptive seal made of a flexible material is disclosed. The seal may be shaped as a combined outer tube and an inner annular ring extending radially along a wavy curve having at least one crest between the outer tube and a central opening of the seal. Such an adaptive seal is thereby configured to sealingly fit to an external surface of a member positioned in the central opening and having a smooth circumference within a range between a first circumference L and a second circumference 1.5 L. A smooth circumference may include a convex curve outlining a convex shape and having no corners or sharp edges.

The forgoing summary provides certain examples of disclosed embodiments to provide a flavor for this disclosure and is not intended to summarize all aspects of the disclosed embodiments. Additional features and advantages of the disclosed embodiments will be set forth in part in the description that follows, and in part will be apparent from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

The accompanying drawings, which are incorporated in and constitute a part of this disclosure, illustrate various disclosed embodiments. Dimensions of components and features shown in the drawings are generally chosen for convenience and clarity of presentation and are not necessarily shown to scale. The drawings are listed below.

DETAILED DESCRIPTION

Figures 1A, 1B:
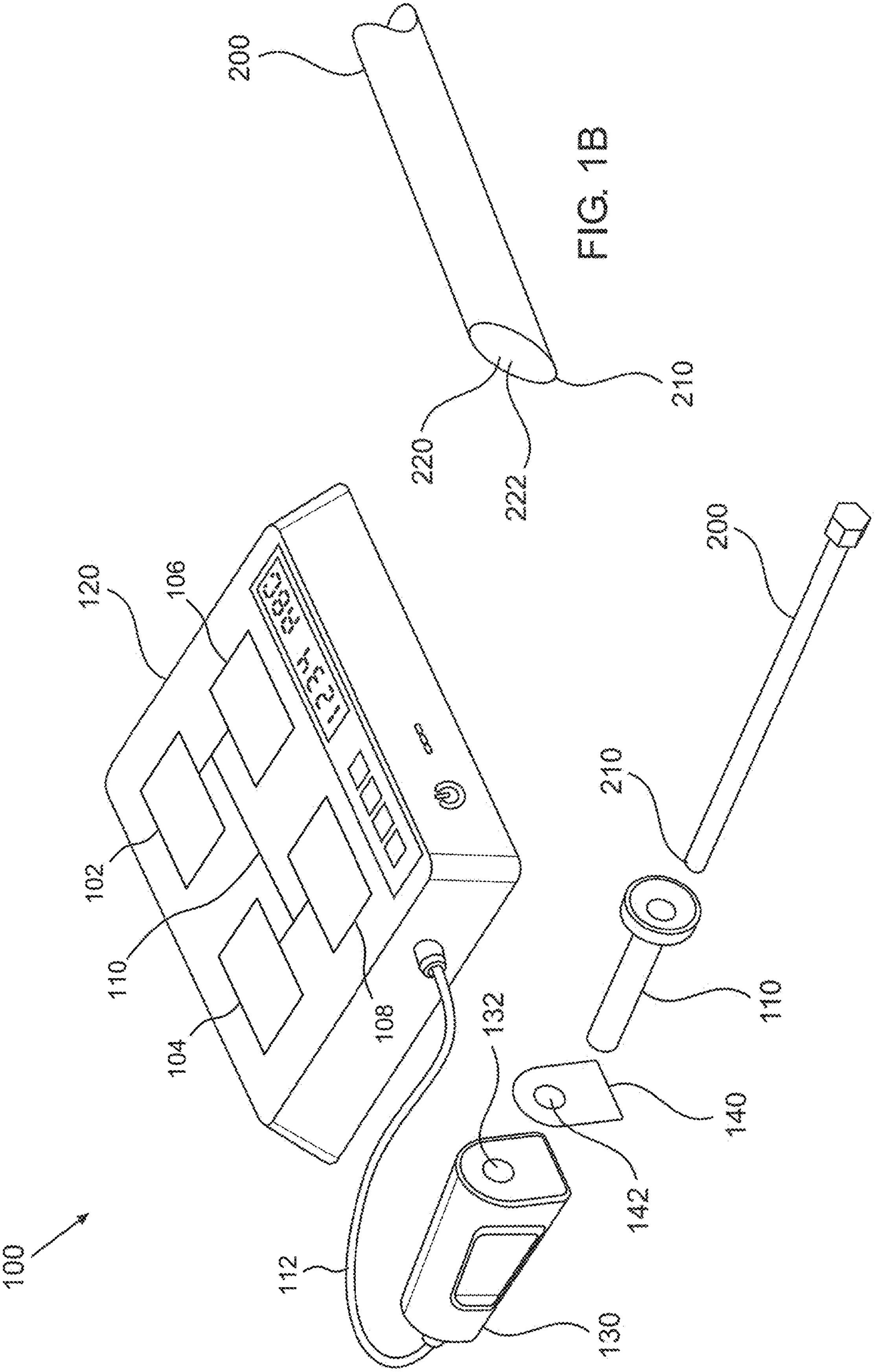
FIG. 1A is a perspective view of an embodiment of an apparatus for preparing a medical instrument to a medical procedure, consistent with some disclosed embodiments.
FIG. 1B is a perspective view of a distal end of an example of an endoscope, the distal end having a viewport suitable to be plasma-treated by the apparatus of FIG. 1A.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items or meant to be limited to only the listed item or items. It should also be noted that as used in the present disclosure and in the appended claims, the singular forms "a," "an," and "the" include plural references unless the context clearly dictates otherwise.

Unless specifically stated otherwise, as apparent from the following description, throughout the specification discussions utilizing terms such as "processing," "calculating," "computing," "determining," "generating," "setting," "configuring," "selecting," "defining," "applying," "obtaining," "monitoring," "providing," "identifying," "segmenting," "classifying," "analyzing," "associating," "extracting," "storing," "receiving," "transmitting," or the like, include actions and/or processes of a computer that manipulate and/or transform data into other data, the data represented as physical quantities, for example such as electronic quantities, and/or the data representing physical objects. The terms "computer," "processor," "controller," "processing unit," "computing unit," and "processing module" should be expansively construed to cover any kind of electronic device, component or unit with data processing capabilities, including, by way of non-limiting example, a personal computer, a wearable computer, smart glasses, a tablet, a smartphone, a server, a computing system, a cloud computing platform, a communication device, a processor (for example, digital signal processor (DSP), an image signal processor (ISR), a microcontroller, a field programmable gate array (FPGA), an application specific integrated circuit (ASIC), a central processing unit (CPA), a graphics processing unit (GPU), a visual processing unit (VPU), and so on), possibly with embedded memory, a single core processor, a multi core processor, a core within a processor, any other electronic computing device, or any combination of the above.

The operations in accordance with the teachings herein may be performed by a computer specially constructed or programmed to perform the described functions.

As used herein, the phrase "for example," "such as," "for instance" and variants thereof describe non-limiting embodiments of the presently disclosed subject matter. Reference in the specification to features of "embodiments," "one case," "some cases," "other cases" or variants thereof means that a particular feature, structure or characteristic described may be included in at least one embodiment of the presently disclosed subject matter. Thus, the appearance of such terms does not necessarily refer to the same embodiment(s). As used herein, the term "and/or" includes any and all combinations of one or more of the associated listed items.

Features of the presently disclosed subject matter, are, for brevity, described in the context of particular embodiments. However, it is to be understood that features described in connection with one embodiment are also applicable to other embodiments. Likewise, features described in the context of a specific combination may be considered separate embodiments, either alone or in a context other than the specific combination.

In embodiments of the presently disclosed subject matter, one or more stages illustrated in the figures may be executed in a different order and/or one or more groups of stages may be executed simultaneously and vice versa. The figures illustrate a general schematic of the system architecture in accordance embodiments of the presently disclosed subject matter. Each module in the figures can be made up of any combination of software, hardware and/or firmware that performs the functions as defined and explained herein. The modules in the figures may be centralized in one location or dispersed over more than one location.

Examples of the presently disclosed subject matter are not limited in application to the details of construction and the arrangement of the components set forth in the following description or illustrated in the drawings. The subject matter may be practiced or carried out in various ways. Also, it is to be understood that the phraseology and terminology employed herein is for the purpose of description and should not be regarded as limiting.

In this document, an element of a drawing that is not described within the scope of the drawing and is labeled with a numeral that has been described in a previous drawing may have the same use and description as in the previous drawings.

The drawings in this document may not be to any scale. Different figures may use different scales and different scales can be used even within the same drawing, for example different scales for different views of the same object or different scales for the two adjacent objects.

Consistent with disclosed embodiments, "at least one processor" may constitute any physical device or group of devices having electric circuitry that performs a logic operation on an input or inputs. For example, the at least one processor may include one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory. The memory may include a Random-Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

Disclosed embodiments may include and/or access a data structure. A data structure consistent with the present disclosure may include any collection of data values and relationships among them. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML database, an RDBMS database, an SQL database or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, that may be owned or operated by the same or different entities. Thus, the term "data structure" as used herein in the singular is inclusive of plural data structures.

Disclosed herein are systems, methods and computer readable media for rendering objects hydrophilic and or treating objects using plasma. Some embodiments involve a plasma generator for carrying out a plasma treatment of an object. Plasma treatment applied to a surface of an object may increase hydrophilicity of the surface, thereby preventing a condensation of fluid droplets (e.g., fog) thereon. The presence of droplets may be particularly relevant when the object includes one or more optical elements since droplets may affect the interaction of the object with light, and cause distortions that hamper optical performance. Each fluid droplet may function as an individual lens that separately distorts light rays transmitted through or reflected off the surface. The collective effect of many individual droplets, each having different optical characteristics, may result in a rough optical surface, which may prevent obtaining a sharp image from light passing through or reflected off the surface, and consequently impair optical quality. However, by increasing hydrophilicity of the object surface to change the surface tension thereon, plasma treatment may be applied to the object surface, preventing fluid from accumulating as droplets. Increased hydrophilicity may cause fluid to coat the object as a thin, even layer of fluid, instead of accumulating as individual droplets. Distributing the fluid as a thin, even coating on the object may reduce the distortion of light waves interacting with the object surface, by maintaining a uniform index of refraction and maintain the optical quality, and/or limit degradation. The plasma treatment may thus reduce variations in the thickness of the fluid coating the object surface and may reduce the variability of the optical path length of light passing through the fluid coating, accordingly.

In some embodiments, the object may be a medical instrument having an optical element, such as a viewport of a laparoscope or endoscope, a lens, a mirror, or any other medical instrument having optical capabilities. Inserting an untreated optical element into a moist body cavity may cause fog to accumulate thereon due to water and/or water-based fluids (e.g., bodily fluids) condensing on the surface of the optical element as droplets. The condensation may distort the interaction of light waves with the optical element and adversely affect visibility via the optical element. Increasing hydrophilicity of the optical element may reduce such distortion by preventing the accumulation of fluid on the optical element as individual droplets.

For ease of discussion herein, references to an endoscope or a laparoscope are intended to broadly refer to both, and disclosures related to one are intended to equally apply to the other unless otherwise stated.

Treating the viewport (e.g., optical element) of the endoscope with plasma may increase hydrophilicity of the viewport to achieve complete wetting of the viewport by water and/or water-based fluid. Complete wetting may be achieved by increasing the surface tension of the treated surface of the viewport to above the surface tension of water, namely above 0.072 N/m. In some embodiments, the plasma treatment may increase the surface tension of the viewport surface to above 0.08 N/m, or above 0.1 N/m, e.g., for a limited time period following the plasma treatment. When the surface tension of the treated surface of the viewport is greater than the surface tension of water, water-based fluid may be prevented from accumulating as droplets on the surface, but rather wet the viewport surface, e.g., such that a contact angle formed between the water-based fluid molecules and the viewport is less than 10 degrees (e.g., less than 5 degrees or substantially 0 degrees). Increasing the hydrophilicity thus may eliminate or significantly reduce blur caused by condensation of moisture on the surface of the viewport as droplets (e.g., fog). Instead, the fluid may form a thin and even layer on the surface of the viewport due to the increased hydrophilicity. This may maintain the optical quality of the viewport in its original (e.g., dry) state, or at least limit degradation of the optical quality when water-based fluid is introduced to the viewport. Similarly, increasing the hydrophilicity of the viewport via the plasma treatment may reduce variations of fluid thickness on the surface of the treated viewport, consequently reducing optical length variability of light waves passing through fluid condensed on the treated viewport. The reduction of optical length variability may improve the optical quality of the treated viewport when coming into contact with a fluid, as compared the diminished optical quality typically associated with an untreated viewport after coming into contact with the fluid.

In some embodiments, the viewport at the distal end of the endoscope may be configured for collecting an image, e.g., when the distal end of the endoscope is inserted into a body. In some embodiments, the viewport may be transparent, e.g., as a viewport of a laparoscope. In some embodiments, the viewport may be reflective, such as a mirror for a dental instrument. In some embodiments, the viewport may be both transparent and reflective (e.g., via a two-way mirror). The viewport may be made of glass, quartz, plastic, semiconductor, metal or any other material suitable for optical applications.

According to some embodiments, to treat an object with plasma, a plasma generation device may be provided. The plasma generation device may be located in a housing having a bore, slot or other opening. Such an opening in the housing may be configured to receive an object, e.g., while shrouded within a sheath for convenience and sterility. Alternatively, the opening in the housing may be configured to receive a shroud or sheath which is configured to subsequently receive an object for treatment. The plasma generation device may apply an electric and/or electromagnetic field suitable for generating plasma inside the bore, thereby permitting treatment of the object, such as the viewport located at the distal end of the object positioned therein, e.g., inside the sheath. According to some embodiments the sheath may be provided with at least one electrode and at least one sheath electric contact configured to electrically contact a corresponding electric contact in the plasma generation device when the sheath is inserted into the bore. The at least one electrode may thus apply an electric and/or electromagnetic field for generating plasma within the sheath. Treating the object with the generated plasma while encased within the sheath may cause the surface tension of the external surface of the object to be higher than the surface tension of water. Consequently, the object may be highly hydrophilic (e.g., super hydrophilic to prevent blurring caused by an accumulation of condensation when in contact with a fluid.

FIG. 1A schematically depicts a plasma generating system 100, according to aspects of some embodiments. Plasma generating system 100 may include an operating unit 120 and a plasma applicator 130 (also referred to herein as a plasma generating field applicator) electrically associated with operating unit 120, e.g., via a cable 112. The term "plasma generator" may refer to any device or system capable of forming plasma. Such a device or system may be configured to treat objects via a plasma cloud by executing one or more actions and/or functions based on computer program instructions that may be generated and/or received from at least one processor. The formation of a plasma cloud may be achieved by subjecting gas to a strong electromagnetic field to the point where an ionized gaseous substance becomes increasingly electrically conductive. Operating unit 120 may be associated with at least one processor 102 (e.g., a controller), a power supply 104, such as a battery, circuitry 106, and at least one memory 108. At least one processor 102 may be commutatively coupled to at least one memory 108 using wired and/or wireless means, e.g., via bus system 110. At least one processor 102 may be further electrically coupled to power supply 104 and circuitry 106, e.g., via a bus system 110. At least one processor 102 may be configured to execute one or more program code instructions with respect to one or more data items stored in at least one memory 106. The at least one program code instruction may facilitate control of one or operational aspects of plasma generation system 100, e.g., to control the generation of plasma via plasma applicator 130. For example, at least one processor 102 may control and moderate one or more attributes of energy supplied by power supply 104 (e.g., as electric power) to plasma applicator 130 for the purpose of generating plasma to treat an object, for example by controlling one or more components (e.g., switches, diodes, and other logical componentry) of circuitry 106. While at least one processor 102, power supply 104, circuitry 106, and at least one memory 108 are shown inside operating unit 120, this is intended for illustrative purposes only and does not limit the invention to the configuration illustrated. For example, at least one processor 102 and at least one memory 108 may include multiple local and/or remote processors and memory units, as known in the art of distributed computing. Similarly, while FIG. 1A shows power supply 104 and circuitry 106 positioned within operating unit 120, this is not required, and power supply 104 and/or circuitry 106 may be external to operating unit 120, e.g., power supply 104 may be within a wall unit that is coupled to operating unit 120 via cable.

FIG. 1B schematically depicts an object 200 (e.g., a medical instrument such as an endoscope), according to aspects of some embodiments. Object 200 may have a surface that may be susceptible to an accumulation of fluid as droplets. Plasma generation system 100 may be used to prepare object 200, e.g., for a medical procedure. Object 200 may include a distal end 210. Distal end 210 may include an optical element (e.g., a viewport) 220 configured to enable collecting light from the surroundings of optical element 220. In some embodiments, optical element 220 may include one or more substantially transparent elements, such as a window or a lens and may be made of material such as glass or quartz, semiconductor, or plastic such as Perspex, allowing light from the outside of object 200 to be collected inside of object 200, e.g. by a light sensitive device (not shown here) such as a camera. Additionally, or alternatively, according to some embodiments optical element 220 may include one or more substantially reflective elements, such as a mirror, that reflects light (e.g., rather than transfers light therethrough) for example towards a light collecting and/or reflecting apparatus (not shown here) or a light sensitive device. Optical element 220 may include a surface 222 which may be exposed to moisture, e.g., during a medical procedure. Consequently, if left untreated, e.g., not immunized against fogging, surface 222 may become covered with fog due to an accumulation of droplets on surface 222, e.g., due to, but not limited to, condensation of vapor.

In some embodiments, plasma generating system 100 may further include a protecting shroud 110 dimensioned to receive therein distal end 210 of object 200. Protecting shroud 110 may be alternatively referred to as a sheath. Plasma applicator 130 may include a slot 132 (e.g., a bore, cavity or other opening) configured to receive therein distal end 210 of object 200, while distal end 210 is shrouded within protecting shroud 110. In some embodiments, for use, distal end 210 of object 200 may be inserted into protecting shroud 110, following which protecting shroud 110, with distal end 210 being shrouded therein, may be inserted into slot 132. According to some embodiments, protecting shroud 110 may be inserted into slot 132, following which distal end 210 may be inserted and advanced into protecting shroud 110.

Figure 1C:
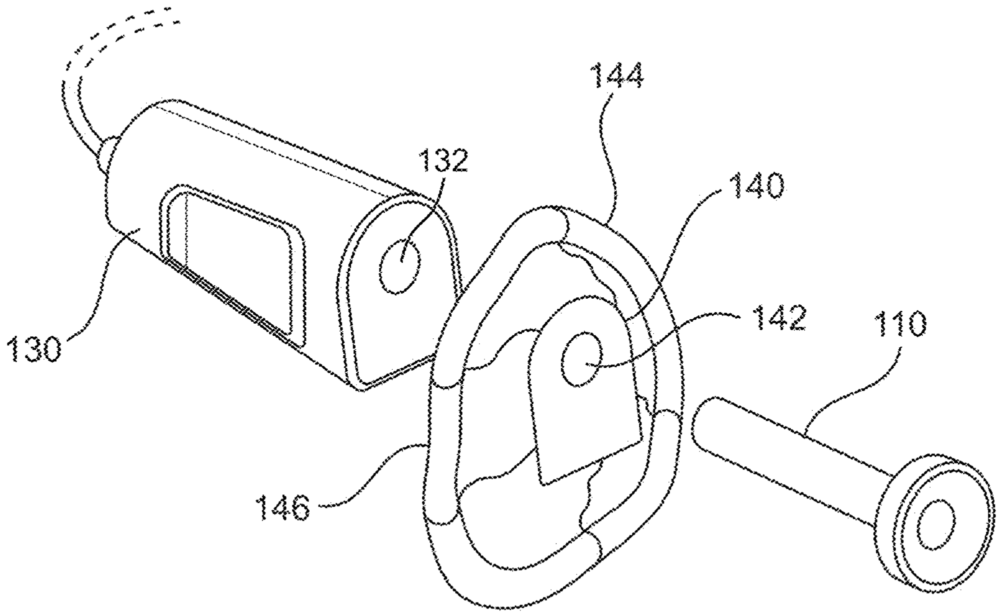
FIG. 1C is a perspective view of an example of a sterility screen of the apparatus of FIG. 1A having a sterility sleeve for covering an example of a plasma applicator of the apparatus of FIG. 1A, the sterility sleeve being rolled prior to use.
Figure 1D:
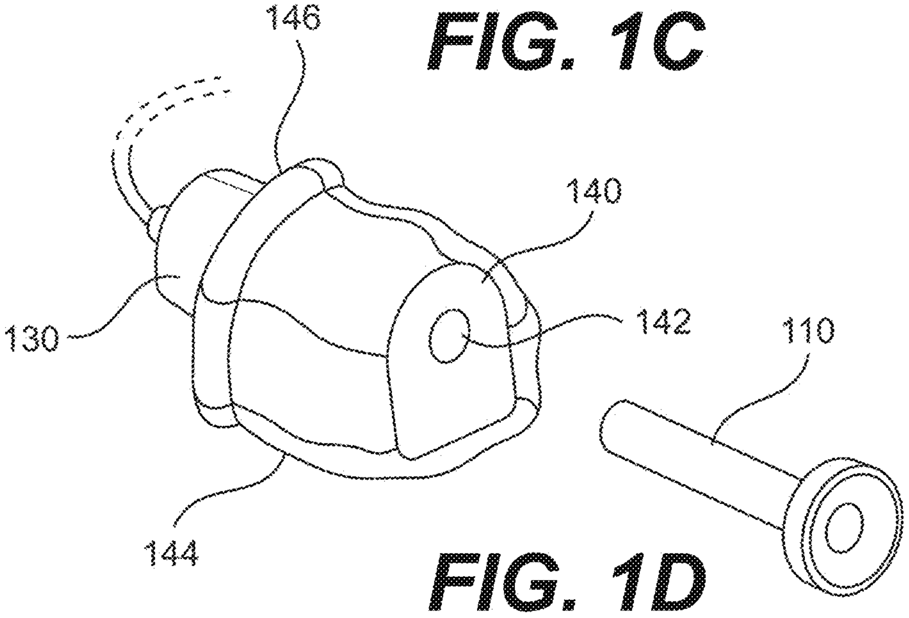
FIG. 1D is a perspective view of the sterility screen of FIG. 1C, wherein the sterility sleeve is partially unrolled to cover the plasma applicator.
Figure 1E:
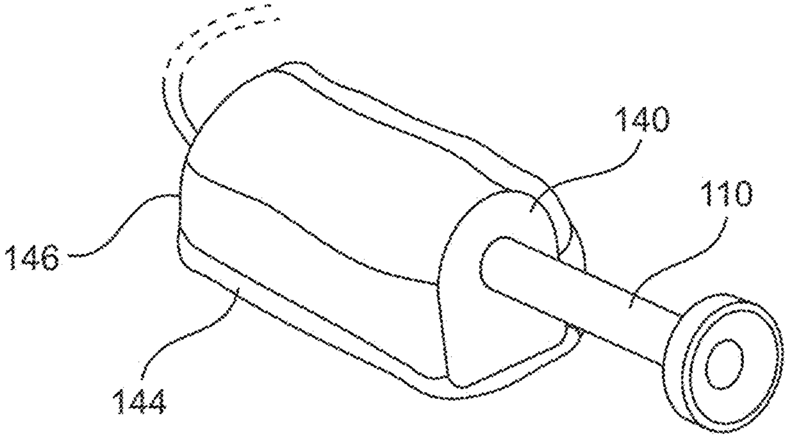
FIG. 1E is a perspective view of the sterility screen of FIG. 1C, wherein the sterility sleeve is unrolled and covering the plasma applicator.

Reference is now made to FIGS. 1C-1E, which taken together illustrate a schematic depiction of a sterility screen 140, according to some disclosed embodiments. According to some embodiments plasma generating system 100 (FIG. 1A) may further include sterility screen 140 having an opening 142. When using sterility screen 140 with plasma generating system 100, protecting shroud 110 may be inserted into slot 132 through opening 142 of sterility screen 140, as is further detailed and explained herein below. According to some embodiments protecting shroud 110 may be a dispensable, disposable, or replaceable part, being configured to be used during a single e.g., partial medical procedure carried out on a single patient. According to some embodiments, protecting shroud 110 may function as a sterility barrier for object 200 (FIG. 1B), preventing exposure of object 200, e.g., to body fluids of a patient during a medical procedure. Protecting shroud 110 may additionally prevent exposure of object 200 to contaminants present within plasma applicator 130, which may or may not be maintained sterile during use and after use. According to some embodiments, sterility screen 140 may facilitate in maintaining plasma applicator 130 clear of fluids (e.g., bodily fluids) that may be transferred via object 200 during use and after use.

According to some embodiments sterility screen 140 may be attached to a sterility sleeve 144, as depicted schematically in FIGS. 1C, 1D, and 1E. Sterility sleeve 144 may extend between sterility screen 140 and a sleeve distal end 146. According to some embodiments sterility sleeve 144 may be soft or flexible, e.g., like a sock. Prior to use, sterility sleeve 144 may be folded or rolled, as schematically depicted in FIG. 1C. For use, sterility sleeve 144 may be unfolded, or unrolled to encompass, envelop, and cover plasma applicator 130 or a portion thereof, e.g., by inserting plasma applicator 130 into sterility sleeve 144 through sleeve distal end 146. During use, sterility sleeve 144 may be disposed around plasma applicator 130 so as to envelop and cover plasma applicator 130. Enveloping plasma applicator 130 thus may ensure that inserting protecting shroud 110 through opening 142 and into slot 132, and/or object 200 into protecting shroud 110, may substantially reduce contamination of plasma applicator 130. According to some embodiments, sterility sleeve 144 may be substantially rigid, having a shape of e.g., a tube, being configured to house protecting shroud 110 therein. According to some embodiments sterility sleeve 144 may include a double-sided sticky pad (not shown here) in a bottom portion thereof, where one side of the double-sided sticky pad may be configured to adhere to plasma applicator 130, and the opposite side of the double-sided sticky pad may be configured to adhere to a flat surface, such as a desk, or a table or another working platform. Attaching plasma applicator 130 thus to the working platform may stabilize plasma applicator 130 and facilitate inserting and extracting protecting shroud 110 (or object 200) from plasma applicator 130. According to some embodiments, sterility screen 140 together with sterility sleeve 144, may be attached to protecting shroud 110, so that insertion of protecting shroud 110 into slot 132 and encapsulating plasma applicator 130 with sterility sleeve 144 may be performed substantially together.

Upon activation of power supply 104, plasma applicator 130 may be further configured to apply an electric and/or electromagnetic field suitable for plasma generation when distal end 210 of object 200 (FIG. 1B), shrouded within protecting shroud 110, is positioned inside slot 132. The electric and/or electromagnetic field may be applied to the inside of protecting shroud 110 inside slot 132 with distal end 210 positioned therein. In some embodiments, distal end 210 includes a viewport 222 (FIG. 1B) including one or more optical elements, e.g., such as a viewport of an endoscope. Thus, the electric and/or electromagnetic field suitable for plasma generation may be applied in proximity to viewport 222.

According to some embodiments plasma applicator 130 may be fluidly associated with a gas pump and additionally or alternatively with a gas reservoir (neither of which is shown here). The gas pump and the gas reservoir may be used to controllably evacuate, or to controllably flush with a preferred gas, respectively, a vicinity of the distal end of the endoscope, to facilitate plasma ignition, as is further detailed and explained below. According to some embodiments, a preferred gas may be argon or nitrogen. According to some embodiments, a gas pressure suitable for plasma ignition after evacuation may be below 0.1 Atm. According to some embodiments, the vicinity of the distal end of the endoscope may be pumped and evacuated and then flushed with a desired gas. According to some embodiments, the gas pump and/or the gas reservoir, as the case may be, may be optionally situated in the operating unit 120 (FIG. 1A).

Operating unit 120 may be configured to enable a user of plasma generating system 100 to operate and control the apparatus. Operating unit 120 may thus include one or more command switches and one or more controllers, such as physical or virtual switches, buttons, and controllers. The control unit may further include indicators for providing a user with required data and information for operating the apparatus, such as indication LEDs, displays and possibly an operating software executable by at least one processor 102 for providing a user with operating and command screens to allow a user to operate and command the apparatus.

Figure 2:
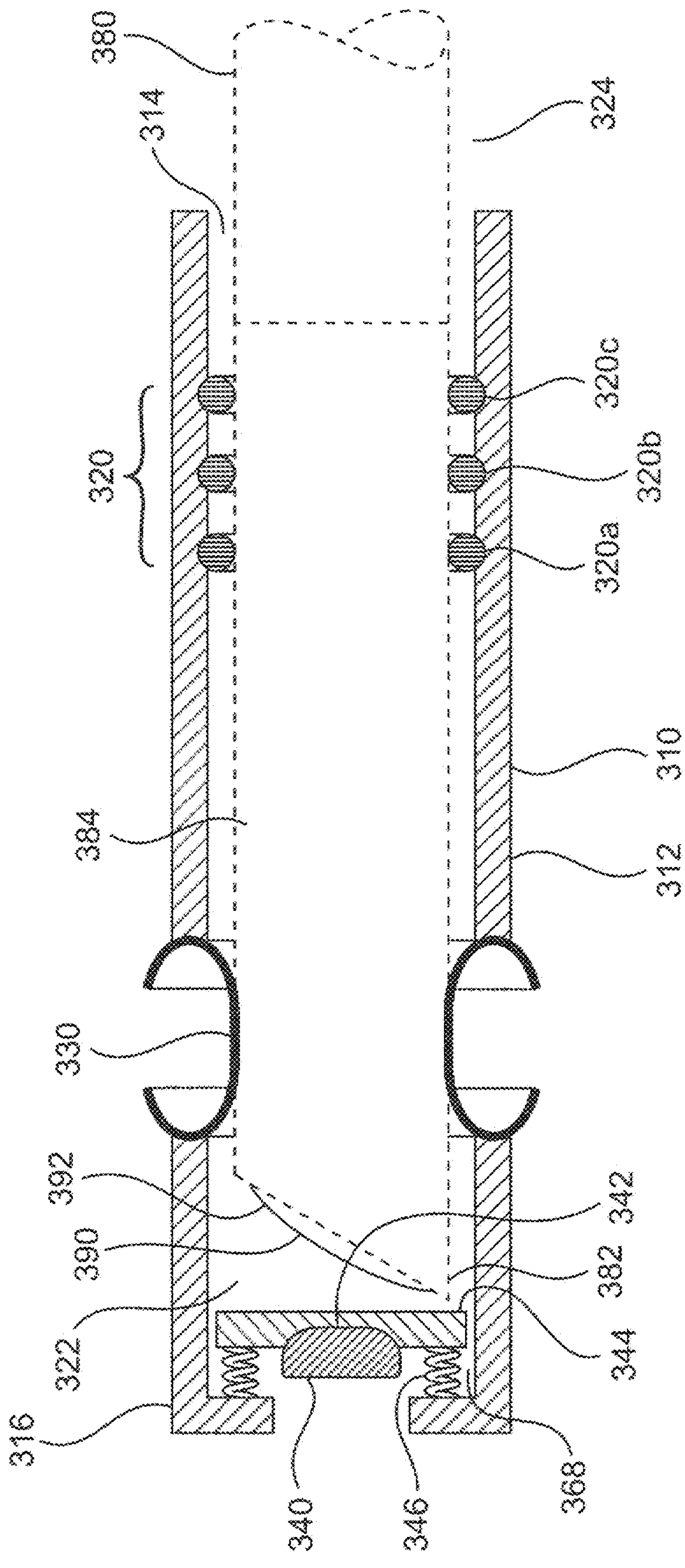
FIG. 2 is a cross-sectional view of an embodiment of a sheath of an apparatus for preparing a medical instrument consistent with some embodiments of the present disclosure.

Reference is now made to FIG. 2 depicting, in a cross-sectional view, an embodiment of a protecting shroud 310 according to an aspect of some embodiments. Protecting shroud 310 may be suitable for use with an object, such as endoscope 380, depicted schematically inside protecting shroud 310 in dashed lines. Endoscope 380 may include a distal end 382 and an electrically conducting surface—e.g., a metallic surface 384—at distal end 382. Distal end 382 of endoscope 380 may be disposed with a viewport 390. Viewport 390 may further include an optical element 392, which may be subject to plasma treatment as described herein.

Protecting shroud 310 may include a hollow cylinder 312 extending between a proximal opening 314 and a cylinder distal end 316. Protecting shroud 310 may further include a vacuum seal 320 having one or more (e.g., three) O-rings, e.g., O-rings 320*a*, 320*b* and 320*c*. Vacuum seal 320 may be adapted to fit an external dimension (e.g. an external diameter) of endoscope 380 so as to allow insertion of endoscope 380 into protecting shroud 310 using a slight force, e.g. by hand, as is known in the art. Accordingly, vacuum seal 320 may be configured to hold a pressure difference (or gas concentration difference) between an inside 322 of protecting shroud 310 and an outside 324 of protecting shroud 310 when endoscope 380 is positioned inside protecting shroud 310. Vacuum seal 320 may also assist in mechanically stabilizing endoscope 380 inside protecting shroud 310, thereby assisting in preventing gas leakage between the inside 322 and the outside 324 of protecting shroud 310. Vacuum seal 320 may further assist in plasma generation in proximity to viewport 390, as is further explained below.

Protecting shroud 310 may further include a cathode 330 arranged on hollow cylinder 312 and configured to establish an electrical feedthrough between the outside 324 of protecting shroud 310 and the inside 322 thereof. Cathode 330 may be flexible and electrically exposed on the inside 322 of protecting shroud 310 and on the outside thereof, thereby allowing insertion of endoscope 380 into protecting shroud 310 while forming an electric contact between cathode 330 and metallic surface 384. Protecting shroud 310 may further include an anode 340 arranged in proximity to cylinder distal end 316. Anode 340 may be shaped as a metallic block having, for example, a circular smooth surface 342 facing the inside 322. According to some embodiments, surface 342 may be curved. According to some embodiments (not shown here), anode 340 may be shaped as a pointed tip pointing towards the inside 322. According to some embodiments, anode 340 may be shaped as a ring. Anode 340 may be mounted on a disk 344 made of a dielectric material, so that disk 344 forms a dielectric barrier between anode 340, positioned on one side of the dielectric barrier, and cathode 330 with metallic surface 384 of endoscope 380, positioned on the other side of the dielectric barrier, where metallic surface 384 is at a same potential as cathode 380. In other words, disk 344 may be configured to ensure plasma generation in a Dielectric Barrier Discharge (DBD) mode of operation, e.g., by interrupting a line-of-sight between anode 340, on one side of the dielectric barrier, and cathode 330 and metallic surface 384 of endoscope 380 on the other side of the dielectric barrier, thereby forming the dielectric barrier. In a DBD mode, plasma may be generated more uniformly over the available space in the vicinity of the view port, whereas arcing or other types of specific and narrow electric transportation trajectories between the anode and the cathode may be prevented. Cathode 330 and/or anode 340 may receive electrical energy for generating an electric and/or electromagnetic field suitable for carrying out a plasma treatment via circuitry 106, power supply 104 and/or 530, at least one processor 102 and cable 112 (FIG. 1A).

It is noted that the thickness of the dielectric barrier may have a substantially strong effect on the uniformity of the plasma generating electric and/or electromagnetic field in the vicinity of viewport 390, and hence on the quality of the plasma treatment. The "quality" of the plasma treatment herein may refer to a level of hydrophilicity attained, and the duration of time during which the electric and/or electromagnetic filed is activated to obtain that hydrophilicity. In other words, a high-quality plasma treatment may achieve a relatively high level of hydrophilicity (e.g., obtaining a surface tension above that of water namely above 0.072N/M on the treated surface) within a relatively short duration (e.g., of 5 minutes, or 1 minute or as short as 10 second or even as short as 5 second of activated electric and/or electromagnetic field). The thickness of the dielectric barrier may generally be as low as possible to facilitate plasma ignition, yet large enough to prevent breakdown and arcing. Exemplary thickness of a dielectric material such as PET or polycarbonate in embodiments described herein may be in the range of about 0.3 mm to about 3 mm for RF electric and/or electromagnetic field at frequencies in the MHz range (e.g., about 2 MHz).

According to some embodiments anode 340 may be configured to displace flexibly relative to hollow cylinder 312, to facilitate a reliable electrical contact between anode 340 and a feeding contactor as is explained further below. According to some embodiments disc 344 may be supported by springs 346 relative to the cylinder 312.

In operation, a plasma generating electric power (e.g., provided by power supply 530) may be supplied between anode 340 and cathode 330. Consequently, a plasma generating electric and/or electromagnetic field in a DBD mode may be generated between anode 340 and metallic surface 384 being in electrical contact with cathode 330. The plasma generating electric and/or electromagnetic field may generate plasma in the space between anode 340 and cathode 330, and particularly in the vicinity of viewport 390 and adjacent optical element 392.

Figures 3A, 3B:
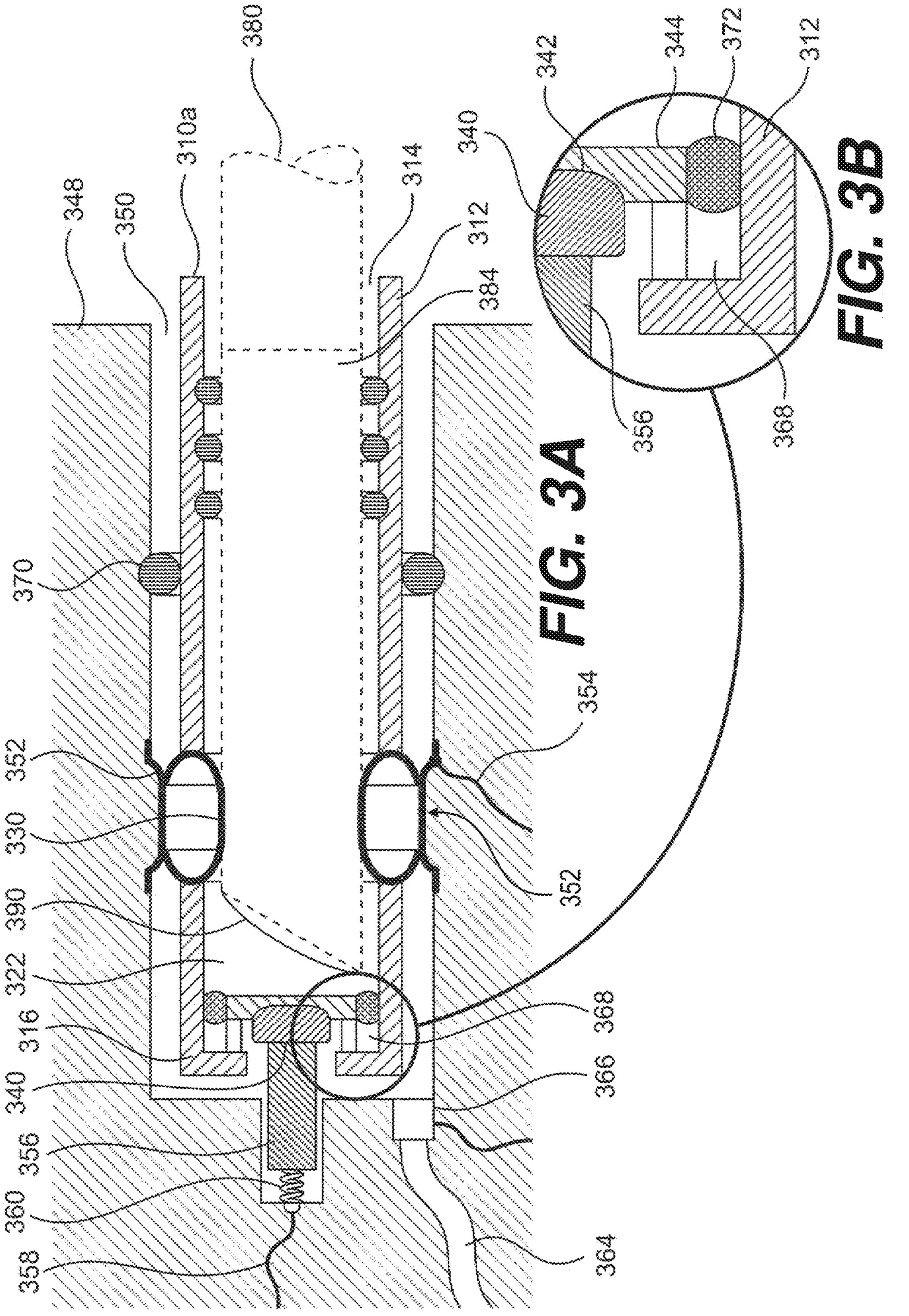
FIG. 3A is a cross-sectional view of a sheath positioned inside a bore of a plasma applicator of the apparatus, consistent with some disclosed embodiments.
FIG. 3B is a cross-sectional view of a detail of the sheath of FIG. 3A.

Reference is now made to FIG. 3A, depicting a portion of an embodiment of a plasma applicator 348 suitable for use with a protecting shroud 310*a*, where protecting shroud 310*a* is slightly different from protecting shroud 310 of FIG. 2, as is detailed below. Plasma applicator 348 may be configured to receive energy for carrying out a plasma treatment, e.g., via circuitry 106, power supply 104, at least one processor 102, and cable 112 (FIG. 1A). Plasma applicator 348 may include a bore 350 configured for receiving therein protecting shroud 310*a*. In some embodiments, endoscope 380 may be shrouded within protecting shroud 310*a*. Plasma applicator 348 may further include a cathode contactor 352 configured to contact a cathode 330 when protecting shroud 310*a* is inside bore 350. An electric conductor 354, such as an electric wire, electrically associated with cathode contactor 352, may be used to supply electric power generated by a power source (e.g., power supply 104) to cathode contactor 352 and to cathode 330. Plasma applicator 348 may further include an anode contactor 356 configured to contact anode 340 when protecting shroud 310*a* is inside bore 350. An electric conductor 358, such as an electric wire, electrically associated with anode contactor 356, may be used to supply electric power generated by the power source to anode 340. Anode contactor 356 may be supported flexibly, e.g., by a spring 360, to facilitate a reliable electric contact between anode contactor 356 and anode 340 when protecting shroud 310*a* is inserted to bore 350.

It is noted that characteristics of an electric and/or electromagnetic field capable of generating plasma from a gas may depend strongly on characteristics of the gas itself, in addition to the geometry of the electrodes involved (such as the shape and configuration of electrodes used to apply the electric and/or electromagnetic field, the distance between the electrodes, and any other physical aspect of the electrode affecting the electric field). Generally, the higher the pressure of the gas, the higher the electric and/or electromagnetic field should be to ignite plasma from the gas. Also, some gases ignite at lower fields than others. For example, plasma may be ignited in helium gas at atmospheric pressure and using an RF field (in a frequency between 1 MHz and 15 MHz) of about 7 KV over a distance of 1 cm between electrodes, and at a voltage of about 200V if the gas is at a pressure of 0.8 KPa. With a similar configuration of electrodes and at similar field frequencies, plasma may be ignited in air at a voltage of about 20 KV in atmospheric pressure and at a voltage of about 800V in 0.8 KPa.

Thus, according to some embodiments, plasma applicator 348 may be configured to stream gas from a gas reservoir (not shown here) to bore 350, or to pump air from bore 350, to generate a low-pressure zone in the space between the electrodes 330 and 340, to facilitate plasma ignition. Thus, according to some embodiments, plasma applicator 348 may be connected to a hose 364 fluidly associating a gas reservoir (not shown here) containing a gas suitable for plasma generation therein such as helium or argon or nitrogen, with bore 350. A valve 366 controlled by a control unit (not shown here) operable by a user, may be used to schedule and regulate the flow of gas into bore 350. During operation, according to some embodiments, after introducing protecting shroud 310*a*, with endoscope 380 positioned therein, into bore 350, valve 366 may be opened to allow gas flow into bore 350. Protecting shroud 310*a* may be penetrable to gas flow through openings 368 between hollow cylinder 312 and disc 344, enabling the gas to flow into protecting shroud 310*a*, and towards viewport 390. Excess of gas flowing into bore 350 may freely escape through the gap in bore 350 between protecting shroud 310*a* and plasma applicator 348 (e.g., the gap being not sealed). Following a suitable time period of gas flow (e.g., 5 seconds or 10 second or 30 second or even 1 minute) the electric power source may be activated to supply power to anode 340 and cathode 330 to generate a plasma generating electric field near viewport 390. According to some embodiments the gas reservoir may be portable and suitable for a single time use.

According to some embodiments, hose 364 may be used to pump gas (e.g., air) from protecting shroud 310*a* and particularly from the space near viewport 390, to facilitate plasma ignition. Air may be sucked from the vicinity of viewport 390 through openings 368 towards bore 350 and into hose 364. A vacuum seal 370 may enable generating vacuum near viewport 390 by withholding a pressure difference between a region near cylinder end 316 and a region near opening 314 of protecting shroud 310*a*. According to some embodiments air may be pumped through hose 364 by a vacuum pump (not shown here), fluidly associated with hose 364. According to some embodiments hose 364 may be fluidly associated to a pumped container (not shown) which may be continuously pumped, e.g., by a small vacuum pump. Fluid association may be provided through hose 364, the hose being in constant fluid communication with the container, thereby being also continuously pumped. Opening valve 366 may result in pumping bore 350 and particularly the space near viewport 390 by the vacuum pump or by the pumped container, depending on the particularities of the embodiment. The volume of the pumped region in fluidly connected parts of bore 350 and of protecting shroud 310*a* may be, according to some embodiments, smaller than 10 cc, and a pumped container and hose of e.g. about 1000 cc (1 liter) may suffice to establish a suitable vacuum level between e.g. about 0.1 atm and about 0.01 atm within less than about 5 or less than about 10 seconds, which may be sufficient for plasma excitation for about 30 seconds or even about 1 minute to satisfactorily plasma-treat optical element 392.

Reference is now made to FIG. 3B which illustrates a close-up depiction of anode 340 interfacing with disc 344, according to some embodiments. Protecting shroud 310*a* may further include a sterility filter 372 positioned in openings 368 for maintaining a sterility barrier between protecting shroud 310*a* and plasma applicator 348. Maintaining a sterility barrier may be understood as meaning that microbial organisms may not penetrate sterility filter 372. For example, microbial organisms may include any form of prokaryotic cells or eukaryotic cells, including fungi and bacteria. Sterility filter 372 may be disposed, according to some embodiments, across cylinder end 316 in openings 368, so that gas flowing from plasma applicator 348 into protecting shroud 310*a* may enter protecting shroud 310*a* without introducing contaminants, e.g., sterile, and/or gas flowing from the inside 322 of protecting shroud 310*a* into plasma applicator 348 enters plasma applicator 348 without introducing contaminants, e.g., sterile. Thus, sterility filter 372 may prevent a transfer of contamination from plasma applicator 348 (e.g., from surroundings of bore 350) onto endoscope 380, and/or may prevent a transfer of contamination from endoscope 380 onto plasma applicator 348. Additionally, or alternatively, a sterility filter may be positioned in plasma applicator 348, or for example in hose 364.

Figure 3C:
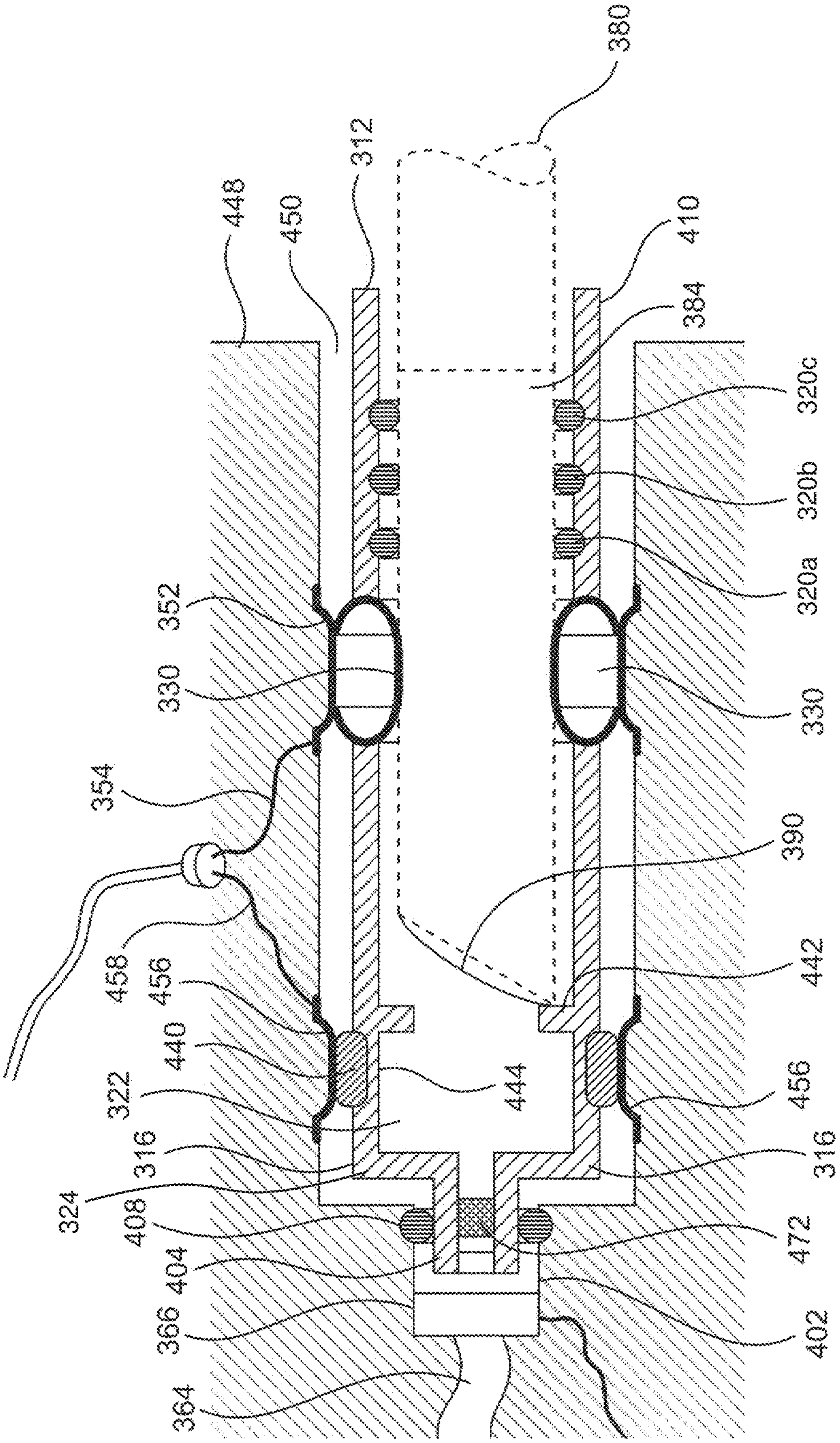
FIG. 3C is a cross-sectional view of another embodiment of a sheath and a generating field applicator for preparing a medical instrument to a medical procedure, consistent with some disclosed embodiments.

FIG. 3C schematically depicts a plasma applicator 448 and a corresponding sheath 410 (e.g., protecting shroud) according to some exemplary embodiments. Plasma applicator 448 differs from plasma applicator 348 by the inclusion of an applicator gas port 402 fluidly associated with hose 364, and by sheath 410 including a sheath gas port 404 configured to fluidly connect to applicator gas port 402. Fluid connectivity between the inside 322 of sheath 410 and the outside 324 of sheath 410—e.g. within the space of bore 450 of plasma applicator 448, may be prevented by a vacuum seal 408, e.g. an O-ring. Thus, when sheath 410 is inserted into plasma applicator 448, sheath gas port 404 may fluidly connect to applicator gas port 402, thereby establishing fluid connectivity of hose 364 to the inside 322 of sheath 410. Consequently, a plasma-ignition facilitating gas (such as helium or argon) may be driven directly into sheath 410 through hose 364, and additionally or alternatively, gas (e.g., air), may be pumped from sheath 410 through hose 364. Fluid connectivity between the bore 450 and the inside 322 of the sheath may thus be prevented. A sterility filter 472 may be positioned inside sheath gas port 404, for maintaining a sterility barrier between the inside 322 of sheath 410 and plasma applicator 448. As explained above regarding sterility filter 372 in FIG. 3B, gas flowing from plasma applicator 448 into the inside 322 of sheath 410 may enter sheath 410 sterile, and/or gas flowing from the inside 322 of sheath 410 into plasma applicator 448 may enter plasma applicator 448 sterile. Thus, sterility filter 472 may prevent contamination from plasma applicator 448 (e.g., from surroundings of bore 450) onto endoscope 380, and/or may prevent contamination from endoscope 380 onto the plasma applicator 448.

Sheath 410 may further differ from protecting shroud 310 in having a ring anode 440 shaped as a ring on an external circumference of hollow cylinder 312 near distal cylinder end 316 (instead of anode 340 in protecting shroud 310). Hence hollow cylinder 312, being made of a dielectric material, may function as a dielectric barrier 444 between anode 440, on one side of dielectric barrier 444, and cathode 330 and metallic surface 384 of the endoscope, on the other side of dielectric barrier 444, so that plasma is generated in sheath 410 in a DBD mode of operation as described above regarding protecting shroud 310. According to some embodiments sheath 410 may include a stopper 442 inside hollow cylinder 412. Stopper 442 may be configured to limit advancement of endoscope 380 into sheath 410, so that a pre-determined, desired gap may be established between anode 440 and metallic surface 384 of endoscope 380, thereby ensuring plasma generation at a known field (the field being determined by the voltage supplied between cathode 330 and anode 440 and the gap there between). Stopper 442 may further be employed as a dielectric barrier on the line of sight between anode 440 and cathode 330, thereby assisting in focusing plasma towards view port 390.

When sheath 410 is inserted into bore 450 of plasma applicator 448, an anode contactor 456 of plasma applicator 448 may contact ring anode 440. Anode contactor 456 may be electrically associated with an electric conductor 458 which is configured to connect to a power supply (e.g., power supply 530) to enable providing energy (e.g., as electric power) to ring anode 440 for generating a plasma generating electric and/or electromagnetic field, as described above. It is noted that cathode 330 of sheath 410 may be electrically associated with cathode contactor 352 when sheath 410 is inserted into bore 450 as described above. Thus, upon activation, a suitably connected power supply may provide a plasma generating electric and/or electromagnetic field (in a DBD mode) between ring anode 440 and metallic surface 384 of endoscope 380 to generated plasma in the vicinity of view port 390.

Figure 4:
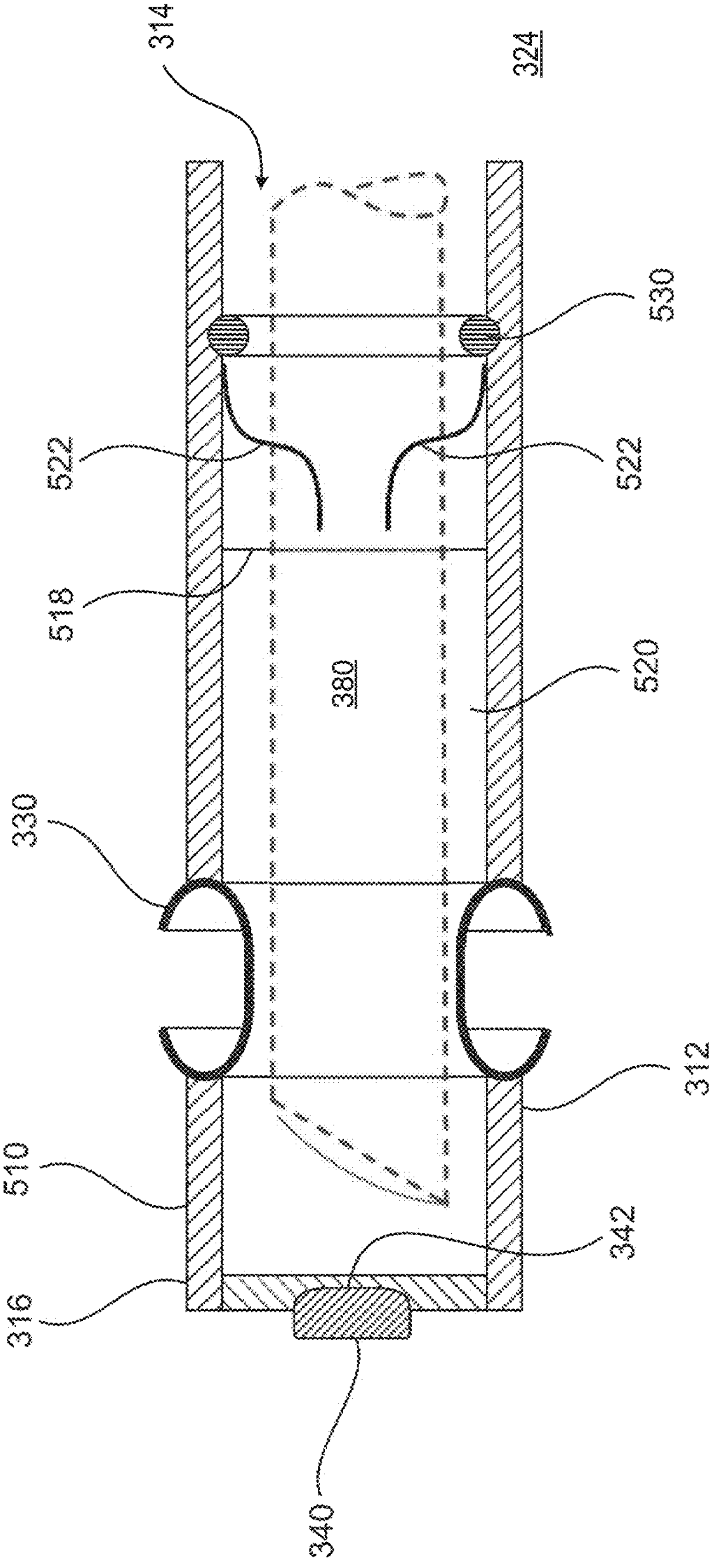
FIG. 4 is a cross-sectional view of yet another embodiment of a sheath of an apparatus for preparing a medical instrument to a medical procedure, consistent with some disclosed embodiments.

FIG. 4 schematically depicts a sheath 510 according to an aspect of some embodiments. Sheath 510 may be configured to facilitate plasma ignition, without pumping the space around the endoscope as described in the embodiments above nor without streaming gas into that space. In other words, sheath 510 may enable providing plasma treatment to a view port of an endoscope according to the teachings herein, using a plasma applicator that is not connected neither to a gas reservoir nor to a gas pump. Accordingly, sheath 510 may not have a gas port, such as gas port 402, and may not be connected to a hose, such as hose 364.

Sheath 510 may include a hollow cylinder 312 extending between an opening 314 and cylinder end 316. Sheath 510 may differ from protecting shroud 310 in that hollow cylinder 312 may be bound and sealed near cylinder end 316, thereby substantially preventing permeation or penetration of gas molecules through cylinder end 316. Sheath 510 may further differ from protecting shroud 310 in having a leakage seal 530 inside hollow cylinder 312, and a hermetic screen 518 in hollow cylinder 312 situated between leakage seal 530 and cylinder end 316. Hermetic screen 518 may be configured to be impermeable to gas molecules, thereby defining a closed space 520, closed between hermetic screen 518 and cylinder end 316. Closed space 520 inside sheath 510 may thus be airtight, namely maintained to remain sealed from the outside 324 of sheath 510. Closed space 520 may contain a gas suitable for plasma ignition, e.g. Argon, at a gas pressure of about 1 atmosphere, so that there is, at most, only minor pressure gradients over the hermetic screen.

Hermetic screen 518 may be breakable, being thereby configured to break (tear down) upon insertion of an endoscope such as endoscope 380 into sheath 510. According to some embodiments, sheath 510 may further include one or more tearing needles 522 attached flexibly to hollow cylinder 312 near hermetic screen 518 outside of closed space 520. Tearing needles 522 may be configured to lean flexibly towards hermetic screen 518 and to tear the hermetic screen when pushed by an object inserted into the sheath. Thus, for use, the endoscope may be inserted into sheath 510 and affecting tearing down of hermetic screen 518 by pushing tearing needles 522 towards hermetic screen 518. The endoscope may be further advanced until the viewport of the endoscope is between cathode 330 and anode 340. It is noted that during insertion, the endoscope may first be advanced through leakage seal 530, and then through hermetic screen 518, which may break. The endoscope may then be further advanced to be positioned in place within sheath 510. Once hermetic screen 518 is broken, the gas inside space 520 may be prevented from freely flowing towards opening 324 by a sealing formed between leakage seal 530 and the endoscope. During further advancement of the endoscope into sheath 510, the free volume of space 520 for the gas may reduce, yet pressure build up in the region of closed space 520 may be prevented, due to gas escaping under a pressure difference across leakage seal 530. As a result, when endoscope 380 is fully inserted into sheath 510, closed space 520 and particularly the space proximal the viewport of the endoscope, between anode 340 and cathode 330, may include substantially the gas that was contained in the space 520 before the tear-up of hermetic screen 518, at approximately atmospheric pressure, thereby facilitating plasma ignition therein. According to some embodiments hermetic screen 518 may be made of Mylar or metalized Mylar or Kapton or metalized Kapton and the like.

There is thus provided according to an aspect of the disclosure an apparatus (e.g., plasma generating system 100 in FIG. 1A) for preparing an endoscope ((200 in FIG. 1, 380 in FIGS. 2, 3A and 3C) for an endoscopy procedure. The apparatus may include a sheath (110 in FIG. 1A, 310, 310*a* in FIGS. 2 and 3A, 410 in FIG. 3C, 510 in FIG. 4) dimensioned to receive therein a distal end (210, 382) of the endoscope. The distal end may include a view port (220, 390) configured to enable collecting an image of the surrounding of the view port there through.

The apparatus may further include a plasma generating field applicator (130, 348, 448), electrically associated with an electric power source. The plasma generating field applicator may have a bore (132, 350, 450) configured to receive therein the distal end of the endoscope shrouded within the sheath. The plasma generating field applicator may be configured to apply electric power suitable for plasma generation within the sheath. The sheath may be detachable from the distal end of the endoscope and from the plasma generating field applicator. According to some embodiments the view port of the endoscope may be transparent or may be a mirror.

According to some embodiments the apparatus may further include a sterility sleeve (144) extending between a first end (146) and a second end (140), configured to encapsulate the plasma generating field applicator, having on the first end a first opening configured to enable inserting the plasma generating field applicator into the sterility sleeve, and on second end a second opening (142) configured to enable inserting the endoscope into the plasma generating field applicator. According to some embodiments the sterility sleeve may be soft and according to some embodiments the sterility sleeve may be rigid. The sterility sleeve may be detached from the plasma generating field applicator. According to some embodiments the sterility sleeve may be attached to the sheath, and according to some embodiments the sterility sleeve may be detached from the sheath.

According to some embodiments the sheath may include at least one electrode (340, 440) and a first sheath electric contact (340, 440) electrically connected to the electrode. The first sheath electric contact may be configured to electrically contact a corresponding first applicator electric contact (356, 456) in the plasma generating field applicator when the sheath is inserted into the bore (350, 450). The at least one electrode may thereby be configured to apply a plasma generating field inside (322) the sheath upon receiving the electric power from the plasma generating field applicator.

According to some embodiments the sheath may further include a second sheath electric contact (330), configured to contact the endoscope when the distal end of the endoscope is received within the sheath. The second sheath electric contact may be configured to electrically contact a second applicator electric contact (352) when the sheath is inserted into the bore (350, 450).

According to some embodiments the sheath may include a hollow, substantially rigid tube (312, 412) extending between an opening (314) configured to receive the distal end of the endoscope, and a distal end (316) of the sheath. According to some embodiments the hollow tube may be a hollow cylinder (312, 412).

According to some embodiments the sheath further may include a seal (320, 530) positioned between the opening and the distal end along an inner circumference of the hollow tube, being dimensioned to encircle the endoscope (380), being thereby configured to sealingly contact the endoscope when the endoscope is received inside the hollow tube. According to some embodiments the seal may include an O-ring.

According to some embodiments the plasma generating field applicator (348, 448) may be connected to a hose (364). The hose may be controllably fluidly connected to the bore (350, 450). According to some embodiments the plasma generating field applicator (348, 448) may include a controlled valve (366), controllably fluidly connecting the hose (364) with the bore (350, 450). According to some embodiments the plasma generating field applicator (348) may include an applicator gas port (402) fluidly connected with the hose, and the sheath (410) comprises a sheath gas port (404). The sheath gas port may be configured to sealingly connect with the applicator gas port for fluidly connecting the hose with an inside (322) of the sheath. The sealed connection between the sheath gas port and the applicator gas port may prevent, e.g. by seal 408, flow communication between the inside (322) of the sheath (fluidly associated with hose 364) and the bore (450), when the sheath is inserted into the bore.

According to some embodiments the sheath (510) may include a seal (530) inside the hollow tube (312) configured to sealingly contact the endoscope when the distal end of the endoscope is inserted into the hollow tube. The sheath (510) may further include a hermetic screen (518) spanning across the hollow tube and configured to thereby define a closed and sealed space (520) between the hermetic screen and the distal end (316) of the hollow tube. According to some embodiments the sheath may further include one or more tearing needles (522) positioned inside the hollow tube between the seal (530) and the hermetic screen (518) being configured to tear down the hermetic seal upon insertion of the endoscope into the hollow tube.

According to an aspect of some embodiments there is provided a method of preparing an endoscope for an endoscopy procedure. The method may include providing a sheath (110, 310, 310*a*, 410, 510) dimensioned to receive therein a distal end (210, 382) of the endoscope, the distal end comprising a view port (220, 390) configured to allow collecting an image of the surrounding of the view port there through. The method may further include providing a plasma generating field applicator (130, 348, 448) electrically associated with an electric power source. The plasma generating field applicator may have a bore (132, 350, 450) configured to receive therein the distal end of the endoscope shrouded within the sheath. The plasma generating field applicator may be configured to apply electric power suitable for plasma generation within the sheath (e.g., by the electrodes 330, 340 and 440). The sheath may be detachable from the plasma generating field applicator and from the distal end of the endoscope. The method may further include positioning the distal end of the endoscope shrouded within the sheath in the bore of the plasma generating field applicator and activating the power source to generate plasma within the sheath, thereby plasma-treating the view port at the distal end of the endoscope.

According to some embodiments, the method may further include preventing, by the sheath, contamination of the plasma generating field applicator with fluids dispersed on the distal end. According to some embodiments, the plasma generation field applicator may include a hose (364) and the method may further include controllably (by closing and opening valve 366) flowing a gas into an inside (322) of the sheath or pumping the inside of the sheath via the hose.

According to an aspect of some embodiments there is further provided a method of preparing an endoscope (380) for an endoscopy procedure, the endoscope comprising a distal end (382) comprising a view port (390). The view port may be made of a dielectric material and is proximal to a metallic segment (384) at the distal end of the endoscope. The method may include placing the distal end of the endoscope in a closed plasma chamber (e.g., sheaths 310, 310*a*, 410 or 510, wherein the insertion of the endoscope seals the inside 322 of the sheaths, thereby defining a closed plasma chamber therein). The closed plasma chamber may have at least an anode (340, 440) and a cathode (330) wherein the cathode electrically contacts the metallic segment. A line-of-sight between the anode and the cathode is interrupted by a dielectric barrier (344, 444), and the method may further include applying a plasma-generating electromagnetic field between the anode and the cathode, thereby generating plasma in a DBD mode in a vicinity (322) of the view port. According to some embodiments, the electric barrier (444) electrically may isolate the anode (440) from gas in the vicinity (322) of the view port. According to some embodiments of the method, the view port may be transparent or alternatively reflective (e.g., a mirror), or semi-transparent (e.g., a two-way mirror both reflecting and transmitting light). According to some embodiments of the method the view port may be made of glass or quartz or plastic.

Figure 5C:
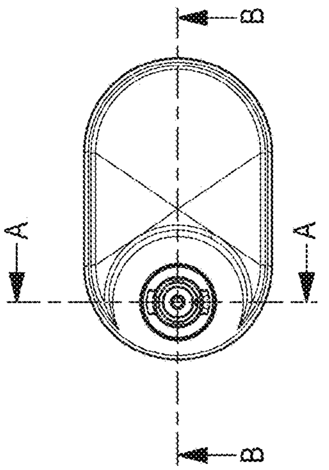
FIGS. 5A, 5B and 5C are respective cross-sectional side, front, and top views of a plasma generating system, consistent with some disclosed embodiments.
Figure 5B:
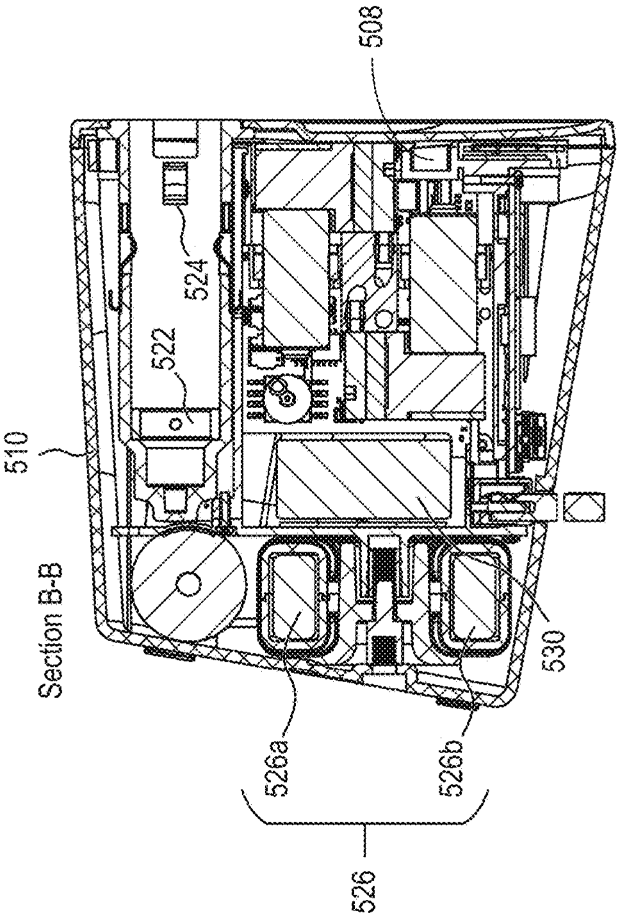
Figure 5A:
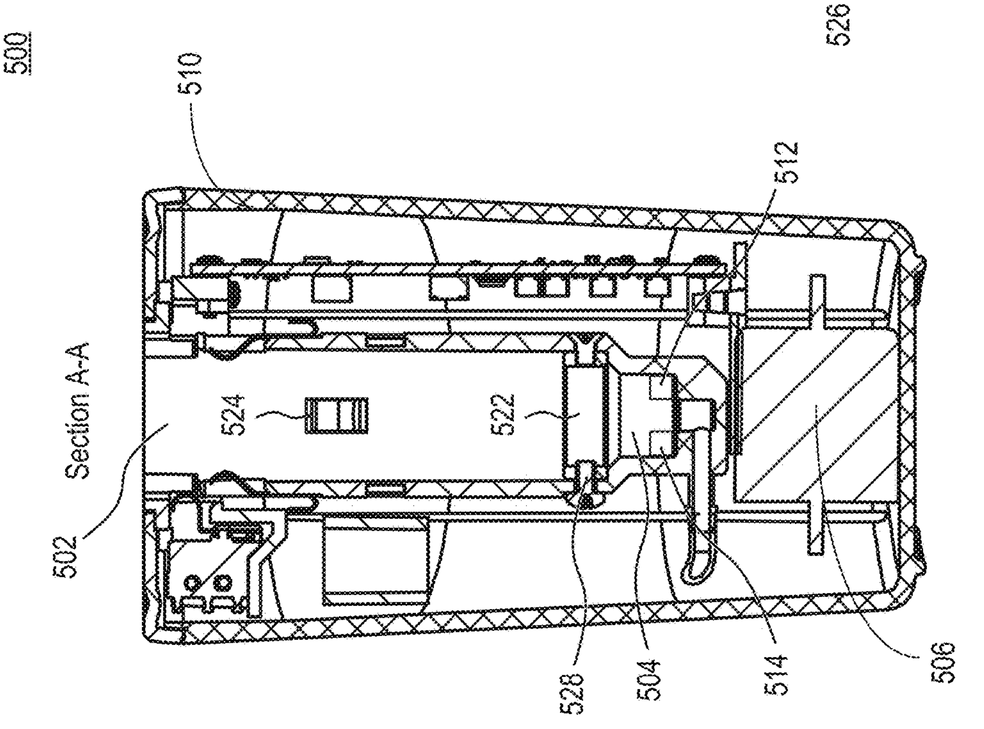

FIGS. 5A, 5B, and 5C illustrate three views of a plasma generating system 500, in accordance with some embodiments of the present disclosure. Plasma generating system 500 may include a housing 510 having a cavity 502 and accommodating a plasma generation zone 504 (e.g., a plasma activation zone) and a plasma generator including at least a first electrical contact 522, a second electrical contact 524, an energy source 530 (e.g., a battery), and a transformer 526. Housing 510 may also accommodate a filter 506 and a controller 508. Transformer 526 may be a ring-shaped solenoid, illustrated in cross section as sections 526*a* and 526*b*. Transformer 526 may be electrically coupled on one side (e.g., an input) to a power source 530 and electrically coupled on the other side (e.g., an output) to first electrical contact 522, for example via one or more conducting wires and screws 528. Transformer 526 may convert an incoming voltage (e.g., 24V) to a substantially higher voltage (e.g., 10 kV to 20 kV). First electrical contact 522 may be electrically coupled to the higher voltage level produced by transformer 526, and second electrical contact 524 may be connected to a lower voltage potential, such as a ground, to generate a substantially high voltage potential between first electrical contact 522 and second electrical contact 524, First electrical contact 522 may be electrically coupled to the external insulating surface of a protecting shroud, such as protecting shroud 310*a* of FIG. 3A encasing viewport 390 and configured for insertion into cavity 502. Second electrical contact 524 may be electrically coupled to an optical element (e.g., viewport 390 of FIG. 3A), internal to insulating protecting shroud, thereby creating a substantial voltage potential between the optical element positioned internal to the insulating protecting shroud and first electrical contact 522.

Plasma generating system 500 may include plasma-generation zone 504 within cavity 502, which may be arranged such that when the at least a portion of an object having an optical element (e.g., endoscope 308 having viewport 392 of FIG. 2) is retained within cavity 502, the optical element is located within plasma-generation zone 504. Plasma-generation zone 504 may thus be subject to the same voltage potential between first electrical contact 522 and second electrical contact 524 thereby facilitating the generation of plasma inside plasma-generation zone 504. The generation of plasma inside plasma-generation zone 504 may be further promoted by creating a low pressure (e.g., vacuum) inside plasma-generation zone 504. The Plasma generator may generate plasma for treating an object (e.g., a medical instrument) within plasma generation zone 504 in accordance with embodiments disclosed herein. Cavity 502 of housing 510 may correspond to one or more of slot 132 (FIG. 1A), opening 142 (FIG. 1D), opening 314 (FIG. 2), bore 350 (FIG. 3A), and bore 450 (FIG. 3C). Plasma generation zone 504 may correspond to plasma applicator 348 (FIG. 3A). Cavity 502 may provide access to plasma generation zone 504, e.g., to enable inserting an object into plasma generation zone 504 for carrying out a plasma treatment to increase the hydrophilicity of the object. Controller 508 may control one or more aspects of the plasma generator, such as the influx and/or outflow of gas into plasma activation zone 504 for the purpose of generating plasma, the generation of an electric and/or electromagnetic field for generating plasma, and any other parameter relevant to the generation of plasma via the plasma generator. Plasma generating system 500 may further include one or more sensors, such as a pressure sensor 1100 (FIG. 11), a voltage sensor 514 and a plasma frequency sensor 512. While voltage sensor 514 and plasma frequency sensor 512 are illustrated inside plasma-generation zone 504, this is but one exemplary implementation and it may be noted that the voltage sensor and plasma frequency sensor may be positioned at any location that is electrically coupled to the voltage source (e.g., transformer 526).

Figure 6:
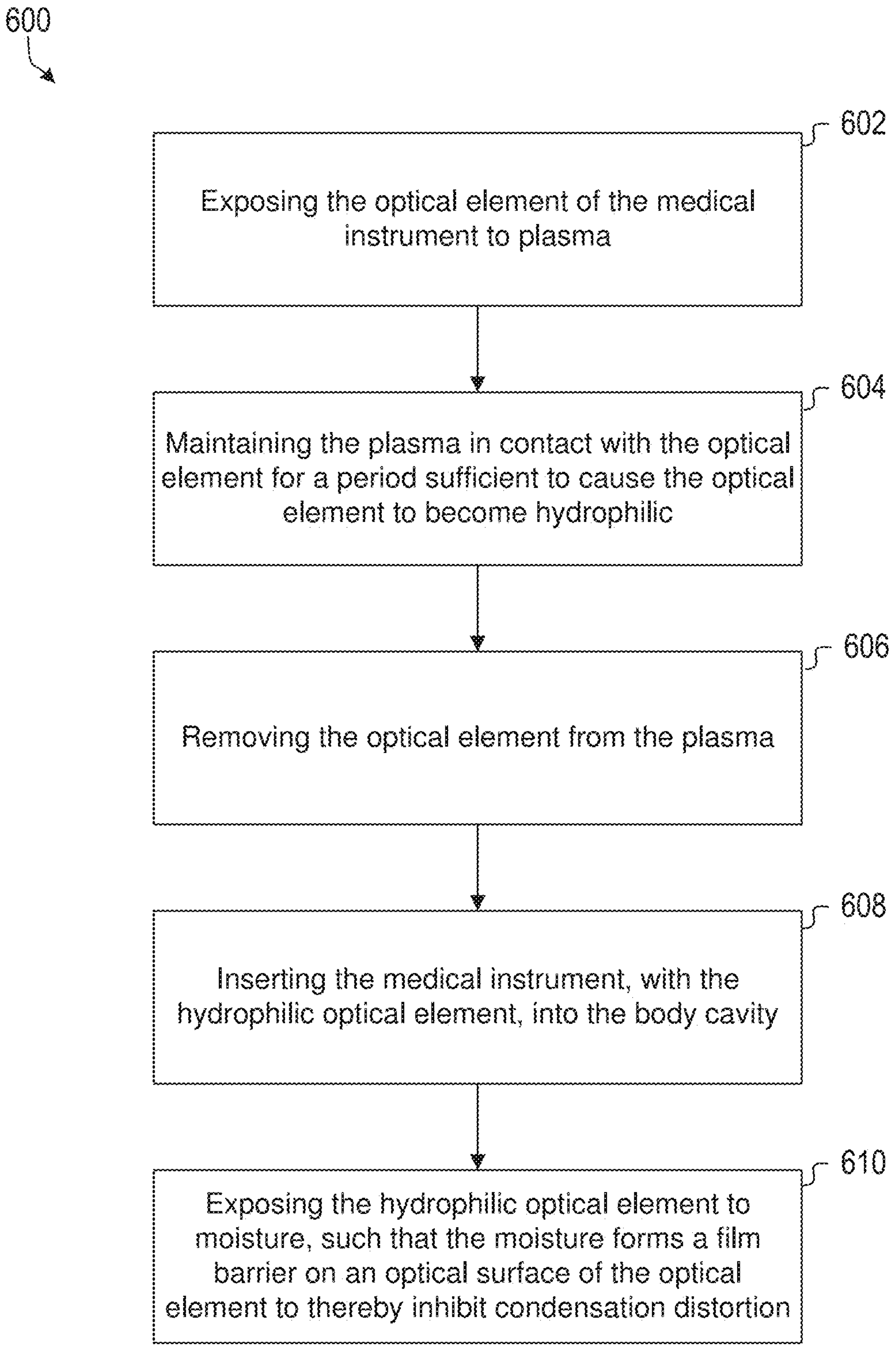
FIG. 6 is a flowchart illustrating a method for inhibiting condensation distortion on an optical element, consistent with some disclosed embodiments.

FIG. 6 is a flowchart that illustrates an example of a method 600 for inhibiting condensation distortion on an optical element of a medical instrument configured for insertion into a body cavity, in accordance with some embodiments of the present disclosure. Step 602 of method 600 may include exposing the optical element of the medical instrument to plasma. Step 604 of method 600 may include maintaining the plasma in contact with the optical element for a period sufficient to cause the optical element to become hydrophilic. Step 606 of method 600 may include removing the optical element from the plasma. Step 608 of method 600 may include inserting the medical instrument, with the hydrophilic optical element, into the body cavity. Step 610 of method 600 may include exposing the hydrophilic optical element to moisture, such that the moisture forms a film barrier on an optical surface of the optical element to thereby inhibit condensation distortion.

Figure 7:
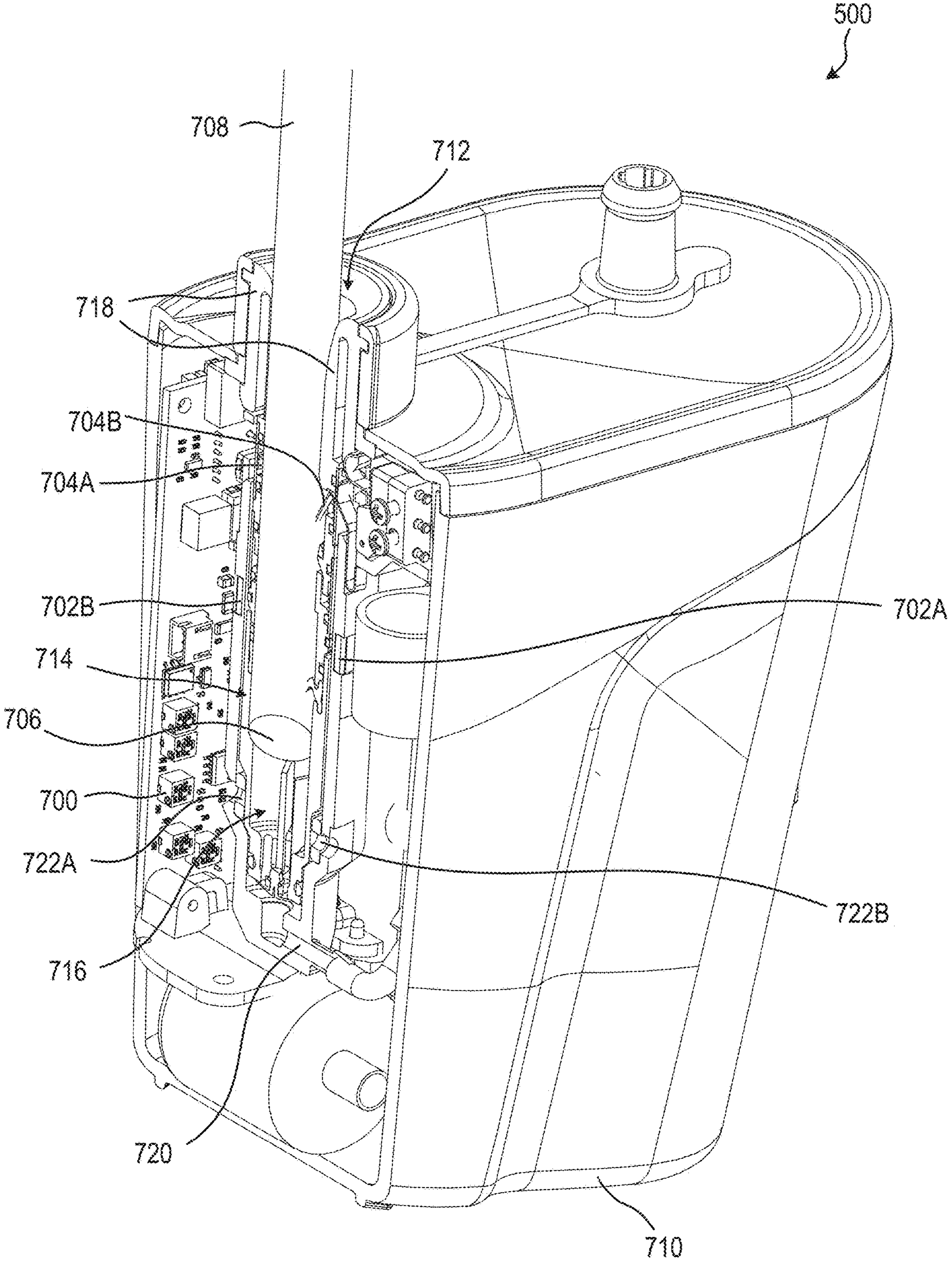
FIG. 7 is a perspective view of the plasma generating system of FIGS. 5A-5C with the front end removed to reveal internal components.

FIG. 7 illustrates another cross-sectional view of plasma generating system 500 (FIGS. 5A-5C), in accordance with some embodiments of the present disclosure. As illustrated in the figure, plasma generating system 500 is configured to treat an optical surface 706 of a medical instrument and may include electrical circuitry 700, a first pair of electrodes 702A and 702B designed to touch the disposable, and a second pair of electrodes 704A and 704B designed to touch the medical instrument.

Figure 8B:
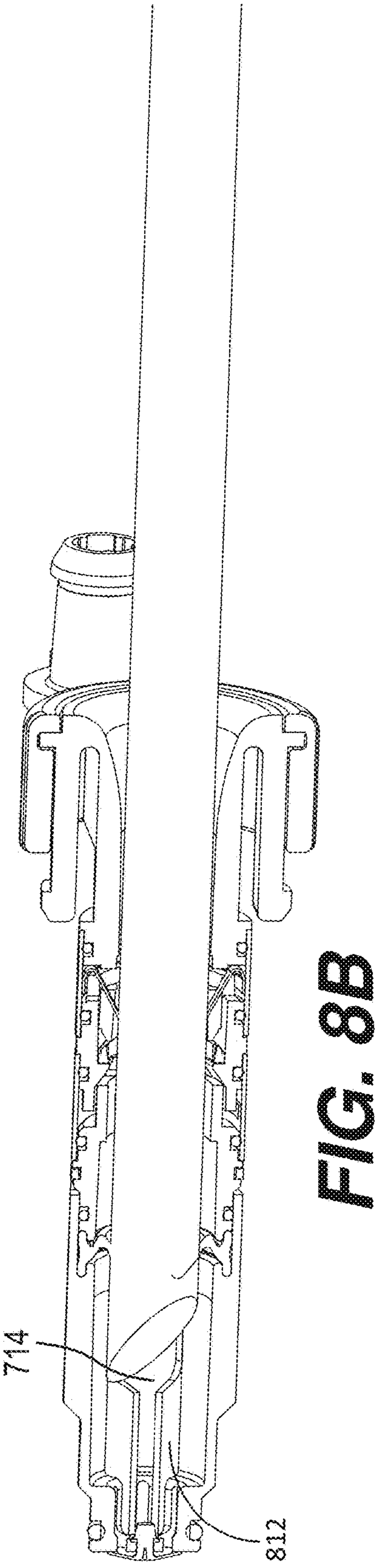
FIGS. 8A and 8B illustrate two views of a sheath containing an inserted medical instrument, consistent with some disclosed embodiments.
Figure 8A:
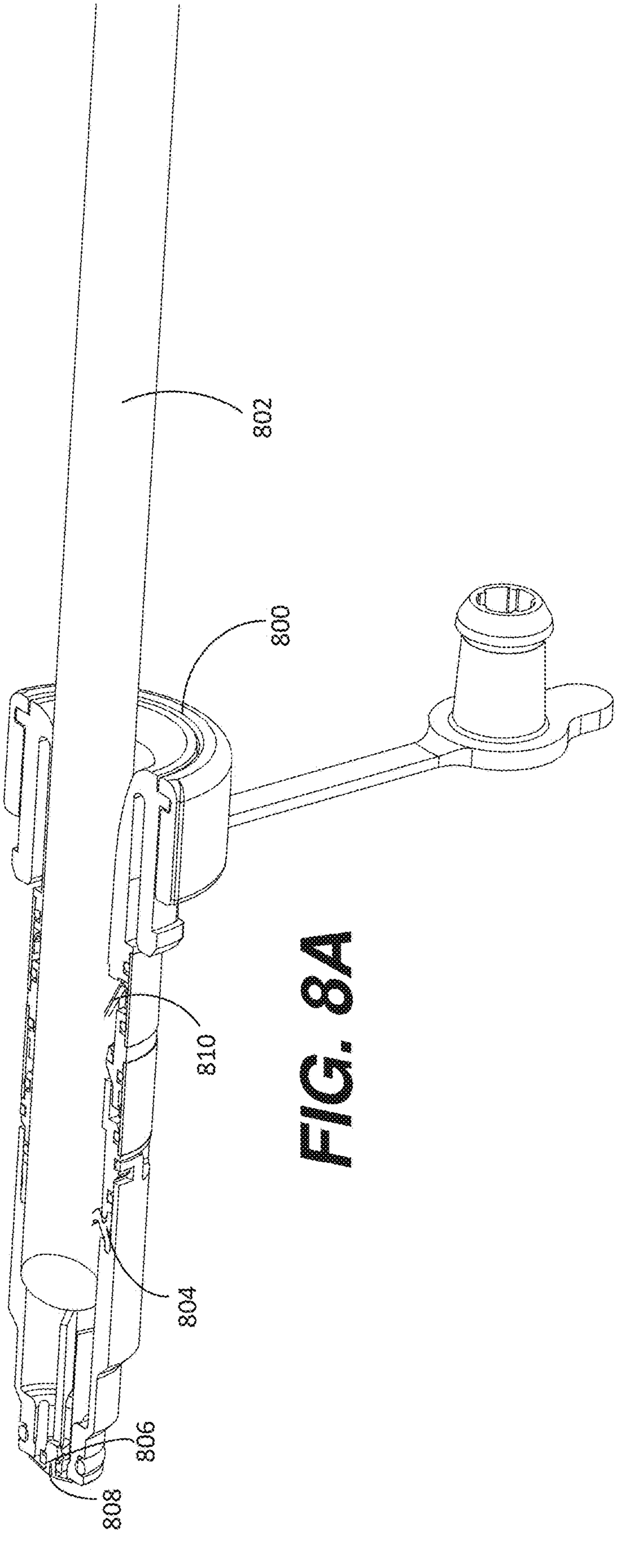

FIG. 8A depicts a cross-sectional view of a sheath 800 with an endoscope 802, in accordance with some embodiments of the present disclosure. As illustrated in the figure, sheath 800 may include an annular seal 804, an opening 806 associated with a one-way valve 808, and an electrode 810. FIG. 8B depicts another cross-sectional view of sheath 800 configured to removably receive an inserted medical instrument therein (e.g., endoscope 802), in accordance with an embodiment of the present disclosure. As illustrated in the figure, sheath 800 may include at least one stopper 812 configured to limit travel of endoscope 802.

Figure 9:
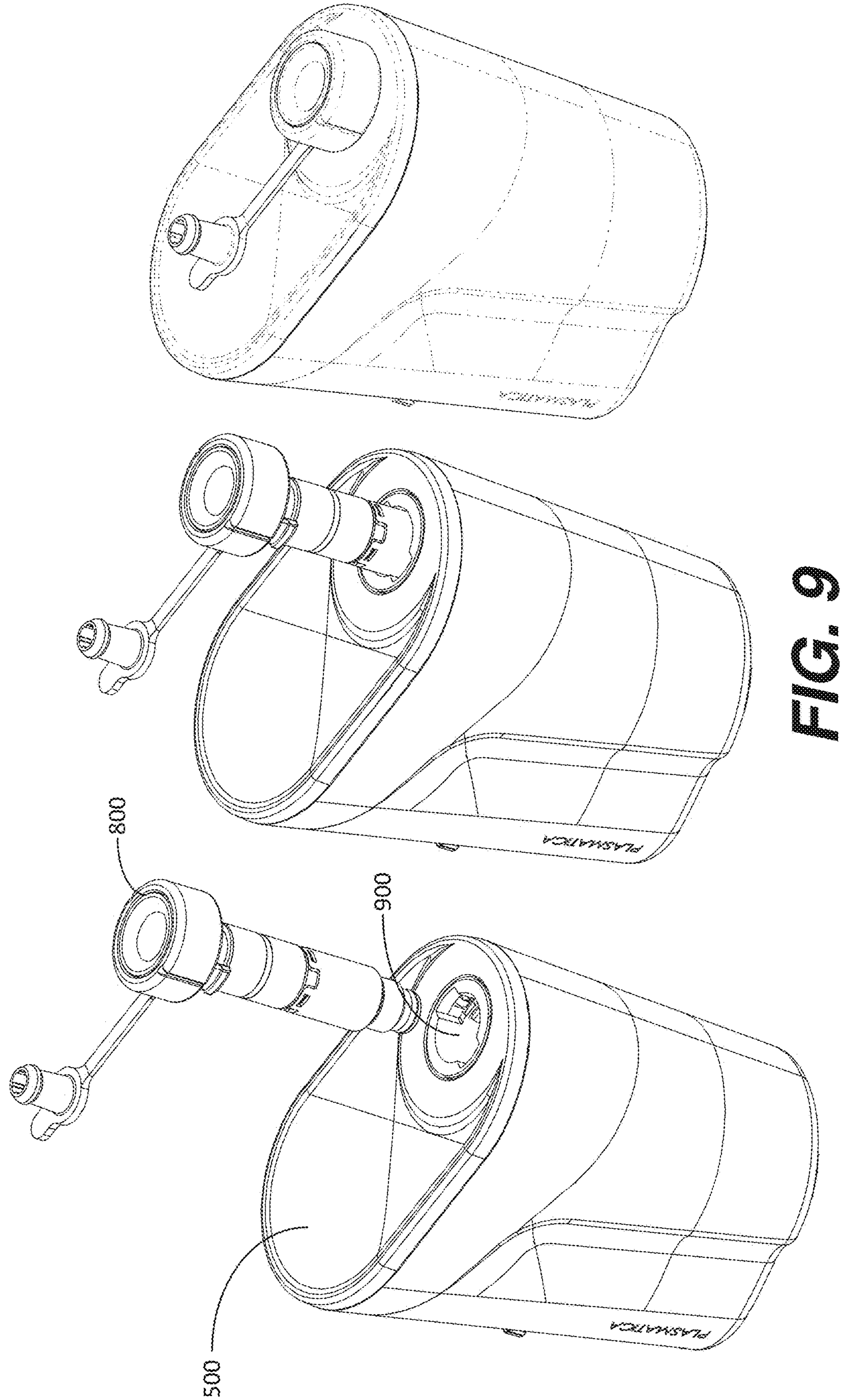
FIG. 9 illustrates how the sheath of FIG. 8 may be inserted into the plasma generating system of FIGS. 5A-5C, consistent with some disclosed embodiments.

FIG. 9 illustrates how sheath 800 may be inserted into plasma generating system 500. As illustrated in the figure, plasma generating system may include a bore 900 sized to retain sheath 800. Other related elements are illustrated in other figures.

Figure 10A:
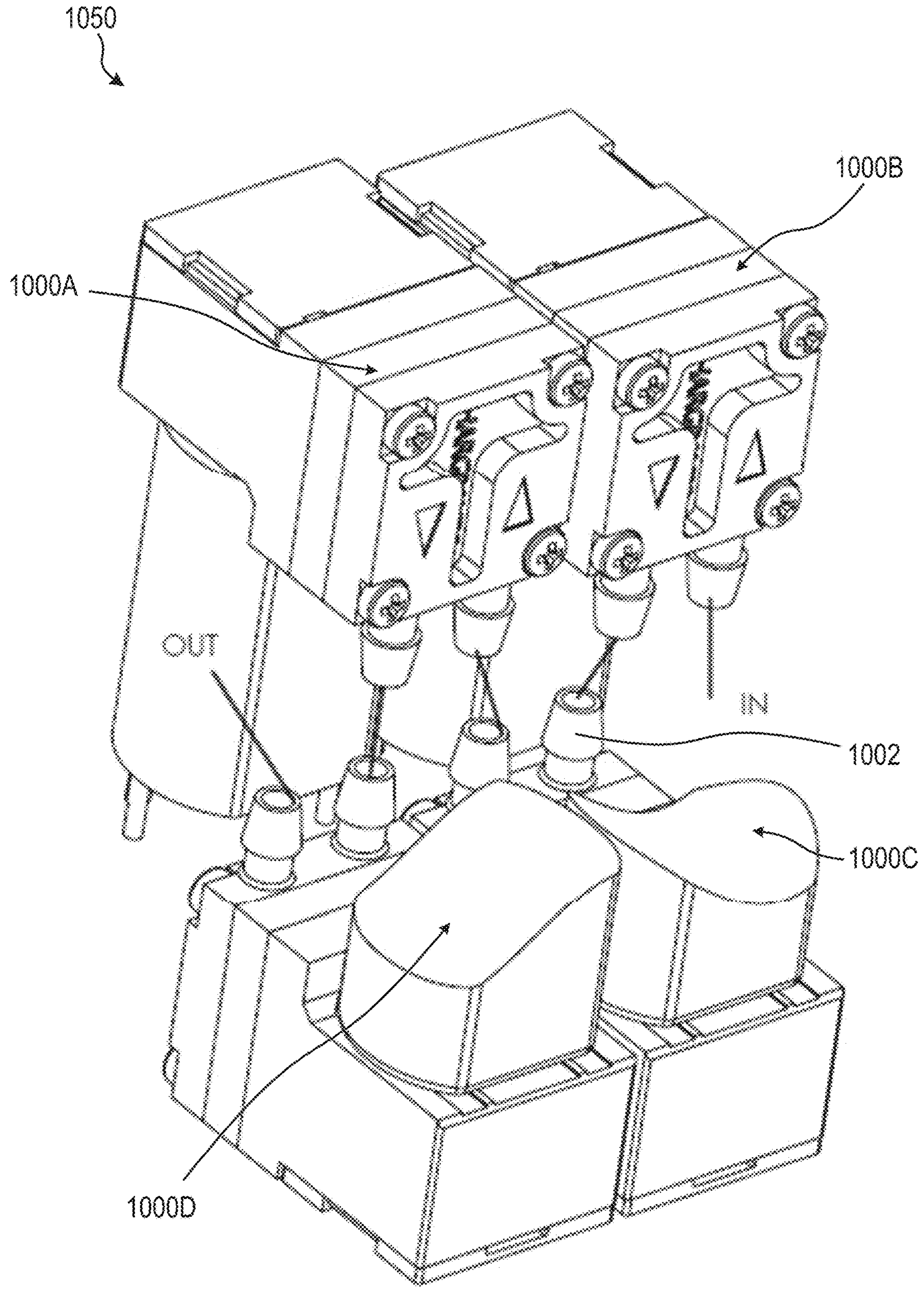
FIG. 10A illustrates a perspective view of a pump assembly consistent with some disclosed embodiments.
Figure 10B:
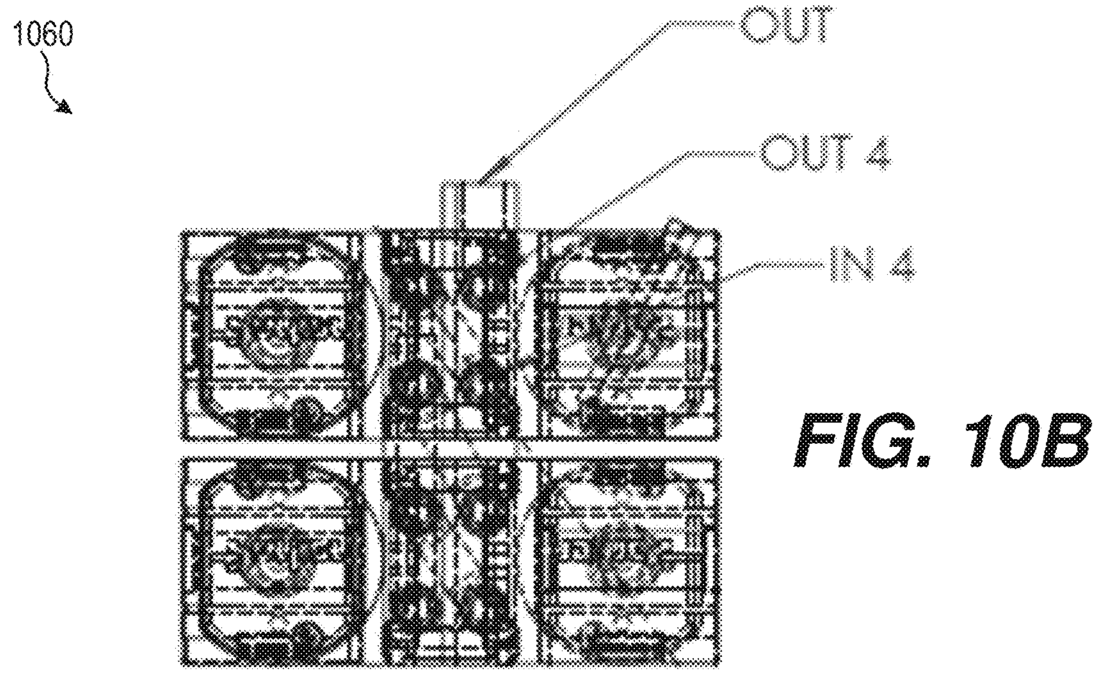
FIG. 10B illustrates a top view of the pump assembly of FIG. 10A.
Figure 10C:
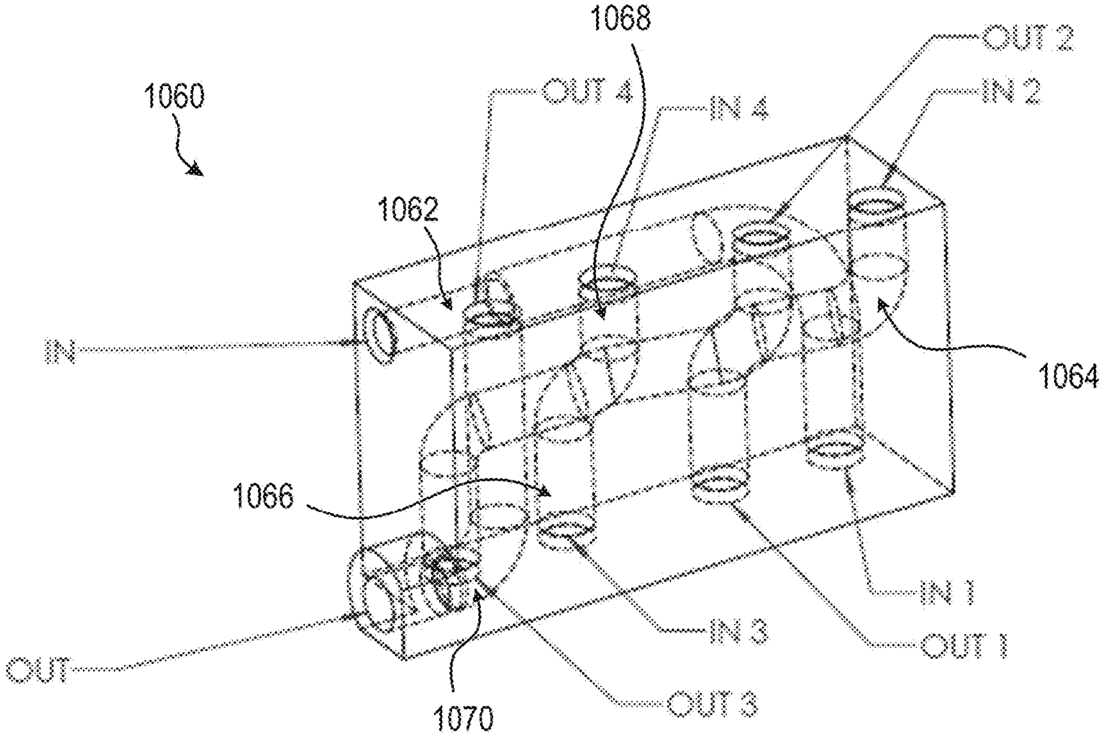
FIG. 10C illustrates a partial perspective view of a pump manifold for use in the pump assembly of FIG. 10A.

FIG. 10A depicts a plurality of vacuum pumps located within plasma generating system 500 in accordance with the following embodiment of the present disclosure. As illustrated in the figure, plasma generating system 500 may include a plurality of vacuum pumps (e.g., vacuum pumps 1000A, 1000B, 1000C, and 1000D) and conduits connecting them in series (e.g., conduit 1002). Other related elements are illustrated in other figures. FIGS. 10B and 10C depict example cross-sectional drawings of the pump manifold of the plasma generating system 500, demonstrating how the plurality of vacuum pumps are connected in series.

Figure 11:
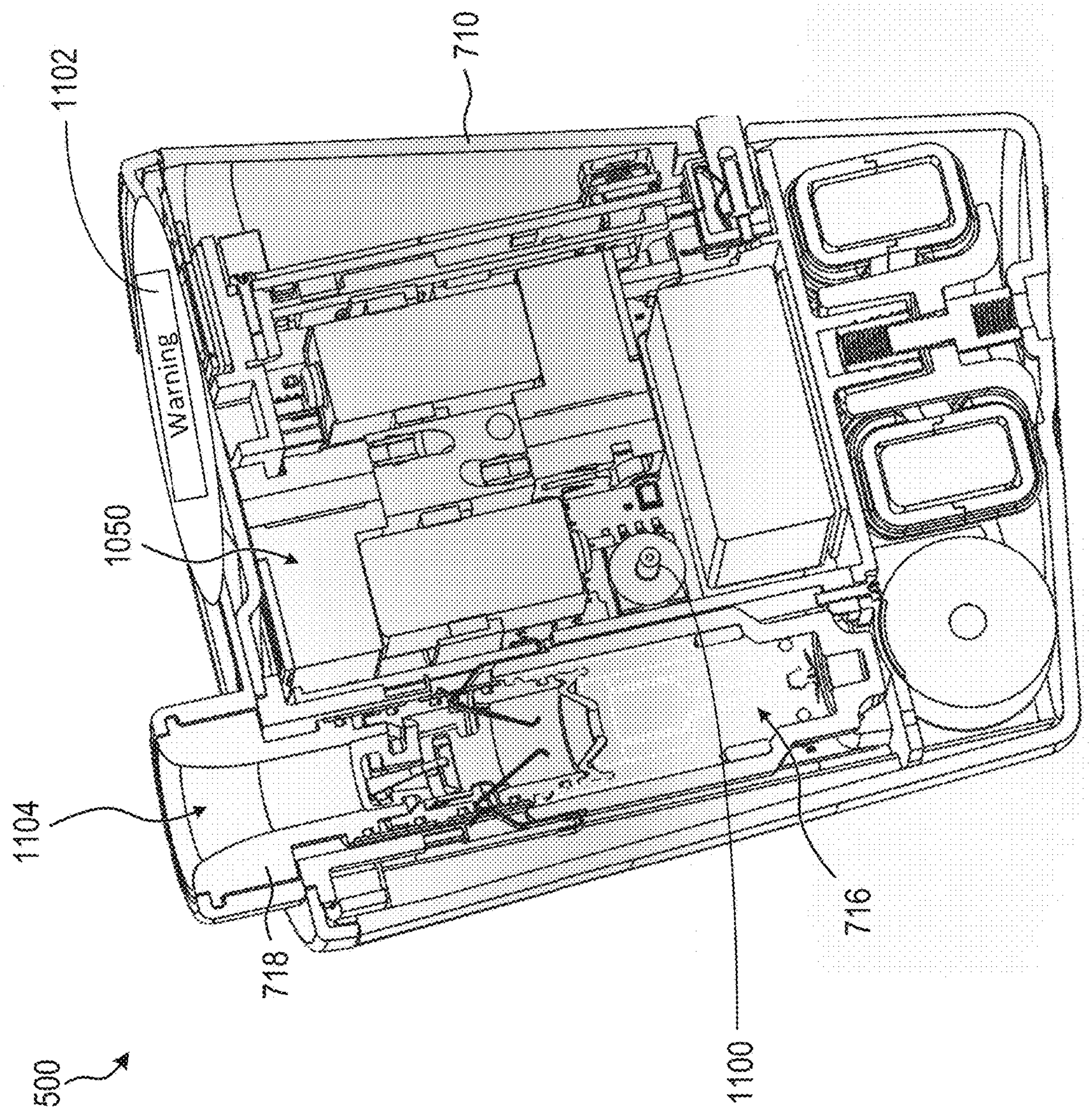
FIG. 11 illustrates a cutaway perspective view of the plasma generating system of FIGS. 5A-5C, consistent with some disclosed embodiments.

FIG. 11 illustrates another cross-sectional view of plasma generating system 500, in accordance the present disclosure. As illustrated in the figure, plasma generating system 500 may further include one or more sensors, such as a pressure sensor 1100 and other sensors configured to measure a plasma-activation parameter) and a display 1102 for displaying a notification.

Figure 12:
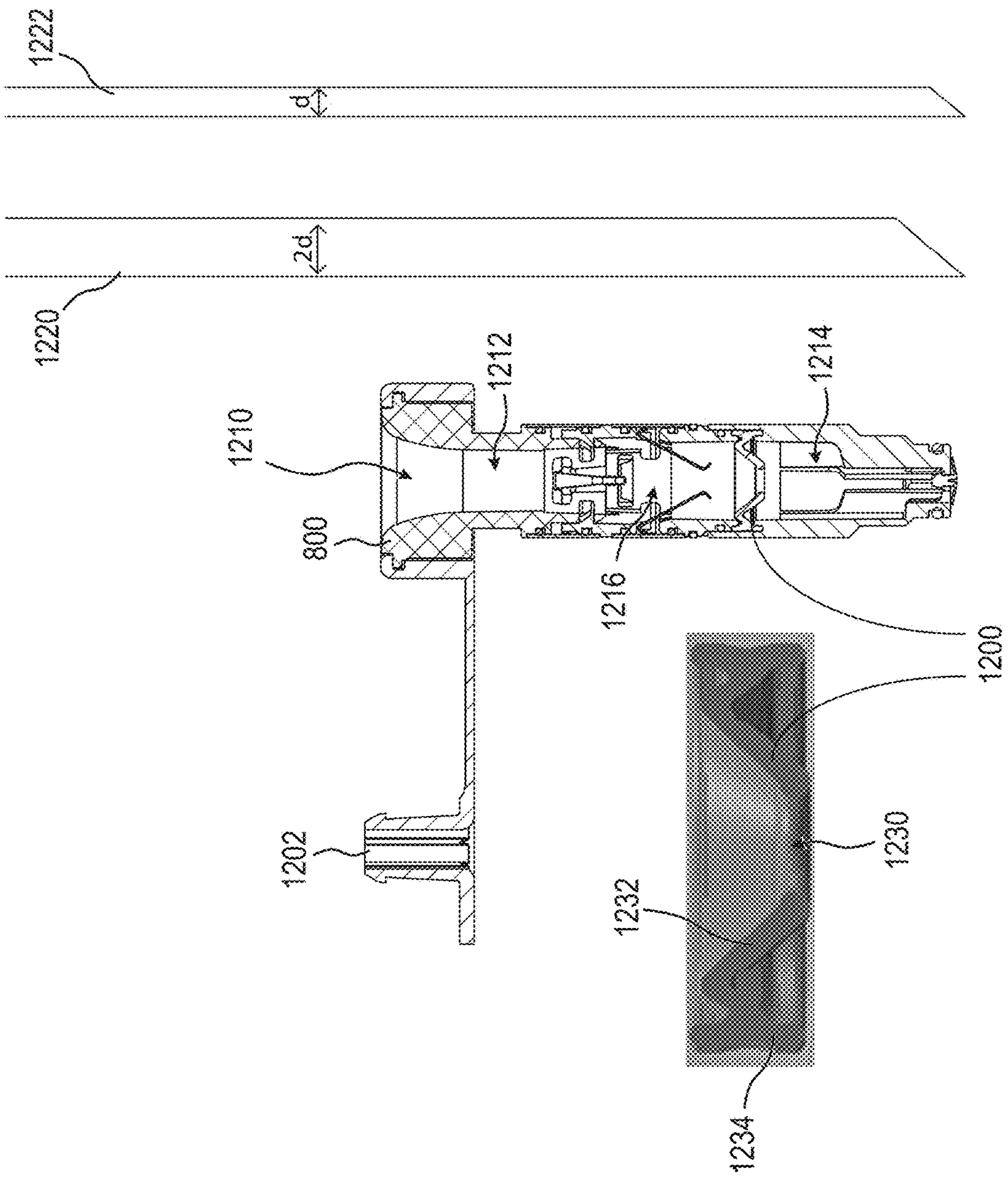
FIG. 12 illustrates a cross-sectional view of a channel in a housing of the device of FIGS. 5A-5C, with two medical instruments of varying dimensions that may be inserted into the channel.

FIG. 12 depicts another cross-sectional view of sheath 800, in accordance with some embodiments. As illustrated in the figure, sheath 800 may include an annular seal 1200 configured to enable formation of a vacuum chamber regardless of the diameter of the scope and an adjusting cap 1202 that may be utilized when using scopes with smaller diameters.

Figure 13:
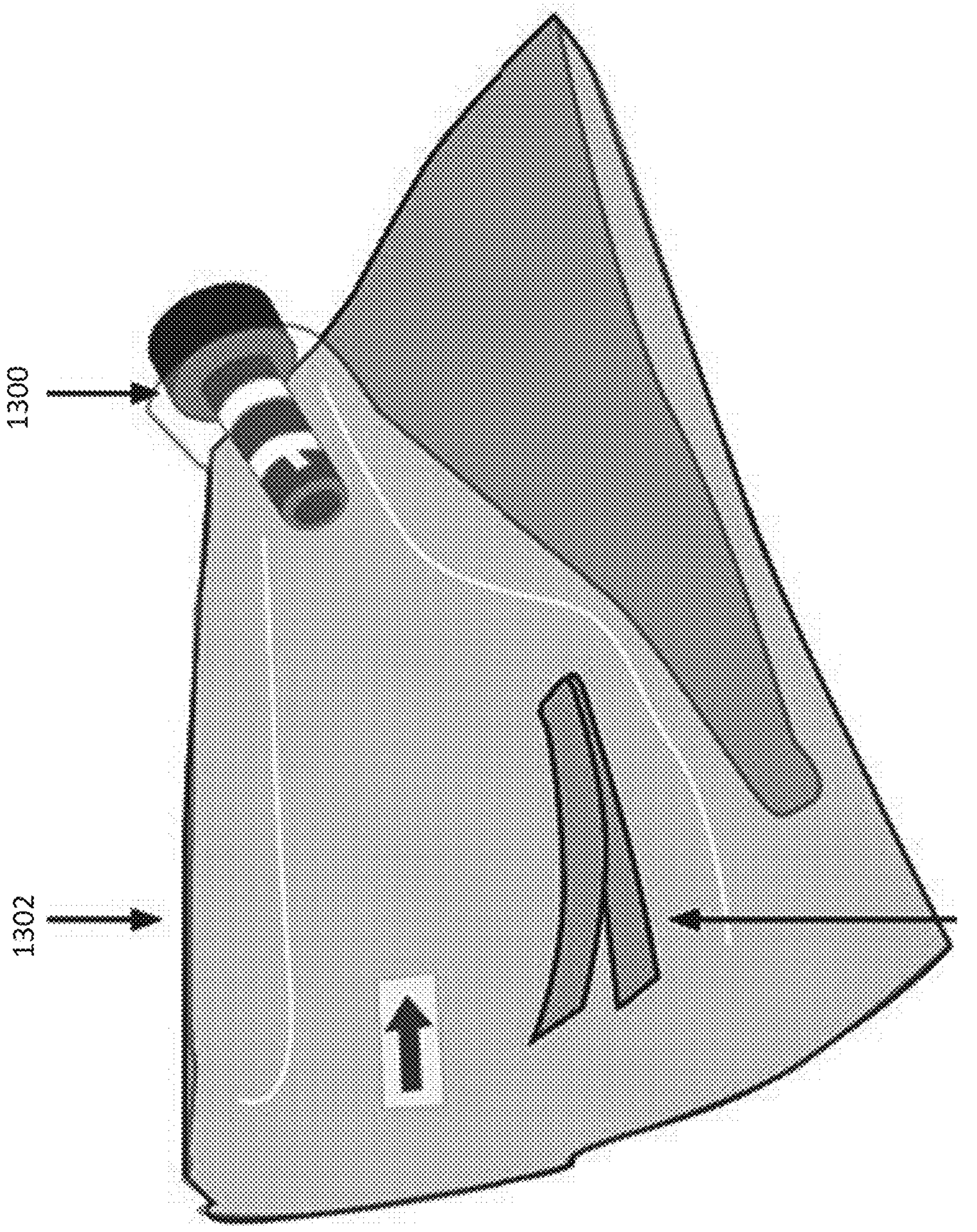
FIG. 13 illustrates a partial perspective view of an integrated sheath and cover consistent with some disclosed embodiments.

FIG. 13 depicts an integrated sheath and cover, in accordance with some embodiments of the present disclosure. Specifically, FIG. 13 illustrates a receptacle 1300 (e.g., sheath 800) configured for insertion into a cavity of plasma generating system 500, a shield 1302 sterilely affixed to the proximal end of receptacle 1300, and an adhesive 1304 for securing shield 1302.

Figure 14:
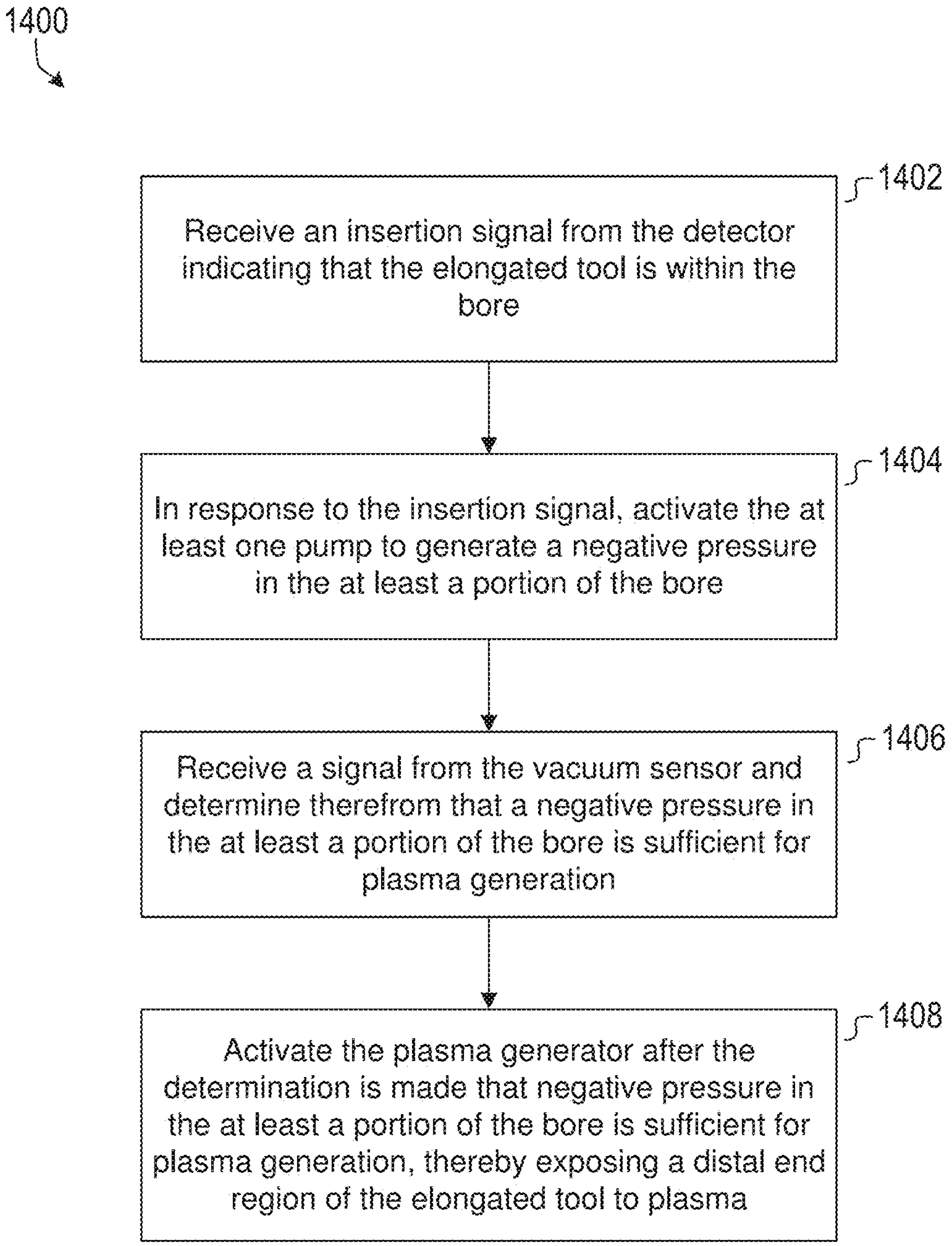
FIG. 14 is a flowchart illustrating a method of treating an elongated tool with plasma, consistent with some disclosed embodiments.

FIG. 14 is a flowchart that illustrates a method 1400 for treating an elongated tool with plasma, in accordance with some embodiments of the present disclosure. Step 1402 of method 1400 may include receiving an insertion signal from the detector indicating that the elongated tool is within the bore. Step 1404 of method 1400 may include activating, in response to the insertion signal, the at least one pump to generate a negative pressure in the at least a portion of the bore. Step 1406 of method 1400 may include receiving a signal from the vacuum sensor and determining therefrom that a negative pressure in the at least a portion of the bore is sufficient for plasma generation. Step 1408 of method 1400 may include activating the plasma generator after the determination is made that negative pressure in the at least a portion of the bore is sufficient for plasma generation, thereby exposing a distal end region of the elongated tool to plasma.

Figure 15:
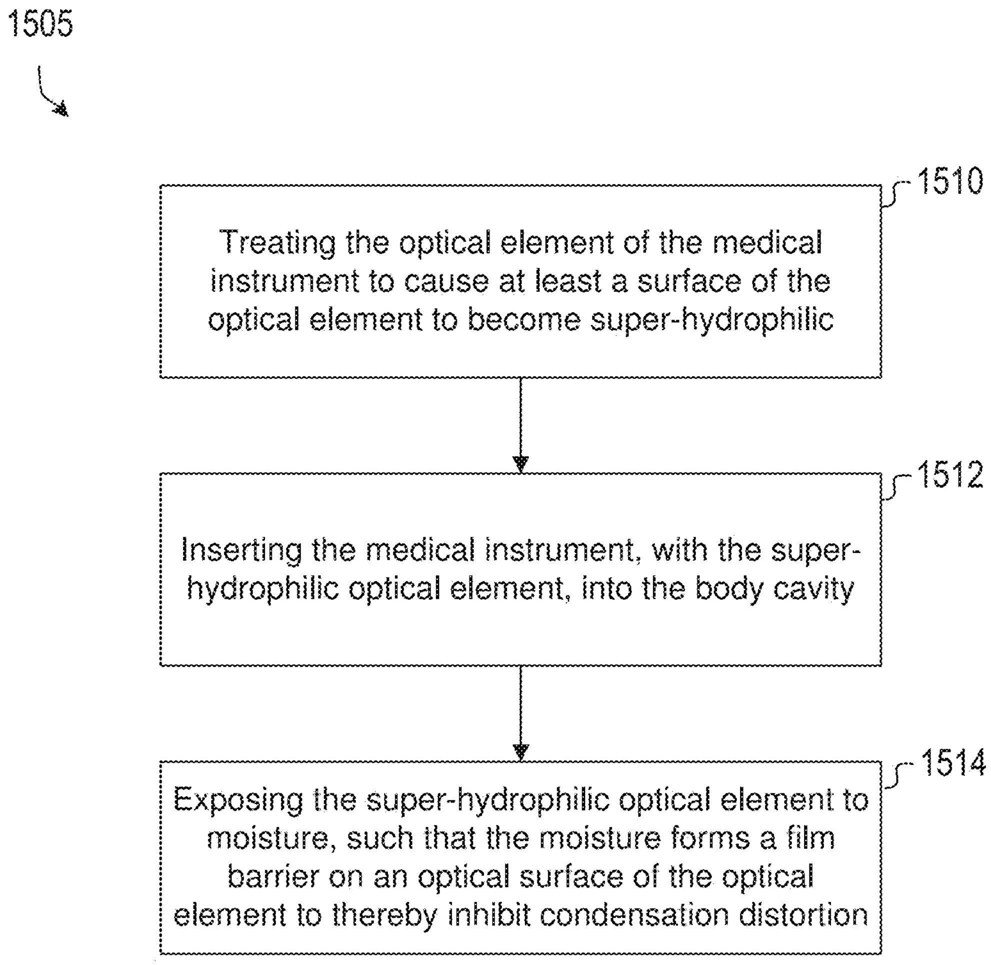
FIG. 15 is a flowchart illustrating a method of inhibiting condensation distortion on an optical element of a medical instrument consistent with some disclosed embodiments.

FIG. 15 is a flowchart that illustrates an example method of inhibiting condensation distortion on an optical element of a medical instrument configured for insertion into a body cavity, in accordance with some embodiments of the present disclosure.

To ensure that a plasma treatment sufficiently increases hydrophilicity of an object to a desired level, at least one processor may execute one or more program code instructions to monitor the plasma treatment. The at least one processor may determine the effectiveness of the plasma treatment based on one or more parameters, such as may be measured by one or more sensors. In some embodiments, when a parameter indicates that the plasma treatment does not sufficiently increase hydrophilicity of the object, the processor may output a notification. In some embodiments, the notification may trigger an adjustment and/or calibration for the plasma treatment.

The following detailed description includes references to the accompanying drawings. Wherever possible, the same reference numbers are used in the drawings and the description to refer to the same or similar parts. While several illustrative embodiments are described herein, modifications, adaptations and other implementations are possible. For example, substitutions, additions, or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

In some embodiments, a plasma generation device for treating objects is provided. The term "plasma" may refer to a state of matter containing an abundance of charged particles, e.g., electrons and ions. Consequently, plasma may be highly electrically conductive and sensitive to electric and/or electromagnetic fields. The term "plasma generation device" may include any apparatus or combination of components capable of generating plasma, e.g., by converting (e.g., igniting) a gas to transform the gas to a plasma state or plasma cloud. The term "treating objects" may refer to a process, procedure or protocol applied to modify one or more properties of a physical object. For example, plasma generating systems 100 (FIG. 1A) and 500 (FIGS. 5A-5C) illustrate exemplary implementations of a plasma generation device in accordance with disclosed embodiments. In some embodiments, the plasma generation device may contain a gas, and two electrodes (e.g., an anode and a cathode) for applying an electric or electromagnetic field to the contained gas. The electric or electromagnetic field may ionize the contained gas to the point that the gas becomes an electrically conductive plasma cloud.

In some embodiments, the object may include an optical element. An "optical element" may include any article of manufacture through which light may either pass and/or be reflected. The optical element may be a combination of one or more of a lens, polarizer, diffraction grating, prism, reflector, filter, viewing window, mirror, protective window, or any other component in which light passes or is reflected. The optical element may modify one or more properties of a light wave directed to or from the optical element, such as the intensity, phase, propagation direction, frequency, wavelength, or polarization of the light wave. For example, the optical element may be formed from metal, glass, plastic, semiconductor, or any other material exhibiting optical properties. The properties modified by the treatment may relate to optical, electric, magnetic, or conductive properties of the object. For example, an object may be treated by exposing the object to a plasma cloud generated by the plasma generation device. The exposure of the object to plasma may modify an optical property of the object by affecting the hydrophilicity of the object, e.g., by causing a fluid to coat the object uniformly (e.g., evenly) instead of forming as individual (e.g., separate) droplets. An example of an optical element is optical element 392 (FIG. 3C), such as may be provided with viewport 390 (FIGS. 2, 3A, and 3C).

In some embodiments the plasma generation device may have a housing. The term "housing" may refer to any supporting structure, frame, cage, enclosure, or encompassment capable of accommodating a plasma generator. The housing may be made of any suitable material, such as plastic, metal, glass, wood, or any other material capable of encasing the plasma generation device. In some embodiments, the housing may include one or more insulating materials to insulate the plasma generation device encased therein from one or more environmental conditions, such as an electric and/or electromagnetic field, light, humidity, temperature, impact, mechanical and/or acoustic vibrations, and any other environmental attribute that may affect the generation of plasma by the plasma generating device. An example of a housing for the plasma generation device is illustrated by housing 510 of FIGS. 5A-5C encasing plasma generation zone 504. Similarly, the exterior of plasma generating field applicator 130 (FIG. 1A) may form a housing consistent with disclosed embodiments.

In some embodiments, the housing may be provided with a bore (e.g., "cavity" or "slot"). In some embodiments, the bore may be sized to removably retain at least a portion of the object. For example, the surface of the housing may expose an entrance into the bore for inserting the object therein. The bore may be any suitable shape or size for containing the object. For example, the bore may be tubular to accommodate a sheath configured to retain an elongated medical instrument. The bore may have a cross-section that is round, triangular, square, rectangular, oval, or any other regular or irregular shape. An example of a bore disposed within the housing for the plasma generation device may be illustrated by slot 132 (FIGS. 1A and 1C), opening 142 (FIG. 1D), opening 314 (FIG. 2), bore 350 (FIG. 3A), bore 450 (FIG. 3C), and bore 900 (FIG. 9).

Some embodiments may involve the plasma generation device including a plasma-generation zone within the housing. As used herein, the term "plasma generation zone" may refer to a physical volume or space in which a plasma cloud may be formed, e.g., by igniting a gas introduced therein. The plasma generation zone may be of any size. For example, the plasma generation zone may be less than 15 $cm^3$, less than 10 $cm^3$, or less than 5 $cm^3$. Plasma generation zone of 504 of FIG. 5A is an exemplary implementation of plasma generation zone, in accordance with disclosed embodiments. In some embodiments, the plasma activation zone may be positioned within a cavity configured to retain at least a portion of the object therein, and thereby expose the at least portion of the object to the plasma treatment. For example, the plasma generation zone (e.g., plasma generation zone 504) may be positioned within bore 350 (FIG. 3A) configured to retain at least a portion of endoscope 380 therein, thereby exposing the at least portion of endoscope 380 to plasma.

In some embodiments, the plasma-generation zone may be associated with a cavity configured to retain the object in a manner exposing at least a portion of the object to the plasma-generation zone. The term "cavity" may refer to a chamber, crevice, or pit capable of containing an object. The chamber within the plasma-generation zone may accommodate at least a portion of an object inside the plasma-generation zone together with a plasma cloud (e.g., generated by igniting a gas streamed therein), thereby exposing the at least portion of the object to the plasma cloud. For example, the cavity may accommodate a viewport of an endoscope within the plasma-generation zone, to expose the viewport to a plasma cloud generated inside the plasma activation zone after a gas has been ignited. Consequently, the hydrophilicity of the viewport may increase to prevent fog from forming when the viewport is subsequently inserted into a body. For example, referring to FIG. 5A, a treatment device may have a cavity 502 disposed within housing 510. Cavity 502 may be configured to retain a medical instrument (e.g., endoscope 380 of FIG. 2) in a manner to expose optical element 392 situated at the distal end of endoscope 380 to plasma generation zone 504.

In some embodiments, the plasma generation zone may be configured to enable accommodation of an object; The term "accommodation" may refer to a capability for surrounding, holding, enclosing, supporting or otherwise containing an object, e.g., within the plasma generation zone. For example, the object may be supported within the plasma generation zone to expose the object to a plasma cloud. The term "object" may be any physical component such as may include an optical element. The optical element may include one or more of a mirror, lens, viewing window or other optical surface. In some embodiments, the term "object" may additionally or alternatively include a medical instrument, such as may be configured for insertion into a patient's body. For example, endoscope 380 (FIG. 3A) illustrates an exemplary implementation of an object in accordance with disclosed embodiments.

In some embodiments, the object is at least a portion of a medical instrument and at least one processor is configured to output a notification indicating of plasma treatment failure prior to using the medical instrument in a medical procedure. The term "medical instrument" may refer to any device or equipment used to perform a medical procedure. For example, the medical instrument may be an endoscope, laparoscope, gastroscope, cystoscope, ureteroscope, arthroscope, colonoscope, mirror (e.g., dental mirror), intraoral scanner, and any other instrument suitable for insertion into a patient's body. In some embodiments, the medical instrument may have an elongated shape. The cross section of the medical instrument may be round, square, triangular, rectangular, oval, or any suitable shape for insertion into a patient's body. The width of the medical instrument may be uniformed or varied, and the edges of the medical instrument may be angular or curved. The term "notification" may refer to conveyed or transmitted information. For example, after determining that the plasma treatment for an endoscope has failed, the at least one processor may convey information indication the failure to a medical practitioner, before the medical practitioner uses the endoscope for performing an endoscopy. The notification may be in the form of text, sound, vibration, visual alert (e.g., flashing light) or any combination thereof. Turning to FIG. 2, optical element 392 positioned at the distal end of endoscope 380 is an exemplary implementation of an object that is at least a portion of a medical instrument, in accordance with disclosed embodiments. Controller 508 (FIG. 5B) may output a notification via display 1102 indicating of plasma treatment failure prior to using endoscope 380 in a medical procedure.

In some embodiments, the plasma generation device may include circuitry for supplying energy to carry out a plasma treatment. The term "circuitry" may include any combination of electronic componentry (e.g., memory units, switches, gates, wires, transformers, and other electronic componentry) for performing one or more operations (e.g., logical operations) in response to receiving an electric signal (e.g., from a processor operating as a controller) as an input. The circuitry may couple an energy source, e.g., a power supply, generator, battery, or rechargeable battery, to the plasma generation device to enable the ignition of the gas for the purpose of converting the gas to a plasma cloud. The energy source may be external to the plasma generation device, e.g., from a wall outlet via a cable. In some embodiments the operational unit may be energized by an internal energy source such as a battery, e.g., a rechargeable battery. The circuitry may control one or more aspects of the energy delivered by the energy source, such as the magnitude, intensity, frequency, phase, timing, polarity, as well as a voltage associated with the energy, a current associated with the energy, and any other attributes characterizing the energy. The circuitry may adapt the energy according to the requirements of the plasma generation device, e.g., for igniting a gas to generate a plasma cloud for carrying out the plasma treatment. The circuitry may thus include a transformer, connecting wires and contacts, and one or more integrated circuits (ICs), including application-specific integrated circuits (ASICs), microchips, microcontrollers, microprocessors, all or part of a central processing unit (CPU), graphics processing unit (GPU), accelerated processing unit (APU), digital signal processor (DSP), field-programmable gate array (FPGA), or other circuits suitable for executing computing instructions and/or capable of performing logical operations, e.g., based on a computing instruction or an input signal. The circuitry may further include one or more memory units, such as Random-Access Memory (RAM), a cache memory, a Read-Only Memory (ROM), a hard disk, an optical disk, a magnetic medium, a flash memory, other permanent, fixed, or volatile memory, or any other mechanism capable of storing data and/or computing instructions for performing a logical operation. The circuitry may further include one or more communication channels coupling the one or more ICs to the memory, thereby enabling the one or more ICs to receive a computing instruction and/or data stored thereon required to perform a corresponding logical operation for controlling energy delivered to the plasma generation device. The communication channels coupling the one or more ICs to the memory may include wired channels, such as one or more cables, fibers, wires, buses, and any other mechanically coupled communication channel. The communication channels may additionally or alternatively include wireless channels such as short, medium, and long-wave radio communication channels (e.g., Wi-Fi, Bluetooth, Zigbee, cellular, satellite), optical, and acoustic communication channels.

The term "energy" may refer to an electric and/or magnetic signal capable of inducing an electric and/or electromagnetic field. The circuitry may control parameters of the energy such as the timing, frequency, intensity, magnitude, and phase of the electric (e.g., voltage, current) and/or magnetic signal (e.g., direction, strength, density) to generate an electric and/or electromagnetic field capable of converting a gas subjected to the electric and/or electromagnetic field to a plasma cloud. For example, a transformer may convert a relatively low voltage supply (e.g., tens of volts) provided from the power supply to a high voltage supplied to the plasma generation zone to generate an electromagnetic field capable of igniting plasma therein. For example, the electric and/or electromagnetic field may ionize the gas until the gas becomes increasingly electrically conductive to the point of reaching a plasma state. The circuitry may thus supply energy in a form that is suitable for carrying out the plasma treatment, e.g., by adapting the energy from the energy source to a signal capable of inducing an electric and/or electromagnetic field capable of converting a gas to a plasma cloud. For example, circuitry 106 (FIG. 1A) may supply energy to carry out a plasma treatment, in accordance with disclosed embodiments. Circuitry 106 may adapt electrical energy supplied by power supply 530, (e.g., in response to one or more control operations by at least one processor 102 or 508) to a form that is suitable for generating an electric and/or electromagnetic field capable of generating plasma. The adapted energy may be provided to any of cathode 330, anode 340, dielectric barrier 344, via any of cathode contactor 352, electric conductor 354, and electric conductor 358 (FIG. 3A). For example, on activating power source 530, circuitry 106 may adapt (e.g., in response to control instructions by at least one processor 102 or 508) electrical energy supplied by power source 530 and deliver the adapted electrical energy to cathode 330 and anode 340 via electric conductors 354 and 358 to generate an electric and/or electromagnetic field suitable for generating plasma from a gas present therein. As another example, circuitry 700 of FIG. 7 may supply energy to carry out the plasma treatment.

Some embodiments may involve supplying energy to carry out a plasma treatment for increasing hydrophilicity of the object to a desired level. The term "hydrophilicity" refers to a tendency or favorability of a molecule to be solvated by water. A hydrophilic compound may have thermodynamic properties that enable the compound to bond with water molecules more readily than a compound that is not hydrophilic, e.g., a hydrophobic compound that does not readily bond with water (e.g., polar) molecules. An object that is hydrophilic may be wettable, enabling a liquid (e.g., water) to maintain contact with the object due to intermolecular interactions that balance adhesive and cohesive forces between the liquid and the object. The term "desired level" may refer to a level of hydrophilicity that achieves a formation of a substantially uniform layer of a fluid on the surface of the object when the fluid comes in contact with the object, thus deterring, inhibiting or at least somewhat preventing the formation of fluid droplets (e.g., fog). The desired level may vary depending on the particular object and the particular intended use. The desired level of hydrophilicity may cause the layer of fluid to be sufficiently uniform to ensure a minimal optical quality. For example, the desired level of hydrophilicity may be associated with a minimal variable thickness of a layer of fluid collecting on the object, or a minimal incident angle between fluid accumulating on the surface of the object and the surface of the object, e.g., less than 30 degrees, less than 15 degrees, or less than 10 degrees. For example, referring to FIG. 3A, circuitry, represented partially by cathode 330, anode 340, dielectric barrier 344, cathode contactor 352, electric conductor 354, and electric conductor 358, may supply energy to carry out a plasma treatment for increasing the hydrophilicity of endoscope 380 to a level whereby visibility via endoscope 380 is not significantly diminished by an accumulation of fog during a medical procedure.

Some embodiments may involve the at least one processor maintaining the plasma treatment for a predefined time duration. For example, to reach the desired level of hydrophilicity, the at least one processor may activate the plasma generator for a time period sufficient to cause the optical element to become hydrophilic prior to insertion into the body cavity. In some embodiments, the predefined time duration may be based on a characteristic of the plasma generated for the plasma treatment, e.g., the type of gas used to generate the plasma, and the conditions under which the plasma is generated (e.g., pressure, temperature, electric and/or electromagnetic field, voltage, current). In some embodiments, the predefined time duration may be based on a physical characteristic of the object, such as the material that the object is made of, the shape of the object, the size of the object, the sharpness or smoothness of the object, the optical characteristics of the object (e.g., transparency, reflectiveness). In some embodiments, the predefined time duration is based on the desired level of hydrophilicity of the object. For example, a first object intended for a medical procedure requiring a high degree of accuracy may demand greater hydrophilicity than a second object intended for a medical procedure requiring a lesser degree of accuracy. Additionally, or alternatively, in some embodiments, the predefined time duration may be based on a desired and/or acceptable level of optical quality, the intended use of the object, and any other parameter (e.g., performance parameter) that may be affected by the hydrophilicity of the object. According to some disclosed embodiments, the time period sufficient to cause the object to become hydrophilic may be less than a minute, less than 45 seconds, less than 30 seconds, or less than 15 seconds.

At least one processor 102 in FIG. 1A illustrates an exemplary implementation of a controller for maintaining a plasma treatment for a predefined time duration, e.g., via a clock internal to at least one processor 102. At least one processor 102 may adapt one or more aspects of energy supplied by power supply 104, e.g., via circuitry 106, and provide the adapted energy to plasma generating field applicator 130 via cable 112. Processor 102 may further base the predefined time duration on a characteristic of plasma generated by plasma generating field applicator 130 for the plasma treatment and/or a physical characteristic of object 200, e.g., such as may be stored in memory 104. In some embodiments, at least one processor may base the predefined time duration on a desired level of hydrophilicity of object 200, e.g., to prevent fog from condensing on an optical element of object 200 when object is inserted into a body during a medical procedure. FIG. 5B additionally illustrates an exemplary implementation of controller 508 (e.g., at least one processor) for maintaining a plasma treatment by plasma generating system 500 for a predefined time duration, depending on the desired level of hydrophilicity of an object. For example, if one object is required for a procedure demanding a high level of accuracy, controller 508 may apply the treatment to the object for a relatively long period of time (e.g., 45 seconds). Whereas if another object is required for a procedure demanding a lesser level of accuracy, controller 508 may apply the treatment to the object for a relatively short period of time (e.g., 15 seconds).

In some embodiments, the at least one processor is further configured to increase a time duration for a subsequent plasma treatment in response to determining that that the plasma treatment is below the threshold. For example, if a first plasma treatment on an object lasting only 15 seconds resulted in the object not reaching a hydrophilic state (e.g., the plasma treatment is below the threshold such that fog can form on the object), the at least one processor may increase a time duration for a second plasma for the object to 30 seconds. The second (e.g., longer) plasma treatment may cause the treated object to become super-hydrophilic (e.g., the plasma treatment is above the threshold and fog no longer forms on the object). For example, at least one processor 102 or 508 may increase a time duration for a subsequent plasma treatment by plasma generating field applicator 130 in response to determining that a previous plasma treatment applied to object 200 is below the threshold for preventing fog from forming on an optical element of object 200.

According to some embodiments, the desired level of hydrophilicity is super-hydrophilic. The term “super-hydrophilic” may refer to a very high level of hydrophilicity, for example sufficiently hydrophilic to substantially decrease a contact angle between a fluid and the surface of the object, e.g., so as to allow the fluid to coat the surface of the object as a substantially uniform (e.g., flat) layer. In some embodiments, after increasing the hydrophilicity of the object to the desired level, the contact angle between the fluid and the super-hydrophilic surface of the object may be less than about 30°, e.g., less than about 15° or less than about 10°, e.g., when measured at 20° C. and atmospheric pressure. Thus, prior to the plasma treatment, droplets may accumulate on the surface of the object to distort an optical behavior of the object, whereas after the plasma treatment, the surface of the object may be coated in a substantially uniform layer of fluid that does not distort the optical behavior of the object in a meaningful manner. In some embodiments, increasing the hydrophilicity of the object to the desired level accentuates a surface charge and surface energy of the object, allowing water molecules to bond to the surface of the object. According to some embodiments, the effect of the plasma treatment on the hydrophilicity of the object may be limited in time, e.g., to less than 48 hours, less than 36 hours, less than 24 hours, or less than 12 hours.

In some embodiments, the desired level of hydrophilicity may relate to a quality of the plasma treatment. The “quality of the plasma treatment” may relate to the level of hydrophilicity attained after activating the electric and/or electromagnetic field for generating the plasma for a given time duration. For example, a high-quality plasma treatment may achieve a relatively high level of hydrophilicity (e.g., obtaining a surface tension above that of water namely above 0.072N/M on the treated surface) after activating the electric and/or electromagnetic field for a relatively short time (e.g., of 5 minutes, or 1 minute or as short as 10 seconds or even as short as 5 seconds).

In some embodiments, the plasma generation device may include at least one sensor configured to measure at least one plasma-activation parameter during the plasma treatment. The term "sensor" may refer to a device or element capable of detection. For example, a sensor may detect an absolute value or a change in a quantity and generate a corresponding signal or data. A sensor may be a physical sensor configured to sense physical (e.g., analog and/or digital) signals, a software sensor configured to sense digital signals (e.g., analog signals converted to a digital format, digital signals generated by the at least one processor, digital signals received from another device), or a combination of a physical sensor and a software sensor. The term "measure" may relate to detecting, checking, assessing, estimating, or quantifying an attribute, e.g., a physical attribute. The sensor may measure the attribute as an instantaneous characteristic, a time-dependent characteristic, or a combination thereof. The term "plasma-activation parameter" may relate to any condition within and/or proximate to the plasma activation zone. For example, the sensor may be a pressure sensor, a voltage sensor, a current sensor, a plasma frequency sensor, touch sensor, time sensor, optical sensor, temperature sensor, electric field sensor, magnetic field sensor, or any other detector for measuring a parameter relevant the plasma treatment. In some embodiments, the sensor may measure a negative pressure in at least a portion of the bore (e.g., via a vacuum sensor). In some embodiments, the sensor may detect when the at least a portion of the object (e.g., the optical element) is within the bore, e.g., ready to be exposed to the plasma. For example, the sensor may be sensitive to touch, pressure, weight, magnetic or electric conductivity, temperature, optical characteristics, or any other physical attribute for detecting the presence of at least a portion of the object. The term "during the plasma treatment" may refer to a time span over which the object is exposed to a plasma cloud for the purpose of increasing the hydrophilicity of the object. The time span may relate to a range of possible times, a minimal time, a maximal time, or a recommended time. In some embodiments, the time span may include a time period needed to generate the plasma cloud from gas present in the plasma-generation zone. In some embodiments, the time span may include a time period needed to introduce gas into the plasma-generation zone. In some embodiments, the time span may include a time period needed to evacuate other gases (e.g., air) from the plasma-generation zone. Turning to FIGS. 5 and 11, plasma generating system 500 include one or more sensors for measuring a plasma-activation parameter, such as pressure sensor 1100 (FIG. 11) for measuring pressure, plasma frequency sensor 512 for measuring a frequency of the plasma generated within plasma-generation zone 504, voltage sensor 514 for measuring voltage, e.g., between anode 340 and cathode 330 (FIG. 4).

In some embodiments, the plasma generation device may include at least one processor. The at least one processor may include electric circuitry for performing logical operations on an input signal. For example, the at least one processor may include one or more integrated circuits (ICs), including ASICs, microchips, microcontrollers, microprocessors, all or part of a CPU, GPU, APU, DSP, FPGA, or other circuits suitable for executing computing instructions and/or capable of performing logical operations, e.g., based on a computing instruction or an input signal. Instructions executed by the at least one processor may be pre-loaded into a memory integrated with or embedded into a controller (e.g., processor) or may be stored in a separate memory. The memory may include a RAM, a cache memory, a ROM, a hard disk, an optical disk, a magnetic medium, a flash memory, other permanent, fixed, or volatile memory, or any other mechanism capable of storing such instructions. In some embodiments, the at least one processor may include multiple processors. Each processor may have a similar construction, or different constructions that may be electrically connected or disconnected from each other. The processors may be separate circuits or integrated in a single circuit. Multiple processors may be configured to operate independently or collaboratively. The processors may be coupled electrically, magnetically, optically, acoustically, mechanically or by other means that permit them to interact. The processors may be physical and/or virtual (i.e., software-based). In some embodiments, multiple processors may be distributed and collectively accessed remotely and/or locally, as known in the art of cloud computing. Turning to FIG. 5B, controller 508 illustrates an exemplary implementation of at least one processor, consistent with disclosed embodiments. Similarly, at least one processor 508 illustrates another exemplary implementation of the at least one processor.

In some embodiments, the at least on processor may be configured to determine, based on the at least one plasma-activation parameter, that the plasma treatment is below a threshold for increasing the hydrophilicity of the object to the desired level. The term "determine" may relate to a measurement, comparison, estimation, or calculation performed by the at least one processor with respect to the at least one plasma-activation parameter and one or more additional values, e.g., stored in memory or received from another device. For example, the at least one processor may determine, based on the at least one plasma-activation parameter by comparing the at least one plasma-activation parameter to a value (e.g., a minimum, maximum, or average value) stored in memory in advance of the plasma treatment. In some embodiments, the term "threshold" may relate to aspects of the plasma treatment, such as a power level, energy level, time duration, intensity, magnitude, pressure, frequency, phase, temperature, or any other attribute that may influence the effectiveness of the plasma treatment in increasing the hydrophilicity of the object. In some embodiments, the term "threshold" may relate to characteristics of the treated object, such as the level of hydrophilicity attained, the incident angle of fluid coming in contact with the treated object, the surface tension of the treated object, the surface charge of the treated object, the variability of fluid condensed on the surface of the treated object, the optical quality attained via the treated object after the treated object comes in contact with fluid, and any other characteristic indicating the level of hydrophilicity achieved by the plasma treatment. For example, controller 508 (FIG. 5B) may determine, based on a plasma activation parameter (e.g., pressure sensed via pressure sensor 1100 of FIG. 11) that the plasma treatment provided by plasma generating system 500 (FIGS. 5A-5C) is not sufficient (e.g., below a threshold) to increase the hydrophilicity of optical element 390 of endoscope 380 (FIG. 2) to a desired level to prevent condensation that diminishes visibility via a viewport of endoscope 380. Consequently, controller 508 may determine failure of the plasma treatment. According to some embodiments, sensor inputs may be pressure and RF voltage measurements. A pressure measurement may be taken prior to igniting plasma, and any change in pressure over time (e.g., above a threshold, such as 0.3 atm) may be reported. Thus, transformer 526 (FIG. 5B) may include a sensor for RF output such that decrease in voltage below a threshold may communicate a failure in the plasma treatment.

In some embodiments, the at least one processor may be configured to output a notification indicating of plasma treatment failure. The term "output" may relate to the indicating of information via an interface. The information may be indicated (i.e., outputted) visually, e.g., via a visual display, printer, one or more light-emitting diodes or light bulbs, dials, gauges, meters, or any other visual indicator. In some embodiments, the information may be indicated audibly, e.g., via a speaker, or in a tactile manner, e.g., as vibrations produced by a direct current motor coupled to an eccentric rotating mass (ERM). In some embodiments, the notification may be a binary indication revealing either success of failure of the plasma treatment. In some embodiments, the notification may further indicate on which of the at least one plasma-activation parameters the determination of failure is based. In some embodiments, the notification may include a recommendation for adjusting or calibrating one or more system parameters to remedy the plasma treatment failure. In some embodiments, the notification may include a recommendation for replacing or fixing one or more components of the plasma generation device to remedy the plasma treatment failure. In some embodiments, the notification may be a warning indicating that a plasma treatment failure is imminent. In some embodiments, the warning may relate to one or more of the system parameters and or system components referred to above. For example, controller 508 (FIG. 5B) may output a notification indicating the plasma treatment failure via display 1102 (FIG. 11).

In some embodiments, the at least one sensor is configured to measure the at least one plasma-activation parameter by detecting a pressure in the plasma-generating zone during the plasma treatment, wherein the at least one processor is further configured to determine that the plasma treatment fails to meet the threshold when the pressure is outside a pressure range. The term "pressure" may relate to a strain or force applied over an area. For example, gas contained within the plasma-generation zone may exert force on the inner walls of the plasma-generation zone. The force exerted by the gas may be measured as a plasma-activation parameter, indicating when the gas is at a suitable pressure for plasma ignition, for example after air is evacuated from the plasma-generating zone, or after the gas for igniting the plasma is streamed into the plasm-generating zone. The term "pressure range" may relate to one or more of a pressure window, a minimal pressure, a maximal pressure, an average pressure, or a tolerance around an average pressure. In some embodiments, a pressure suitable for plasma ignition may be below 0.1 Atm. The at least one processor may compare the detected pressure to a predefined pressure range (e.g., below 0.1 Atm) stored in memory and determine that the detected pressure does not meet conditions necessary to successfully generate plasma. Consequently, the at least one processor may determine that the plasma treatment may fail. For example, controller 508 (FIG. 5B) may determine, based on a pressure sensed via pressure sensor 1100 (FIG. 11) that the plasma treatment provided by plasma generating system 500 (FIGS. 5A-5C) to an object is not sufficient (e.g., fails to meet a threshold) for increasing the hydrophilicity of the object to a desired level, e.g., that may prevent condensation diminishing visibility via the object.

In some embodiments, the at least one sensor is configured to measure the at least one plasma-activation parameter by detecting a voltage at an electrode generating the plasma during the plasma treatment, wherein the at least one processor is further configured to determine that the plasma treatment fails to meet the threshold when the detected voltage is outside a voltage range. The term "voltage" may relate to an electric potential difference between two points (e.g., measure in units of volts), such as between two electrodes (e.g., between an anode and a cathode). The term "voltage range" may relate to one or more of minimal voltage, a maximal voltage, an average voltage, or a tolerance around an average voltage. For example, the voltage detected in the vicinity of the plasma-generation zone may determine aspects of the electric and/or electro-magnetic field for generating the plasma. The term "electrode" may relate to an electrical contact made of a conductive material, such as metal, a semiconductor, graphite, conductive polymers, and any other material capable of conducting an electric current. An electrode may be an anode or a cathode, where electric current typically flows out of a cathode and towards an anode. Thus, in some embodiments, the at least one sensor may include a voltage sensor that measures the voltage inside or in proximity to the plasma-generation zone. The at least one processor may receive the measured voltage to determine if the voltage is sufficient to drive an electric and/or electromagnetic field capable of generating plasma to increase the hydrophilicity of the object to the desired level. The at least one processor may compare the detected voltage to a predefined voltage range stored in memory and determine that the detected voltage does not meet conditions necessary to successfully generate plasma. Consequently, the at least one processor may determine that the plasma treatment may fail. Turning to FIG. 5A, voltage sensor 514 may measure a voltage, e.g., between anode 340 and cathode 330 (FIG. 4). Controller 508 may receive the measurement from voltage sensor 514, and determine, based on the measurement if the plasma treatment fails to meet the threshold.

In some embodiments, characteristics of an electric and/or electromagnetic field capable of generating plasma from a gas may depend on the geometry of the electrodes, such as the shape, configuration, and distance between the electrodes provided for inducing the electric field. Additionally, or alternatively, the electric and/or electromagnetic field needed to generate the plasma may depend on the gas used to generate the plasma. Typically, gas at a high pressure requires a higher electric and/or electromagnetic field (e.g., measured as voltage per unit area) to ignite plasma in the gas. However, some gases may require lower electric and/or electromagnetic fields to ignite to form plasma than other gases. For example, plasma may be ignited in helium gas at atmospheric pressure using a radio frequency (RF) field (e.g., in a frequency between 1 MHz and 15 MHz) of about 7 KV over a distance of 1 cm between electrodes, whereas if the helium gas is at a pressure of 0.8 KPa, a voltage of about 200V may suffice. Using a similar configuration of electrodes with similar field frequencies, plasma may be ignited in air at atmospheric pressure using a voltage of about 20 KV, whereas if the air is at a pressure of 0.8 KPa, a lower voltage, e.g., 800V may be sufficient.

In some embodiments, the at least one sensor is configured to measure the at least one plasma-activation parameter by detecting a plasma frequency during the plasma treatment, and wherein the at least one processor is configured to determine that the plasma treatment fails to meet the threshold when the detected plasma frequency is outside a plasma frequency range. The term "plasma frequency", e.g., "electron plasma frequency", may relate to the frequency at which electrons (e.g., negatively charged particles) in a plasma naturally oscillate relative to ions (e.g., positive and negatively charged particles) present in the plasma. The plasma frequency may range between 2 and 20 MHz. Each type, e.g., species, of plasma may have a different frequency. The term "plasma frequency range" may relate to one or more of minimal plasma frequency, a maximal plasma frequency, an average plasma frequency, or a tolerance around an average plasma frequency. Turning to FIG. 5A, plasma frequency sensor 512 may measure a frequency of the plasma generated within plasma generation zone 504. Controller 508 may receive the measurement from plasma frequency sensor 512, and determine, based on the measurement if the plasma treatment fails to meet the threshold.

In some embodiments, the at least one sensor includes at least one of a pressure sensor, a voltage sensor, or a plasma frequency sensor. The pressure sensor may include one or more of a pressure transducer, a pressure transmitter, a pressure sender, a pressure indicator, a piezometer, a manometer, or any other device capable of detecting or measuring pressure. The pressure sensor may be an absolute pressure sensor that measures pressure relative to a perfect vacuum, e.g., for situations where a constant reference is required, such as to monitor a vacuum pump. Alternatively, the pressure sensor may measure pressure relative to atmospheric pressure or ambient pressure, or relative to a pressure that is different than the ambient pressure. The pressure sensor may include a force collector to measure a compression, load, or stress caused by gas pushing or pressing against the pressure sensor (e.g., when the pressure sensor is located inside the plasma-generation zone). Additionally, or alternatively, the pressure sensor may include one or more vibrating components to measure a change in resonant frequency of a gas, such as vibrating wires, crystals (e.g., quartz), micro-electromechanical systems (MEMS), and any other vibrating component sensitive to a resonant frequency. The voltage sensor may detect a magnetic field, an electric field, or an electromagnetic field to calculate the amount of voltage (e.g., electric potential) in an object. In some embodiments, the voltage sensor may be a contact sensor having a test probe configured to touch an electric circuit. In some embodiments, the voltage sensor may be a non-contact voltage sensor configured for sensing a weak electric current that is capacitively coupled from a circuit to the voltage sensor. The plasma frequency sensor may be a resonance frequency detector configured to measure an electron density of the plasma. Turning to FIGS. 5 and 11, voltage sensor 514 and a plasma frequency sensor 512 (FIG. 5A) may measure voltage and plasma frequency, respectively with respect to the plasma generated within plasma generation zone 504. Similarly, frequency sensor 1100 (FIG. 11) may measure a frequency of the plasma generated within plasma generation zone 504 (FIG. 5A). Controller 508 (FIG. 5B) may receive a measurement from one or more of voltage sensor 514, plasma frequency sensor 512, or frequency sensor 1100, and determine, based on the measurement if the plasma treatment fails to meet the threshold.

In some embodiments, the plasma generation device may further include a gas reservoir configured to stream a gas into the plasma-generation zone for carrying out the plasma treatment, wherein the at least one processor is further configured to determine that the plasma treatment fails to meet the threshold based on a characteristic of the gas. The term "gas reservoir" may refer to a sealable tank, balloon, or canister configured to contain a gas, e.g., at a higher pressure or lower pressure than atmospheric pressure. In some embodiments, the gas reservoir may be portable, e.g., for a single plasma treatment. In some embodiments, the gas reservoir is a central gas reservoir that is not portable. The gas reservoir may be configured to be fluidly coupled to the plasma-generation zone of the plasma generation device, e.g., via a hose. The gas reservoir may be further configured to be fluidly coupled to one or more pumps and/or valves for controlling and moderating a stream of gas from the gas reservoir to the plasma-generation zone.

In some embodiments, the object is an endoscope, wherein the plasma generation device further includes a detachable sheath dimensioned to receive a distal end of the endoscope, and wherein the plasma-generation zone is configured to apply the plasma treatment to the distal end of the endoscope within the sheath. The term "detachable" may refer to removeable or capable of separation. For example, the sheath may be removeable from the distal end of the endoscope and from the plasma generation device. The term "sheath", or "protecting shroud" may refer to a covering or supporting structure that fits around an object. For example, the sheath may enclose an optical element of a medical instrument. In one exemplary embodiment, the sheath may be a slender, flexible, disposable tube that retains within the sheath a portion of the medical instrument when the medical instrument is inserted into the plasma-generation zone. In some embodiments, the sheath may include an authentication element (e.g., an RFID tag or any other automatically detectable identification device) enabling the at least one processor to test the sheath prior to operating the plasma generation device with the sheath. The authentication element may enable the at least one processor to determine if the sheath is new and/or if it has been used a permissible number of times. Additionally or alternatively, the authentication element may enable the at least one processor to test the sheath to determine if the sheath is from an approved manufacturer. Without such verification, an unauthorized sheath may be used, compromising sterility and/or effectiveness in inhibiting fog on the object. The term "dimensioned" may refer to sized or designed (e.g., configured or constructed) according to a measured proportion, e.g., length, width, and/or height. For example, the sheath may be sized to accommodate a distal end of the endoscope. The term "endoscope" may include any of the medical scopes previously described. For example, an endoscope includes an elongated tubular instrument having an optical sensor (e.g., camera) and light source disposed at a distal end. The endoscope may be used to look inside a human body, e.g., during medical procedures commonly referred to as endoscopy. For example, the distal end of an endoscope may be placed inside a removeable sheath, and the sheath with the distal end of the endoscope may be placed inside the plasma-generation zone such that the distal end of the endoscope is exposed to a plasma cloud while inside the sheath, e.g., to carry out the plasma treatment. After the plasma treatment is complete, the endoscope may be removed from the plasma-generation zone while inside the sheath to preserve sterility, or, the endoscope may be removed completely from the housing while the sheath remains within the housing. Protecting shroud 110 in FIG. 1A, protecting shroud 310 in FIG. 2, and sheath 800 in FIG. 8A are some examples of sheaths, in accordance with disclosed embodiments. As another example, protecting shroud 310 may be sized (e.g., dimensioned) to receive distal end 382 of endoscope 380 (FIG. 2), where distal end 382 is provided with viewport 390. Plasma-generation zone 504 (FIG. 5A) may apply the plasma treatment to distal end 382, thereby applying the plasma treatment to viewport 390, while viewport 390 is within protecting shroud 310.

In some embodiments, the plasma generation zone is configured to contain a plasma cloud on a first side of a dielectric barrier while the object is located on a second side of the dielectric barrier. Disk 344 of FIGS. 3A-3B depicts an exemplary implementation for a dielectric barrier separating anode 340, positioned on one side of disk 344, from cathode 330 positioned on the other side of disk 344. A plasma cloud may be formed on the cathode side 330, exposing viewport 390 of endoscope 380 while preventing arc formation.

In some embodiments, the plasma generation device further includes a plasma generator configured to be activated to cause formation of a plasma cloud in the plasma-generation zone, and wherein the at least one processor is further configured to activate the plasma generator for a time period sufficient to increase the hydrophilicity of the object to the desired level. The Plasma generator of FIGS. 5A-5C illustrates an exemplary implementation of a plasma generator in accordance with disclosed embodiments. Plasma generator 506 may be activated, e.g., via controller 508, to cause a plasma cloud to be formed in plasma generation zone 504. Controller 508 may further activate the plasma generator for a time period sufficient to increase the hydrophilicity of viewport 390 of endoscope 380 (FIG. 2) to the desired level, e.g., to prevent fog from forming on viewport 390 during an endoscopy procedure.

In some embodiments, the desired level of hydrophilicity of the object is such that at least one hour after the plasma treatment, droplets hitting a surface of the object have contact angles of less than 10 degrees. In some embodiments, the contact angles of droplets hitting the surface after at least an hour of treatment may be less than 8.5 degrees, or less than 7.5 degrees.

The contact angle may indicate a degree of hydrophilicity, for example a desired, or threshold level of hydrophilicity required to use the object, e.g., for a medical procedure. The desired contact angle (e.g., less than 10 degrees, less than 8.5 degrees, or less than 7.5 degrees) may be associated with a desired optical quality of an optical element of the object when the object is used for a medical procedure. Turning to FIG. 2, viewport 390 of endoscope 380 may be treated by plasma in accordance with the present disclosure such that at least one hour after the plasma treatment, the surface tension of viewport 390 is greater than the surface tension of water, and results in a contact angle of less than 10 degrees for water droplets hitting the surface of viewport 390. Consequently, at least one an hour of the plasma treatment viewport 390 may be substantially immunized from an accumulation of fog, and endoscope 380 may be used for a medical procedure and provide a high optical quality.

Figure 16:
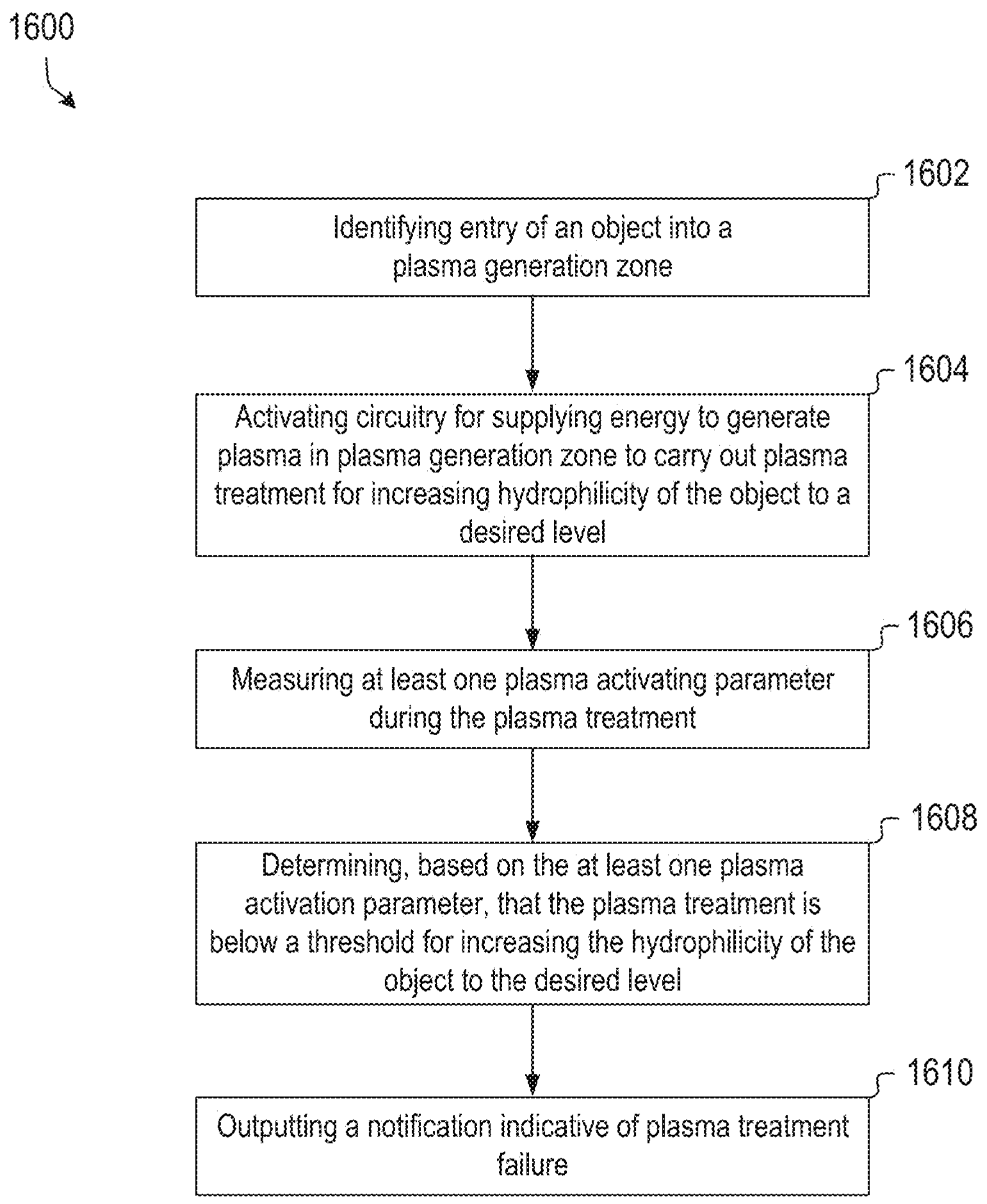
FIG. 16 is a flowchart illustrating a method for determining when a plasma treatment is insufficient, and outputting a notification of such, consistent with some disclosed embodiments.

FIG. 16 is a block diagram of an example process 1600 for generating plasma to treat an object, consistent with embodiments of the present disclosure. While the block diagram may be described below in connection with certain implementation embodiments presented in other figures, those implementations are provided for illustrative purposes only, and are not intended to serve as a limitation on the block diagram of FIG. 16. As examples of the process are described throughout this disclosure, those aspects are not repeated or are simply summarized in connection with FIG. 16. In some embodiments, the process 1600 may be performed by at least one processor (e.g., controller 508 of FIG. 5B) to perform operations or functions described herein. In some embodiments, some aspects of the process 1600 may be implemented as software (e.g., program codes or instructions) that are stored in a memory provided with the at least one processor, or a non-transitory computer readable medium. In some embodiments, some aspects of the process 1600 may be implemented as hardware (e.g., a specific-purpose circuit). In some embodiments, the process 1600 may be implemented as a combination of software and hardware.

FIG. 16 includes process blocks 1602 to 1610. At block 1602, entry of an object into a plasma-generation zone is identified. This may occur, for example, via a processing means (e.g., controller 508 of FIG. 5B). For example, controller 508 may identify entry of distal end 382 disposed with viewport 390 of endoscope 380 (FIG. 2), into plasma-generation zone 504 of plasma generating system 500.

At block 1604, circuitry may be activated for supplying energy to generate plasma in the plasma-generation zone to carry out a plasma treatment for increasing hydrophilicity of the object to a desired level. For example, at least one processor 508 may activate circuitry 106 for supply energy from power supply 104 to device 130 to generate plasma in a plasma-generation zone of device 130 to carry out a plasma treatment on object 200. Circuit activation may alternatively occur via a switch or sensor that determines entry of the object. The plasma treatment may be controlled by at least one processor 508 to increase hydrophilicity of object 200 to the desired level, e.g., to prevent fluid from condensing as droplets on an optical surface of object 200. As another example, controller 508 (FIG. 5B) may activate circuitry, e.g., (circuitry 700 of FIG. 7) for supplying energy (e.g., via cable 112 of FIG. 1A) to cathode 330 and anode 340 via electric conductor 354, and electric conductor 358 (FIG. 3A) to generate plasma in plasma-generation zone 504 of plasma generating system 500. The plasma treatment may increase hydrophilicity of viewport 390 (FIG. 3A) of endoscope 380 to a desired level. The desired level may be associated with a desired optical quality when subsequently using endoscope 380 in a medical procedure.

At block 1606, at least one plasma-activation parameter is measured during the plasma treatment. As used in this context, "measuring" may refer to one or more of detecting, sensing, determining, or obtaining a value indicative of a plasma-activation parameter. For example, controller 508 (FIG. 5B) may measure a pressure parameter associated with the plasma treatment via pressure sensor 1100 (FIG. 11). Additionally, or alternatively, controller 508 may measure a voltage parameter associated with the plasma treatment via voltage sensor 514. Similarly, controller 508 may measure a plasma frequency parameter associated with the plasma treatment via plasma frequency sensor 514.

At block 1608, a determination is made that the plasma treatment is below a threshold for increasing the hydrophilicity of the object to the desired level. For example, controller 508 (FIG. 5B) may determine, based on the pressure parameter measured via pressure sensor 1100 (FIG. 11) that the plasma treatment provided by plasma generating system 500 is below a threshold for increasing the hydrophilicity of viewport 390 of endoscope 380 to the desired level (e.g., to ensure the desired optical quality when endoscope 380 is subsequently used for a medical procedure. In a similar manner, controller 508 may make determine, based on a voltage parameter measured via voltage sensor 514, and/or a plasma frequency parameter measured via plasma frequency sensor 512 that the plasma treatment provided by plasma generating system 500 is below the threshold.

At block 1610, a notification may be output indicating plasma treatment failure. For example, controller 508 (FIG. 5B) may display a notification via display 1102 (FIG. 11) indicating that the plasma treatment has failed.

To facilitate treating an object with plasma, a plasma generation device may automatically trigger the generation of plasma upon detecting the insertion of the object, i.e., within a bore of a housing of the plasma generation device. The bore may be provided with one or more sensors for detecting the insertion of the object. The one or more sensors may communicate information associated with the detection to at least one processor configured to trigger, e.g., automatically, a plasma treatment for the object. When plasma generation occurs in a vacuum (e.g., a partial vacuum), a signal may be received from a vacuum sensor and determination may be made that there is a sufficient negative pressure for plasma generation. Once a sufficient negative pressure determination is made, energy may be supplied to an electrode to cause plasma generation and to expose the object to plasma. In the case of medical scopes where a premium is placed on speed, efficiency, and sterility, an ability to treat optics with plasma and with limited human intervention may provide a significant benefit.

In some embodiments, at least one processor may trigger a plasma treatment to correspond to the object type, e.g., based on the information received from the one or more sensors. For example, a first object may be of a type requiring a shorter plasma treatment than a second object requiring a longer plasma treatment. Alternatively, the first object may have a different hydrophilicity threshold than the second object (e.g., corresponding to preventing fogging for different applications and uses). The at least one processor may thus trigger a different plasma treatment for each of the first and second objects, corresponding to the different hydrophilicity thresholds.

In some embodiments, a device for treating an elongated tool with plasma may be provided. The term “device” may include any apparatus or combination of components capable of treating an object with plasma, e.g., by converting (e.g., igniting) a gas to transform the gas to a plasma state or plasma cloud and exposing the object to the plasma cloud. Plasma generating systems 100 (FIG. 1A) and 500 (FIGS. 5A-5C), as well as plasma applicator 348 (FIG. 3A) illustrate exemplary implementations of a plasma generation device in accordance with disclosed embodiments. The term “elongated tool” may refer to an object having a length that is substantially longer than the width of the object. Object 200 (FIG. 1B), endoscope 380 (FIG. 2), and endoscope 802 (FIG. 8A) illustrate exemplary implementations of an elongated tool. The term “plasma” may refer to a state of matter containing an abundance of charged particles, e.g., electrons and ions. Consequently, plasma may be highly electrically conductive and sensitive to electric and/or electromagnetic fields.

In some embodiments, the device may include a bore within the housing, the bore having an open end on a surface of the housing for insertion of the elongated tool therein. The term “bore” may refer to may refer to a cavity, chamber, crevice, or pit capable of containing an object. The bore may accommodate at least a portion of an object inside a plasma-generation zone to expose the at least portion of the object to the plasma cloud. For example, the bore may accommodate an optical element of an endoscope to expose the optical element to a plasma cloud generated by igniting a gas streamed into the bore. Consequently, the hydrophilicity of the optical element may increase to prevent fog from forming when the optical element is subsequently inserted into a body. In some embodiments, the bore may have an elongated shape, such as to accommodate the elongated tool. The surface of the housing may include an opening, exposing an entrance into the elongated bore. The opening may enable insertion of the elongated tool within the bore. Examples of a bore disposed within the housing for the plasma generation device may be illustrated by slot 132 (FIGS. 1A and 1C), bore 350 (FIG. 3A), bore 450 (FIG. 3C), cavity 502 (FIGS. 5A-5C) and bore 900 (FIG. 9). Proximal openings 142 (FIG. 1D) and 314 (FIG. 2) illustrate exemplary implementations of an open end of the bore, on the surface of the housing, consistent with disclosed embodiments.

In some embodiments, a device includes at least one vacuum pump for causing a vacuum in at least a portion of the bore. The term “vacuum” may refer to a region having a gaseous pressure that is substantially lower than atmospheric or ambient pressure. As used herein, the term “vacuum” is intended to include partial vacuums. That is, in the context of this disclosure, a vacuum encompasses an enclosed space where at least some of the air or other gas is removed. The term “vacuum pump” may refer to a device that draws or suctions particles from a sealed volume in order to cause a vacuum in the volume. Examples of vacuum pumps for causing a vacuum may be seen in FIG. 10A, which depicts a plurality of vacuum pumps (e.g., vacuum pumps 1000A, 1000B, 1000C, and 1000D). One or more of vacuum pumps 1000A, 1000B, 1000C, and 1000D may be configured to cause a vacuum in at least a portion of a bore, such as in a portion of any of slot 132 (FIGS. 1A and 1C), bore 350 (FIG. 3A), bore 450 (FIG. 3C), cavity 502 (FIGS. 5A-5C) and bore 900 (FIG. 9).

In some embodiments, a device includes an insertion detector for determining when the elongated tool is inserted within the bore. An “insertion detector” may refer to any sensor capable of detecting the insertion of an object within the bore, such as a touch (contact) sensor detecting contact with the object, an optical sensor, e.g., capable of detecting the obstruction of a line of sight by the object within the bore or a reflection of light by the object within the bore, a pressure sensor capable of detecting pressure exerted by the object, a weight sensor capable of sensing the weight of the object, a voltage and/or current sensor capable of detecting a change in potential and/or current caused by insertion of the object into the bore, and any other sensor capable of sensing the object. In some embodiments, the insertion detector may include a radio receiver for detecting an identifying tag associated with the object, such as an RFID tag (e.g., authenticating tag), such as may be included with a sheath provided to retain the object within the bore. In some embodiments, the insertion detector may include a mechanical sensor such as to detect the tearing of a hermetic seal covering the entrance to the bore. Non-limiting examples of an insertion detector include one or both of the transmitter 24650 and transponder 24654 depicted in FIGS. 25A through 25E.

For example, electrodes 704A and 704B (FIG. 7), configured to come in physical contact with the object, illustrate an exemplary implementation of a sensor (e.g., voltage sensor) for detecting the insertion of the object within the bore. Electrodes 704A and 704B may be configured to electrically couple the inserted object with a cathode and/or anode associated with the bore, and thereby facilitate detecting when object is inserted within the bore. As another example, a sensor (not shown) associated with breakable hermetic screen 518 (FIG. 4) and configured to emit a signal when breakable hermetic screen 518 breaks upon insertion of the elongated object within the bore, may illustrate another exemplary implementation for detecting when the object is inserted into the bore. As another example, pressure sensor 1100 (FIG. 11) may illustrate another exemplary implementation for the insertion sensor, in accordance with disclosed embodiments. A signal sensed by the insertion sensor may be provided to at least one processor (e.g., at least one processor 102 of FIG. 1A and/or controller 508 of FIG. 5B) using wired and/or wireless communications means. Based on the insertion signal, the at least one processor may determine the insertion of an object (e.g., object 200 of FIG. 1B, endoscope 380 of FIG. 2, or endoscope 802 of FIG. 8A) within the bore (e.g., slot 132 of FIG. 1A, bore 350 of FIG. 3A, bore 450 of FIG. 3C cavity 502 of FIGS. 5A-5C, or bore 900 of FIG. 9).

In some embodiments, a device includes a vacuum sensor associated with the housing for determining an extent of negative pressure in the at least a portion of the bore. In some embodiments, the vacuum sensor may include a pressure transducer, e.g., for measuring pressure and converting the pressure to an electrical signal via one or more strain gauges. In some embodiments, the vacuum sensor may detect pressure relative to a threshold and output a binary signal indicating that the pressure is above or below the threshold. In some embodiments, the vacuum sensor may output an electric signal proportional to the measured pressure. The vacuum sensor may be positioned in proximity to the bore, e.g., while being in fluid communication with the bore, to determine the extent of the negative pressure inside the bore. Pressure sensor 1100 (FIG. 11) illustrates an exemplary implementation for a vacuum sensor in accordance with disclosed embodiments. Pressure sensor 1100 may be enclosed within (e.g., associated with) housing 510 (FIGS. 5A-5C) and may determine the extent of negative pressure within cavity (e.g., bore) 502.

In some embodiments, the device may include a plasma generator for generating plasma within the bore. The term "plasma generator" may refer to a device configured to generate plasma, e.g., inside a plasma generation zone The term "plasma generation zone" may refer to a physical volume or space in which a plasma cloud may be formed, e.g., by igniting a gas introduced therein. The plasma generation zone may be of any size. For example, the plasma generation zone may be less than 15 $cm^3$, less than 10 $cm^3$, or less than 5 $cm^3$. The plasma generator may generate an electromagnetic field within the plasma generation zone, such that exposing a gas to the electromagnetic field ignites the gas to generate plasma. Plasma applicators 130 (FIG. 1A) and 348 (FIG. 3A), and the plasma generator of FIGS. 5A-5C, (e.g., including at least a first electrical contact 522, a second electrical contact 524, an energy source such as a battery 530, and a transformer 526) illustrate exemplary implementations of a plasma generator in accordance with disclosed embodiments. Plasma applicators 130 and 348, and the plasma generator of FIGS. 5A-5C may be configured to generate plasma within slot 132, bore 350, and cavity 502, respectively.

In some embodiments, a device includes at least one processor. In some embodiments, the at least one processor is configured to receive an insertion signal from the insertion detector indicating that the elongated tool is within the bore. The term "insertion signal" may refer to any signal indicating a presence of the elongated tool in the bore. For example, outputs of any of the insertion detectors described above may constitute insertion signals. In some embodiments, the insertion signal may be an analog signal (e.g., as an analog value or signal received from an analog insertion detector). In some embodiments, the insertion signal may be a digital signal (e.g., received by a digital device such as a digital processor, digital filter, diode, and any other device capable of providing a digital signal). In some embodiments, the insertion signal may be a binary signal indicating whether the elongated tool has been inserted within the bore. In some embodiments, the insertion signal may be a value that is comparable (e.g., via the at least one processor) to one or more threshold values (e.g., store in memory) to determine if the elongated tool has been inserted within the bore. In some embodiments, the insertion signal may include one or more of: a touch signal by a touch (contact) sensor indicating physical contact between the elongated tool (or a sheath enclosing the elongated tool) and the bore, an optical signal by an optical sensor indicating an obstruction of a line of sight or a reflection of light by the elongated object within the bore, a pressure signal by a pressure sensor indicating pressure exerted by the elongated object within the bore, a weight signal by a weight sensor indication weight exerted by the elongated object within the bore, a voltage (and/or current) signal by a voltage (and/or current) sensor indicating a voltage (and/or current) level caused by inserting the elongated object into the bore, a radio signal by a radio receiver indicating insertion of the elongated object into the bore (e.g., in association with an authenticating tag such as an RFID tag), or any other measure indicating the insertion of the elongated object into the bore. For example, an identification signal from transponder 24654, as discussed herein in reference to FIGS. 24 and 25A through 25E, may correspond to an insertion signal from an insertion detector.

In some embodiments, the insertion signal may be associated with an insertion detector configured with a sheath encasing the elongated tool. For example, the sheath may be provided with at least one electrode and at least one sheath electric contact configured to electrically contact a corresponding contact in the plasma generation device when the sheath is inserted into the bore. As another example, the sheath may be provided with an authenticating tag, such as an RFID tag, that sends a radio signal receivable by a radio receiver associated with the bore. In some embodiments, the insertion signal may be mechanical in nature, e.g., in association with the tearing of a hermetic seal covering the entrance to the bore. In some embodiments, the insertion signal may relate to a portion of the elongated tool, such as the distal end of the elongated tool. For example, the insertion detector may emit an insertion signal when the distal end of the elongated tool is inserted into the bore.

An exemplary implementation of an insertion sensor configured to send an insertion signal may be seen in FIG. 7. For example, on inserting medical instrument 708 (e.g., an elongated tool) into bore 712, electrodes 702A and 702B may become electrically coupled to medical instrument 708 via electrodes 704A and 704B, e.g., thereby electrically coupling medical instrument 708 or 200 (FIG. 1A) to power supply 530. Consequently, any of electrodes 702A and 702B or 704A and 704B may transmit a voltage signal as an insertion signal indication insertion of the object within the bore. Similarly, detecting breakage of hermetic screen 518 (FIG. 4) by endoscope 380 (e.g., an elongated tool) when endoscope 380 is inserted within sheath 510 (e.g., with sheath 510 fitted inside the bore of the device) may be another exemplary implementation of an insertion signal for detecting when the object is inserted into the bore. As another example, pressure sensed by pressure sensor 1100 (FIG. 11) when endoscope 810 (FIG. 8) is inserted into sheath 800, (e.g., with sheath 800 fitted inside the bore of the device) may constitute an additional exemplary implementation for the insertion signal received from the insertion detector, in accordance with disclosed embodiments. The insertion sensor may transmit an insertion signal indication the insertion to at least one processor (e.g., at least one processor 102 of FIG. 1A and/or controller 508 (FIG. 5B) using wired and/or wireless communications means. A least one processor 102 and/or controller 508 may determine, based on the insertion signal, that the elongated object (e.g., object 200 of FIG. 1B, endoscope 380 of FIG. 2, medical instrument 708 (FIG. 7), or endoscope 802 of FIG. 8A) has been inserted within the bore (e.g., slot 132 of FIG. 1A, bore 350 of FIG. 3A, bore 450 of FIG. 3C, cavity 502 of FIGS. 5A-5C, and bore 900 of FIG. 9).

In some embodiments, at least one processor may be further configured to, in response to the insertion signal, activate the at least one vacuum pump to generate a negative pressure in the at least a portion of the bore. The term "activate" may refer to trigger, turn or switch on (e.g., by emitting an electric signal), or perform any other action for initiating pumping by the vacuum pump. The term "negative pressure" may refer to air or gas pressure that is smaller or lower relative to a reference pressure, such as atmospheric or ambient pressure. In some embodiments, the pressure may be less than 0.3 atm, or less than 0.2 atm, or less than 0.1 atm. In some embodiments, the effective pressure range may be between 0.300 to 0.001 atm. In some embodiments, the effective pressure range may be between 0.1 to 0.01 atm. The term "at least a portion of the bore" may refer to a section or region of the bore that is in proximity to the elongated tool such that the negative pressure is at least partially exerted in the region of the elongated tool within the bore. On activation by the at least one processor and in response to receiving the insertion signal, the vacuum pump may generate a relatively low pressure (e.g., negative pressure) to draw out (e.g., suction) air and/or gas present within the bore, such that the pressure of air and/or gas within the bore, at least in the region surrounding the elongated tool, is lower relative to the reference pressure.

For example, at least one processor 102 (FIG. 1A) or controller 508 (FIG. 5B) may receive the insertion signal from the insertion detector, e.g., a pressure signal from pressure sensor 1100 (FIG. 11), a voltage signal from one or more of electrodes 704A and 704B (FIG. 7), a signal indicating breakage of hermetic screen 518 (FIG. 4), and any of the other pressure sensing implementations described above. In response to the insertion signal, at least one processor 102 and/or controller 508 may activate the at least one vacuum pump (e.g., vacuum pumps 1000A, 1000B, 1000C, and 1000D of FIG. 10A) to generate a negative pressure (e.g., suction) in at least a portion of the bore (e.g., slot 132 of FIGS. 1A and 1C, bore 350 of FIG. 3A, bore 450 of FIG. 3C, cavity 502 of FIG. 5A, or bore 900 of FIG. 9). In some embodiments, the at least portion of the bore may be in the vicinity of the elongated object. Thus, the negative pressure may be generated in proximity to the elongated tool (e.g., object 200 of FIG. 1B, endoscope 380 of FIG. 2, or endoscope 802 of FIG. 8A) within the bore.

In some embodiments, at least one processor is configured to receive a signal from the vacuum sensor and determine therefrom that a negative pressure in at least a portion of the bore is sufficient for plasma generation. The term "sufficient for plasma generation" may refer to a gas pressure that is low enough to allow any gas remaining, or any gas introduced after generating the negative pressure in the bore, to ionize and generate plasma. Additionally, or alternatively, the negative pressure generated by the vacuum pump may be sufficiently low such that a proportion or percentage of a specific type of gas (e.g., helium, argon, or nitrogen) introduced into the bore after the negative pressure is generated (e.g., drawing out air from the bore) meets a gas concentration threshold needed to produce a specific type of plasma corresponding to the specific type of gas.

For example, at least one processor 102 (FIG. 1A), and/or controller 508 (FIG. 5B) may receive a signal from one or more of vacuum pumps 1000A, 1000B, 1000C, and 1000D (FIG. 10A), and determine from the signal that the pressure in at least a portion of the bore, e.g., a portion of slot 132 (FIGS. 1A and 1C), bore 350 (FIG. 3A), bore 450 (FIG. 3C), cavity 502 (FIGS. 5A-5C), bore 712 (FIG. 7), and bore 90 0 (FIG. 9) is low enough to generate plasma, such as via plasma applicator 130 (FIG. 1A), plasma applicator 348 (FIG. 3A), or the plasma generator of FIGS. 5A-5C. In some embodiments, the negative pressure may be facilitated by hose 364 (FIG. 3A) fluidly coupling the bore to the vacuum pump. In some embodiments, the negative pressure may be maintained by a seal, such as vacuum seal 370 (FIG. 3A). In some embodiments, low pressure (e.g., negative relative to the reference pressure) that is sufficient for plasma generation may be less than 0.3 atm, or less than 0.2 atm, or less than 0.1 atm. In some embodiments, the effective pressure range may be between 0.300 to 0.001 atm. In some embodiments, the effective pressure range may be between 0.1 to 0.01 atm.

In some embodiments, generating of the negative pressure and the activating of the plasma generator occur automatically in response to detecting that the elongated tool is within the bore. The term "automatically" may refer to directly, spontaneously, or consequent to, e.g., without intervention or necessitating an action external to the plasma generating system, such as by a human operator. Thus, the plasma generator may be activated automatically, e.g., directly and consequent to detecting that the elongated tool is inserted within the bore, without intervention by an agent and/or component external to the plasma generating device. For example, in response to detecting, via the insertion sensor, that the elongated tool, (e.g., object 200 of FIG. 1B, endoscope 380 of FIG. 3A, medical instrument 708 of FIG. 7, or endoscope 802 of FIG. 8A is within the bore, (e.g., slot 132 of FIGS. 1A, bore 350 of FIG. 3A, bore 450 of FIG. 3C, cavity 502 of FIGS. 5A-5C, bore 712 of FIG. 7, and bore 900 of FIG. 9), at least one processor (e.g., processor 102 or controller 508) may automatically, e.g., without intervention by an agent or component external to the plasma generating device (such as plasma applicator 130 of FIG. 1A, plasma applicator 348 of FIG. 3A, or the plasma generator of FIGS. 5A-5C, activate one or more of vacuum pumps 1000A, 1000B, 1000C, and 1000D (FIG. 10A) to generate the negative pressure within the bore, and additionally activate the plasma generator, e.g., the plasma generator of FIGS. 5A-5C or plasma applicator 130.

In some embodiments, the at least one processor is configured to activate the plasma generator after the determination is made that negative pressure in the at least a portion of bore is sufficient for plasma generation, thereby exposing a distal end region of the elongated tool to plasma. The term "activate" may refer to trigger, turn or switch on (e.g., by emitting an electric signal), or perform any other action that initiates the generation of plasma by the plasma generator, e.g., by initiating the generation of an electric and/or electromagnetic field by the plasma generator capable of igniting plasma within the bore. For example, after determining that the pressure within the bore, e.g., any one of slot 132 (FIGS. 1A and 1C), bore 350 (FIG. 3A), bore 450 (FIG. 3C), cavity 502 (FIGS. 5A-5C) and bore 900 (FIG. 9), is low enough to generate plasma, at least one processor (e.g., processor 102 or controller 508) may send an activation signal to any of plasma applicator 130, plasma applicator 348 (FIG. 3A), or the plasma generator of FIGS. 5A-5C to initiate the generation of plasma within at least a portion of the bore, e.g., in proximity to distal end 210 of object 200 (FIG. 1B), distal end 382 with optical element 392 of endoscope 380 (FIG. 2), or optical surface 706 of medical instrument 708 (FIG. 7), thereby exposing the distal end of the elongated object to plasma.

According to some embodiments, the bore is configured to receive a sheath therein, the sheath being sized to receive the elongated tool, and wherein the device is further configured to cause plasma generation within the sheath. The term "sheath" or "protecting shroud" may synonymously refer to a covering or supporting structure that contains an object or a portion thereof. For example, the sheath may enclose an optical element of a medical instrument. In one exemplary embodiment, the sheath may be a slender, disposable tube for containing a portion of the medical instrument when the medical instrument is inserted into the plasma-generation zone. In some embodiments, the sheath may include an authentication element (e.g., an RFID tag or any other automatically detectable identification device) enabling at least one processor to test the sheath prior to operating the plasma generation device with the sheath. The authentication element may enable the at least one processor to determine if the sheath is new and/or if it has been used a permissible number of times. Additionally, or alternatively, the authentication element may enable the at least one processor to test the sheath to determine if the sheath is from an approved manufacturer to prevent an unauthorized sheath to be used, compromising sterility and/or effectiveness in inhibiting fog on the object. The term "sized to receive the elongated tool" may refer to formed, constructed, or shaped to accommodate an object having dimensions corresponding to the elongated tool. The sheath may thus be formed to enable inserting the elongated tool therein. Similarly, the bore may be shaped and/or sized to accommodate the sheath with the elongated tool inserted therein. The sheath may be further configured to enable the distal end of the elongated tool to be exposed to a plasma cloud while the distal end is encased within the sheath.

For example, protecting shrouds (a/k/a sheaths) 310 (FIG. 2) and 310*a* (FIG. 3A), and 410 (FIG. 3C) and 800 (FIG. 9) are exemplary implementations of a sheath sized to receive an elongated tool, such as endoscope 380, consistent with disclosed embodiments. In some embodiments, the distal end of the elongated tool may be introduced into the sheath first. Plasma applicator 130 (FIG. 1A), plasma applicator 348, or the plasma generator of FIGS. 5A-5C may be provided with a bore, such as slot 132, bore 350, or cavity 502, respectively, which may be configured to receive therein the sheath referred to above. In addition, the sheath may be provided with one or more electrodes (e.g., cathode 330 and anode 340 of FIGS. 3A and 3C) configured to electrically couple to a power supply (e.g., power supply 104 and/or 530), such as via conductors 354 and 356, respectively. Cathode 330 and anode 340 may maintain a voltage potential for generating a plasma-generating an electric and/or electromagnetic field in the vicinity of the distal end (e.g., viewport 390) of endoscope 380, positioned therein inside the sheath. A gas for generating the plasma (e.g., helium, argon, nitrogen) may be streamed, e.g., via hose 364 into sheath 410 in the vicinity of viewport 390 at the distal end of endoscope 380. The electric and/or electromagnetic field thus generated may ignite the gas streamed into the sheath to form the plasma cloud in the vicinity of viewport 390, thereby exposing viewport 390 at the distal end of endoscope 380 to plasma.

In some embodiments, the insertion detector is configured to sense insertion of the elongated tool within the sheath in the bore and to automatically initiate a plasma generation process upon sensed insertion of the elongated tool within the sheath. The term "automatically" may refer to directly consequent to, without requiring intervention external to the plasma generation device, as described above. According to some embodiments, the term "automatically initiate a plasma generation process" may refer to generating the plasma independent of (e.g., by circumventing) a controller such that the detector directly triggers the plasma generation. Thus, the plasma generation process may be triggered automatically on inserting the elongated tool within the sheath positioned within the bore of the plasma generation device. For example, FIGS. 1A, 3C and 5A, taken together, illustrates an exemplary implementation for an insertion detector configured to sense insertion of the elongated tool within the sheath in the bore and automatically initiate plasma generation, consistent with disclosed embodiments. Sheath 410 (FIG. 3C) includes cathode 330 configured to contact metallic surface 384 for example at the distal end of endoscope 380. On inserting endoscope 380 into sheath 410 positioned within bore 450, cathode 330 may become electrically coupled to endoscope 380 via metallic surface 384. Cathode 330 may additionally be electrically coupled to power supply 530, thereby electrically coupling endoscope 380 to power supply 530 on inserting endoscope 380 into sheath 410 within bore 450. Electrically coupled thus, the insertion of endoscope 380 within sheath 410 inside bore 450 may be detected, such as by at least one processor 102 (FIG. 1A), or controller 508 (FIG. 5B) receiving an electric signal from cathode 330, e.g., via circuitry 106 or 700. On receiving the electric signal (e.g., the insertion signal), the at least one processor may automatically activate the plasma generator, e.g., plasma applicator 130 (FIG. 1A), plasma applicator 348 (FIG. 3A), or the plasma generator of FIGS. 5A-5C.

According to some embodiments, the bore includes an electrical contact therein configured to engage a contact on the sheath, to thereby enable plasma generation within the sheath. The term "electrical contact" may refer to an electrical circuit component having an electrically conductive section (e.g., made from metal or semiconductor) that allows an electrical current to pass through when the electrical contact is electrically coupled to (e.g., physically touches) another electrical contact. The term "engage" may refer to couple, attach, or connect for the purpose of interacting. Thus, electrically coupling the electric contact of the bore to the electrical contact of the sheath, thereby engaging the electrical contact of the bore with the contact on the sheath, may allow passage of an electric current from an external power supply into the interior of the sheath, for example for the purpose of generating an electromagnetic field within the sheath to generate plasma.

FIG. 3A illustrates an exemplary implementation of a bore including an electrical contact therein configured to engage a contact on the sheath, consistent with disclosed embodiments. Bore 350 may include cathode contactor 352 configured to be coupled to an external power source (e.g., power supply 104 and/or 530) via electric conductor 354. Cathode contactor 352 may additionally be configured to be electrically coupled to, and thus engage with cathode 330 of protecting shroud 310*a* (e.g., a sheath), thereby electrically coupling cathode 330 of protecting shroud 310*a* to the external power supply. Bore 350 may additionally include anode contactor 356 configured to be electrically coupled to, and thus engage with anode 340 of protecting shroud 310*a* while protecting shroud 310*a* is positioned within bore 350. Consequently, a voltage potential may be generated within protecting shroud 310*a*, e.g., between cathode 330 (electrically coupled to the power supply) and anode 340. The voltage potential may enable generating a plasma-generating electromagnetic field within protecting shroud 310*a*. The electromagnetic field may ignite a gas present within protecting shroud 310*a* to generate a plasma cloud within.

In some embodiments, the sheath includes a vacuum port and a vacuum seal therein, the vacuum port being flow-connectable to the at least one vacuum pump to enable causation of the negative pressure within the sheath when located within the bore, and wherein the vacuum seal is configured to engage with the elongated tool upon insertion of the elongated tool into the sheath to maintain the negative pressure on a distal side of the elongated tool (i.e., proximate the distal end of the elongated tool when inserted in the sheath within the bore). The term "vacuum port" may refer to an opening configured to be fluidly coupled to a vacuum source or pump, e.g., via a hose, to enable suctioning of gas or fluid, e.g., from the sheath. The term "vacuum seal" may refer to a plug, closure, ring, flap, engagement, or fastening that is substantially immune to leakage of gas or fluid when the system is used within normal operating parameters. The term "flow-connectable" may refer to fluidly coupled, e.g., joined or attached in a manner that allows streaming a fluid (e.g., including gas) there through. The sheath may thus be fluidly coupled (e.g., flow-connectable) to the at least one vacuum pump via the vacuum port and vacuum seal. This configuration may allow the suctioning of gas and/or air present within the sheath to generate a low-pressure zone within the sheath (e.g., relative vacuum with respect to a reference pressure) for the purpose of generating plasma. In some embodiments, one or more vacuum seals may be provided with the sheath encasing the elongated tool. The one or more vacuum seals may be adapted to fit an external diameter of the elongated tool, such that inserting the elongated tool into the sheath may engage the elongated tool with the one or more vacuum seals, thereby sealing the interior of the sheath from the exterior of the sheath (e.g., via the elongated tool surrounded by the vacuum seal). Such sealing may allow maintaining a pressure difference (e.g., gas concentration difference) between the interior and exterior of the sheath, which may assist in generating plasma for the plasma treatment.

FIG. 3C and FIG. 10A, taken together, illustrates an exemplary implementation of a sheath including a vacuum port and vacuum seal, the vacuum port being flow-connectable to the at least one vacuum pump, consistent with disclosed embodiments. Sheath 410 may be configured with sheath gas port 404 (e.g., a vacuum port) and vacuum seal 408. Sheath gas port 404 may fluidly connect to applicator gas port 402 of plasma applicator 448, which may be fluidly connected via hose 364 to a vacuum source, such as one or vacuum pumps 1000A, 1000B, 1000C, and 1000D of FIG. 10A, thereby fluidly coupling the vacuum source to the interior of sheath 410. Vacuum seal 408, e.g., an O-ring, may prevent leakage of gas or air flowing through hose 364, e.g., from the inside of sheath 410, into the space of bore 450 outside of sheath 410. Consequently, gas (e.g., air), may be pumped out of sheath 410 via hose 364, to create a low-pressure zone within sheath 410 relative to the ambient pressure. Additionally, vacuum seals 320 may engage with endoscope 380 to seal the interior of sheath 410 (e.g., encasing the distal end of endoscope 380 therein) from the exterior of sheath 410 (e.g., the space between sheath 410 and bore 450). Sealing sheath 410 thus may facilitate in maintaining negative pressure (e.g., relative to the ambient pressure) inside sheath 410.

In some embodiments, the elongated tool is a scope having an optical element located in the distal end region. The term "scope" may refer to a medical instrument, such as an arthroscope, endoscope (as defined earlier), laparascope, stethoscope, or microscope, configure to enable examination or observation. The term "optical element" may refer to a component through which light passes or is reflected, as described above. The scope may be configured with an optical element to enable examination by viewing. The optical element may be disposed at the distal end region of the scope, such that when the scope is inserted into the bore, e.g., starting from the distal end region, the optical element may be immersed within the bore, e.g., in proximity to a plasma generation zone associated with the bore. The optical element may thus be exposed to a plasma cloud after activating the plasma generator. FIG. 3A illustrates an exemplary implementation of a scope having an optical element located in the distal end region, consistent with disclosed embodiments. Optical element 392 may be configured with viewport 390 located at the distal end of endoscope 380. When endoscope 380 is inserted distal-end-first into protecting shroud 310*a* inside bore 450, viewport 390 with optical element 392 may be immersed within protecting shroud 310*a* between cathode 330 and anode 340. Positioned thus, optical element 392, located at the distal end region of endoscope 380, may be exposed to a plasma cloud, e.g., produced by an electromagnetic field generated via a voltage potential between cathode 330 and anode.

In some embodiments, the at least one processor is configured to maintain activation of the plasma generator for a period sufficient to cause an external surface of the optical element to become hydrophilic. The term "hydrophilic" may refer to a tendency or favorability of a molecule to be solvated by water. A hydrophilic compound may have thermodynamic properties that enable the compound to bond with water molecules more readily than a compound that is not hydrophilic, e.g., a hydrophobic compound that does not readily bond with water (e.g., polar) molecules. An object that is hydrophilic may be wettable, enabling a liquid (e.g., water) to maintain contact with the object due to intermolecular interactions that balance adhesive and cohesive forces between the liquid and the object. The plasma generator of FIGS. 5A, 5B, and 5C illustrate an exemplary implementation of a plasma generator in accordance with disclosed embodiments. At least one processor 102 (FIG. 1A) or controller 508 may maintain activation of plasma applicator 130 or the plasma generator of FIGS. 5A, 5B, respectively, for a sufficient length of time to cause the external surface of optical element 392 of viewport 390 to become hydrophilic, such as prevent fog from forming on viewport 390 during an endoscopy procedure. According to some disclosed embodiments, the time period sufficient to cause optical element 392 to become hydrophilic may be less than a minute, less than 45 seconds, less than 30 seconds, or less than 15 seconds.

In some embodiments at least one processor is further configured to output a signal to a display indicating a status of a plasma generator treatment. The term "display" may refer to an output device that visually presents information. A display may include one or more LEDs, e.g., configured with a screen, or light bulbs, dials, gauges, meters, or any other means for rendering data visually. FIGS. 5A and 11, taken together, illustrate an exemplary embodiment of display 1102 in FIG. 11 outputting a signal (e.g., "Warning") indicating a status of a plasma generator treatment, consistent with disclosed embodiments. Controller 508 (FIG. 5B) may output a signal to display 1102 indicating the status of a plasma treatment by the plasma generator of FIGS. 5A-5C.

In some embodiments, at least one processor is further configured to calculate a number of plasma treatments remaining before required maintenance. The term "maintenance" may refer to fixing, repairing, restoring, or otherwise ensuring continued functionality. For example, required maintenance of a plasma generator may relate to any of: recharging a battery, replacing a power supply, replacing a seal, replacing or cleaning an electrical contact, replacing or cleaning a filter, refilling a gas canister, replacing a hose, fixing a wire, or performing any other action affecting the plasma treatment by the plasma generator. At least one processor 102 (FIG. 1A) or controller 508 (FIG. 5B) illustrate exemplary implementations of at least one processor configured to calculate a number of remaining plasma treatments before maintenance is required for the device, according to disclosed embodiments. For example, at least one processor 102 may monitor one or more factors affecting subsequent plasma treatments by plasma applicator 130, such as by recording the number of plasma treatments already performed, monitoring a state of power supply (e.g., battery) 530, monitoring the duration of the plasma treatments, monitoring an amount of gas remaining in the gas reservoir, monitoring the pressure within the plasma generation zone, monitoring a state (e.g., conductivity) of cathode 330 and anode 340, monitoring the pressure maintained within the bore indicating a broken seal, and monitoring any other measure that may affect the plasma treatment by the plasma applicator. Based on the one or more factors, at least one processor 102 may determine how many more treatments may be performed by plasma applicator 130 before a maintenance is required. Controller 508 may similarly monitor one or more factors affecting subsequent plasma treatments by plasma generating system 500 to determine how many plasma treatments remain before a maintenance is required.

In some embodiments, at least one processor is further configured to detect a malfunction of at least one of the plasma generator or the at least one vacuum pump and to output a malfunction indicator. The term "malfunction" may refer to an impairment or defect that negatively affects performance. The term "output a malfunction indicator" may refer to indicating a malfunction via a user interface, such as visually (e.g., via a display screen, warning light, gauge, or dial), audibly (e.g., via a speaker emitting a beep), as a vibration produced using an ERM, and the like. At least one processor 102 (FIG. 1A) and controller 508 (FIG. 5B) illustrate exemplary implementations of at least one processor configured to detect a malfunction of the plasma generator or vacuum pump and output a malfunction indicator, according to disclosed embodiments. For example, controller 508 may detect a malfunction of plasma generating system 500 (e.g., by detecting insufficient power stored in power supply 530, insufficient gas retained within the gas reservoir, an insufficiently low pressure within plasma generation zone 502, a malfunctioning seal, a malfunctioning wire or electrical contact, an insufficient electromagnetic field generated in plasma generation zone 502, and any other factor affecting the performance of plasma generating system 500). Similarly, controller 508 may detect a malfunction of one or more of vacuum pumps 1000A, 1000B, 1000C, and 1000D, e.g., by detecting insufficiently low pressure within plasma generation zone 502 or detecting insufficient plasma-generating gas streamed into plasma generation zone 502. Consequently, controller 508 may output a malfunction indicator (e.g., "warning") via display 1102 (FIG. 11). In a similar manner, at least one processor 102 may detect a malfunction of plasma applicator 130 and any of vacuum pumps 1000A, 1000B, 1000C, and 1000D, and output a malfunction indicator via display 1102.

In some embodiments, at least one processor is further configured to output a warning signal when the optical element is insufficiently treated to achieve a predetermined level of hydrophilicity. The term "predetermined level of hydrophilicity" may refer to a level of hydrophilicity that enables a sufficient level of performance (e.g., optical quality) when the elongated object is used for a procedure, such as a medical procedure. For example, if the elongated tool is an endoscope, the predetermined level of hydrophilicity may correspond to a level of hydrophilicity to allow sufficiently unobstructed viewing (e.g., due to fog) through the endoscope throughout the duration of a colonoscopy, e.g., 1 hour. However, if the elongated tool is a dental mirror, the predetermined level of hydrophilicity may correspond to an unobstructed viewing via the mirror of several minutes. In some embodiments, the predetermined level of hydrophilicity may be stored in memory corresponding to one or more system parameters needed to achieve the predetermined level of hydrophilicity. Such system parameters may include time, temperature, pressure level, electromagnetic field parameters, gas type, gas level, battery level, and any other parameter affect the plasma treatment. The at least one processor may identify the elongated tool, e.g., based on an RFID tag, and may retrieve the one or more system parameters required to achieve the predetermined level of hydrophilicity corresponding to the elongated tool. The at least one processor may measure the one or more system parameters to determine if the optical element is insufficiently treated and output the warning signal accordingly.

FIG. 11 illustrates an exemplary embodiment of display 1102 outputting a warning signal to indicate that an optical element, e.g., optical element 392 of FIG. 3A, is insufficiently treated to achieve a predetermined level of hydrophilicity. For example, at least one processor 102 (FIG. 1A), or controller 508 (FIGS. 5A-5C) may retrieve the predetermined hydrophilicity level, e.g., from memory 108 after identifying the elongated tool based on an RFID tag, and determine that the plasma treatment applied to optical element 392 of endoscope 380 by plasma applicator 130 or the plasma generator of FIGS. 5A-5C is not sufficient to achieve the predetermined level of hydrophilicity, e.g., based on the timing of the treatment, type of gas used, type of material treated, expected use, pressure level, electromagnetic field properties, or any other parameter affecting the plasma treatment.

In some embodiments, a warning signal is outputted if the optical element is insufficiently treated to achieve sufficient hydrophilicity. The term "sufficient hydrophilicity" may refer to a level of hydrophilicity that enables a threshold optical quality for viewing, such as during a medical procedure. For example, if the elongated tool is an endoscope, sufficient hydrophilicity may correspond to enabling unobstructed viewing (e.g., due to fog) through a viewport of the endoscope throughout a colonoscopy procedure. As another example, if the elongated tool is configured for a procedure where the viewport of the elongated tool is to be immersed in air, such as a laparoscopic procedure, sufficient hydrophilicity may correspond to enabling unobstructed viewing through the viewport throughout the procedure due to fogging or condensation. FIGS. 5A, 5B, and 5C and 11, taken together, illustrate an exemplary embodiment of display 1102 outputting a warning signal to indicate that an optical element, e.g., optical element 392 of FIG. 3A, is insufficiently treated to achieve sufficient hydrophilicity, e.g., a level of hydrophilicity to enable viewing through optical element 392 when using endoscope 380 to perform a colonoscopy.

In some embodiments, the elongated tool includes a lens and at least one processor is configured to activate the plasma generator for a period sufficient to cause the lens to become super-hydrophilic. The term "lens" may refer to an optical element through which light is transmitted. The lens may be made of glass, plastic, or other crystal with refraction properties. A lens may also include a protective transparent covering with minimal or no refractive properties. The term "super-hydrophilic" may refer to a very high level of hydrophilicity, for example sufficiently hydrophilic to substantially decrease a contact angle between a fluid and the surface of the object, e.g., so as to allow the fluid to coat the surface of the object as a substantially uniform (e.g., flat) layer. In some embodiments, after increasing the hydrophilicity of the object to the desired level, the contact angle between the fluid and the super-hydrophilic surface of the object may be less than about 5°, e.g., less than about 4°, less than about 3°, less than about 2°, less than about 10, or may be about 0°, e.g., when measured at 20° C. and atmospheric pressure. For example, the at least one processor may detect insertion of the lens (or an element associated with the lens), and based on that detection, activate the plasma generator to expose the lens to plasma for a period that causes the lens to become super-hydrophilic. FIG. 3A illustrates an exemplary embodiment of an elongated tool (e.g., endoscope 380) including a lens (e.g., optical element 392 of viewport 390). At least one processor 102 (FIG. 1A) or controller 508 (FIG. 5B) may, on detecting optical element 392 (e.g., via an RFID tag disposed with endoscope 380), activate plasma generator 130 or the plasma generator of FIGS. 5A-5C for a sufficiently long period of time (e.g., between 15 seconds and 1 minute) to cause optical element 392 to become super-hydrophilic.

In some embodiments, the time period sufficient to cause a surface of the optical element to become hydrophilic is a time period sufficient to cause the surface of the optical element to become super-hydrophilic. For example, when processor 102 (FIG. 1A) or controller 508 (FIG. 5B) activates plasma generator 130 or the plasma generator of FIGS. 5A-5C, respectively, to cause the surface of optical element 392 of endoscope 380 to become hydrophilic, the surface of optical element 392 of endoscope 380 may become super-hydrophilic. The processor may determine that super-hydrophilicity is reached based on one or more of duration of plasma exposure, pressure, temperature and identity of the object being treated.

In some embodiments, the plasma generator is configured for causing a dielectric barrier discharge. The term "dielectric barrier discharge" may refer to the electrical discharge between two electrodes when the electrodes are separated by an insulating dielectric barrier. FIGS. 3A-3B illustrate a plasma generator that when activated, may cause a dielectric barrier discharge, consistent with disclosed embodiments. Cathode 330 and anode 340 of plasma applicator 348 are separated by dielectric barrier 344. Generating an electric potential between cathode 330 and anode 340, when separated by dielectric barrier 344, may cause or result in a dielectric barrier discharge. Cathode 330 separated from anode 440 by dielectric barrier 444 of FIG. 3C illustrate another exemplary implementation of a plasma generator that when activated, results, and thereby causes, a dielectric barrier discharge, consistent with disclosed embodiments.

In some embodiments, the at least one processor is configured to control the plasma generator in a manner causing a voltage drop of at least 1000 volts. The term "voltage drop" may refer to the difference in voltage, or potential, between two electrodes, such as between a cathode and anode. At least one processor 102 (FIG. 1A) or controller 508 (FIG. 5B) illustrate exemplary implementations of at least one processor configured to control the plasma generator (e.g., plasma generators 130 and the plasma generator of FIGS. 5A-5C, or plasma applicator 348). For example, the at least one processor may cause a voltage drop of at least 1000 volts between cathode 330 and any one of anode 340 or anode 440 by modifying, via circuitry 106 or 700, an electric signal provided to cathode 330 from power supply 530.

Figure 17:
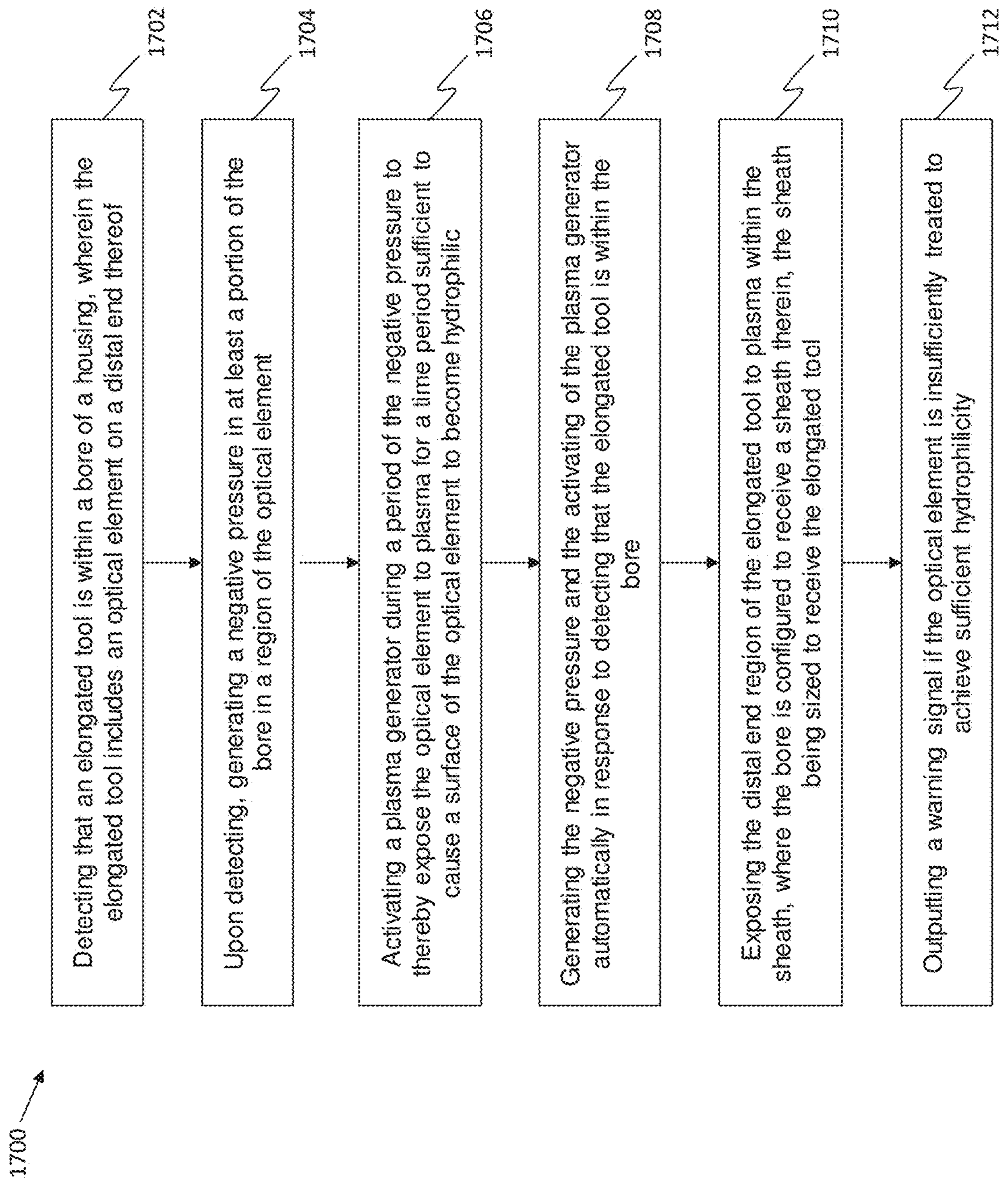
FIG. 17 is a flowchart that illustrates a method for treating an elongated tool with plasma, in accordance with an embodiment of the present disclosure.

FIG. 17 is a block diagram of an example process 1700 for treating an elongated tool with plasma, consistent with embodiments of the present disclosure. While the block diagram may be described below in connection with certain implementation embodiments presented in other figures, those implementations are provided for illustrative purposes only, and are not intended to serve as a limitation on the block diagram. As examples of the process are described throughout this disclosure, those aspects are not repeated or are simply summarized in connection with FIG. 17. In some embodiments, the process 1700 may be performed by at least one processor (e.g., at least one processor 102 of FIG. 1A or controller 508 of FIG. 5B) to perform operations or functions described herein. In some embodiments, some aspects of the process 1700 may be implemented as software (e.g., program codes or instructions) that are stored in a memory (e.g., memory 108) provided with the at least one processor, or a non-transitory computer readable medium. In some embodiments, some aspects of the process 1700 may be implemented as hardware (e.g., a specific-purpose circuit). In some embodiments, the process 1700 may be implemented as a combination of software and hardware. Unless otherwise indicated, the sequence of the process blocks may be arbitrary and the order for performing one or more process blocks may be changed. Similarly, one or more process blocks may be omitted.

FIG. 17 includes process blocks 1702 to 1710. At block 1702, an elongated tool is detected within a bore of a housing, wherein the elongated tool includes an optical element on a distal end thereof. Detecting may involve determining, sensing, or identifying an elongated tool within the bore. The detecting may further involve detecting the elongated tool within a sheath contained in the bore. For example, controller 508 (FIG. 5B) may identify that endoscope 380 (FIG. 3A) is within bore 502 of housing 510. Endoscope 380 may include optical element 392 configured with viewport 390 positioned at a distal end of endoscope 380. When endoscope 380 is inserted into bore 502, optical element 392 may be located in plasma generation zone 504 of bore 502. The detecting may also involve determining that a protective sheath (e.g., 310 or 410) surrounding the elongated tool 380, is also within the bore 450.

At block 1704, upon detecting of the tool within the bore, a negative pressure is generated in at least a portion of the bore in a region of the optical element. The generation of a negative pressure may involve removal or gas or air so that in at least some area of the bore (e.g., an area within a sheath in the bore), the pressure is caused to be sub-atmospheric. For example, upon detecting that endoscope 380 (FIG. 2) is inserted within bore 502 of housing 510 (FIG. 5A), controller 508 may activate one or more of vacuum pumps 1000A, 1000B, 1000C, and 1000D (FIG. 10A). This may generate a negative pressure in plasma generation zone 504 of bore 502, e.g., in the region of optical element 392 of endoscope 380.

At block 1706, a plasma generator is activated during a period of the negative pressure to thereby expose the optical element to plasma for a time period sufficient to cause a surface of the optical element to become hydrophilic. The activation of the plasma generator may occur in any of the ways described earlier. For example, controller 508 (FIG. 5B) may activate the plasma generator of FIGS. 5A-5C during the period when one or more of vacuum pumps 1000A, 1000B, 1000C, and 1000D (FIG. 10A) cause a negative pressure inside plasma generation zone 504. This may expose optical element 392 of endoscope 380 to plasma for a time period (e.g., ranging from 15 seconds to 1 minute) to cause the surface of optical element 392 to become hydrophilic, thereby preventing an accumulation of fog on optical element 392 during a subsequent endoscopy.

At block 1708, the generating of the negative pressure and the activating of the plasma generator occur automatically in response to detecting that the elongated tool is within the bore. These automatic occurrences may occur in any of the ways described earlier. For example, in response to detecting that endoscope 380 (FIG. 3A) is within cavity 502 (FIG. 5A), controller 508 may automatically, e.g., without intervention external to system 500, activate one or more of vacuum pumps 1000A, 1000B, 1000C, and 1000D (FIG. 10A) to generate the negative pressure within cavity 502, and activate the plasma generator (e.g., plasma generator of FIGS. 5A-5C).

At block 1710, the distal end region of the elongated tool is exposed to plasma within the sheath, wherein the bore is configured to receive a sheath therein, the sheath being sized to receive the elongated tool. The foregoing can occur in any of the manners described earlier. For example, sheath 410 (FIG. 3C) may be sized to receive (e.g., accommodate) endoscope 380. Additionally, bore 350 may be configured to receive sheath 410 therein, such as by being sized to accommodate sheath 410 and by being configured to electrically couple cathode 330 of sheath 410 with power supply 530, e.g., via cathode contactor 352 and electric conductor 354. Electrically coupling cathode 330 of sheath 410 thus may allow generating an electromagnetic field within sheath 410 to generate plasma in proximity to the distal end region (e.g., optical element 392) of endoscope 380. This may allow exposing the distal end region of endoscope 380 to plasma within sheath 410.

At block 1712, a warning signal is outputted if the optical element is insufficiently treated to achieve sufficient hydrophilicity. The warning signal and the insufficiency determination may occur in any of the ways described earlier. For example, controller 508 (FIG. 5B) may determine a tool type corresponding to optical element 392 of endoscope 380 (FIG. 3C), such as via an RFID tag or camera provided with sheath 410. Controller 508 may obtain one or more parameters, e.g., from memory 108 (FIG. 1A) for performing a treatment to achieve sufficient hydrophilicity for optical element 392. For example, the one or more parameters may relate to an amount of power available via power supply 530, a level of negative pressure generated by any of vacuum pumps 1000A, 1000B, 1000C, and 1000D (FIG. 10A), a type of gas streamed into plasma generating zone 504, a pressure of gas or air within plasma generating zone 504, properties of the electromagnetic field generated between cathode 330 and any of anode 340 or 440, a timing parameter, a temperature parameter, and any other parameter affecting plasma treatment by system 100 or 500. Controller 508 may obtain one or more measurements relating to the plasma treatment applied to optical element 392 (e.g., via one or more sensors), and determine, based on the one or more measurements and the one or more parameters, that the hydrophilicity of optical element 392 is insufficient. Controller 508 may thus output a warning, such as via display 1102 (FIG. 11).

Some disclosed embodiments involve inhibiting condensation distortion on an optical element of a medical instrument configured for insertion into a body cavity. Condensation may include moisture, dampness, wetness, beading, or any other manifestation of water or other fluid collecting on a surface. For example, condensation may include the formation of water droplets on a surface, such as glass. Condensation distortion may include an exaggeration, blurring, misrepresentation, contortion, or any other change, caused by condensation, that makes something appear different from an actual appearance. For example, condensation distortion may include a foggy image visualized through a glass surface when the glass surface is covered with water droplets. In surgical procedures, condensation distortion poses various problems, including lens fogging, which limits clear visualization during such procedures. Thus, it is desirable to inhibit condensation distortion. Inhibiting condensation distortion may include constraining, curbing, discouraging, hindering, obstructing, suppressing, preventing, minimizing, or any other manner of restraining condensation distortion. For example, inhibiting condensation distortion on a glass surface may include reducing fogging on the surface by limiting the number or size of water droplets that accumulate on the surface. Some disclosed embodiments involve the use of a device. A device may include any individual or combination of one or more of an accessory, apparatus, appliance, equipment, machine, mechanism, or arrangement configured to achieve any of the functions disclosed herein.

An optical element may include a lens, prism, mirror, or any other part of an optical instrument which either reflects light or permits the passage of light. It may be desirable to inhibit condensation distortion on an optical element because the characteristics of light passing through an optical element may be distorted by water collected on a surface of the optical element. For example, an optical element may include a lens of medical instrument, such as an endoscope. A medical instrument may include a scope, catheter, tube, or any other device used on the inner or outer part of the body for diagnosis or treatment of a medical condition. A body cavity may include a peritoneum, dorsal cavity, back body cavity, cranial cavity, spinal cavity, ventral cavity, thoracic cavity, abdominopelvic cavity, abdominal cavity, pelvic cavity, bowel, stomach, esophagus, lung, blood vessel, organ, or any other space or compartment in a body. In some examples, a body cavity may include a space housing multiple organs, such as a thoracic cavity. In other examples, a body cavity may include a single organ, such as a heart. In yet other examples, a body cavity may include a blood vessel, such as an aorta. Insertion into a body cavity may include introducing, injecting, entering, embedding, implanting, or any other manner of placement into a body cavity. In one example, insertion into a body cavity may include introducing an endoscope into a blood vessel by guiding the endoscope into the blood vessel.

Some disclosed embodiments involve a housing. A housing may include any supporting structure, frame, cage, enclosure, encompassment capable of accommodating any component of any devices or methods disclosed herein. The housing may be made of any suitable material, such as plastic, metal, glass, wood, or any other material capable of encasing a plasma generation device. In some embodiments, the housing may include one or more insulating materials to insulate a plasma generation device encased therein from one or more environmental conditions, such as an electric and/or electromagnetic field, light, humidity, temperature, impact, mechanical and/or acoustic vibrations, and any other environmental attribute that may affect the generation of plasma by the plasma generating device.

Some disclosed embodiments involve a cavity within the housing, the cavity being sized to removably retain at least a portion of the medical instrument therein, wherein the portion includes the optical element. A cavity may include a chamber, depression, hap, hole, pocket, bore, sinus, socket, or any other type of empty space within the housing. Removably retaining at least a portion of the medical instrument within the housing may include containing, keeping, maintaining, detaining, collecting, reserving, or in any other way holding any piece, section, segment, component, element, factor, unit, or any other part of the whole medical instrument within the housing. The portion including the optical element may include an entirety of the portion including the optical element or a part of the portion including the optical element. For example, the cavity may include a bore formed within the housing, and the portion of the medical instrument may include a distal end of an endoscope including a lens that is configured to slide in and out of the bore.

Some disclosed embodiments involve a plasma activation zone within the cavity and arranged such that when the at least a portion of the medical instrument is retained within the cavity, the optical element is located within the plasma activation zone. A plasma activation zone may include a physical volume or space in which a plasma cloud may be formed, e.g., by igniting a gas introduced therein. The plasma activation zone may be of any size. For example, the plasma activation zone may be less than 15 $cm^3$, less than 10 $cm^3$, less than 5 $cm^3$, less than 3 $cm^3$, less than 2 $cm^3$, or less than 1.4 $cm^3$. In some examples, an electromagnetic field may be generated within the plasma activation zone, such that exposing a gas to the electromagnetic field ignites the gas to generate plasma. The term "plasma" may refer to a state of matter containing an abundance of charged particles, e.g., electrons and ions. Consequently, plasma may be highly electrically conductive and sensitive to electric and/or electromagnetic fields. In some examples, the plasma is cold plasma, i.e., the plasma contains electrons which have much higher energy than ions. Cold plasma may be especially advantageous in applications involving frequent use of medical devices which may be sensitive to harsh treatment. It may be desirable to expose the optical surface to plasma in order to improve the hydrophilicity of the optical element. Specifically, during a hydrophilic treatment, a surface undergoes oxidation and the bombarding plasma ions form hydroxyl groups on the surface. These hydroxyl groups are polar, and since water is polar, it is attracted to the hydroxyl groups. Ultimately, this is what enhances the surface's wettability and adhesion, which in turn makes it more hydrophilic.

Some disclosed embodiments involve a plasma generator configured to be activated to cause formation of a plasma cloud in the plasma activation zone in a vicinity of the optical element. A plasma generator may include a device configured to generate plasma, e.g., inside a plasma activation zone. In some examples, plasma is formed inside a plasma generator by creating a vacuum inside a chamber. In some embodiments, a small amount of gas may be channeled into the chamber and changes phases from gas to plasma when its molecules become ionized. Inside the chamber of a plasma generator, surfaces get bombarded by plasma ions modifying the surface on a very small scale. These plasma processes may change the surface by enhancing their adhesion capabilities, such as making the surface hydrophilic or even super-hydrophilic. In other examples, the plasma may be created within a nozzle and then expelled out in a stream of compressed air. A plasma cloud may include any volume of plasma created by the plasma generator. The plasma generator may cause formation of the plasma cloud in the plasma activation zone through any manner of creating or activating plasma, including arc discharge, or corona discharge.

In some embodiments, the plasma generator causes formation of the plasma cloud through Dielectric Barrier Discharge. Dielectric barrier discharge occurs between two electrodes separated by a dielectric. Due to the presence of the dielectric barrier, such plasma sources may operate with sine-wave or pulsed high voltages. The discharge may consist of multiple micro-discharges, although in some cases uniform discharges may be created as well. To increase the uniformity and the discharge gap, a pre-ionization system may be used. In a Dielectric Barrier Discharge embodiment, air (as opposed to another gas stream) may serve as a basis for plasma formation. A vicinity of the optical element may include a range within the optical element, an environment of the optical element, or any area near or surrounding the optical element. In one example, a plasma cloud in the vicinity of the optical element may include a plasma cloud surrounding the optical element. In another example, a plasma cloud in the vicinity of the optical element may include a plasma cloud near one portion of the optical element.

Some disclosed embodiments include a controller configured to activate the plasma generator for a time period sufficient to cause the optical element to become hydrophilic prior to insertion into the body cavity. A controller may be configured to enable a user of device to operate and control the device in order to activate the plasma generator. The controller may thus include one or more command switches and one or more controllers, such as physical or virtual switches, buttons and controllers. The controller may further include indicators for providing a user with required data and information for operating the device, such as indication LEDs, displays and possibly an operating software executable by at least one processor for providing a user with operating and command screens to allow a user to operate and command the device in order to activate the plasma generator. The controller (e.g., at least one processor) may include electric circuitry for performing logical operations on an input signal. For example, the controller may include one or more integrated circuits (ICs), including ASICs, microchips, microcontrollers, microprocessors, all or part of a CPU, GPU, APU, DSP, FPGA, or other circuits suitable for executing computing instructions and/or capable of performing logical operations, e.g., based on a computing instruction or an input signal. Instructions executed by controller may be pre-loaded into a memory integrated with or embedded into a processor or may be stored in a separate memory. The memory may comprise a RAM, a cache memory, a ROM, a hard disk, an optical disk, a magnetic medium, a flash memory, other permanent, fixed, or volatile memory, or any other mechanism capable of storing such instructions. The memory may additionally store data, which may include one or more inputs for executing the one or more program code instructions, and one or more outputs produced by executing the one or more program code instructions. In some embodiments, the controller may include multiple processors. Each processor may have a similar construction, or different constructions that may be electrically connected or disconnected from each other. The processors may be separate circuits or integrated in a single circuit. Multiple processors may be configured to operate independently or collaboratively. The processors may be coupled electrically, magnetically, optically, acoustically, mechanically or by other means that permit them to interact. The processors may be physical and/or virtual (i.e., software-based).

FIGS. 5A-5C illustrate three views of a plasma generating system 500, in accordance with some embodiments of the present disclosure. As illustrated in the figure, plasma generating system 500 may include a housing 510 having, a cavity 502 and accommodating, a plasma activation zone 504, a plasma generator 506, and a controller 508. Plasma generating system 500 may include a plasma activation zone 504 within the cavity 502, and arranged such that when at least a portion of a medical instrument having an optical element (e.g., an endoscope having a viewport) is retained within the cavity 502, the optical element is located within the plasma plasma-activation activation zone 504. Plasma generator 506 may generate plasma for treating an object (e.g., a medical instrument) within plasma activation zone 504 in accordance with embodiments disclosed herein. Cavity 502 may provide access to plasma activation zone 504, e.g., to enable inserting an object into plasma activation zone 504 for carrying out a plasma treatment to increase the hydrophilicity of the object. Controller 508 may control one or more aspects of plasma generator 506, such as the influx and/or outflow of gas into plasma activation zone 504 for the purpose of generating plasma, the generation of an electric and/or electromagnetic field for generating plasma, and any other parameter relevant to the generation of plasma via plasma generator 506. Plasma generating system 500 may further include one or more sensors, such as a pressure sensor, a voltage sensor 514 and a plasma frequency sensor 512.

A time period sufficient to cause the optical element to become hydrophilic prior to insertion into the body cavity may include any amount of time required for a desired level of hydrophilicity of the optical element to occur for any desired procedure associated with the optical element. In some examples, a time period sufficient to cause the optical element to become hydrophilic prior to insertion into the body cavity may be less than a minute, less than 45 seconds, less than 30 seconds, or less than 15 seconds.

In some embodiments, the medical instrument includes a scope having an elongated shaft, the cavity includes an elongated channel for receiving the elongated shaft, and the plasma activation zone is located proximate a distal end of the elongated channel. A scope may include any instrument, as described in greater detail herein, for viewing or examining any part of a body. An elongated shaft may include any long, narrow part or section of the scope. An elongated channel may include any open or closed passage. In some examples, the elongated channel may be tubular. A distal end of the elongated channel may include any site located away from a specific area of the elongated channel, including the center of the elongated channel. In some examples, a distal end may include parts of the elongated channel further away from the center of the elongated channel. In some examples, a distal end of the elongated channel may include either end of the elongated channel.

In some embodiments, the scope includes a laparoscope or an endoscope. As used herein, "endoscope" may include any scope that has a distal end configured to be inserted into a patient's body, and a proximal end configured to remain outside the patient's body during the procedure. In some embodiments, the optical element includes a lens element on a distal end of the elongated shaft. A lens element may include any transmissive optical device which focuses or disperses a light beam by means of refraction. A lens element may consist of a single piece of transparent material, or several lenses, usually arranged along a common axis. A lens element may be made from materials such as glass or plastic. Typically, the distal end includes a viewport such as a lens or a window or a bare end of an optical fiber or even a mirror (such as a dentist mirror for example). Through the viewport, the scope enables collecting an image of the surrounding of the viewport, e.g., using a light-sensitive device such as a CCD. The viewport may be aimed to collect light from in front of the device (namely from a region coinciding with the longitudinal axis of the device), or the viewport may be slanted in an angle relative to the longitudinal axis or may be facing perpendicular to the longitudinal axis of the device (as is demonstrated for example in colonoscopies). The proximal end typically includes or is connected to a handle to be held by a medical practitioner, possibly including user interface components such as switches, navigating sticks, touch screens and touch pads. Endoscopes include a vast range of scopes, for example bronchoscopes, colonoscopes, cystoscopes and laparoscopes. A laparoscope—as a specific example—includes a rigid or relatively rigid rod or shaft having a viewport, possibly including an objective lens, at the distal end, and an eyepiece and/or an integrated visual display at the proximal end. The scope may also be connected to a remote visual display device or a video camera to record surgical procedures.

In some embodiments, the elongated channel is sized to receive a sheath surrounding a portion of the elongated shaft including the optical element. A sheath may include any covering or supporting structure that fits around an object. For example, the sheath may enclose an optical element of a medical instrument. In one exemplary embodiment, the sheath may be a slender, flexible, disposable tube that retains within the sheath a portion of the medical instrument when the medical instrument is inserted into the plasma activation zone. The term "sized to receive the sheath" may refer to formed, constructed, or shaped to accommodate an object having dimensions corresponding to the sheath. The elongated may thus be formed to enable inserting the sheath therein.

In some embodiments, the sheath is formed of a dielectric material. A dielectric material may include any electrical insulator that can be polarized by an applied electric field. A dielectric material may include glass, quartz, ceramics, or polymers. The dielectric material be of any thickness required to achieve a desired dielectric effect. In some examples, a dielectric material may make up the entirety of the sheath. In other examples, a dielectric material may make up only a portion of the sheath.

In some embodiments, the housing is configured such that the sheath surrounds the optical element when the optical element is in the plasma activation zone. The sheath surrounding the optical element when the optical element is in the plasma activation zone may include the sheath enclosing, encircling, encompassing, or in any other way being located at any of the surroundings of the optical element when the optical element is in the plasma activation zone. In some examples, the sheath may surround the entirety of the optical element when the optical element is in the plasma activation zone. In other examples, the sheath may surround only a portion of the optical element when the optical element is in the plasma activation zone.

In some embodiments, the device is further configured to cause the plasma cloud to occur within the sheath. Causing the plasma cloud to occur within the sheath may include causing the generation, activation, extension, or any form of presence of the plasma cloud within the sheath. In some examples, the plasma cloud may be generated within the sheath. In other examples, the plasma cloud may be generated outside of the sheath and then transported within the sheath. In some examples, the entirety of the plasma cloud may occur within the sheath. In other examples, only a portion of the plasma cloud may occur within the sheath.

In some embodiments, the cavity is configured to receive a sheath having a sheath electrode therein and having an external electrical contact, and wherein the cavity includes an internal contact configured to form an electrical connection with the external contact when the sheath is located within the cavity, to thereby enable a supply of energy to the sheath electrode. A sheath may include any covering or supporting structure that fits around an object, as mentioned earlier. A sheath electrode may include any electrical conductor used to make an electrical connection. For example, the electrical connection may be with a nonmetallic part of a circuit that is associated with the sheath. An electrical contact may include any electrical circuit component having an electrically conductive section (e.g., made from metal or semiconductor) that allows an electrical current to pass through when the electrical contact is electrically coupled to (e.g., physically touches or enables circuitry completion without physically touching) another electrical circuit component. An external electrical contact may include any electrical contact that may be located on an outer surface of the sheath. An internal contact may include any electrical contact that may be located on an inner surface of the cavity. An electrical connection may include any structure that allows electricity to flow through it. A supply of energy may include any source of electrical energy, such as a battery. Creating an electrical connection between the internal contact of the cavity and the external contact of the sheath may allow passage of an electric current from an external power supply into the interior of the sheath, for example for the purpose of generating an electromagnetic field within the sheath to generate plasma.

In some embodiments, at least a partial vacuum is established in a region containing the plasma activation zone. A vacuum (referred to synonymously herein as at least a partial vacuum) may include any region having a gaseous pressure that is substantially lower than atmospheric or ambient pressure. In some examples, a vacuum includes any free space sufficiently devoid of particle obstruction to enable formation of plasma.

Some embodiments involve at least one pump configured to establish at least a partial vacuum within the sheath in an area of the sheath electrode. A pump configured to establish at least a partial vacuum within the sheath in an area of the sheath electrode may include any device that draws or suctions particles from a sealed volume in order to cause sub-ambient pressure in the volume. In some examples, the pump may establish at least a partial vacuum by exerting a negative pressure between 0.1 atm and about 0.01 atm. An area of the sheath electrode may include any region within a desired range of the sheath electrode. In some examples, the pump may establish a partial vacuum within the sheath directly on the sheath electrode. In other examples, the pump may establish a partial vacuum within the sheath electrode at a small distance away from the sheath electrode.

In some embodiments, the housing includes a housing electrode therein. A housing electrode may include any electrical conductor used to make electrical connection with another part of the circuit. For example, it may contact or otherwise electrically connect with a metallic or nonmetallic part of a circuit that is associated with the sheath. The housing electrode may be positioned at any location on the housing. In some examples, the housing electrode may be connected to the housing. In other examples, the housing electrode may be incorporated into either an interior or an exterior of the body of the housing.

In some embodiments, the housing electrode is configured to form an electrical circuit with the sheath electrode when the sheath is inserted in the elongated channel. An electrical circuit may include any closed loop network which provides a return path for the flow of current. In some examples, the housing electrode may form an electrical circuit with the sheath electrode when the entirety of the sheath is inserted in the elongated channel. In other examples, the housing electrode may form an electrical circuit with the sheath electrode when a portion of the sheath is inserted in the elongated channel. In certain examples, partial contact between the sheath electrode and the housing electrode may be sufficient to form an electrical circuit. In other examples, the sheath electrode and the housing electrode may be spaced apart and the closed loop may occur when current passes through a gap between the housing electrode and the sheath electrode. Such a gap may coincide, at least partially with the plasma generation zone.

Some embodiments further involve a circuit for electrically transferring power to the sheath electrode. A circuit may include any closed loop network which provides a return path for the flow of current, as described herein. Electrically transferring power to the sheath electrode may include any manner of providing power to the sheath electrode from a power supply, such as a battery. For example, creating an electrical connection between the internal contact of the cavity and the external contact of the sheath may allow passage of an electric current from a battery into the interior of the sheath, thereby transferring power from the battery to the sheath electrode. As mentioned previously, a closed loop includes loops where gaps exist between electrodes, so long as current may flow through the gap, such as occurs when plasma is formed in the gap.

In some embodiments, at least one pump includes a plurality of interconnected pumps. A plurality of interconnected pumps may include two or more pumps, as described herein, that are connected to one another. In some instances, it may be desirable to use a plurality of interconnected pumps instead of a single pump, in order to achieve a higher vacuum level than the vacuum level possible using a single pump. In other instances, it may be desirable to use a plurality of interconnected pumps instead of a single pump, in order to reduce the load or strain on a single pump. In yet other instances, it may be desirable to use a plurality of interconnected pumps instead of a single pump, in order to provide a back-up source of negative pressure, in case one of the pumps fails during plasma generation. For example, the at least one pump may include two interconnected pumps. In the case of the failure of the first pump, the second pump may be activated to continue plasma generation without significant interruption.

In some embodiments, the plasma cloud is maintained for a time period sufficient to cause the optical element to become super-hydrophilic prior to insertion into the body cavity. The term "super-hydrophilic" may refer to a very high level of hydrophilicity, for example sufficiently hydrophilic to substantially decrease a contact angle between a fluid and the surface of the object, e.g., so as to allow the fluid to coat the surface of the object as a substantially uniform (e.g., flat) layer. In some embodiments, after increasing the hydrophilicity of the object to the desired level, the contact angle between the fluid and the super-hydrophilic surface of the object may be less than about 100 or less than 5°, e.g., less than about 4°, less than about 30, less than about 2°, less than about 1°, or may be about 0°, e.g., when measured at 20° C. and atmospheric pressure. A time period sufficient to cause the optical element to become super-hydrophilic prior to insertion into the body cavity may include any amount of time required for a desired level of super-hydrophilicity of the optical element to occur for any desired procedure associated with the optical element. In some examples, a time period sufficient to cause the optical element to become super-hydrophilic prior to insertion into the body cavity may be less than a minute, less than 45 seconds, less than 30 seconds, or less than 15 seconds.

In some embodiments, the controller activates the plasma generator for a time period sufficient to cause the optical element to become super-hydrophilic prior to insertion into the body cavity. The term "activate" may refer to triggering, turning or switching on (e.g., by emitting an electric signal), or performing any other action that initiates the generation of plasma by the plasma generator, e.g., by initiating the generation of an electric and/or electromagnetic field by the plasma generator capable of igniting plasma within the cavity. The controller may activate the plasma generator for a time period sufficient to cause the optical element to become super-hydrophilic prior to insertion into the body cavity either automatically or upon input by a user of the device. In one example, the controller may automatically activate the plasma generator for 30 seconds upon a certain threshold condition being met. In another example, the controller may activate the plasma generator for 45 seconds in response to user input in the form of the user pressing of a button on the controller.

Figure 18:
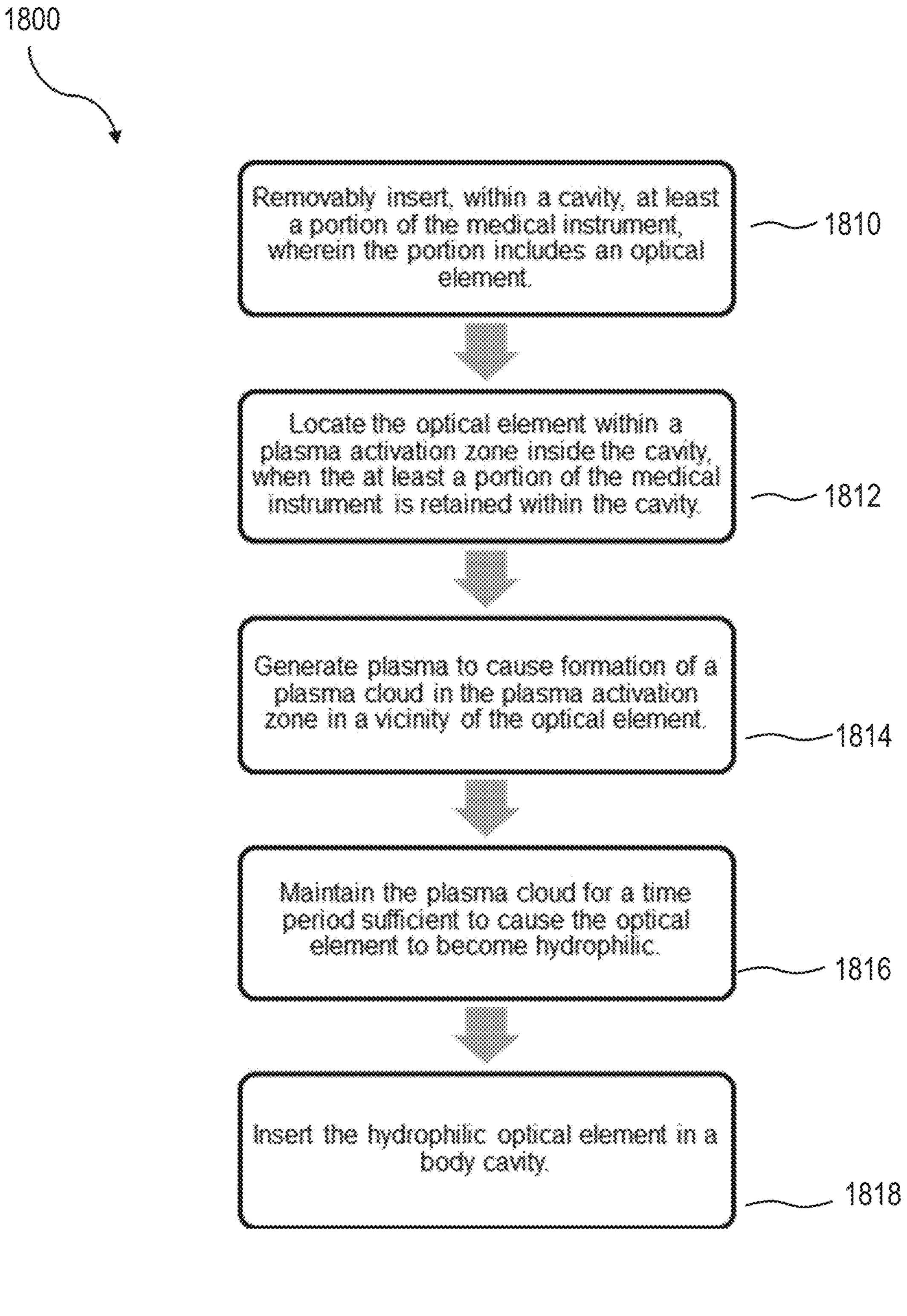
FIG. 18 is a flowchart that illustrates a method for inhibiting condensation distortion on an optical element of a medical instrument configured for insertion into a body cavity, in accordance with an embodiment of the present disclosure.

Disclosed embodiments may involve methods for inhibiting condensation distortion on an optical element of a medical instrument configured for insertion into a body cavity. FIG. 18 illustrates an exemplary method 1800 for inhibiting condensation distortion on an optical element of a medical instrument configured for insertion into a body cavity, consistent with some embodiments of the present disclosure. As shown in step 1810, the method 1800 may involve removably inserting, within a cavity, at least a portion of the medical instrument, wherein the portion includes an optical element. The method 1800 may also involve locating the optical element within a plasma activation zone inside the cavity, when the at least a portion of the medical instrument is retained within the cavity, as shown in step 1812. Step 1814 shows that the method 1800 may also involve generating plasma to cause formation of a plasma cloud in the plasma activation zone in a vicinity of the optical element. Step 1816 shows that the method 1800 may further involve maintaining the plasma cloud for a time period sufficient to cause the optical element to become hydrophilic. Method 1800 may additionally involve inserting the hydrophilic optical element in a body cavity, as shown in step 1818.

As noted, a Dielectric Barrier Discharge (DBD) mode of operation may provide one or more advantages, such as ensuring uniformity of an electric and/or electromagnetic field during plasma treatment in the vicinity of a view port thereby enhancing plasma treatment quality. This may be useful for treating optical surfaces where a high level of hydrophilicity may be desirable. Systems and methods are described herein below that may provide a plasma treatment in a DBD mode of operation. Moreover, when, in some embodiments, air plasma may be used in a DBD mode, the DBD mode of operation described herein below may simplify the plasma generator, for example by avoiding the need for costly gas cannisters requiring periodic refilling or replacement.

Some embodiments involve inhibiting condensation distortion on an optical element. The term "inhibiting" may refer to curbing, impeding, limiting, or otherwise hindering an event from occurring. The term "distortion"" may refer to an altered, skewed, or otherwise imprecise representation. The term "optical element" may refer to any component of an optical system designed to manipulate light, such as a window or a lens, a mirror reflecting light, or viewport (e.g., of a medical scope). The optical element may be made of material such as glass, quartz, or plastic such as Perspex allowing some or most visible light to pass through. In some embodiments, the optical element may be made of a reflective or semi-reflective material such as metal or a semiconductor. Moisture may accumulate as droplets on the surface of the optical element (e.g., as condensation or fog), causing an object viewed via the optical element to appear different (e.g., distorted) compared with how the object would appear if viewed via the optical element without condensation accumulated thereon. Some disclosed embodiments may hinder an accumulation of droplets on the optical element by providing a plasma treatment that achieves a relatively high level of hydrophilicity to immunize the optical element against fogging, or to significantly reduce fogging that might otherwise occur in an absence of a plasma treatment. In other words, by applying the plasma treatment to the optical element, condensation distortion may be inhibited when using the optical element, for example during a medical procedure. Plasma applicator 130 of FIG. 1A illustrates an exemplary implementation of a device for inhibiting condensation distortion on an optical element. Plasma applicator 130 may immunize viewport 222 of medical device 200 against fogging (or at least significantly reduce fogging) by exposing viewport 222 to plasma. The exposure to plasma may increase the hydrophilicity of viewport 222 to prevent or limit droplets from accumulating thereon. In other words, plasma applicator 130 may inhibit condensation distortion of viewport 22.

Some embodiments involve a chamber within the housing. The term "chamber" may refer to a slot, cavity, crevice, or pit capable of containing an object. The chamber within the plasma-generation zone may be sized to accommodate at least a portion of an object inside the plasma-generation zone together with a plasma cloud (e.g., generated by igniting a gas streamed therein), thereby exposing the at least portion of the object to the plasma cloud. For example, the chamber may accommodate a viewport of an endoscope within the plasma-generation zone, to expose the viewport to a plasma cloud generated inside the plasma activation zone after a gas has been ignited. Consequently, the hydrophilicity of the viewport may increase to limit or prevent fog from forming when the viewport is subsequently inserted into a body. According to some embodiments, a protecting shroud may form a chamber, and the insertion of an object into the protecting shroud may seal the inside of the protecting shroud containing the object, thereby defining a closed plasma chamber therein. For example, slot 132 exposing an opening on the external surface of plasma applicator 130 of FIG. 1A may illustrate an exemplary implementation of a chamber (i.e., slot) within the housing (i.e., external surface) of a device inhibiting condensation distortion on an optical element, consistent with disclosed embodiments. While, in some embodiments a removable shroud may serve as a chamber, in other embodiments, the shroud may be omitted, and the slot or concavity in the housing may itself constitute a chamber.

According to some embodiments, the chamber is configured to receive an elongated tool with the optical element proximate a distal end of the elongated tool. The term "elongated tool" may refer to an object having a length that is substantially longer that the width of the object. Examples of elongated tools, include cannulas, probes, or tubes for use in medical procedure. Thus, the optical element undergoing the plasma treatment may be positioned towards a distal end of an elongated tool, such as an optical element integrated with a camera positioned the distal end of an endoscope, or a dental mirror positioned at the distal end of a handle. The chamber may have an elongated shape to accommodate the elongated tool. The surface of the housing may include a slot or opening, exposing an entrance into the elongated chamber. The slot or opening may enable insertion of the elongated tool within the chamber. For example, FIG. 3A illustrates an exemplary implementation of a chamber configured to receive an elongated tool with the optical element proximal proximate to a distal end of the elongated tool, consistent with disclosed embodiments. Endoscope 380 (e.g., an elongated tool) may be provided with viewport 390 (e.g., an optical element) having external surface 392 (FIG. 2). Viewport 390 may be positioned proximate to the distal end of endoscope 380. Slot 350 may expose an entrance into the chamber (e.g. or may form at least a portion of the chamber) and may be configured with an elongated shape to allow placing the distal end of endoscope 380 with viewport 390 affixed thereto into the chamber.

Some embodiments involve electrical circuitry in the housing. The electric circuitry may include one or more electronic components, such as wires, virtual and/or physical switches, and/or controllers configured to electrically associate a plasma generating field applicator with an electric power source used to supply electric power. The circuitry may additionally be facilitated by one or more software instructions for controlling the device. In other words, the term "electric circuitry" may include any combination of electronic componentry (e.g., conductors, memory units, switches, gates, wires, and/or other electronic componentry) for conveying electrical energy or signals. Depending on the embodiment, the electrical circuitry may facilitate performance of one or more operations (e.g., logical and/or arithmetic operations) in response to receiving an electric signal (e.g., from a processor operating as a controller) as an input. The circuitry may couple an energy source, e.g., a power supply, generator, battery, or rechargeable battery, to the plasma generation device to enable the ignition of the gas for the purpose of converting the gas to a plasma cloud. The energy source may be external to the plasma generation device, e.g., from a wall outlet via a cable. In some embodiments the operational unit may be energized by an internal energy source such as a battery, e.g., a rechargeable battery. The circuitry may control one or more aspects of the energy delivered by the energy source, such as the magnitude, intensity, frequency, phase, timing, polarity, as well as a voltage associated with the energy, a current associated with the energy, and any other attributes characterizing the energy. The circuitry may adapt the energy according to the requirements of the plasma generation device, e.g., for igniting a gas to generate a plasma cloud for carrying out the plasma treatment. The circuitry may thus include one or more integrated circuits (ICs), including application-specific integrated circuits (ASICs), microchips, microcontrollers, microprocessors, all or part of a central processing unit (CPU), graphics processing unit (GPU), accelerated processing unit (APU), digital signal processor (DSP), field-programmable gate array (FPGA), or other circuits suitable for executing computing instructions and/or capable of performing logical operations, e.g., based on a computing instruction or an input signal. The circuitry may further include one or more memory units, such as Random-Access Memory (RAM), a cache memory, a Read-Only Memory (ROM), a hard disk, an optical disk, a magnetic medium, a flash memory, other permanent, fixed, or volatile memory, or any other mechanism capable of storing data and/or computing instructions for performing a logical operation. The circuitry may further include one or more communication channels coupling the one or more ICs to the memory, thereby enabling the one or more ICs to receive a computing instruction and/or data stored thereon required to perform a corresponding logical operation for controlling energy delivered to the plasma generation device. The communication channels coupling the one or more ICs to the memory may include wired channels, such as one or more cables, fibers, wires, buses, and any other mechanically coupled communication channel. The communication channels may additionally or alternatively include wireless channels such as short, medium, and long-wave radio communication channels (e.g., Wi-Fi, Bluetooth, Zigbee, cellular, satellite), optical, and acoustic communication channels.

In some embodiments a plasma activation region is associated with the chamber. The term "plasma activation region" may refer to a physical volume, space, or zone where plasma may be generated. In some embodiments, the region may be an electrically isolated space or volume within the chamber conducive to generation plasma in a DBD mode. The electrically isolated region may be realized by a dielectric layer, thereby associating the region with the chamber. For example, turning to FIGS. 3A-3B, vicinity 322 around viewport 390 illustrates an exemplary implementation of a plasma activation region associated with the chamber, consistent with disclosed embodiments. Vicinity 322 is located inside (e.g., associated with) protecting shroud 310*a* (e.g., a chamber). Disk 344 may form a dielectric barrier interrupting a line-of-sight between anode 340 and cathode 330, electrically isolating anode 340 from gas flowing into vicinity 322. Vicinity 322 is thus a plasma activation region associated with the chamber.

Some embodiments involve the plasma activation region associated with the chamber and being configured to retain the optical element in a manner exposing an optical surface of the optical element thereof to the plasma activation region. The term "retain" may refer to contain, house, hold, or otherwise position in place. For example, the optical element (e.g., viewport) may be housed (e.g., retained) inside the closed chamber where a plasma-generating electromagnetic field is applied. The term "exposing" may refer to revealing, uncovering, causing a coincidence, or otherwise baring an object such that the object interfaces with the surrounding environment, e.g., a plasm cloud. The term "optical surface" may refer to an exterior or outer portion of an optical element, such as the surface of the viewport of a medical instrument, or a surface of a lens, mirror, or pane. Thus, the viewport surface (e.g., optical surface) may be housed (e.g., retained) within a chamber where a plasma-generating electromagnetic field is applied, thereby exposing the viewport surface to the plasma activation region. For example, turning to FIGS. 3A-3B, viewport 390 (e.g., an optical element) of endoscope 380 may be housed (e.g., retained) in vicinity 322 (e.g., a plasma activation region), thereby exposing surface 392 (e.g., an optical surface) of viewport 390 to the plasma activation region of protecting shroud 310*a*.

According to some embodiments, the optical element includes a lens, and the optical surface is a surface of the lens. The term "lens" may include one or more optical components capable of transmitting, focusing, refracting, dispersing, filtering, magnifying, miniaturizing, or otherwise manipulating the transmission of light waves therethrough. For example, an endoscope may be provided with one or more lenses to collect and focus lights waves for capturing images during an endoscopy. To prevent the surface of the lens from fogging up during an endoscopy, the surface lens of the endoscope may be treated with plasma using the techniques described herein. Surface 222 of viewport 220 of FIG. 1A illustrates an exemplary implementation of an optical surface of a lens, consistent with disclosed embodiments. Surface 222 may be treated with plasma according to any of the techniques described herein to increase the hydrophilicity of surface 222 and prevent fogging when using viewport 222, e.g., for a medical procedure.

Some embodiments involve wherein the plasma-activation region is configured to contain gas on a first side of a dielectric barrier. The term "contain" may refer to enclose, store, or otherwise hold within a confined or closed space. For example, a plasma-generating gas may be enclosed within the plasma-activation region. The term "dielectric barrier" may refer to a layer made of a dielectric (e.g., insulating) material that may interrupt a line-of-sight between two electrodes between which the plasma-generating field is applied. Plasma generation in a DBD mode may be effected, for example, by electrically isolating one of the electrodes used for applying the field. Such isolation may be realized by a dielectric layer that isolates the electrode from the gas in the region where plasma is generated. In other words, one electrode may be located on a first side of the dielectric barrier, and the other electrode may be located on a second side of the dielectric barrier. Thus, the dielectric barrier may divide a space into two sides with the first electrode positioned in the first side, and the second electrode positioned in the second side. For example, the two electrodes may be a cathode and anode. The cathode may be positioned one side of the dielectric barrier (e.g., the first side), and the anode may be positioned on the other side of the dielectric barrier (e.g., the second side). According to some embodiments, the plasma-activation region may enclose or store gas on the cathode side (e.g., first side) of a dielectric barrier. FIGS. 3A-3B illustrate an exemplary implementation of a plasma-activation region configured to contain gas on a first side of a dielectric barrier, consistent with disclosed embodiments. Disk 344 may form a dielectric barrier between anode 340 and cathode 330 by interrupting a line-of-sight there between. Plasma applicator 348 may stream gas into slot. Protecting shroud may be penetrable to gas flow, enabling the gas to flow into protecting shroud 310*a* towards viewport 390, e.g., in vicinity 322 of cathode 330. Alternatively, air may be contained in protecting shroud 310*a*. Either way, vicinity 322 (e.g., the plasma-activation region) is configured to contain gas on the side of disk 344 (e.g., a dielectric barrier) where cathode 330 is positioned (e.g., the first side).

According to some embodiments, the gas that the plasma-activation region is configured to contain is air. While gases such as argon or helium are commonly used for igniting a plasma cloud, these gases may prove costly and inconvenient for multiple, repeated uses. Thus, disclosed embodiments provide a plasma generating field applicator that is capable of igniting a plasma cloud from air encased within the chamber or protecting shroud 310*a*. For example, depending on the volume of the chamber, plasma may be ignited in air (e.g., without using gas from an external source) at atmospheric pressure using a voltage of about 10-20 KV. When the air pressure is reduced to about 0.8 KPa, a plasma cloud may be ignited from air using a voltage of about 800V. FIG. 3A illustrates an exemplary implementation of a plasma-activation configured to contain air, consistent with disclosed embodiments. Hose 364 may pump some air out of protecting shroud 310*a* (e.g., a chamber) to reduce the air pressure therein, such that the voltage differential maintained between cathode 330 and anode 340 induces an electric field capable of igniting a plasma cloud from the remaining low-pressure air.

According to some embodiments, the gas that the plasma-activation region is configured to contain is inert. Inert, or noble gases made from elements such as Helium or Argon may be used in plasma technology since they do not form radicals that can react with other atoms or molecules, such as the surface of an optical element. For this reason, inert gas such as Helium or Argon may be streamed into the plasma-activation region via a tube or hose. FIG. 3C illustrates an exemplary implementation of a plasma activation region configured to contain an inert gas, consistent with disclosed embodiments. Hose 364 may be fluidly associated with a reservoir containing an inert gas, such as Helium or Argon. Hose 364 may stream the inert gas into protecting shroud 310*a* to vicinity 322 (FIG. 3A) near viewport 390 via applicator gas port 402 and shroud gas port 404. A vacuum seal 408 may establish fluid connectivity between hose 364 and the vicinity 322 of protecting shroud 310*a* to stream the inert gas directly into protecting shroud 310*a* via hose.

Some embodiments involve at least one pump for causing at least a partial vacuum in the plasma activation region. The term "vacuum" may refer to a region having a gaseous pressure that is lower than atmospheric or ambient pressure. As used herein, the term "vacuum" is intended to include partial vacuums. That is, in the context of this disclosure, a vacuum encompasses an enclosed space where at least some of the air or other gas is removed. The term "pump" may refer to a device that draws or suctions particles from a sealed volume in order to cause a vacuum or partial vacuum in the volume. For example, a hose fluidly connected to the interior of the device may remove air to cause a partial vacuum therein. The partial vacuum may facilitate the generation of plasma, e.g., by allowing the gas to ionize to form plasma. FIG. 3A illustrates an exemplary implementation of a device including a pump for causing at least a partial vacuum in the plasma activation region, consistent with disclosed embodiments. Hose 364 may pump gas (air) from protecting shroud 310*a* in vicinity 322 of viewport 390 through openings 368. Air may be pumped through hose 364 by a vacuum pump fluidly associated with hose 364.

In some embodiments a gas pressure associated with the partial vacuum is below 0.3 Atm or below 0.1 Atm. As noted, a lower pressure (e.g., partial vacuum) may facilitate in generating plasma by enabling a plasma-generating gas to ionize. Thus, after pumping out air or gas as described above, the pressure inside the plasma activation region may be considerably lower than atmospheric pressure. Turning to FIG. 3A, vacuum seal 370 may enable generating a partial vacuum near viewport 390 by maintaining a pressure difference between the interior and exterior of protecting shroud 310*a* below 0.1 Atm.

Some embodiments involve the plasma-activation region containing gas on a first side of a dielectric barrier and the electrical circuitry is configured to form an electrical connection with a first electrode located on the first side of the dielectric barrier. The term "electrode" refers to a conductor through which electricity enters or leaves an object, substance, or region. Electrodes are typically configured in pairs, with one electrode being the cathode (e.g., a sink for a conventional current, and source for an electron flow) and the other electrode being the anode (e.g., a source for a conventional current, and sink for an electron flow). Thus, the cathode may be the first electrode of the pair, and the anode may be the second electrode of the pair. For example, the electric circuitry delivering electric current to a device may be electrically coupled to the cathode (e.g., first electrode positioned on the first side of the dielectric barrier) via one or more wires. FIG. 1A taken with 3A illustrates an exemplary implementation of electrical circuitry configured to form an electrical connection with a first electrode located on the first side of the dielectric barrier, consistent with disclosed embodiments. Plasma generating field applicator 348 (FIG. 3A) may be electrically associated with an electrical power source, such as via operating unit 120 (FIG. 1A) containing electrical circuitry. An electric conductor 354 such as an electric wire, electrically associated with cathode contactor 352, may supply electric power from the power source to cathode contactor 352 and to cathode 330, e.g., on the cathode side of disk 344. In other words, the electrical circuitry of operating unit 120 may form an electrical connection with cathode 330, which is located on the first (e.g., cathode) side of the dielectric barrier formed by disk 344.

Some embodiments involve a second electrode connected to the electrical circuitry, The term "second electrode" may refer to the second electrode of the cathode-anode pair described above. Thus, the second electrode may correspond to the anode electrode which may be connected to the electrical circuitry via one or more contactors or wires. FIG. 1A taken with 3A illustrates an exemplary implementation of a second electrode connected to the electrical circuitry, consistent with some disclosed embodiments. Plasma generating field applicator 348 (FIG. 3A) may be electrically associated with an electrical power source, such as via operating unit 120 (FIG. 1A) containing electrical circuitry. Anode contactor 356 may be in contact with anode 340 while protecting shroud 310*a* is inside slot 350. Electric conductor 358 may be electrically connect anode contactor 356 with a supply of electric power (e.g., via the electrical circuitry of operating unit 120), thereby connecting anode 340 (e.g., the second electrode) to the electrical circuitry. In other words, anode 340 may be connected to the electric circuitry of operating unit 120 via electrical conductor 358 and anode contactor 356.

According to some embodiments, the second electrode is connected to the electric circuitry and is located on a second side of the dielectric barrier, opposite the plasma activation region. The term "second side of the dielectric barrier" may refer to the side opposite the first side of the dielectric barrier described above. Thus, if the first side corresponds to the side of the barrier where the cathode is positioned, the second side may correspond to the side of the barrier where the anode is positioned. The term "opposite the plasma activation region" may refer to the zone or area that is on the side of the dielectric barrier opposite the zone where the plasma is activated. Thus, if the plasma is activated on the cathode side (e.g., first side) of the dielectric barrier, the anode (e.g., second electrode) may be positioned on the other (e.g., opposite) side of the dielectric barrier. FIG. 3A illustrates an exemplary implementation of the second electrode being located on a second side of the dielectric barrier, opposite the plasma activation region, consistent with some disclosed embodiments. Anode 340 may be mounted on disk 344 forming a dielectric barrier between anode 340 and cathode 330. Thus, anode 340 is located on the other (e.g., second side) of disk 344 to cathode 330, which is located on the first side of disk 344. Moreover, the side of disk 344 where anode 340 is located is opposite to the side of disk 344 of vicinity 322 of viewport 390 corresponding to the plasma activation region.

According to some embodiments, the dielectric barrier and the first electrode are removable from the housing. The term "removable" may refer to detachable, separable, or transferrable. For example, the dielectric barrier may be detached (e.g., removed) from the housing, for example to change the mode of operation from a DBD to a non-DBD mode of operation. As another example, the first electrode may be detached from the housing to allow replacing or cleaning the electrode, e.g., from a build-up of sediment. FIGS. 3A-3B illustrate an exemplary implementation of a dielectric barrier and first electrode that may be removable from the housing, consistent with disclosed embodiments. Cathode 330 (FIG. 3A) and disk 344 (FIG. 3B) may be removable from the housing of application 348.

According to some embodiment, the dielectric barrier is configured to isolate the second electrode from gas in the chamber. The term "isolate" may refer to insulate, sequester, or otherwise prevent something from interacting with nearby matter or energy. For example, the anode (e.g., second electrode), positioned on one side of a dielectric barrier, may be insulated by the dielectric barrier from interacting with gas present on the other side of the dielectric barrier. FIGS. 3A-3B illustrates an exemplary embodiment of a dielectric barrier configured to isolate the second electrode from gas in the chamber, consistent with disclosed techniques. Disk 344 may form a dielectric barrier between anode 340 and cathode 330. Disk 344 may be an electric barrier that electrically isolates anode 340 from gas present in vicinity 322 of viewport 390.

According to some embodiments, a thickness of the dielectric barrier is between about 0.3 mm to about 3 mm. The thickness of the dielectric barrier may affect the quality of the plasma treatment, which may be measured by the level of hydrophilicity attained, and the time to activate the electric field to reach that hydrophilicity. In other words, a high-quality plasma treatment may correspond to a relatively high level of hydrophilicity. The thickness of the dielectric barrier may be sufficiently low to facilitate plasma ignition, yet sufficiently thick to prevent breakdown and arcing, e.g., between the anode and cathode. Exemplary thicknesses for dielectric materials such as PET or polycarbonate may range between 0.3 mm to about 3 mm for RF electric field at frequencies in the MHz range (e.g., about 2 MHz).

Some embodiments include a stopper for maintaining a gap between the optical element and the second electrode, the stopper acting as the dielectric barrier between the first electrode and the second electrode. The term "stopper" may refer to any type of barrier that may be positioned inside a container to isolate or separate one portion of the container from another portion of the container. For example, a stopper or barrier may be positioned inside the plasma activation region to control the advancement of the optical element, e.g., to ensure a predetermined gap between the optical element and the anode for generating the plasma. The stopper may additionally function as a dielectric barrier between the cathode and anode by interrupting the line of sight there between, such as to enable a DBD mode of operation. FIG. 3C illustrates an exemplary implementation of a plasma generating device further including a stopper for maintaining a gap between the optical element and the second electrode, the stopper acting as the dielectric barrier between the first electrode and the second electrode, consistent with disclosed embodiments. Protecting shroud 410 may be provided with stopper 442. Stopper 442 may limit the advancement of viewport 390 into protecting shroud 410 to ensure a predetermined gap between surface 392 (FIG. 3A) of viewport 390 and ring anode 440. The predetermined gap may facilitate the generation of plasma therein. In addition, stopper 442 may interrupt a line-of-sight between cathode 330 and anode 440, functioning as a dielectric barrier there between, e.g., to enable a DBD mode of operation.

Some embodiments involve at least one processor. The at least one processor may include electric circuitry for performing logical operations on an input signal. For example, the at least one processor may include one or more controllers, integrated circuits (ICs), including ASICs, microchips, microcontrollers, microprocessors, all or part of a CPU, GPU, APU, DSP, FPGA, or other circuits suitable for executing computing instructions and/or capable of performing logical operations, e.g., based on a computing instruction or an input signal. Instructions executed by the at least one processor may be pre-loaded into a memory integrated with or embedded into a controller (e.g., processor) or may be stored in a separate memory. The memory may comprise a RAM, a cache memory, a ROM, a hard disk, an optical disk, a magnetic medium, a flash memory, other permanent, fixed, or volatile memory, or any other mechanism capable of storing such instructions. The memory may additionally store data, which may include one or more inputs for executing the one or more program code instructions, and one or more outputs produced by executing the one or more program code instructions. In some embodiments, the at least one processor may include multiple processors. Each processor may have a similar construction, or different constructions that may be electrically connected or disconnected from each other. The processors may be separate circuits or integrated in a single circuit. Multiple processors may be configured to operate independently or collaboratively. The processors may be coupled electrically, magnetically, optically, acoustically, mechanically or by other means that permit them to interact. The processors may be physical and/or virtual (i.e., software-based). Operating unit 120 of FIG. 1A may illustrate an exemplary implementation of at least one processor, consistent with disclosed embodiments. Operating unit 120 includes one or more command switches and controller (e.g., processors).

Some embodiments are configured to control electricity flow through the circuitry. The term "control" may refer to administering, governing, or otherwise regulating. For example, the at least one processor may regulate the electricity flowing through the circuitry, and thereby regulate (e.g., control) a voltage difference between the cathode and anode. The voltage difference may affect the electromagnetic field generated in the plasma activation region, and thereby influence the generation of plasma therein. Since characteristics of the gas and electrodes may determine the attributes of the electromagnetic field needed to ignite the plasma, the at least one processor may regulate the electricity flow through the circuitry to generate an electromagnetic field suitable for the type of gas and electrode characteristics. For example, plasma may be ignited in helium gas at atmospheric pressure using an RF field of about 7 KV over a distance of 1 cm between the cathode and anode, and at a voltage of about 200V if the gas is at a pressure of 0.8 KPa. Operating unit 120 of FIG. 1A may illustrate an exemplary implementation of at least one processor configured to control electricity through the circuitry, consistent with disclosed embodiments. Operating unit 120 includes one or more command switches and controller (e.g., processors) that may regulate the flow of electricity throughout apparatus 100.

Some embodiments involve controlling the electricity flowing the circuitry to cause an electric and/or electromagnetic field associated with a voltage drop between the first electrode and a second electrode. The term "voltage drop" may refer to an electrical potential difference or a gap between the voltage levels of the two electrodes. The voltage drop, or potential difference, may define an electric and/or electromagnetic field between the two electrodes that may induce charged particles to move. Thus, the at least one processor may control parameters of the electricity such as the timing, frequency, intensity, magnitude, and phase of the electric (e.g., voltage, current) and/or magnetic signal (e.g., direction, strength, density). By controlling the electricity flowing through the circuitry, the at least one processor may control a voltage potential difference between the two electrodes, and thereby control an electric field therebetween. Operating unit 120 of FIG. 1A illustrates an exemplary implementation of at least one processor (e.g., controller) that may control electricity flowing through the circuitry of plasma generating system 100, consistent with disclosed embodiments. Turning to FIG. 3A, controlling the electricity (e.g., via operating unit 120 of FIG. 1A) may cause a voltage drop (e.g., potential difference) between cathode 330 and anode 340. The voltage drop may be associated with an electric field between cathode 330 and anode 340.

According to some embodiments, the electrical circuitry in the housing includes a plasma generating field applicator configured to cause the voltage drop to be at least 800 V. According to some embodiments, the electrical circuitry in the housing includes a plasma generating field applicator configured to cause the voltage drop to be at least 1000 V. Characteristics of the gas (e.g., type, pressure, temperature) may determine one or more aspects of an electric field suitable for generating plasma from the gas. This in turn may determine a voltage level corresponding to the electric field. For example, when electrodes are approximately 1 cm apart, plasma may be ignited in air (e.g., a gas) at a voltage of about 800V in 0.8 KPa for RF frequencies ranging between 1 MHz and 15 MHz. Similarly, plasma may be ignited at a voltage of about 1000V. Thus, causing a voltage potential difference (e.g., voltage drop) between the two electrodes of at least 800V, or at least 1000V may facilitate plasma ignition inside the plasma generating field applicator. FIG. 3A illustrates an exemplary implementation of a plasma generating field applicator configured to cause a voltage drop, (e.g., potential difference) to be at least 800V, or at least 1000V, consistent with disclosed embodiments. The foregoing are provided as examples only, as there is an interrelationship between parameters impacting plasma ignition, and thus parameters can be variably altered depending on design constraints so long as plasma is ignited and maintained for a period sufficient to achieve a desired level of hydrophilicity.

In some embodiments an electric field is caused between the first electrode and a second electrode to thereby generate plasma within the plasma-activation region. The term "plasma" may refer to a state of matter containing an abundance of charged particles, e.g., electrons and ions. Consequently, plasma may be highly electrically conductive and sensitive to electric and/or electromagnetic fields. Thus, the at least one processor may control the electricity to generate an electric and/or electromagnetic field inside the plasma-activation region capable of converting a gas subjected to the electric and/or electromagnetic field to a plasma cloud. For example, the electric and/or electromagnetic field may ionize the gas until the gas becomes increasingly electrically conductive to the point of reaching a plasma state. The circuitry may thus control the electricity to be suitable for carrying out the plasma treatment, e.g., by adapting the electricity from the power source to a signal capable of inducing an electric and/or electromagnetic field capable of converting a gas to a plasma cloud. Operating unit 120 (FIG. 1A) illustrates an exemplary implementation of at least one processor controlling electricity to carry out a plasma treatment, in accordance with disclosed embodiments. Operating unit 120 may adapt (e.g., control) electricity supplied by the power supply to be suitable for generating an electric and/or electromagnetic field capable of generating plasma. The electricity may be provided to any of cathode 330, anode 340, dielectric barrier 344, via any of cathode contactor 352, electric conductor 354, and electric conductor 358 (FIG. 3A). For example, electricity controlled by operating unit 120 may be delivered to cathode 330 and anode 340 via electric conductors 354 and 358 to generate an electric and/or electromagnetic field suitable for converting a gas present therein to a plasma cloud.

Some embodiments involve maintaining the generated plasma in the plasma-generating region for time period sufficient to cause the optical surface to become hydrophilic. As noted, the "quality" of the plasma treatment may correspond to the level of hydrophilicity attained due to the plasma treatment. The duration (e.g., time period) during which the electric field is activated, and thus capable of igniting plasma for treating an optical surface, may correspond to the level of hydrophilicity (e.g., the quality) required for a given application. For example, different applications (short versus long) and optical elements (e.g., varying shapes, sizes, and materials) may require varying qualities of treatment (e.g., levels of hydrophilicity). Some optical elements may require a very high level of hydrophilicity (e.g., corresponding to a lengthier treatment) and other optical elements may suffice with a lower level of hydrophilicity (e.g., corresponding to a shorter treatment). In a similar manner, to attain the same level of hydrophilicity, different materials, shapes, or sizes of optical elements may require different durations (e.g., time periods) of plasma treatment. Thus, the "time period sufficient to cause the optical surface to become hydrophilic" may depend on the material being treated (e.g., plastic, glass, metal), the shape of the optical element (e.g., flat or rounded), the use type and duration (e.g., a short dental procedure versus lengthy abdominal surgery) the type of gas used (e.g., Helium, Argon, or air), the pressure of the gas (e.g., atmospheric pressure or lower pressure generated via a vacuum pump), the ambient temperature, and any other factor that may affect the hydrophilicity of the optical element. The at least one processor may thus control the electricity in the circuitry to maintain plasma within the plasma-generating region for a time duration that meets the hydrophilicity requirements for a given optical element. A user may enter the hydrophilicity requirements for a specific optical element via a user interface of a control unit. Operating unit 120 (FIG. 1A) illustrates an exemplary implementation of at least one processor for maintaining the generated plasma in the plasma-generating region for time period sufficient to cause the optical surface to become hydrophilic, consistent with disclosed embodiments. Operating unit 120 may include a user interface (e.g., switches, controllers, buttons, indications, displays) allowing the user to enter one or more criterion for a plasma treatment for object 200, e.g., an optical element. For example, the user may provide one or more criterion to operating unit 120, such as a target treatment quality level, the type of material to be treated, the size and shape of the optical element to be treated, and any other criterion relevant to the plasma treatment for the optical element. At least one processor of operating unit 120 may control characteristics of the electricity flowing through the circuitry to generate plasma in any of plasma generating field applicator (130, 348, 448) based on the criterion, for example by controlling the duration (e.g., time period) for the treatment. In other words, operating unit 120 (e.g., at least one processor) may maintain the generated plasma in the plasma-generating region (e.g., vicinity 322 of FIG. 3A) for time period sufficient to cause optical surface 392 of optical element 390 to become hydrophilic.

Figure 19:
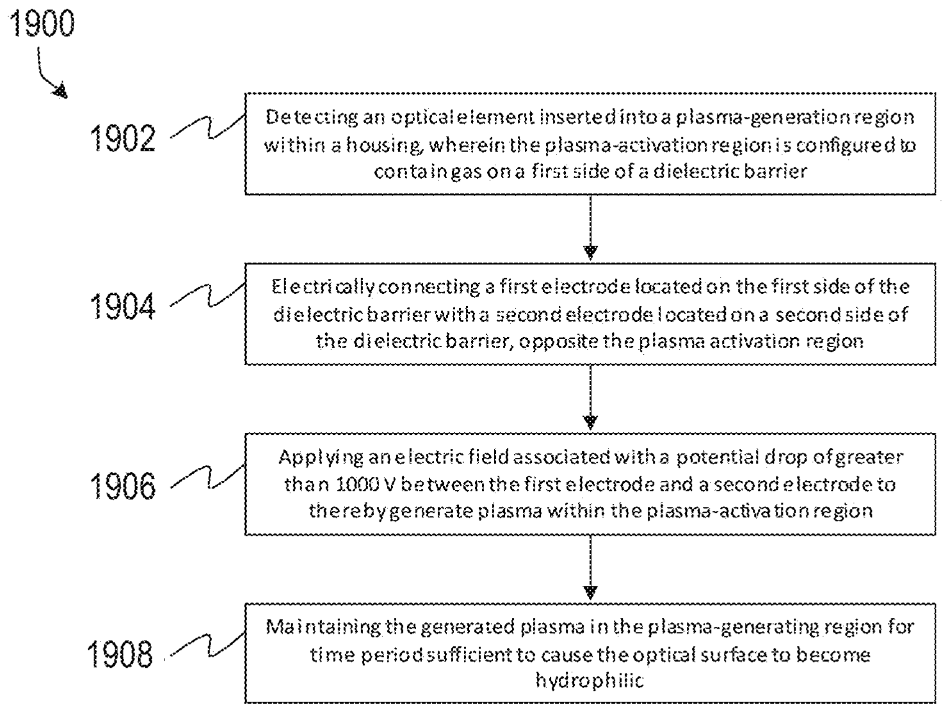
FIG. 19 is a block diagram of an example process for inhibiting condensation distortion on an optical element, consistent with embodiments of the present disclosure.

FIG. 19 is a block diagram of an example process 1900 for inhibiting condensation distortion on an optical element, consistent with embodiments of the present disclosure. While the block diagram may be described below in connection with certain implementation embodiments presented in other figures, those implementations are provided for illustrative purposes only, and are not intended to serve as a limitation on the block diagram. As examples of the process are described throughout this disclosure, those aspects are not repeated or are simply summarized in connection with FIG. 19. In some embodiments, the process 1900 may be performed by at least one processor (e.g., at least one processor operating unit 120 of FIG. 1A) to perform operations or functions described herein. In some embodiments, some aspects of the process 1900 may be implemented as software (e.g., program codes or instructions) that are stored in a memory provided with the at least one processor, or a non-transitory computer readable medium. In some embodiments, some aspects of the process 1900 may be implemented as hardware (e.g., a specific-purpose circuit). In some embodiments, the process 1900 may be implemented as a combination of software and hardware.

FIG. 19 includes process block 1902 to 1908. At block 1902 the method may involve, detecting an optical element inserted into a plasma-generation region within a housing, wherein the plasma-activation region is configured to contain gas on a first side of a dielectric barrier. The term "detecting" may refer to determining, sensing, or identifying, for example sensing the insertion of an optical element in a plasma-generation region. The detecting may further involve sensing the insertion of the optical element within a sheath that contains the plasma-generation region. The sheath may be contained within a housing encasing component of the plasma generating device. The plasma generating device may include a dielectric barrier that divides the plasma-activation region from other internal regions of the plasma generating. In this manner, the plasma-activation region may contain gas on only one side of the dielectric barrier. For example, cathode 330 (FIG. 3A) may come into physical contact with a metallic surface 384 of endoscope 380. The electrical contact may allow detecting the insertion of endoscope 380 into protecting shroud 310*a*, and thereby detect the insertion of optical surface 392 of viewport 390 (e.g., an optical element) within vicinity 322 (e.g., a plasma-generation zone) within the housing (e.g., applicator 130 of FIG. 1A). Vicinity 322 may contain gas on one side (e.g., of cathode 330) of disk 344 (e.g., a dielectric barrier).

In some embodiments, the optical element is part of a medical instrument having an elongated shaft and the optical element includes a lens on a distal end of the elongated shaft. For example, the medical instrument may be configured for insertion into a body, the insertion facilitated by an elongated cannula or handle (e.g., shaft), the distal end of which may be suited for insertion into the body, and the proximal end may be suited for control, external to the body, by a medical practitioner. The distal end may include a camera configured with an optical element including one or more lenses. The cannula may include one or more wires, fibers, or cables to enable controlling (e.g., maneuvering) the distal end of the medical instrument within the body, and to enable communicating information to and from the distal end, such as to transfer images collected by the camera (e.g., at the distal end) to a memory (e.g., at the proximal end). FIG. 2 illustrates the optical element being part of a medical instrument having an elongated shaft and including a lens on a distal end of the elongated shaft, consistent with disclosed embodiments. Endoscope 380 (e.g., a medical instrument) includes an elongated shaft, such as may be suited for inserting into a body. The distal end of the elongated shaft of endoscope 380 includes a viewport 390 (e.g., an optical element). External surface 392 which may be subject to a plasma treatment may be an external surface of a lens.

In some embodiments, the medical instrument is a laparoscope or an endoscope. For example, medical instruments such as laparoscopes and endoscopes may benefit from undergoing a plasma treatment to immunize a viewport of these instruments from fogging during use. FIG. 3A illustrates an exemplary implementation of endoscope 380 for undergoing a plasma treatment consistent with disclosed embodiments. The distal end of endoscope 380 includes a viewport 390. Protective shroud 310*a* is sized to accommodate the elongated shape of endoscope 380, or any other elongated medical instrument, such as a laparoscope.

At block 1904, the process may involve electrically connecting a first electrode located on the first side of the dielectric barrier with a second electrode located on a second side of the dielectric barrier, opposite the plasma activation region. Electrically connecting may refer to the inclusion of components within a circuit, and may not necessarily require a physical connection. For example, while two electrodes may not physically connect, their spaced apart proximity to each other may enable a voltage drop to occur within a common circuit, and in such instance, the two spaced apart electrodes are considered to be electrically connected. By electrically connecting the electrodes located at opposite sides of a dielectric barrier, plasma may be generated in the plasma-activation region in a DBD mode of operation, which may result in a more uniform generation of plasma and prevent arcing and other non-predictable and/or undesirable electric transmissions between the first and second electrodes. FIG. 3A, illustrates an exemplary implementation of electrically connected first and second electrodes, where the first electrode is located on a first side of a dielectric barrier and the second electrode located on the other (e.g., second) side of the dielectric barrier, opposite the plasma activation region, consistent with disclosed embodiments. Disk 344 (e.g., a dielectric barrier) separates cathode 330 (e.g., a first electrode) and anode 340 (e.g., a second electrode). Cathode 330 is electrically connected to protecting shroud 310*a* in proximity to vicinity 322 (e.g., the plasma activation region), whereas anode 340 is located on the opposite (e.g., second) side of disk 344, opposite vicinity 322.

At block 1906, an electric field associated with a potential drop of greater than 1000 V is applied between the first electrode and a second electrode to thereby generate plasma within the plasma-activation region. As noted above, the voltage suitable for generating an electric field capable of igniting a plasma cloud may depend on multiple factors, such as the type of gas used (e.g., Argon, Helium, or air), the pressure of the gas, and the geometry of the electrodes, with examples given for applying voltages of 7 KV and 20 KV to generate plasma. In other words, in some embodiments, a voltage of greater than 1000V may be applied between the first and second electrodes to generate plasma within the plasma-activation region. FIG. 3A illustrates an exemplary implementation for applying an electric field associated with a potential drop of greater than 1000 V between the first electrode and a second electrode to thereby generate plasma within the plasma-activation region, consistent with disclosed embodiments. A voltage of greater than 1000V may be applied between cathode 330 (e.g., first electrode) and anode 340 (e.g., second electrode) via conductors 354 and 358 to generate an electric field capable of generating plasma in vicinity 322 (e.g., the plasma-activation region).

At block 1908, the process may involve maintaining the generated plasma in the plasma-generating region for time period sufficient to cause the optical surface to become hydrophilic. As noted, the quality of a plasma treatment may correspond to the level of hydrophilicity attained. For example, certain materials, devices or applications may be associated with one or more hydrophilicity thresholds. The electric field may be maintained in the plasma-generating region for a long enough (e.g., sufficient) duration to ensure that the level of hydrophilicity attained meets the threshold. For example, operating unit 120 (FIG. 1A) may include one or more processors, controllers and switches that maintain the plasma inside the plasma-generation region for a sufficient duration to cause optical surface 390 (FIG. 3A) to become hydrophilic. Operating unit 120 may achieve this by controlling the electricity delivered to cathode 330 and anode 340 via conductors 354 and 358, respectively, and contactors 352 and 356, respectively, thereby controlling the electric field there between. For example, for one set of applications and/or configurations of the plasma-generation region, the time period sufficient to cause the optical surface to become hydrophilic is less than 1 minute of activated electric field. For a second set of applications and/or configurations of the plasma-generation region, the time period sufficient to cause the optical surface to become hydrophilic is less than 10 seconds of activated electric field. For a third set of applications and/or configurations of the plasma-generation region, the time period sufficient to cause the optical surface to become hydrophilic is less than 5 seconds of activated electric field. The time periods may be based on the type of material treated (e.g., metal, glass or plastic), the type and length of treatment the optical surface is slated to be used for (e.g., a mirror for quick dental procedure versus an endoscope for a lengthy abdominal surgery), the size and shape of the optical surface (flat dental mirror versus rounded camera lens), and any other factor that may affect the condensation of droplets on the optical surface.

Embodiments of the present disclosure may relate to systems, devices, methods, and computer readable media for generating plasma and for treating objects with plasma. For ease of discussion, in some instances related embodiments are described below in connection with a system or method with the understanding that the disclosed aspects of the system and method apply equally to each other as well as devices and computer readable media. Some aspects of a related method may occur electronically over a network that is either wired, wireless, or both. Other aspects of such a method may occur using non-electronic means. In the broadest sense, the systems, methods, and computer readable media disclosed herein are not limited to particular physical and/or electronic instrumentalities, but rather may be accomplished using many differing instrumentalities.

Some disclosed embodiments include a plasma generation device. As discussed elsewhere in the present disclosure, a plasma generation device may include any apparatus or combination of components capable of generating plasma, e.g., by converting a gas to transform the gas to a plasma state or plasma cloud. In some embodiments, the plasma generation device may include a mechanism for supplying gas such as helium or argon, and two electrodes (e.g., an anode and a cathode) or any other suitable means for applying an electric or electromagnetic field to the supplied gas. The electric or electromagnetic field may ionize the gas to the point that the gas becomes an electrically conductive plasma cloud.

In some embodiments, the plasma generation device is configured for treating objects. For example, plasma generated by the plasma generation device may be applied to an object, such that the plasma may react with molecules on the object's surface. In some embodiments, plasma may be applied to modify properties of the object's surface, such as by rendering the surface hydrophilic or hydrophobic or by altering the surface's electrical conductivity. Additionally, or alternatively, plasma may be applied to clean the object's surface by breaking down and removing organic residues. For example, plasma generation system 500 depicted in FIGS. 5 and 7 illustrates an exemplary implementation of a plasma generation device, in accordance with disclosed embodiments. As shown in FIG. 7, plasma generating system 500 may be configured to generate plasma to treat a surface of an object, such as an optical surface 706 of an endoscope 708 or another medical instrument. In some embodiments, plasma generating system 500 may be configured to apply plasma to an object (e.g., optical surface 706) to modify a hydrophilic property and/or another surface property of the object.

Some disclosed embodiments include a housing. In some embodiments, a housing may include any structure, casing, frame, enclosure, or support that covers and/or protects other components of the plasma generation device. For example, the housing may cover and protect the components of the plasma generation device that are configured to cause the reaction that creates the plasma (e.g., a vacuum chamber, one or more electrode pairs, and a mechanism for supplying reaction gas). As discussed elsewhere in the present disclosure, the housing may be made of any suitable material, such as plastic, metal, glass, wood, or any other material capable of encasing the plasma generation device, or any combination thereof. In some embodiments, the housing may be hollow so that the housing may hold or accommodate one or more other components. For example, the housing may include at least one bore, cavity, or hollow internal chamber that may hold or accommodate at least a portion of the object to be treated with plasma, and may optionally also hold or accommodate at least a portion of a protective sheath or shroud surrounding the object to be treated.

As an example, FIG. 7 illustrates an exemplary plasma generation device 500 including a housing 710, which may cover the outer surface of the plasma generation device and which may enclose other components of the plasma generation device. Housing 710 may include an opening 712 through which a sheath 718 (also referred to as a protecting shroud sheath 718) and an object to be treated (e.g., object 708) may be introduced into an inner cavity 714 of the housing (also referred to as a bore 714). Cavity 714 may be sized and configured to removably retain at least a portion of sheath 718 which may, in turn, accommodate at least a portion of object 708.

Some disclosed embodiments include a plasma generation zone within the housing. As discussed elsewhere in the present disclosure, the term "plasma generation zone" may refer to a physical volume or space within the housing in which a plasma cloud may be formed, e.g., by igniting a gas introduced therein. For example, the plasma generation zone may include a volume or space within the housing within which a reaction may occur for generating plasma. In some embodiments, the plasma generation zone may be located between an electrode pair configured to apply an electric or electromagnetic field to ionize gas within the plasma generation zone, thus generating plasma. In some embodiments, the plasma generation zone may be fluidly connected to a mechanism (e.g., a reservoir and/or pump) for supplying the reaction gas for generating the plasma, so that the gas may be delivered into the plasma generation zone.

In some disclosed embodiments, the plasma generation zone is configured to enable accommodation of an object, such as an object to be treated with plasma. As disclosed elsewhere in the present disclosure, the term "accommodation" may refer to a capability for holding, enclosing, supporting, or otherwise containing an object, e.g., within the plasma generation zone. For example, the object may be supported within the plasma generation zone to expose at least a portion of the object to a plasma cloud. In some embodiments, the plasma generation zone may be sized and configured to accommodate the entire object. Additionally, or alternatively, the plasma generation zone may be sized and configured to accommodate a portion of the object, such as a distal end of the object, while another portion of the object remains outside of the plasma generation zone (and, optionally, outside of the plasma generation device). In some embodiments, the object may be removable from the plasma generation zone. For example, the object may be delivered into, and accommodated within, the plasma generation zone for treatment with plasma, after which the object may be removed from the plasma generation zone.

In some embodiments, the plasma generation zone may be completely sealed from the external environment while the object is accommodated within the plasma generation zone. As a result, the plasma generation zone may be airtight. For example, one or more seals may be provided in the housing and/or in the sheath to form a vacuum seal about the external diameter of the object to be treated. The vacuum seal may be configured to hold a pressure differential between the plasma generation zone and the external environment, while the distal end of the object (or any other desired portion) is accommodated within the plasma generation zone. Accordingly, the internal pressure and/or the contents of the plasma generation zone may be controlled (e.g., by at least one processor of the plasma generation device). In alternative embodiments, the plasma generation zone may be open to the outer environment.

As an example, FIG. 7 illustrates a plasma generation device 500 including a plasma generation zone 716 located within housing 710. In some embodiments, plasma generation zone 716 may include an inner volume of sheath 718 at or near the distal end of sheath 718, such that plasma generation zone 716 may be configured to accommodate at least a portion of object 708 (including optical surface 706) during plasma treatment. Since sheath 718 may be accommodated within housing cavity 714, plasma generation zone 716 may also be located within cavity 714, at or near the end of the cavity that is opposite from opening 712. In some embodiments, plasma generation zone 716 may be located between an electrode pair configured to ionize gas within plasma generation zone 716 to generate plasma. As a non-limiting example, the anode 722A, 722B may be located within housing 710 and may include one electrode, two electrodes, or any other suitable number of electrodes or electrical contacts. Additionally, or alternatively, sheath 718 may include first electrode pair 702A, 702B and second electrode pair 704A, 704B, one or both of which may be configured as the cathode. For example, in some embodiments the first electrode pair 702A, 702B may be configured as the cathode. Electric power may be supplied between the anode and cathode to generate the electric or electromagnetic field for plasma generation.

In some embodiments, plasma generation zone 716 may be fluidly connected to a hose 720, which may be fluidly connected to a gas reservoir or container (not shown) containing a gas suitable for plasma generation, such as helium, argon, or nitrogen. Thus, hose 720 may stream the reaction gas from the gas reservoir into cavity 714 and plasma generation zone 716. Additionally, or alternatively, hose 720 may be fluidly connected to at least one vacuum pump configured to remove gas from plasma generation zone 716 in order to control the pressure within the plasma generation zone 716.

In some disclosed embodiments, the object to be treated with plasma includes a medical device or instrument configured to be inserted into, or implanted within, the body of a patient. For example, the object may include an optical surface of an endoscope. As used herein, an endoscope may refer to an instrument configured to be inserted into a body opening (such as a surgical opening or a preexisting opening such as the mouth or anus) in order to visualize an interior body cavity or organ or to assist with a medical procedure. The endoscope may include at least one imaging mechanism (e.g., a small camera) at or near the distal end of the endoscope. As also used herein, an optical surface of an endoscope may include a component positioned on the endoscope, or connected to the endoscope, through which light passes and/or is reflected. The optical surface may include one or more of a lens, polarizer, diffraction grating, prism, reflector, filter, viewing window, mirror, protective window, or any other component through which light passes or is reflected. In some embodiments, the optical surface may be part of a camera or other imaging mechanism of the endoscope, such that the optical surface may be configured to focus light in order to capture images of a body cavity or internal organ. The optical surface may be situated at the distal end of the endoscope or at any other location along the length of the endoscope from which it may be advantageous to capture images.

The optical surface of the endoscope may be treated with plasma to alter one or more characteristics of the optical surface. In some embodiments, the plasma treatment may minimize, inhibit, or prevent fogging of the optical surface that is caused by water droplets formed on the optical surface. Specifically, treatment with plasma may elevate the surface energy of the optical surface, thus rendering the surface super-hydrophilic (i.e., attracted to water). As a result, the water droplets may consolidate into a thin water layer on the optical surface so that light passing through the optical surface is not distorted by individual water droplets. Thus, fogging on the optical surface may be minimized or eliminated because the thin water layer formed on the hydrophilic optical surface does not distort light the way that water droplets do.

In some disclosed embodiments, the plasma generation zone is configured to enable accommodation of the optical surface of the endoscope surrounded by a dielectric barrier. As used herein, a dielectric barrier may refer to an insulating material structure located in the discharge path between an electrode pair. In some embodiments, a dielectric barrier may be provided in the plasma generating device between the electrodes used to apply an electric or electromagnetic field for generating plasma. The presence of the dielectric barrier may suppress excessive and rapid discharge between the electrodes, thus preventing sparks and are formation during plasma generation. In some embodiments, the plasma generation zone enables accommodation of the optical surface surrounded by a dielectric barrier (i.e., the protective sheath) because the plasma generation zone may be formed when the object to be treated and the protective sheath are accommodated within the internal cavity of the housing.

The dielectric barrier may be made from one or more dielectric materials such as glass, quartz, ceramics, enamel, mica, plastics, silicon rubber, or Teflon. In some embodiments, the dielectric barrier may be a planar structure provided in the gap between the electrodes, such as a plate or sheet of insulating material. Additionally, or alternatively, the dielectric barrier may partially or entirely surround or encircle the optical surface of the electrode. For example, the protective sheath or shroud provided around the optical surface (or another object to be treated with plasma) may be constructed from a dielectric material, such that the sheath may be configured as a dielectric barrier between the plasma-generating electrode pair. In some embodiments, the protective sheath may have a cylindrical side wall encircling the optical surface, as well as a cap or end wall that may form a dielectric barrier in between the electrodes. Alternatively, the protective sheath may have another shape or configuration that may enable the sheath to surround the optical surface.

By way of example, FIG. 1B shows an object 200 (e.g., an endoscope) including an optical surface 222 of an optical element 220 such as a window or lens of an imaging mechanism, which may be situated at the distal end 210 of the object. As another example, FIG. 7 depicts an optical surface 706 of an object 708, such as an endoscope. Optical surface 706 may be a lens of an imaging mechanism configured to capture images of a hollow body organ or cavity. In some embodiments, optical surfaces 222 and 706 may be treated with plasma (e.g., plasma generated by the exemplary plasma generating device) to render the surfaces hydrophilic and to thereby prevent fogging of the surfaces. In some embodiments, optical element 706 may be surrounded by protective sheath 718 while the optical element is positioned in the plasma generation zone 716 (see FIG. 7). Protective sheath 718 may be constructed from a dielectric material and may be situated in between the plasma-generating electrode pair of plasma generation device 500; thus, protective sheath 718 may be configured as a dielectric barrier.

Some disclosed embodiments include a plasma generator. As used herein, a plasma generator may include a mechanism configured to ionize gas in order to produce plasma. In some embodiments, a plasma generator may a power source, and circuitry connecting at least two electrodes so that a potential difference is established between the electrodes. The electrodes may be configured to subject gas to a strong electromagnetic field that ionizes the gas to the point that the gas becomes an electrically conductive plasma cloud. Additionally, or alternatively, a plasma generator may include any other mechanism configured to ionize gas particles to generate plasma. In some embodiments, the plasma generator may enable formation of plasma within the plasma generation zone. For example, the plasma generator may be configured to subject gas contained within the plasma generation zone to an electromagnetic field that ionizes the gas, thus producing plasma within the plasma generation zone.

As an example, FIG. 7 illustrates a plasma generation device 500 including a plasma generation zone 716 and a plasma generator that may include at least one high-voltage electrode 722A, 722B (which may be configured as the anode in device 500), a first electrode pair 702A, 702B, a second electrode pair 704A, 704B, a ground electrode (not pictured), a power supply (e.g., power supply 530), and electrical circuitry 700. In some embodiments, the at least one high-voltage electrode 722A, 722B may be configured as the anode and may include any suitable structure, such as a metal ring or a pair of metal rings provided in the housing 710. In some embodiments, the first electrode pair 702A, 702B and the second electrode pair 704A, 704B may be associated with (e.g., connected to or mounted upon) the protective sheath 718 and may be configured to establish electrical feedthrough between object 708 and electrical circuitry 700 located outside of the sheath. For example, second electrode pair 704A, 704B may extend inward from sheath 718 to contact object 708. First electrode pair 702A, 702B may electrically couple circuitry 700 and the power supply to sheath 718 (and to object 708 via second electrode pair 704A, 704B), thus closing the circuit and driving current between the electrodes to produce the ionizing field.

Some disclosed embodiments include a plurality of vacuum pumps within the housing. As used herein, a vacuum pump may refer to a device configured to draw fluid (e.g., gas such as air) from a sealed volume in order to produce a partial vacuum within the sealed volume. In some embodiments, the vacuum pumps may be fluidly connected with the plasma generation zone and may be configured to remove fluid (e.g., air or other gas) from the plasma generation zone to create a partial vacuum. The plurality of vacuum pumps may include at least one of a centrifugal pump, positive displacement pump, diaphragm pump, gear pump, screw pump, peristaltic pump, lobe pump, piston pump, or any other kind of pump suitable for removing air from the plasma generation zone to create a partial vacuum, or any combination thereof. In some disclosed embodiments, each pump may have a vacuum inlet (i.e., a suction inlet) through which fluid (e.g., air) that was removed from the plasma generation zone may flow into the vacuum pump body. Each pump may also have an outlet from which fluid may be discharged from the pump body at a higher pressure.

The vacuum pumps may be contained (partially or entirely) within the housing and may include two or more vacuum pumps. In some embodiments, the plurality of vacuum pumps may include at least three vacuum pumps. Alternatively, the plurality of vacuum pumps may include at least four vacuum pumps. Alternatively, the plurality of vacuum pumps may include at least five vacuum pumps. Alternatively, the plurality of vacuum pumps may include any other number of pumps suitable for creating a vacuum within the plasma generation zone. In some embodiments, the plurality of vacuum pumps may be controlled by at least one processor of the plasma generation device (as discussed in further detail herein). For example, the at least one processor may be configured to control the vacuum pumps based on sensor feedback, a predetermined program or schedule, and/or input received from a user. Additionally, or alternatively, the plasma generation device may include a user interface (e.g., buttons or a touch screen) which a user may operate to control operations of the vacuum pumps.

Some disclosed embodiments also include a plurality of conduits within the housing connecting the plurality of vacuum pumps. For example, one or more conduits may fluidly connect the plasma generation zone and the plurality of vacuum pumps. The conduits may include fluid control valves that may be controlled, e.g., by a processor. Additionally, or alternatively, conduits may be provided within the housing to fluidly connect some or all of the vacuum pumps, so that fluid may be conveyed between individual pumps. These conduits may also include flow control valves that may be controlled, e.g., by a processor.

As an example, FIG. 10A illustrates a vacuum pump assembly 1050 of plasma generation device 500 that includes a plurality of vacuum pumps 1000A, 1000B, 1000C, and 1000D. In the embodiment shown, vacuum pump assembly 1050 may include four pumps; however, the vacuum pump assembly 1050 may alternatively include any other suitable number of pumps. Vacuum pumps 1000A-1000D may be fluidly connected to plasma generation zone 716 (e.g., via hose 720 of FIG. 7) and may be configured to remove air from plasma generation zone 716 to create a vacuum for the generation of cold plasma. Vacuum pump assembly 1050 may also include pump manifold 1060 (see FIGS. 10B and 10C), which may include an arrangement of conduits and valves configured to direct air from plasma generation zone 716 to the pump assembly 1050 and between some or all of the individual pumps of pump assembly 1050. As shown in FIG. 11, vacuum pump assembly 1050 (including the plurality of vacuum pumps and the plurality of conduits) may be contained within housing 710 of plasma generation device 500.

In some disclosed embodiments, the plurality of conduits connects the plurality of vacuum pumps in series. As used herein, a connection "in series" may refer to an arrangement in which the vacuum pumps are fluidly connected along a single line, such that fluid (e.g., air) removed from the plasma generation zone flows through each vacuum pump consecutively. Thus, the discharge or outlet pressure of a first pump in the series is equal to the suction or inlet pressure of a second pump in the series, the discharge or outlet pressure of the second pump is equal to the suction or inlet pressure of a third pump in the series, etc. Connecting the pumps in series may have an additive effect on the head from each pump, thus enabling the series of pumps to create a large differential pressure between the inlet of the first pump and the outlet of the final pump. As a result, when the vacuum pumps are activated, the pumps may be configured to cause a vacuum within the plasma generation zone due to the large differential pressure allowing the removal of most or all air from the plasma generation zone.

In some disclosed embodiments, the series of pumps may be configured to cause a vacuum of between 0.1 atm and 0.01 atm, such as within the plasma generation zone. For example, the series of pumps may be configured to remove air from the plasma generation zone until a vacuum of between 0.1 atm and 0.01 atm is achieved. Then, the reaction gas may be introduced into the plasma generation zone until a desired vacuum pressure suitable for plasma generation is achieved. In some embodiments, the desired vacuum pressure for plasma generation may be a pressure within the range of between 0.1 atm and 0.01 atm. As the gas is excited to a plasma state, the series of pumps may remove air from the plasma generation zone as required to maintain a vacuum pressure within the desired range for generating plasma.

Because a vacuum (significantly below atmospheric pressure) may be created within the plasma generation zone, the plasma generation device may be configured to produce non-thermal or cold plasma with temperatures close to ambient temperature. Advantageously, treatment of a device with cold plasma (rather than high temperature, atmospheric plasma) is less likely to cause surface defects or damage the quality of the surface being treated, allowing the same device to be treated with plasma multiple times without the plasma damaging or otherwise negatively affecting the device. Further, a plurality of vacuum pumps in series is lower cost, requires less power, and is smaller than a single, larger pump that produces the same head as the vacuum pumps connected in series. Thus, the plasma generation device may be configured to produce cold plasma in a vacuum, while also being smaller, lighter, less expensive to produce, and more portable than a device that uses a single, larger pump to create a vacuum.

As an example, FIG. 10C depicts an exemplary pump manifold 1060 including conduits fluidly connecting vacuum pumps 1000A-1000D in series. For example, a first conduit 1062 may connect a discharge from the plasma generation zone ("IN") to an inlet ("IN 1") of a first vacuum pump in the series, such as pump 1000C of FIG. 10A. The pump manifold may additionally include a second conduit 1064 connecting an outlet ("OUT 1") of the first pump with the inlet ("IN 2") of a second vacuum pump in the series, such as pump 1000B of FIG. 10A. A third conduit 1066 may similarly connect the second pump with the third pump in the series (e.g., pump 1000D), and a fourth conduit 1068 may similarly connect the third pump with the fourth pump in the series (e.g., pump 1000A). A fifth conduit 1070 may be provided between the outlet ("OUT 4") of the fourth pump and an assembly outlet ("OUT"), from which the fluid (e.g., air) may exit the plasma generation device.

Some disclosed embodiments involve at least one processor. Consistent with disclosed embodiments, "at least one processor" may include any physical device or group of devices having electric circuitry that performs a logic operation on an input or inputs. For example, the at least one processor may include one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory. The memory may include a Random-Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction, or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact. As a non-limiting example, the at least one processor may include processor 102 of FIG. 1A.

The at least one processor may be configured to individually control each of the vacuum pumps of the plasma generation device. For example, the at least one processor may send control signals to each of the vacuum pumps to activate the pump, deactivate the pump, or control one or more operational parameters of the pump (e.g., the pump speed). In some disclosed embodiments, the at least one processor may be configured to simultaneously operate the plurality of vacuum pumps. For example, the at least one processor may cause some or all of the vacuum pumps in the series to operate (i.e., perform a pumping operation) at the same time while the object to be treated is in a region of the plasma generation zone. The simultaneous operation of the pumps may create a vacuum in the plasma generation zone so that plasma (e.g., cold plasma) may be generated for treating the object. As a non-limiting example, processor 102 of FIG. 1A may be configured to cause each of the vacuum pumps 1000A-1000D to operate (i.e., perform a pumping operation) simultaneously, while optical surface 706 is accommodated within plasma generation zone 716. The simultaneous operation of vacuum pumps 1000A-1000D may produce a vacuum of between 0.1 atm and 0.01 atm within plasma generation zone 716. After reaction gas is introduced into the plasma generation zone, the electrode pair may be controlled to deliver an ionizing electromagnetic field to the gas (e.g., for 10 seconds) to produce plasma for treating optical surface 706.

In some disclosed embodiments, the at least one processor is configured to activate the plasma generator after the vacuum is caused by the series of pumps. For example, the at least one processor may be configured to activate the series of vacuum pumps (e.g., simultaneously activate) to remove air from the plasma generation zone in order to produce a vacuum. Then, the at least one processor may cause a gas delivery mechanism to deliver the reaction gas into the plasma generation zone and may activate the plasma generator to ionize the gas and produce plasma.

In some disclosed embodiments, the at least one processor is configured to cause plasma to be generated for a period of time sufficient to cause a portion of the object to become hydrophilic. As discussed elsewhere in the present disclosure, the term "hydrophilic" may refer to a tendency or favorability of a molecule to be solvated by water. The at least one processor may be configured to maintain activation of the plasma generator for a sufficient length of time to cause the external surface, or any other desired portion, of the object to become hydrophilic. In some embodiments, the length of time may vary depending on the shape, size, and other properties of the object that is to be treated with plasma; accordingly, the at least one processor may be configured to alter the activation time of the plasma generator as required for the particular object. As a non-limiting example, the at least one processor 102 (FIG. 1A) may maintain activation of the plasma generator for a sufficient length of time to cause the external surface of optical element 392 of viewport 390 to become hydrophilic, such as prevent fog from forming on viewport 390 during an endoscopy procedure. According to some disclosed embodiments, the time period sufficient to cause optical element 392 to become hydrophilic may be less than a minute, less than 45 seconds, less than 30 seconds, less than 15 seconds, or any other suitable length of time.

In some disclosed embodiments, the at least one processor is configured to receive an insertion signal indicating that the object is within the region of the plasma generation zone. As discussed elsewhere in the present disclosure, an "insertion signal" may refer to any signal received from an insertion detector, for example any of the insertion detectors described herein, which may indicate that the object to be treated is accommodated within the region of the plasma generation zone. Once the insertion signal is received, the at least one processor may determine that plasma generation may begin. Accordingly, the at least one processor may be configured to activate the series of pumps to cause the vacuum within the plasma generation zone in response to the insertion signal. Once the desired pressure is achieved within the plasma generation zone, the at least one processor may activate the plasma generator to ionize the reaction gas in order to generate plasma.

In some disclosed embodiments, the at least one processor is configured to determine that the vacuum in the plasma generation zone is sufficient for plasma generation. As discussed elsewhere in the present disclosure, the term "sufficient for plasma generation" may refer to a gas pressure that is low enough to allow any gas remaining within the plasma generation zone, or any reaction gas introduced after emptying the plasma generation zone, to ionize and generate plasma. In some embodiments, and as also discussed elsewhere in the present disclosure, the at least one processor may be configured to determine that the vacuum is sufficient for plasma generation based on pressure sensor data obtained from within the plasma generation zone and/or another area within the housing. In some disclosed embodiments, the at least one processor is configured to activate the plasma generator after the determination is made that the vacuum in the plasma generation zone is sufficient for plasma generation, thereby exposing at least a portion of the object to plasma. In some embodiments, due to the vacuum in the plasma generation zone, cold plasma may be generated for treating the object.

Some disclosed embodiments may include at least one filter configured to filter air pumped from the plasma generation zone. As used herein, an air filter may refer to a device configured to remove particles such as dust, pollen, bacteria, and/or other impurities from the air. In some embodiments, the at least one air filter may be composed of a fibrous or porous material through which air may pass to be filtered. In some embodiments, the at least one filter may be a high efficiency particulate air (HEPA) filter, that is, a pleated mechanical air filter configured to remove at least 99.97% of dust, pollen, mold, bacteria, and any airborne particles with a size of 0.3 microns. The at least one filter may be situated at any suitable location within the housing, including and not limited to a location within hose 720, an inlet of vacuum pump assembly 1050, at one or more locations within pump manifold 1060, at an outlet of vacuum pump assembly 1050, or at a fluid discharge port of housing 710.

In some disclosed embodiments, the plasma generation zone is configured to enable accommodation of the object surrounded by a dielectric casing. As used herein, a dielectric casing may refer to a dielectric barrier (discussed in detail elsewhere in the present disclosure) that is shaped and configured to at least partially surround an object, such as an object to be treated with plasma. In some embodiments, the protective sheath or shroud provided around the object to be treated (e.g., sheath 718 of FIG. 7) may be constructed from a dielectric material, such that the sheath may be configured as a dielectric casing that may surround the object to be treated. The plasma generation zone may be configured to enable accommodation of the object surrounded by the dielectric casing since the plasma generation zone may be formed when the object to be treated and the protective sheath (i.e., the dielectric casing) are accommodated within the internal cavity of the housing. In some disclosed embodiments, the plasma generator is configured to enable formation of plasma within the plasma generation zone to treat the object when the object and the dielectric casing are inserted into the housing. As a non-limiting example, FIG. 7 depicts a configuration of plasma generating device 500 in which endoscope 708 (including optical surface 706) and protective sheath 718 (i.e., the dielectric casing) are inserted into cavity 714 of housing 710. In this configuration, an airtight plasma generation zone 716 may be formed within sheath 718, such that optical surface 706 may be exposed to the gas within the plasma generation zone. The at least one processor may activate the plasma generator to ionize the gas within plasma generation zone 716 in order to treat optical surface 706.

In some disclosed embodiments, the dielectric casing includes a one-way valve for enabling vacuum formation within the casing. As used herein, a one-way valve may include a check valve, or a fluid-control device configured to only allow fluid flow in one direction. In some embodiments, the one-way valve may include a stop-check valve, swing check valve, ball check valve, or any other structure configured to limit fluid flow to a single direction. In some embodiments, and as discussed above, the dielectric casing may include a protective sheath or shroud provided around the object to be treated with plasma. The protective sheath (i.e., the dielectric casing) may include a one-way valve permitting fluid to pass from inside of the plasma generation zone to an area outside, but not to pass in the opposite direction. As a result, an airtight seal of the plasma generation zone may be maintained so that a vacuum may be formed. As a non-limiting example, FIG. 8A depicts an example of a protective sheath 800 that is provided around an endoscope 802 and which may include a one-way valve 808 at or near a closed end of the sheath 800. One-way valve 808 may be configured to allow fluid to pass from the interior of the sheath to an area outside of the sheath but may prevent fluid from passing in the opposite direction.

In some disclosed embodiments, the series of pumps may be configured to cause at least a partial vacuum within a portion of the dielectric casing. As discussed herein, the series of pumps may be configured to cause a vacuum within the plasma generation zone, which may be located within the protective sheath (i.e., the dielectric casing) near the object that is to be treated with plasma. For example, the series of pumps may be configured to cause a vacuum of between 0.1 atm and 0.01 atm within a portion of the dielectric casing (i.e., within the plasma generation zone).

Figure 20:
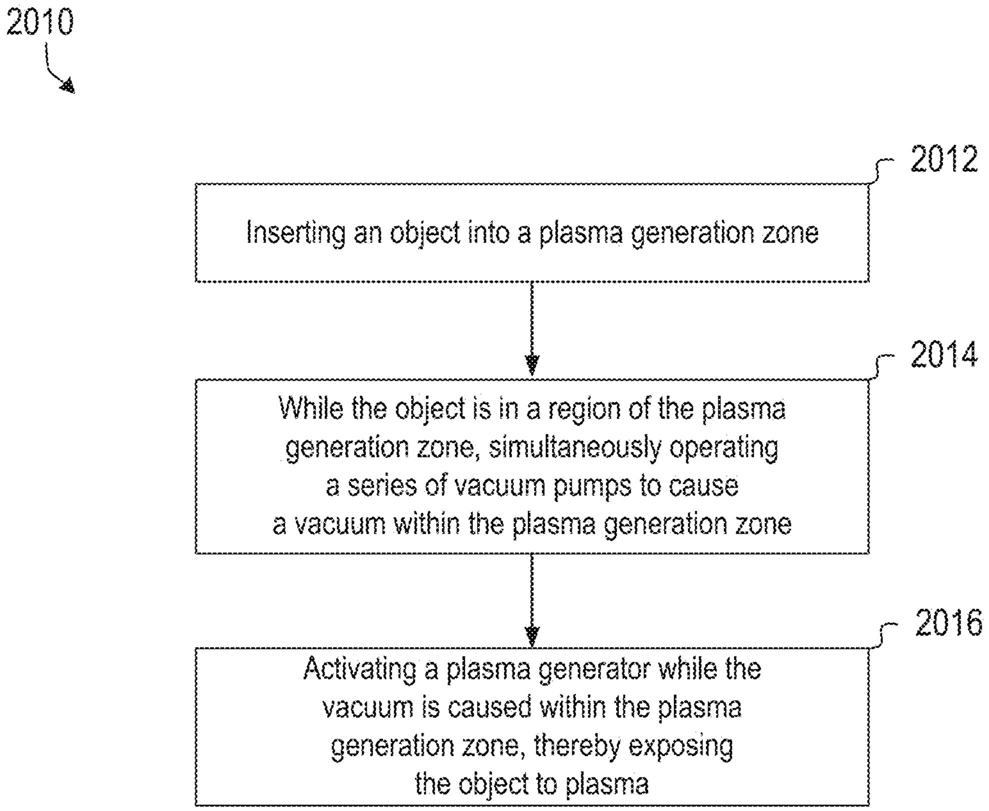
FIG. 20 depicts a flow chart of a method for generating plasma for treating objects, consistent with disclosed embodiments.

FIG. 20 is a block diagram illustrating a method 2010 consistent with a disclosed embodiment. The method 2010 of FIG. 20 may be implemented through software and/or using the hardware previously described.

At block 2012, an object is inserted into a plasma generation zone. The object may, for example, be a medical instrument as described earlier. At block 2014, while the object is in a region of the plasma generation zone, a plurality of vacuum pumps is simultaneously operated to cause a vacuum within the plasma generation zone. As described earlier, the vacuum pumps may be connected in series. At block 2016, while the vacuum is caused within the plasma generation zone, plasma is activated thereby exposing the object to plasma. The plasma activation may occur as described earlier.

Disclosed embodiments may involve inhibiting condensation distortion on an optical element of a medical instrument configured for insertion into a body cavity. Condensation may include moisture, dampness, wetness, beading, or any other manifestation of water or other fluid collecting on a surface. For example, condensation may include the formation of water droplets on a surface, such as glass. Condensation distortion may include an exaggeration, blurring, misrepresentation, contortion, or any other change, caused by condensation, that makes something appear different from an actual appearance. For example, condensation distortion may include a foggy image visualized through a glass surface when the glass surface is covered with water droplets. In surgical procedures, condensation distortion poses various problems, including lens fogging, which limits clear visualization during such procedures. Thus, it is desirable to inhibit condensation distortion. Inhibiting condensation distortion may include constraining, curbing, discouraging, hindering, obstructing, suppressing, preventing, minimizing, or any other manner of restraining condensation distortion. For example, inhibiting condensation distortion on a glass surface may include reducing fogging on the surface by limiting the number or size of water droplets that accumulate on the surface.

An optical element may include a lens, prism, mirror, or any other part of an optical instrument which either reflects light or permits the passage of light. It may be desirable to inhibit condensation distortion on an optical element because the characteristics of light passing through an optical element may be distorted by water collected on a surface of the optical element. For example, an optical element may include a lens of medical instrument, such as an endoscope. A medical instrument may include a scope, catheter, tube, or any other device used on the inner or outer part of the body for diagnosis or treatment of a medical condition. In some embodiments, the medical instrument is exposed to air which is greater than room temperature such as air located in the inner orifice of a human during a medical procedure. In some embodiments, the medical instrument includes a scope and the optical element may be located on a distal end of the scope. A scope may include any instrument for viewing or examining any part of a body. A distal end of the scope may include any site located away from a specific area of the scope (i.e., located a distance from the end controlled or handled by medical personnel or robot controlled by medical personnel), including the center of the scope. In some examples, a distal end may include parts of the scope further away from the center of the scope. In some embodiments, the scope may be at least one of an endoscope, duodenoscope, or a laparoscope. In other examples, the scope may include a laparoscope, fiberscope, bronchoscope, arthroscope, cystoscope, anoscope, gastroscope, sigmoidoscope, or any other medical device used to look inside a body cavity or organ.

As used herein, "endoscope" may include any scope that has a distal end configured to be inserted into a patient's body, and a proximal end configured to remain outside the patient's body during the procedure. Typically, the distal end includes a viewport such as a lens or a window or a bare end of an optical fiber or even a mirror (such as a dentist mirror for example). Through the viewport, the scope enables collecting an image of the surrounding of the viewport, e.g., using a light-sensitive device such as a CCD. The viewport may be aimed to collect light from in front of the device (namely from a region coinciding with the longitudinal axis of the device), or the viewport may be slanted in an angle relative to the longitudinal axis or may be facing perpendicular to the longitudinal axis of the device (as is demonstrated for example in colonoscopies). The proximal end typically includes or is connected to a handle to be held by a medical practitioner, possibly including user interface components such as switches, navigating sticks, touch screens and touch pads. Endoscopes include a vast range of scopes, for example bronchoscopes, colonoscopes, cystoscopes and laparoscopes. A laparoscope—as a specific example—comprises a rigid or relatively rigid rod or shaft having a viewport, possibly including an objective lens, at the distal end, and an eyepiece and/or an integrated visual display at the proximal end. The scope may also be connected to a remote visual display device or a video camera to record surgical procedures. A body cavity may include a peritoneum, dorsal cavity, back body cavity, cranial cavity, spinal cavity, ventral cavity, thoracic cavity, abdominopelvic cavity, abdominal cavity, pelvic cavity, bowel, stomach, esophagus, lung, blood vessel, organ, or any other space or compartment in a body. In some examples, a body cavity may include a space housing multiple organs, such as a thoracic cavity. In other examples, a body cavity may include a single organ, such as a heart. In yet other examples, a body cavity may include a blood vessel, such as an aorta. Insertion into a body cavity may include introducing, injecting, entering, embedding, implanting, or any other manner of placement into a body cavity. In one example, insertion into a body cavity may include introducing an endoscope into a blood vessel by guiding the endoscope into the blood vessel. In some embodiments, the body cavity may be a surgical cavity or natural orifice. It may be desirable to inhibit condensation distortion when a medical instrument is used within a surgical cavity in order to visually examine an organ during surgery without having to make a large incision. It may also be desirable to inhibit condensation distortion when a medical instrument is used with a natural orifice in order to visually examine an organ during incisionless surgery or for non-surgical procedures such as diagnosis based on organ visualization. A surgical cavity may include a hollow area or hole created for or as part of a procedure in which a part of the body is cut, usually to expose internal parts such as organs. For example, a surgical cavity may include a hole in an abdomen created when a surgeon makes an incision through the skin and muscle of the abdomen, so that the underlying organs can be viewed. A natural orifice may include a hollow area or hole that exists in a body from birth or by nature and is not caused by any incision. For example, a natural orifice may include the oral cavity or the vaginal cavity. In one example, an endoscope may be used in accordance with transvaginal gall bladder removal through the natural orifice of the vagina in order to inspect the inner organs that are visible through the vaginal cavity.

Disclosed embodiments may include treating the optical element of the medical instrument to cause at least one surface of the optical element to become super-hydrophilic. The term "treating" may refer to a process, procedure or protocol applied to modify one or more properties of a physical object. In some embodiments, treating the optical element may include applying a substance (e.g., plasma) to the optical element, exposing the optical element to a condition, or any other interaction with the optical element that may cause the optical element to become super-hydrophilic. The term "super-hydrophilic" may refer to a very high level of hydrophilicity, for example sufficiently hydrophilic to substantially decrease a contact angle between a fluid and the surface of the object, e.g., so as to allow the fluid to coat the surface of the object as a substantially uniform (e.g., flat) layer. It may be desirable to treat the optical element of the medical instrument to cause at least one surface of the optical element to become super-hydrophilic because super-hydrophilic surfaces are less prone to fogging caused by condensation, which may limit condensation distortion of the optical element. A substance may include any material that possesses physical properties, such as a liquid, solid, gas, or plasma. Applying a substance to the optical element to treat the optical element may be desirable because an amount of the substance may be controlled, such that the amount of the substance applied may be increased or decreased to achieve a desired level of hydrophilicity or super-hydrophilicity. In one example, treating the optical element may include applying a liquid coating to the optical element. In another example, treating the optical element may include exposing the optical element to a gaseous or plasma-based substance. A condition may include a temperature, location, habitat, setting, or any other factor associated with the circumstances of the optical element. In one example, exposing the optical element to a condition may include increasing the temperature of the optical element. In another example, exposing the optical element to a condition may include reducing the pressure of the region around the optical element. An interaction with the optical element may include a communication, contact, cooperation, movement, or any other type of action performed in association with the optical element. In one example, an interaction with the optical element may include moving the optical element. In another example, an interaction with the optical element may include contacting the optical element with any substance or object.

In some embodiments, treating the optical element may occur in a vacuum chamber. A vacuum chamber may include any rigid enclosure from which air or other gases are removed to some degree by a vacuum pump, resulting in a low-pressure environment within the enclosure (e.g., a sub-atmospheric pressure environment). In some examples, the pressure within the vacuum chamber may be less than 0.3 atm. In other examples, the pressure within the vacuum chamber may be less than 0.1 atm. In yet other examples, the pressure within the vacuum chamber may be between 0.1 to 0.01 atm. It may be desirable to treat the optical element in a vacuum chamber in order to improve the resulting hydrophilicity of the optical element. In some examples, the vacuum chamber may be incorporated into the medical instrument. In other examples, the vacuum chamber may include an additional device used in conjunction with the medical instrument.

In some embodiments, treating the optical element may include exposing the optical surface to plasma. The term "plasma" may refer to a state of matter containing an abundance of charged particles, e.g., electrons and ions. Consequently, plasma may be highly electrically conductive and sensitive to electric and/or electromagnetic fields. It may be desirable to expose the optical surface to plasma in order to improve the hydrophilicity of the optical element. Specifically, during a hydrophilic treatment, the surface undergoes oxidation and the bombarding plasma ions form hydroxyl groups on the surface. These hydroxyl groups are polar, and since water is polar, it is attracted to them. Ultimately, this is what enhances the surface's wettability and adhesion, which in turn makes it more hydrophilic. Exposing the optical surface to plasma may include continuously contacting the optical surface with plasma. Exposing the optical surface to plasma may also include intermittently contacting the optical surface with plasma.

In some embodiments, treating the optical element may include coating the optical surface with a liquid solution. A liquid solution may include any homogenous mixture composed of two or more components. For example, a liquid solution may include a hydrophilic mixture that forms a covalent bond to create water-attracting surfaces. Coating the optical surface with a liquid solution may include dip coating, spray coating, reel-to-reel coating, robotic coating, spin coating, submersion coating, or any other manner of contacting the optical surface with the liquid solution.

In some embodiments, causing the at least one surface of the optical element to become super-hydrophilic may include enabling, for at least one hour after treating the optical element, droplets hitting the at least one surface of the optical element to have contact angles of less than 10 degrees. For example, causing the at least one surface of the optical element to become super-hydrophilic may include sufficiently treating the at least one surface to enable for 45 minutes after treating the optical element, droplets hitting the at least one surface of the optical element to have contact angles of less than 10 degrees. The contact angle is a quantitative measure of the hydrophilicity of a surface or material. If the contact angle of water is less than a certain degree, the surface may be designated hydrophilic since the forces of interaction between water and the surface nearly equal the cohesive forces of bulk water and water does not cleanly drain from the surface. If the liquid molecules are strongly attracted to the solid molecules then the liquid drop will completely spread out on the solid surface and create a completely hydrophilic surface, corresponding to a contact angle of 0°. In some embodiments, the contact angles may be less than 30 degrees. In some embodiments, the contact angles may be less than 20 degrees. In some embodiments, the contact angles may be less than 8.5 degrees. In some embodiments, the contact angles may be less than 7.5 degrees. For example, causing the at least one surface of the optical element to become super-hydrophilic may include sufficiently treating the at least one surface such that for forty-five minutes after treating the optical element, droplets hitting the at least one surface of the optical element to have contact angles of 7 degrees or less. In some embodiments, the contact angles may be less than 5 degrees.

In some embodiments, causing the at least one surface of the optical element to become super-hydrophilic may include treating the optical element for less than 30 seconds. It may be desirable to treat the optical element for less than 30 seconds when using a treatment that is highly effective within a short period of time. It may also be desirable to treat the optical element for less than 30 seconds when there is an urgent need for an endoscope with improved condensation distortion inhibition in a surgical procedure. For example, causing the at least one surface of the optical element to become super-hydrophilic may include treating the optical element for 20 seconds.

In some embodiments, treating the optical element may include causing a super-hydrophilic state of the at least one surface of the optical element that deteriorates over time. Over time, a super-hydrophilic state of the at least one surface of the optical element may deteriorate, such that the degree of hydrophilicity changes. In some instances, it may be desirable (or at least acceptable) to have a super-hydrophilic state such that droplets hitting the at least one surface of the optical element have contact angles of 7 degrees. In other instances, it may be desirable (or acceptable) to have a super-hydrophilic state such that droplets hitting the at least one surface of the optical element have contact angles of 10 degrees. In such situations, deterioration of the super-hydrophilic state may be acceptable so that the same medical instrument can be used in both instances. Deterioration may include decline, degradation, worsening, lessening, retrogression, decay, or any other process of becoming impaired or inferior in the quality, functioning, or condition of being super-hydrophilic. For example, causing a super-hydrophilic state of the at least one surface of the optical element that deteriorates over time may include causing the super-hydrophilic state to reduce to a hydrophilic state within 48 hours. In another example, causing a super-hydrophilic state of the at least one surface of the optical element that deteriorates over time may include causing the super-hydrophilic state to reduce to a hydrophobic state within 48 hours.

In some embodiments, the deterioration of the super-hydrophilic state of the at least one surface of the optical element may occur within 24 hours. For example, the same medical instrument may be used for various visualization or surgical procedures within a single day (e.g., for surgeries with long durations). For example, causing a super-hydrophilic state of the at least one surface of the optical element that deteriorates over time may include treating the at least one surface so that its super-hydrophilic state remains for about 24 hours. In another example, causing a super-hydrophilic state of the at least one surface of the optical element that deteriorates over time may include causing the super-hydrophilic state to reduce to a water neutral or hydrophobic state within 24 hours.

In some embodiments, treating the optical element includes maintaining a liquid in contact with the optical element for a period sufficient to cause the at least one surface of the optical element to become super-hydrophilic. The liquid may include any fluid that may cause the at least one surface of the optical element to become super-hydrophilic, including any fluid capable of participating in dynamic hydrogen bonding with surrounding water. In some embodiments, the liquid may be used to provide a hydrophilic coating to the hydrophilic surface of the optical element prior to exposure to hot air. In some examples, the liquid may be ionic. In other examples, the liquid may be negatively charged in order to further facilitate aqueous interactions, which in some instances may give rise to hydrogel materials that may exhibit low coefficients of friction. As one example, the liquid may be VitreOx™. Maintaining the liquid in contact with the optical element may include coating the optical element with the liquid, submerging the optical element in the liquid, continuously exposing a flow of the liquid to the optical element, or in any other way continuing contact between the liquid or the optical element. A period sufficient to cause the at least one surface of the optical element to become super-hydrophilic may include a single period or a plurality of periods. In some examples, the period may be the same for a plurality of liquids. In other examples the period may be different for a plurality of liquids. In some examples, the period may be the same for a plurality of types of optical elements. In other examples, the period may be different for a plurality of types of optical elements.

Disclosed embodiments may include inserting the medical instrument, with the super-hydrophilic element, into the body cavity. Inserting the medical instrument into the body cavity may include embedding, entering, implanting, injecting, introducing, admitting, interposing, placing, setting, or in any other way bringing optics of the medical instrument to a location within a body cavity. It may be desirable to insert the medical instrument, with the super-hydrophilic element, into the body cavity in order to improve the functioning of an endoscope inserted into the body by improving image visualization through the reduction of image distortion by fogging. In some examples, the entire super-hydrophilic element may be inserted into the body cavity. In other examples, only a portion of the super-hydrophilic element may be inserted into the body cavity.

Some embodiments further include applying a liquid to the optical element prior to inserting the medical instrument into the body cavity. A liquid may include any fluid material, such as water or hydrophilic substance. Applying a liquid to the optical element prior to inserting the medical instrument into the body cavity may be desirable in order to verify that the treatment of the optical element to cause the at least one surface of the optical element to become super-hydrophilic was successful. If after applying the liquid to the optical element prior to inserting the medical instrument into the body cavity, the optical element still experiences condensation distortion, then it may be desirable to again treat the optical element prior to inserting the medical instrument into the body cavity, in order to improve visualization using the optical element.

Some disclosed embodiments include exposing the super-hydrophilic optical element to moisture, such that the moisture forms a film barrier on the at least one surface of the optical element to thereby inhibit condensation distortion. Moisture may include a liquid, fog, humidity, dampness, wetness, or any other presence of a liquid caused by exposure to liquids, such as one or more body fluids or moisture within the body. Exposing the super-hydrophilic optical element to moisture may include introducing, contacting, touching, or in any other way causing an interaction between the super-hydrophilic optical element and moisture. In one example, exposing the super-hydrophilic optical element to moisture may include contacting a portion of the super-hydrophilic optical element with moisture. In another example, exposing the super-hydrophilic optical element to moisture may include locating the optical element in an environment and facilitating condensation on the optical element. A film barrier may include a covering, lamination, coating, covering, membrane, partition, sheet, or any other thin separation layer. The film barrier may inhibit condensation distortion by reducing or even eliminating the formation of water droplets on the at least one surface of the optical element.

In some embodiments, the method may further include, after inserting the medical instrument into the body cavity, re-treating the optical element to cause the at least one surface of the optical element to become super-hydrophilic. It may be desirable to re-treat the optical element to cause the at least one surface of the optical element to become super-hydrophilic after inserting the medical instrument into the body cavity in order to return the surface to a super-hydrophilic state following a deterioration of the super-hydrophilic state. It may also be desirable to re-treat the optical element to cause the at least one surface of the optical element to become super-hydrophilic after inserting the medical instrument into the body cavity in order to achieve a higher level of super-hydrophilicity if the medical instrument is still experiencing an unwanted amount of condensation distortion. For example, the initial treatment of the optical element may cause the at least one surface of the optical element to become super-hydrophilic such that droplets hitting the at least one surface of the optical element have contact angles of less than 10 degrees. The super-hydrophilic state of the surface of the optical element may then deteriorate over time such that droplets hitting the at least one surface of the optical element have contact angles greater than 10 degrees and less than 30 degrees. In this example, re-treating the optical element to cause the at least one surface of the optical element to become super-hydrophilic may include causing the droplets hitting the at least one surface of the optical element to have contact angles of less than 10 degrees, in order to return the surface to a desired super-hydrophilic state for the procedure.

Some embodiments further include re-treating the optical element to cause the at least one surface of the optical element to become super-hydrophilic at least one additional time within 24 hours of treating the optical element. It may be desirable to re-treat the optical element to cause the at least one surface of the optical element to become super-hydrophilic at least one additional time within 24 hours of treating the optical element so that the same medical instrument may continue to be used in a lengthy surgical procedure. For example, the initial treatment of the optical element may cause the at least one surface of the optical element to become super-hydrophilic such that droplets hitting the at least one surface of the optical element have contact angles of less than 10 degrees, where the super-hydrophilic state deteriorates over time. The super-hydrophilic state of the surface of the optical element may then deteriorate throughout the day such that droplets hitting the at least one surface of the optical element have contact angles greater than 10 degrees. In this example, re-treating the optical element to cause the at least one surface of the optical element to become super-hydrophilic may include causing the droplets hitting the at least one surface of the optical element to have contact angles of less than 10 degrees within 15 hours, in order to return the surface to a desired super-hydrophilic state for the procedure within the same day.

In some embodiments, the at least one additional re-treatment of the optical element includes executing the at least one additional re-treatment by a battery-powered plasma generator. The term "plasma generator" may refer to a device configured to generate plasma, e.g., inside a plasma generation zone. The term "plasma generation zone" may refer to a physical volume or space in which a plasma cloud may be formed, e.g., by igniting a gas introduced therein. The plasma generation zone may be of any size. For example, the plasma generation zone may be less than 15 $cm^3$, less than 10 $cm^3$, or less than 5 $cm^3$. The plasma generator may generate an electromagnetic field within the plasma generation zone, such that exposing a gas to the electromagnetic field ignites the gas to generate plasma.

A battery-powered plasma generator may include any device or system that includes a battery for powering the device and is capable of forming plasma. Such a device or system may be configured to treat objects with a plasma cloud by executing one or more actions and/or functions based on computer program instructions that may be generated and/or received from at least one processor. The formation of a plasma cloud may be achieved by subjecting gas to a strong electromagnetic field to the point where an ionized gaseous substance becomes increasingly electrically conductive. FIG. 1 schematically depicts a plasma generator 100, according to an aspects of some embodiments. Plasma generator 100 may include an operating unit 120 and a plasma applicator 130 electrically associated with operating unit 120, e.g., via a cable 112. Operating unit 120 may be associated with at least one processor 102 (e.g., a controller), a power supply 104 and/or 530, which may be a battery, circuitry 106, and at least one memory 108. At least one processor 102 may be communicatively coupled to at least one memory 108 using wired and/or wireless means, e.g., via bus system 110. At least one processor 102 may be further electrically coupled to power supply 530 and circuitry 106, e.g., via a bus system 110. At least one processor 102 may be configured to execute one or more program code instructions with respect to one or more data items stored in at least one memory 108. The at least one program code instruction may facilitate in controlling one or operational aspects of plasma generation system 100, e.g., to control the generation of plasma via plasma applicator 130. For example, at least one processor 102 may control and moderate one or more attributes of energy supplied by power supply 530 (e.g., as electric power) to plasma applicator 130 for the purpose of generating plasma to treat an object, for example by controlling one or more components (e.g., switches, diodes, and other logical componentry) of circuitry 106. While at least one processor 102, power supply 530, circuitry 106, and at least one memory 108 are shown inside operating unit 120, this is intended for illustrative purposes only and does not limit the invention to the configuration illustrated. For example, at least one processor 102 and at least one memory 108 may include multiple local and/or remote processors and memory units, as known in the art of distributed computing. Similarly, while FIG. 1 shows power supply 104 and circuitry 106 positioned within operating unit 120, this is not required, and power supply 104 and/or circuitry 106 may be external to operating unit 120, e.g., power supply 104 may be within a wall unit that is coupled to operating unit 120 via cable.

FIGS. 5A-5C illustrate three views of a plasma generating system 500, in accordance with some embodiments of the present disclosure. In some embodiments, plasma generating system 500 may correspond to plasma generating field applicator 130 (FIG. 1) in that plasma generating system 500 may be configured to receive energy for carrying out a plasma treatment, e.g., via circuitry 106, power supply (battery) 530, at least one processor 102, and cable 112 (FIG. 1). As illustrated in the figure, Plasma generating system 500 may include a housing 510 having, a cavity 502 and accommodating, a plasma activation generation zone 504 (e.g., plasma activation zone), a plasma generator 506, and a controller 508. Plasma generating system 500 may include a plasma-generation activation zone 504 within the cavity 502 and arranged such that when the at least a portion of the medical instrument having an optical element is retained within the cavity 502, the optical element is located within the plasma plasma-activation generation zone 504. Plasma generator 506 may generate plasma for treating an object (e.g., a medical instrument) within plasma generation zone 504 in accordance with embodiments disclosed herein. Cavity 502 of housing 510 may correspond to slot 132 (FIG. 1). Cavity 502 may provide access to plasma generation zone 504, e.g., to enable inserting an object into plasma generation zone 504 for carrying out a plasma treatment to increase the hydrophilicity of the object. Controller 508 may control one or more aspects of plasma generator 506, such as the influx and/or outflow of gas into plasma activation zone 504 for the purpose of generating plasma, the generation of an electric and/or electromagnetic field for generating plasma, and any other parameter relevant to the generation of plasma via plasma generator 506. Plasma generating system 500 may further include one or more sensors, such as a pressure sensor, a voltage sensor 514 and a plasma frequency sensor 512.

In some embodiments, the at least one additional re-treatment of the optical element includes using the battery-powered plasma generator without charging the battery-powered plasma generator between the treatment and the at least one additional re-treatment. Charging may include storing energy in the battery of the battery-powered plasma generator by running an electrical protocol. The charging protocol, including how much voltage or current is introduced and for how long it is introduced, may depend on the size and type of the battery being charged. It may be desirable to use the battery-powered plasma generator without charging the battery-powered plasma generator between the treatment and the at least one additional re-treatment in order to improve energy efficiency while using the battery-powered plasma generator. In one example, the at least one additional re-treatment of the optical element may include using the battery-powered plasma generator without charging the battery-powered plasma generator between the treatment and one additional re-treatment. In another example, the at least one additional re-treatment of the optical element may include using the battery-powered plasma generator without charging the battery-powered plasma generator between the treatment and two additional re-treatments.

Some embodiments further include estimating a number of remaining treatments of the optical element that can be performed before maintenance is required. Estimating a number of remaining treatments of the optical element that can be performed before maintenance is required may be performed either manually by a user of the plasma generator or automatically by the plasma generator. For example, a user may estimate based on the charge-holding history of the associated battery, that a remaining four treatments of the optical element can be performed before maintenance is required. In another example, the plasma generator may automatically determine, based on the charge-holding history of the associated battery, that a remaining three treatments of the optical element can be performed before maintenance is required. Maintenance may include maintenance of the plasma generator or any other device used in conjunction with the disclosed embodiments. Maintenance may include updating, fixing, replacing, or repairing the battery or any other component of the plasma generator. In one example, maintenance may include charging the battery when it is estimated that no remaining treatments of the optical element can be performed before maintenance is required. In another example, maintenance may include replacing the battery when it is estimated that no remaining treatments of the optical element can be performed before maintenance is required. By way of other examples, maintenance may include replacing a filter or a gas canister or replacing an electrode.

Disclosed embodiments may involve methods for treating an endoscope to make it super hydrophilic. FIG. 15 illustrates an exemplary method 1505 for inhibiting condensation distortion on an optical element of a medical instrument configured for insertion into a body cavity, consistent with some embodiments of the present disclosure. As shown in step 1510, the method 1505 may involve treating the optical element of the medical instrument to cause at least one surface of the optical element to become super-hydrophilic. The method 1505 may also involve inserting the medical instrument, with the super-hydrophilic optical element, into the body cavity, as shown in step 1512. Step 1514 shows that the method 1505 may also involve exposing the super-hydrophilic optical element to moisture, such that the moisture forms a film barrier on the at least one surface of the optical element to thereby inhibit condensation distortion.

Minimally invasive surgery involves a variety of techniques to operate with less damage to the body compared to open surgery. Generally, minimally invasive surgery is associated with less pain, shorter hospital stays, and fewer complications. Laparoscopy—surgery done through one or more small incisions, using small tubes and tiny cameras and surgical instruments—was one of the first types of minimally invasive surgery. Another type of minimally invasive surgery is robotic surgery. It provides a magnified 3D view of the surgical site and helps the surgeon operate with precision, flexibility and control.

Experience shows that images collected by optical instruments inserted to the patient's body tend to blur due to accumulation of fog on the surface of the optical element of the instrument. As discussed above, the local environment within the patient's body is generally humid and warm compared to ambient conditions. Consequently, the optical element of the instrument, following insertion to the body, tends to accumulate fog, that is to say to accumulate condensed vapor on the surface of the optical element.

One reason that condensation of vapor on an optical element might cause blur, is that the condensed liquid—e.g. water, possibly mixed with body fluids—condenses into droplets which distort the light rays passing through the droplets, thereby ruining the optical quality of the optical element. In other words, each droplet might function as a lens, focusing or diverging or generally distorting the light rays passing therethrough in uncontrolled manner. The total effect of the multitude of droplets on the optical element is thus generating an optically rough surface, thereby preventing obtaining a sharp image from light passing the optical element (or reflecting therefrom).

It is noted that some medical instruments intended for collecting images as described herein may operate outside the visible spectrum of light, namely with non-visible radiation, such as in the near infra-red (IR) spectrum, using optical elements. Such optical elements may suffer deterioration in optical quality due to accumulation of fog similarly to optical elements operating in the visible spectrum. Consequently, the teachings herein should be understood as applicable to optical elements and optical systems in the wide sense, including such that operate with non-visible light. It is further noted that accumulation of fog on a surface of an optical element may affect not only incoming light rays but may also divert or even absorb light rays extending out from an optical device and may thus hinder the operation of light-emitting elements, too. Aspects of the invention thus relate to treating an optical element of a medical device, as detailed below, be it a light collecting device or a light emitting device or a combination of both.

There is thus provided, according to an aspect of some embodiments, a method of treating an optical to prevent it from fogging during use. According to some embodiments the optical element may be an optical element of a medical device that is inserted into the patient's body during use, such as an endoscope. The method includes increasing hydrophilicity of the optical surface of the optical element. In some embodiments the method includes applying a plasma-generating electromagnetic field in close vicinity to the optical element, so as to cause such increase in hydrophilicity. The treatment process may be provided prior using the medical device in the medical procedure. According to some embodiments the method may be applied during the medical procedure as the medical device is removed from the patient's body for treatment and consequently re-introduced to the patient's body.

Increasing hydrophilicity of the optical surface is achieved by increasing the surface tension of the optical surface. As the surface tension of the treated surface increases and approaches the surface tension of water, the contact angle of water droplets on the optical surface decreases, and each droplet tends to spread on the surface and form a more flattened and less curved structure. Complete wetting is achieved by increasing the surface tension of the treated surface to above the surface tension of water, namely above 0.072 N/m. When the surface tension of the treated surface is higher than the surface tension of water, water does not accumulate in droplets on the surface but rather wet the surface, having a contact angle of substantially 0 degrees. Thus, the method eliminates or at least significantly reduces blur due to fogging because condensation of moisture on the hydrophilic surface of the optical element results in a thin and even layer of fluid, thereby maintaining the optical quality of the optical element or at least limiting the degradation of the optical quality. Variations of fluid thickness on the optical element is reduced by the plasma treatment, and thereby variability in optical lengths associated with passing of light through the condensed fluid on the optical element is reduced as well.

The effects of plasma treatment on hydrophilicity of a treated surface are often temporary, so that hydrophilicity of a treated surface tends to decrease over time after the exposure to plasma ends. The method may thus further include using the optical element (or the device in which the optical element is installed)—namely exposing the optical element to moisture—soon after applying the plasma. "Soon after" means within 24 hours, preferably within 6 hours and even more preferably using the optical element within less than an hour after applying the plasma thereto. Moreover, other treatments or processes applied to the instrument's surface after such plasma treatment—sterilization as one example—might decrease or eliminate altogether the effects of the plasma treatment. It is therefore most preferable to apply the method of increasing hydrophilicity according to the teachings herein immediately prior to the medical procedure itself, to apply it on a medical device that has already been sterilized and carry it out under sterile conditions while maintaining the sterility of the medical device.

Medical devices having an optical element that may require plasma treatment as described herein, may have a variety of shapes and sizes. For example, laparoscopes have diameters in the range of 5-10 mm and even beyond. In some laparoscopy procedures, two laparoscopes may be used, typically sequentially, during a single procedure applied to a single patient. For example, entering the abdominal cavity under vision is a known technique which may be performed with a direct vision trocar. A first laparoscope may be placed directly into the trocar sheath so that the trocar end can be seen and followed. As the trocar is pushed and advanced into the peritoneal cavity, each layer of the abdominal wall may be visualized and registered. Following insertion of the trocar, a second laparoscope may be inserted over the trocar to allow inspection of the procedure inside the abdominal cavity. When robotic surgery is employed, the second laparoscope, being part of the robot, is evidently different from the first, and may consequently have a different diameter. It is therefore advantageous that a system, an apparatus or a device for treating an endoscope prior to or during a medical procedure, would be compatible with medical devices intended for use in a same procedure, of various shapes and dimensions. Particularly, it is advantageous if endoscopes having distal segments of different diameters, may be treated according to the teachings herein in a single system, apparatus or device.

Medical devices that may require treatment according to the teachings herein vary greatly not only in dimensions but also in types. For example, some endoscopes—e.g. laparoscopes—are rigid, having a metallic sheath in the distal segment thereof. Other endoscopes—e.g. colonoscopes—are typically flexible, having a non-rigid distal segment, namely such that does not include a metallic tube enveloping the distal segment, thus their distal segment has a substantially dielectric surface. Yet some types of endoscopes exist in both rigid and flexible configurations. Further, endoscopes of various types may have distal segments with very different diameters. For example, pediatric colonoscopes have distal segments with outer diameters in the range of 11-12 mm. Adult colonoscopes are even wider, with an outer diameter of 12.8 mm. Cystoscopes are available in both flexible and rigid configurations, the rigid ones typically having metallic external sheaths. Distal segments' diameters of flexible cystoscopes range between 14 F and 16.2 F (1F=0.33 mm). Diameters of rigid cystoscopes vary between 6 F and 27 F whereas the most commonly used cystoscopes in adults have diameters ranging between 15 F and 25 F. Rigid bronchoscopes may have outside dimeters ranging from 8.2 mm (size 6) for adolescents, down to 3.7 mm (size 2.5) for premature infants. Arthroscopes sheaths (used for diagnosing and treating joint problems) have outer diameters ranging from 6 mm and more, down to 2.5 mm and even 1.9 mm.

It is thus advantageous to have a system that requires only minor adaptations to allow the system treating a large variety of medical devices. It is further advantageous to have a method of treating a medical device according to the teachings herein, that may employ a system capable of providing such a treatment, requiring only minor adaptations to treat medical devices that are different from one another. For example, it is advantageous to have a system including a universal operational unit and an adapter—or a set of adapters—each configured to adapt the universal operational unit to treating a specific medical device or a specific type of medical devices or a group of medical devices used in a same procedure given to a single patient. Different adapters may be needed to treat different types of medical devices or treat devices that differ in some other parameter. It is noted that in the description herein, differences between medical devices may include—but are not necessarily limited to—differences in shape, in dimension and in mechanical structure and electrical properties. Difference in electrical properties may include for example having a distal segment that is electrically conducting (e.g. due to an enveloping metallic sheath) or alternatively a distal segment that is electrically insulating (having a dielectric material on the external surface). It may further be advantageous that such a universal operational unit could identify and/or certify an adapter in use, to adapt certain operational parameters to the specific adapter and/or to the medical device being treated with the adapter.

Figure 21B:
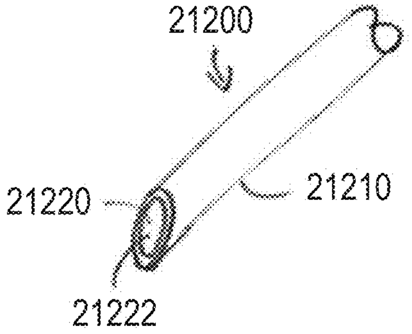
FIG. 21B depicts a perspective view of a distal segment of a medical device, the distal segment having an optical element suitable for plasma treatment with the apparatus of FIG. 21A, consistent with some disclosed embodiments.
Figure 21A:
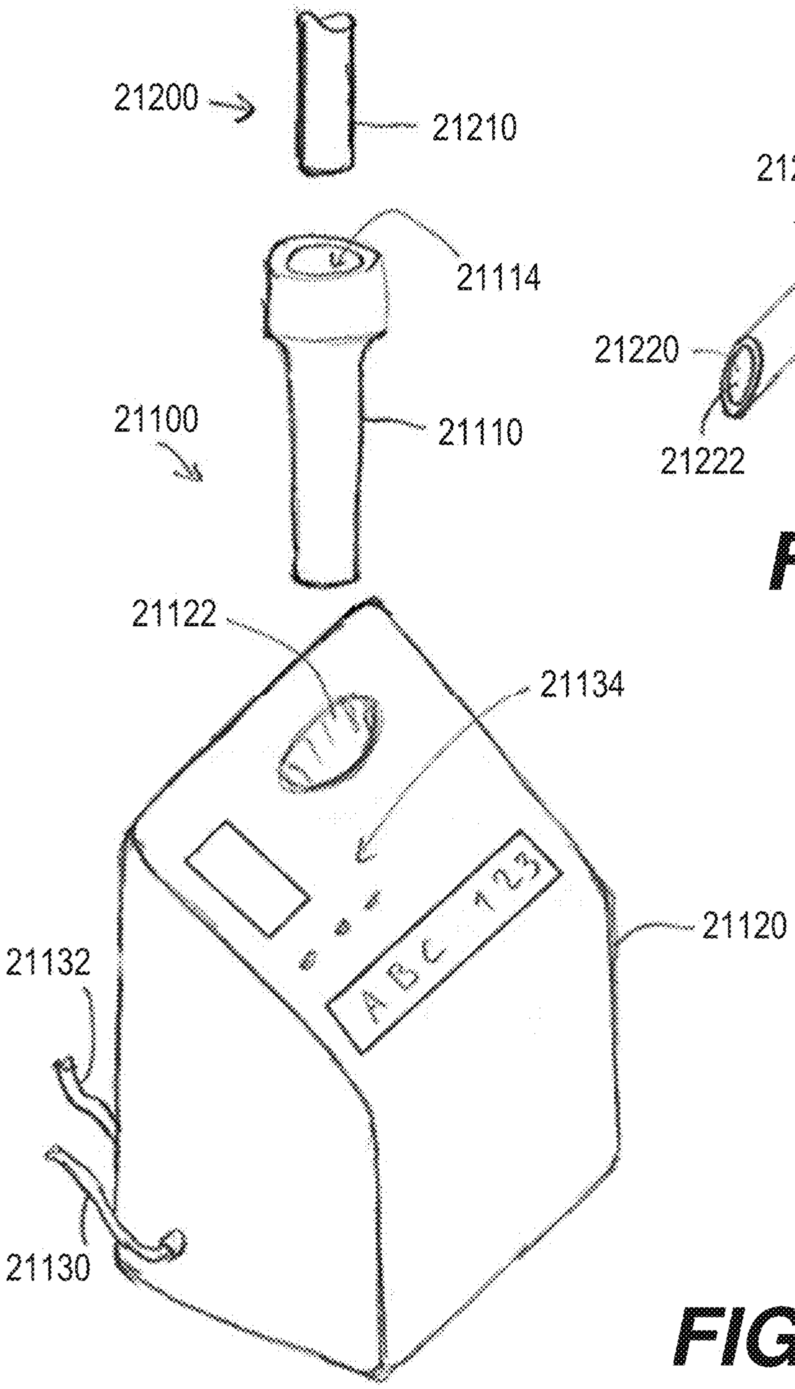
FIG. 21A depicts a perspective view of an apparatus, including an operational unit and an adapter, for preparing a medical device for a medical procedure, consistent with some disclosed embodiments.

FIG. 21A schematically depicts an apparatus 21100, according to an aspect of some embodiments, for preparing a medical device 21200 such as an endoscope, to a medical procedure. Medical device 21200 includes a distal segment 21210, schematically depicted also in FIG. 21B. Distal segment 21210 includes an optical element 21220 configured to enable collecting an image of the surroundings of the optical element. Optical element 21220 may be in some embodiments a transparent sheet such as a window or a lens, of material such as glass or quartz, or plastic such as Perspex, thereby allowing light from the outside of the medical device 21200 to be collected in the inside of medical device 21200, e.g. by a light sensitive device (not shown here) such as a camera. According to some embodiments optical element 21220 may be a mirror, reflecting light (rather than transferring light there through) towards a light collecting apparatus (not shown here) or a light sensitive device. Optical element 21220 includes an optical surface 21222 which during a medical procedure may be exposed to moisture. Consequently, if not treated to prevent fogging, optical surface 21222 may thereby become covered with fog, such fog being the result of accumulation of droplets on the optical surface 21222, e.g. (but not limited to) due to condensation of vapor.

Apparatus 21100 includes an adapter 21110 dimensioned to receive therein distal segment 21210 of the medical device 21200. Apparatus 21100 further includes an operational unit 21120 detached from adapter 21110. Operational unit 21120 includes a slot 21122 configured to receive therein distal segment 21210 of medical device 21200, whereas distal segment 21210 is shrouded within adapter 21110. In other words, for use, distal segment 21210 of medical device 21200 is inserted into adapter 21110, and adapter 21110, with distal segment 21210 being shrouded therein, is inserted into slot 21122. According to some embodiments adapter 21110 is inserted into slot 21122, and then distal segment 21210 is inserted and advanced into adapter 21110.

Operational unit 21120 includes an electric power source (not shown here). Operational unit 21120 is further configured, when distal segment 21210, shrouded within adapter 21110, is positioned inside slot 21122, and upon activation of the power source, to apply inside adapter 21110 inside slot 21122 an electric field suitable for plasma generation proximal optical surface 21222. In some embodiments operational unit 21120 is energized from an external energy source e.g. from a wall outlet via a cable 21130. In some embodiments the operational unit may be energized by an internal energy source such as a battery, for example a rechargeable battery.

According to some embodiments operational unit 21120 may be fluidly associated with a gas pump and additionally or alternatively with a gas reservoir (neither one is shown here) via one or more gas tube(s) 21132. The gas pump and the gas reservoir may be used to controllably evacuate, or to controllably flush with a preferred gas, respectively, a vicinity of the distal segment of the endoscope, to facilitate plasma ignition, as is further detailed and explained below. According to some embodiments, a preferred gas may be helium, argon or nitrogen. According to some embodiments, a gas pressure suitable for plasma ignition after evacuation may be below 0.1 Atm. According to some embodiments, the vicinity of the distal segment of the endoscope may be pumped and evacuated and then flushed with a desired gas. According to some embodiments, the gas pump and/or the gas reservoir, as the case may be, may be optionally situated in the operational unit 21120.

Operational unit 21120 is configured to enable a user of apparatus 21100 to operate and control the apparatus. Operational unit 21120 may thus include command switches 21134, such as physical or virtual switches. Operational unit 21120 may further include indicators 136 for providing a user with required data and information for operating the apparatus, such as indication LEDs, displays and possibly an operating software for providing a user with operating and command screens to allow a user to operate and command the apparatus.

According to some embodiments operational unit 21120 is required to be portable, so it can be freely moved and positioned in any required location in the operation room. In other words operational unit 21120 is required to be operable while being disconnected from any other object, particularly from a fixed object such as a wall outlet. In such embodiments, operational unit 21120 may be energized by an internal battery, and in some embodiments, which require gas pumping or flushing, operational unit 21120 may include a gas pump and/or a gas reservoir (neither are shown here). Embodiments of operational unit 21120 wherein the operational unit is portable as described herein, may be void of cable 21130 and of gas tube(s) 21132, or the cable and the gas tube(s) may be out of use.

Figure 21C:
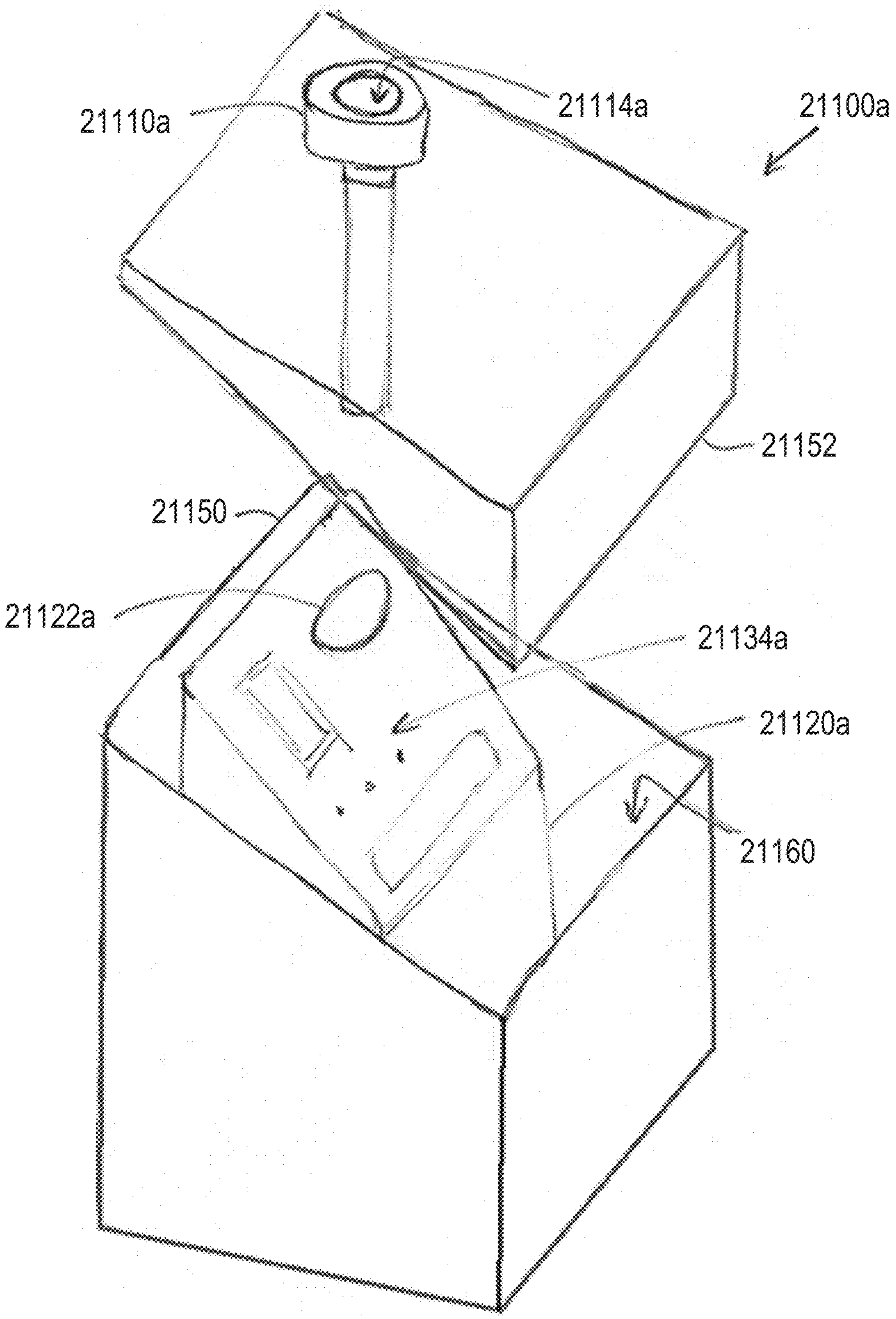
FIG. 21C depicts a perspective view of the apparatus of FIG. 21A inside a sterility cup and covered with a cup cover, consistent with some disclosed embodiments.

FIG. 21C schematically depicts an apparatus 21100*a* including an operational unit 21120*a* which is portable as described above. Apparatus 21100*a* further includes a sterility cup 21150 and an adapter 21110 including a cup cover 21152 configured to close sterility cup 21150. Sterility cup 21150 and cup cover 21152 are intended to provide a sterile environment for treating the medical device, prior or during a medical operation, while using operational unit 21120*a* which may be non-sterile. sterility cup 21150, cup cover 21152 and adapter 21110*a* may be dispensable, disposable or replaceable parts, being configured to be used during a single medical procedure carried out on a single patient. According to some embodiments, the adapter functions as a sterility barrier between the medical device which should be kept clear of contamination, and the operational unit, which may be exposed to contamination and is considered non-sterile.

For use, the sterility cup 21150, cup cover 21152 and adapter 21110 may be supplied in one or more sterile packages which are opened in a sterile environment prior to activating the apparatus. Operational unit 21120 may then be inserted into sterility cup 21150 as is depicted in FIG. 21C. Further, adapter 21110 may be attached to cup cover 21152 as is depicted in FIG. 21C. Additionally or alternatively, adapter 21110 and cup cover 21152 may be supplied being attached together as depicted in the Figure. By inserting the adapter to the slot 21122, while closing the sterility cup 21150 with the cup cover 21152, sterile environment may be provided in the surroundings outside of the cup. In other words, sterility cup 21150, closed by cup cover 21152, functions as a microbially sealed case enclosing the operational unit there within and preventing spreading contamination originating from the operational unit outside the cup. Furthermore, the medical device' distal segment 21210 may be inserted into the sterile adapter 21110, for treatment.

According to some embodiments, inserting the distal segment 21210 to the adapter activates the operational unit, as is further detailed and explained below. In some embodiments, the user may turn on the operational unit using a physical switch, prior to closing the cup with the cup cover, thereby switching the operational unit into a 'standby' state. Then, inserting the distal segment into the adapter, may activate the operational unit to perform plasma treatment. In some embodiments the cup cover 21152, and optionally the sterility cup 21150, are transparent so the user may see the operational indicators 136 and monitor the progress of the treatment.

Figure 22A:
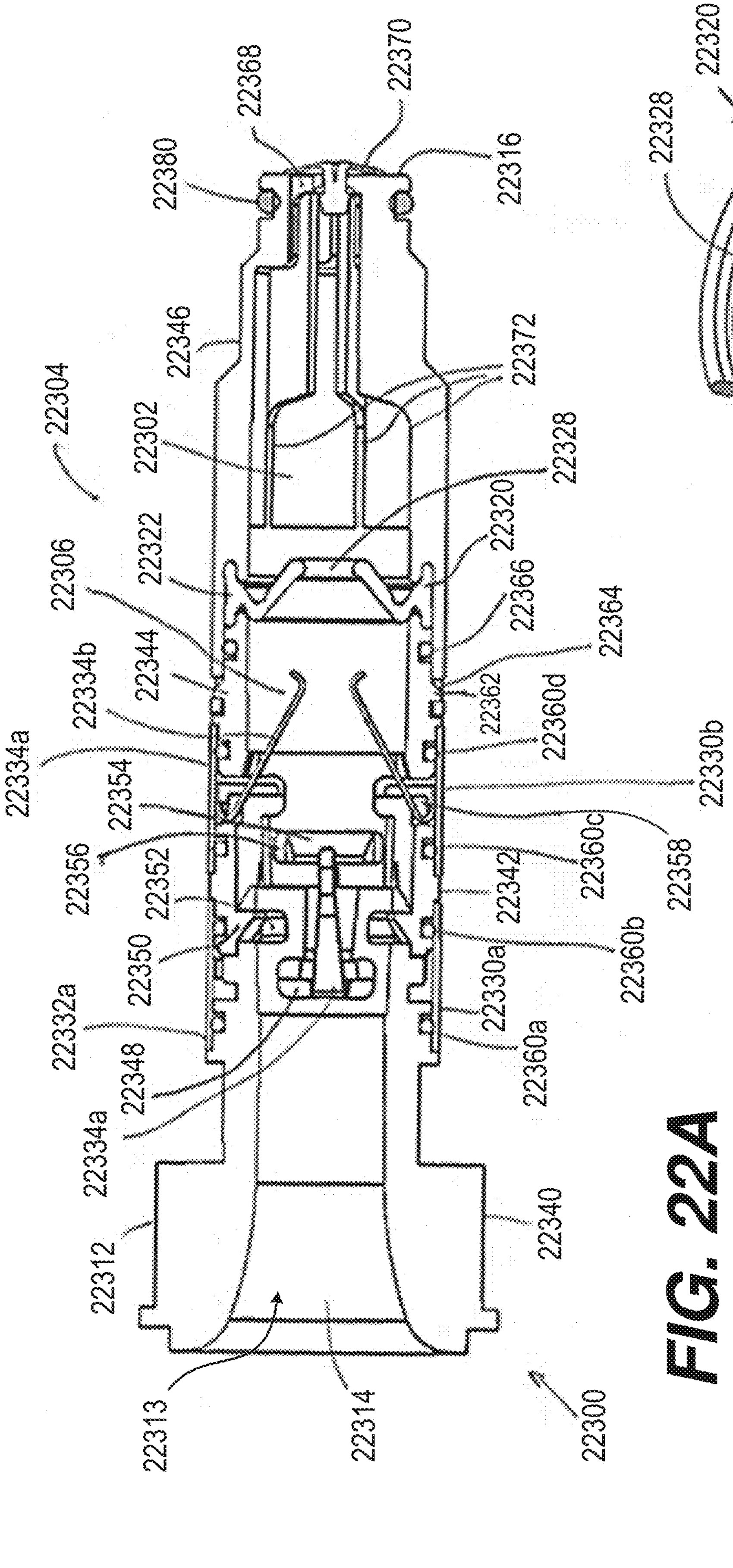
FIG. 22A depicts an internal view of an adapter of an apparatus for preparing a medical device for a medical procedure, consistent with some disclosed embodiments.
Figure 22B:
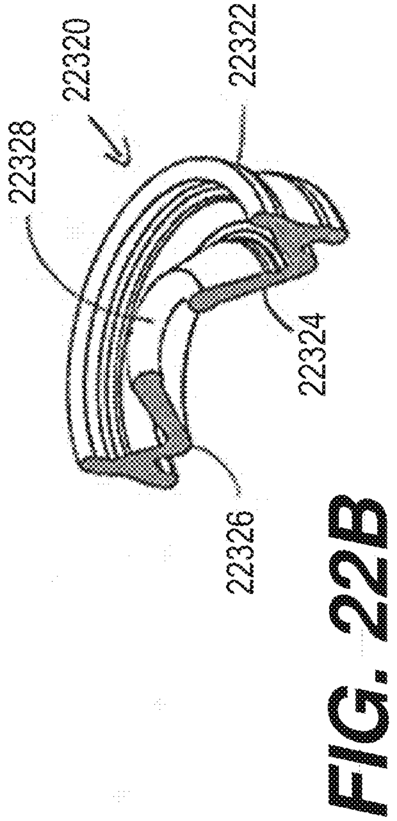
FIG. 22B depicts a cross-sectional, perspective view of an adaptive vacuum seal of the adapter of FIG. 22A, consistent with some disclosed embodiments.
Figure 22C:
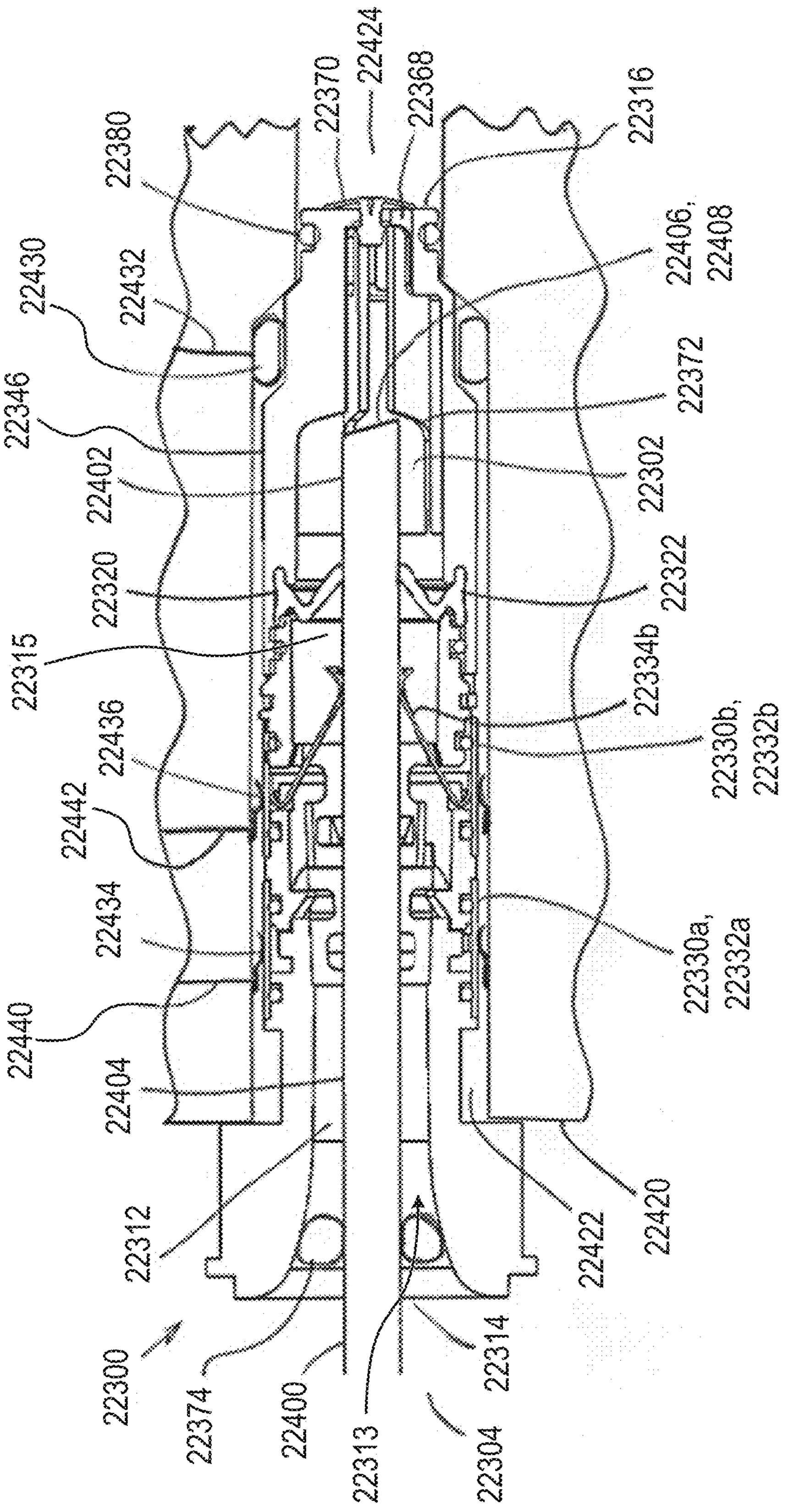
FIG. 22C depicts an internal view of the adapter of FIG. 22A inside an operational unit and housing the distal segment of an endoscope, consistent with some disclosed embodiments.

FIGS. 22A and 22C schematically depict in a cross-sectional view, an embodiment of an adapter 22300 according to an aspect of the invention. Adapter 22300 is particularly suitable for use with a medical device such as an endoscope 22400, depicted schematically inside a hollow cylinder 22312 of adapter 22300 in FIG. 22C whereas adapter 22300 is inside a slot 22422 of an operational unit 22420. Endoscope 22400 includes a distal segment 22402 and an electrically conducting surface—e.g. a metallic surface 22404—at distal segment 22402, proximal an optical element 22406. Optical element 22406 further includes an optical surface 22408, which may be subject to plasma treatment as described herein.

Adapter 22300 is configured to provide a sterile environment to a medical device inserted thereto, hence it is microbially sealed to external contaminants. In other words, adapter 22300 is configured to prevent penetration of contaminants from the surroundings of the adapter—e.g. from the operational unit—through the walls of the hollow cylinder to the inside thereof, when the adapter is in the slot of the operational unit. Further, adapter 22300 is configured to provide a confined space which is gas sealed when the medical device is inserted into the hollow cylinder of the adapter. The confined space which is gas-sealed may be fluidly associated, via one or more pumping openings, to a gas pump, thereby enabling pumping the confined space. Furthermore, adapter 22300 is configured as a disposable part intended for use during one operational procedure to a single patient. Accordingly, adapter 22300 is configured to be manufactured and assembled at a low cost, as is detailed further below.

Drawing attention to FIG. 22A, hollow cylinder 22312 is made substantially of a dielectric material, and extends between a cylinder proximal opening 22314 and a cylinder distal end 22316. Adapter 22300 further includes an adaptive vacuum seal 22320 depicted schematically also in FIG. 22B. Adaptive vacuum seal 22320 is positioned inside hollow cylinder 22312 and adapted to fit an external dimension (e.g. an external circumference) of endoscopes such as endoscope 22400 so as to allow insertion of the endoscope into adapter 22300 using a slight force, e.g. by hand, as is known in the art. Accordingly, adaptive vacuum seal 22320 is configured to hold a pressure difference (or gas concentration difference) between a distal portion 22302 of hollow cylinder 22312 and an outside 22304 of adapter 22300 when endoscope 22400 is positioned inside adapter 22300.

Adaptive vacuum seal 22320 is constructed of a seal outer ring 22322 shaped as a short cylinder, and a seal inner ring 22324 extending radially between seal outer ring 22322 and a seal central opening 22328 of the adaptive vacuum seal 22320, along a wavy curve having at least one crest 22326. Adaptive vacuum seal 22320 may be formed of a flexible material such as rubber or silicone and may therefore fit an external circumference of endoscopes (or other devices) within a range of circumferences. In other words, adaptive vacuum seal 22320 may seal against a first medical device, having a first circumference, inserted into hollow cylinder 22312 and through central opening 22328, and also against a second medical device, having a second circumference different from the first circumference, inserted through central opening 22328 after the first device is removed from the adapter. According to some embodiments, the ratio between the two circumferences may be at least 1.5. Accordingly, if the first and second medical devices have circular cross-sections, then adaptive vacuum seal 22320 may vacuum seal against the first and second medical devices even if their cross-sectional diameters have a ratio of at least 150%. Further, adaptive vacuum seal 22320 may vacuum seal against a devise having a non-circular cross-section.

Adapter 22300 further includes feedthroughs 22330*a* and 22330*b* arranged on hollow cylinder 22312 along the cylinder's longitudinal axis and configured to establish an electrical connection between the outside 22304 of adapter 22300 and an inside 22306 of the hollow cylinder. Feedthroughs 22330 are constructed of a metallic outer ring 22332 (that is, metallic rings 22332*a* and 22332*b* respectively) shaped as a short cylinder and two opposing flexible metallic stripes 22334 extending inwards from the metallic ring and slanted at an angle relative to the plane of the metallic ring. Feedthroughs 22330 may be made of a flexible metal, preferably inert and medically approved, for example stainless steel.

To allow low-cost manufacturing, hollow cylinder 22312 is constructed of four segments—a proximal segment 22340, a first middle segment 22342, a second middle segment 22344 and a cylinder distal segment 22346, which are made of a dielectric material or dielectric materials, and configured to be sealingly assembled together during manufacturing as is explained below.

When the segments are separated, an O-ring 22360*a* is positioned in a corresponding groove in proximal segment 22340 and an O-ring 22360*b* is positioned in a corresponding groove in first middle segment 22342. Feedthrough 22330*a* may then be appended by sliding the metallic outer ring 22332*a* over the O-ring 22360*a* while adjusting the metallic stripes 22334*a* into corresponding proximal segment slits 22348 in proximal segment 22340. The proximal segment and the first middle segment may then be assembled together in a snap-fit manner by sliding the first middle segment into the metallic outer ring 22332*a* while adjusting first protrusions 22350 of first middle segment 22342 into corresponding proximal depressions 22352 in proximal segment 22340. When assembled together, O-rings 22360*a* and 22360*b*, between the proximal segment and the metallic outer ring 22332*a* and between the first middle segment 22342 and the metallic outer ring 22332*a*, respectively, seal the gap between the two segments, and particularly prevent the penetration of contaminants, through the gap, from the outside 22304 into the hollow cylinder 22312.

Second middle segment 22344 may be assembled with first middle segment 22342 in a similar snap-fit manner, as second protrusions 22354 of first middle segment 22342 are adjusted into corresponding second depressions 22356 in second middle segment 22344. The gap between second middle segment 22344 and first middle segment 22342 is sealed by O-rings 22360*c* and 22360*d*, between the first middle segment and the metallic outer ring 22332*b* and between the second middle segment 22344 and the metallic outer ring 22332*b*, respectively. The metallic stripes 22334*b* of feedthrough 22330*b* are adjusted into corresponding first slits 22358 in first middle segment 22342.

Cylinder distal segment 22346 may also be assembled with second middle segment 22344 using a snap-fit manner, as second protrusions 22362 are engaged into distal segment depressions 22364. O-ring 22366 seals the gap between second middle segment 22344 and cylinder distal segment 22346. When second middle segment 22344 and cylinder distal segment 22346 are assembled together, outer ring 22322 of adaptive vacuum seal 22320 is held tight between opposing grooves of second middle segment 22344 and cylinder distal segment 22346 so that inserting a medical device into central opening 22328 or extracting a medical device therefrom does not displace the adaptive vacuum seal from position.

Adapter 22300 includes pumping opening 22368 in cylinder distal segment 22346, allowing pumping gas through the pumping openings from distal portion 22302. Openings 22368 are equipped with a unidirectional valve 22370 allowing extracting gas from the distal portion 22302 through the pumping openings, but preventing penetration of gas through the pumping openings into the distal portion. Thus, unidirectional valve 22370 allows pumping gas from the distal portion while preventing penetration of contamination into the hollow cylinder through the pumping openings.

Figure 23C:
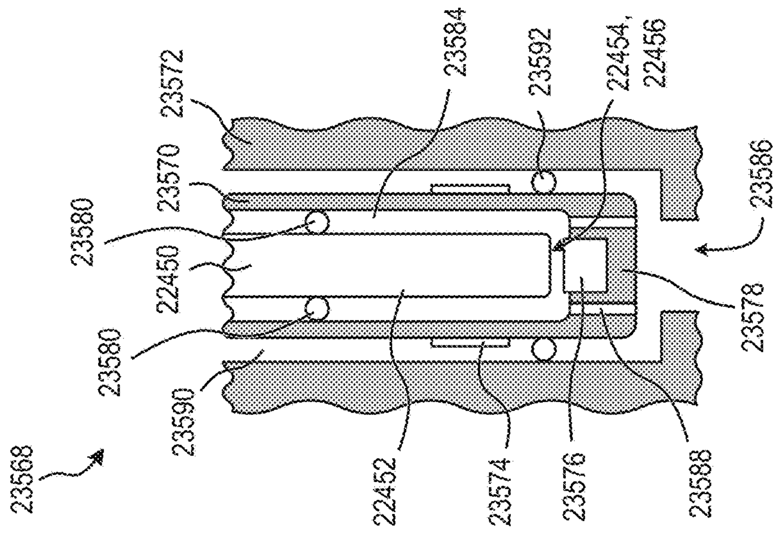
FIG. 23C depicts a further electrode arrangement configured for treating an optical element of a medical device with plasma, consistent with some disclosed embodiments.

FIG. 23C schematically depicts adapter 22300 positioned inside slot 22422 of operational unit 22420, wherein endoscope 22400 is inside the hollow cylinder 22312 of the adapter. Endoscope 22400 is advanced in the hollow cylinder until distal segment 22402 contacts fins 22372 of the adapter. Thus fins 22372 are employed as a stopper for the advancement of the endoscope into the adapter, so as to determine a proper position of the endoscope during plasma generation.

During insertion of endoscope 22400 into the adapter, the endoscope is advanced through central opening 22328 of adaptive vacuum seal 22320. The edges of the inner ring 22324 around the central opening sealingly contact the metallic surface 22404 of the endoscope, thus allowing pumping air from the distal portion 22302 while maintaining a pressure difference across the adaptive vacuum seal. In some embodiments adapter 22300 includes a stabilizer 22374 positioned near opening 22314 of the hollow cylinder and configured to stabilize the endoscope in a center position of the hollow cylinder during insertion into the hollow cylinder and during the endoscope's residing in the adapter. Stabilizer 22374 is configured as an annular ring of a soft and flexible material, e.g., soft silicone or a sponge, and is configured to allow insertion of endoscopes having different diameters into the hollow cylinder. Stabilizer 22374 should not necessarily seal against the walls of the endoscope, but rather maintain the endoscope stabilized along the longitudinal (symmetry) axis of the hollow cylinder so as to prevent deviations of the endoscope from the center of the adaptive vacuum seal 22320 during insertion or during residence of the endoscope therein, so as to prevent air leaks through an accidental gap between the adaptive vacuum seal 22320 and the endoscope.

Operational unit 22420 includes a pumping channel 22424 fluidly associated with a vacuum pump (not shown here) of the operational unit. Channel 22424 is fluidly associated to pumping openings 22368 via unidirectional valve 22370, thus enabling pumping air from the distal portion 22302, to enable or to facilitate generating plasma therein. An external seal 22380 positioned on the external wall of the hollow cylinder, preferably near the distal end 22316 of hollow cylinder 22312, seals against the walls of the slot 22312 thereby preventing air leaks from the outside 22304 via the slot 22312 into the channel 22424 and thus allowing pumping air from the distal portion.

Operational unit 22420 further includes an anode 22430, electrically associated, e.g., via a HV cable 22432, with a RF high voltage (HV) power source (not shown here). Anode 22430 is annular, being arranged around the longitudinal axis of the slot, that is to say around the longitudinal axis of hollow cylinder 22312 and opposite the distal portion 22302 of the hollow cylinder, when the adapter is inserted to the slot. Operational unit 22420 further includes electrical contacts 22434 and 22436, configured to electrically contact the metallic outer rings 22332*a* and 22332*b*, respectively, of feedthroughs 22330*a* and 22330*b* of the adapter. Electrical contacts 22434 and 22436 may be electrically associated, via HV cables 22440 and 22442 respectively, to electrical circuitry of the operational unit. In some embodiments electrical contact 22434 may be electrically associated to the RF HV power source, so that when the RF HV power source is activated, a RF high voltage is applied between anode 22430 and electrical contact 22434. In some embodiments electrical contact 22434 is fixedly connected to a ground potential.

When the distal segment of the endoscope is in the hollow cylinder as detailed above, flexible stripes 22334*a* and 22334*b* electrically contact the metallic surface 22404, so that when the RF HV power source is activated, a plasma generating HV is applied between the anode and the metallic surface 22404. The plasma generating EM field may generate plasma in the vicinity of the optical element 22406. It is noted that the dielectric walls of the cylinder distal segment 22346 are positioned between the anode and the metallic surface 22404 of the endoscope, hence plasma is activated in the distal portion 22302 in a Dielectric Breakdown Discharge (DBD) mode of operation. It is further noted that fins 22372 may be employed to focus and unify the plasma onto the optical surface 22408.

In some embodiments the electrical connection formed by the metallic surface between flexible stripes 22334*a* and 22334*b*, as the endoscope is inserted into the hollow cylinder (and when the adapter is in the slot of the operational unit) may be employed for automatic activation of the HV power source. For example, in embodiments wherein electrical contact 22434 is fixedly connected to a ground potential as described above, electrical contact 22436 may be electrically associated with a controller (not shown here) of the operational unit, wherein the controller may consequently control activating or deactivating the RF HV source. Insertion of the endoscope into the hollow cylinder may force a ground potential at electrical contact 22436 to command the controller activating the RF HV power source thereby generating plasma in the vicinity of the distal segment of the endoscope. Plasma may so be generated for a pre-determined time duration required for a proper plasma treatment as is dictated by the controller, and, alternatively of additionally, plasma may be generated until the endoscope is removed from the hollow cylinder and ground potential ceases at electrical contact 22436.

Figure 23B:
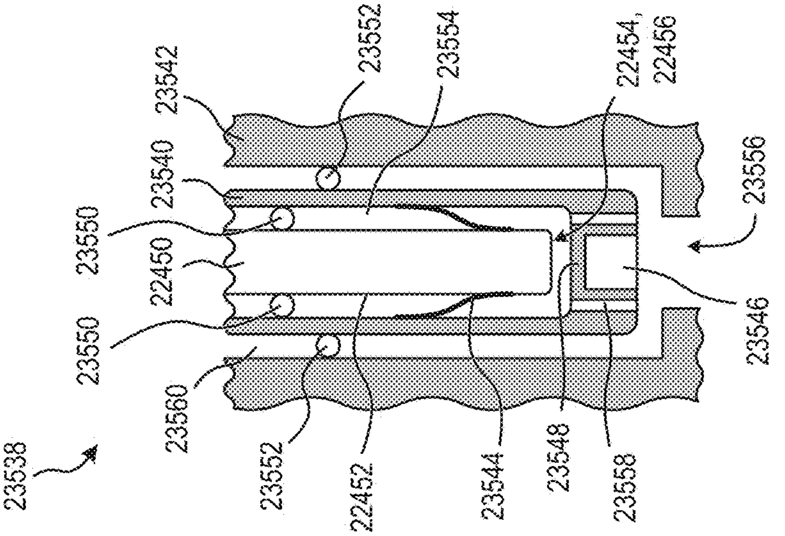
FIG. 23B depicts another electrode arrangement configured for treating an optical element of a medical device with plasma, consistent with some disclosed embodiments.
Figure 23A:
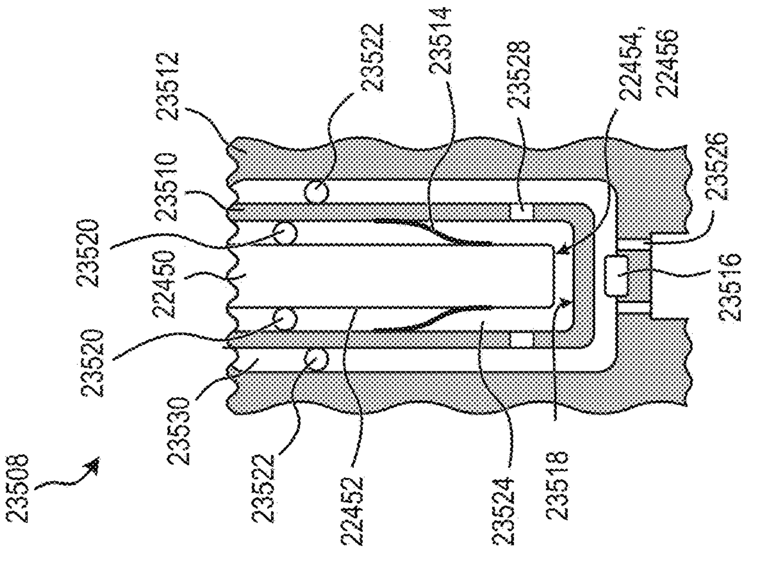
FIG. 23A depicts an electrode arrangement configured for treating an optical element of a medical device with plasma, consistent with some disclosed embodiments.

FIGS. 23A, 23B, and 23C depict schematically various electrode arrangements that can be employed to treat a medical device 22450 having, on a distal segment 22452 thereof an optical element 22454 having an optical surface 22456 that may be treated against accumulation of fog. For the sake of simplicity the distal segment 22452 is depicted as an elongated member, however this should not be construed as limiting and the teachings herein may apply to medical devices having other shapes and dimensions. Medical device 22450 is different from medical device 22400 of FIG. 22C in that medical device 22450 does not have a metallic surface at the distal segment 22452 thereof, in other words the surface of the distal segment is not electrically conducting. FIGS. 23A, 23B, and 23C depict apparatuses 23508, 23538 and 23568, respectively. In the Figures, medical device 22450 is inserted in adapters 23510, 23540 and 23570, respectively, wherein the adapters are positioned in corresponding slots 23530, 23560 and 23590 of operational units 23512, 23542 and 23572, respectively, substantially as described above.

In FIG. 23A, an annular electrode 23514 is included by adapter 23510, and a second electrode 23516 is included by the operational unit 23512. Electric connections of the electrodes to a power source (not shown here) are implied and are not explicitly shown. Annular electrode 23514 may be made flexible to tightly contact the surface of the distal segment of the medical device, or it may be dimensioned to allow a gap between the electrode and the medical device. The second electrode 23516 is shaped as a plate, however other shapes are readily contemplated. In some embodiments the second electrode may be annular, having a ring-like shape. In some embodiments the second electrode may be pointed, having a tip pointing towards the adapter, to amplify the field and focus the field in the vicinity of the center of the optical surface. Because the distal segment of the endoscope does not have a conducting surface, a plasma generating electric field is applied between the electrodes, in other words the geometry of the electrodes and the distance between the electrodes are dominant in determining the field. Plasma is generated in the vicinity of the optical surface 22456 in a DBD mode, due to a dielectric barrier formed by the distal end 23518 of the hollow cylinder. Vacuum seals 23520 and 23522, between the distal segment and the hollow cylinder of the adapter, and between the adapter and the slot of the operational unit, respectively, assist in maintaining vacuum in the distal portion 23524 of the hollow cylinder, substantially as explained above regarding FIG. 22C. Pumping the distal portion is made possible via channels 23526 of the operational unit and via pumping openings 23528 in the adapter.

In FIG. 23B, an annular electrode 23544 and a second electrode 23546 are included by adapter 23540. As in FIG. 23A, electric connections of the electrodes to a power source (not shown here) are implied. Annular electrode 23544 and second electrode 23546 may be shaped similarly to annular electrode 23514 and second electrode 23516, respectively, in FIG. 23A, and according the description above. Plasma is generated in the vicinity of the optical surface 22456 in a DBD mode, due to a dielectric barrier formed by the distal end 23548 of the hollow cylinder. Also, vacuum seals 23550 and 23552 and pumping arrangements are substantially similar to the corresponding seals and pumping method described above to FIG. 23A. In operation, the electrode arrangement of FIG. 23B is advantageous over that of FIG. 23A in that both the annular electrode 23544 and second electrode 23546 are included by the adapter 23540, hence the plasma generating electric field applied between the electrodes is more accurately determined and is less subject to in consistencies or uncertainty involving the relative position of the adapter in the slot. A disadvantage of the arrangement in FIG. 23B is that the adapter 23540 might be more expensive relative to adapter 23510 of FIG. 23A, due to the inclusion of the second electrode 23546 in the adapter.

The electrodes arrangement in FIG. 23C is different from that of FIG. 23B in that an annular electrode 23574 in an adapter 23570 is located outside the hollow cylinder of the adapter 23570 and not inside hollow cylinder as in FIG. 23B. Also, a second electrode 23576 included by the adapter 23570, is not separated from the optical element 22454 of the endoscope by a dielectric layer as in FIG. 23B. Thus, in the arrangement of FIG. 23C, plasma is generated in a DBD mode due to the dielectric layer of the walls of the adapter 23570 next to the annular electrode 23574.

According to an aspect of the invention, it would be advantageous to certify an adapter housing a medical device therein, for activating plasma, prior to such plasma activation and/or during such plasma activation. For example, it may be necessary or at least advantageous to certify that an adapter is properly positioned in the slot of an operational unit, to ensure proper plasma activation inside the adapter. For example it may be advantageous to prevent the generation of high-voltage (intended to induce a plasma-generating EM field or to generate plasma or to maintain plasma inside the adapter), if the adapter in absent from the slot or misplaced in the slot. Such prevention of high-voltage generation may be needed to prevent accidental electrification of a user or undesired arcing, or other undesired results of unsuccessful delivery of the plasma generating field to the adapter. According to some embodiments accurate positioning of the adapter inside the slot may be necessary to ensure suitable coupling of the electric voltage generated by the operational unit to the adapter. For example, it may be necessary or at least desired to ensure electric contact of the RF power supply in the operational unit with electrodes of the adapter. In some embodiments such accurate positioning of the adapter in the slot may be necessary to ensure suitable and proper impedance matching between the adapter and the HV generator. According to some embodiments, it is necessary or at least desirable to ensure that plasma is actually being generated inside the adapter, to validate the plasma treatment and to prevent mistaken use of a medical device that did not undergo plasma treatment.

According to some embodiments it may be necessary, or at least desirable, to associate and apply a particular plasma treatment protocol to a particular type of medical device, by identifying the adapter used with the medical device. In other words, different types of medical devices may undergo plasma treatment in different adapters, wherein each type of medical device may be identified by an identification component embedded in the corresponding adapter. When the adapter is positioned in the slot of the operational unit, the operational unit may identify the type of the medical device by recognizing the identification component of the adapter, thereby preventing applying plasma according to a wrong protocol, and ensuring applying plasma according to a correct and suitable protocol.

Thus, according to an aspect of the invention, an apparatus for plasma treatment of a medical device is provided including an operational unit and an adapter (detachable from the operational unit). The apparatus further includes an adapter certification system including a field transponder attached to one of the operational unit and the adapter, and a receiver, attached to the other of the operational unit and the adapter. A signal transmitted from the field transponder may be received by the receiver, thereby certifying the identity of the adapter or the position thereof relative to the operational unit. According to some embodiments the certification system further includes a transmitter positioned also on the other one of the operational unit and an adapter. According to some embodiments, the transmitter may transmit a transmitted signal to which the field transponder may respond with a response signal which is received by the receiver. The field transponder may be passive (such as a reflector) or may be active (powered by an energy source).

Figure 24:
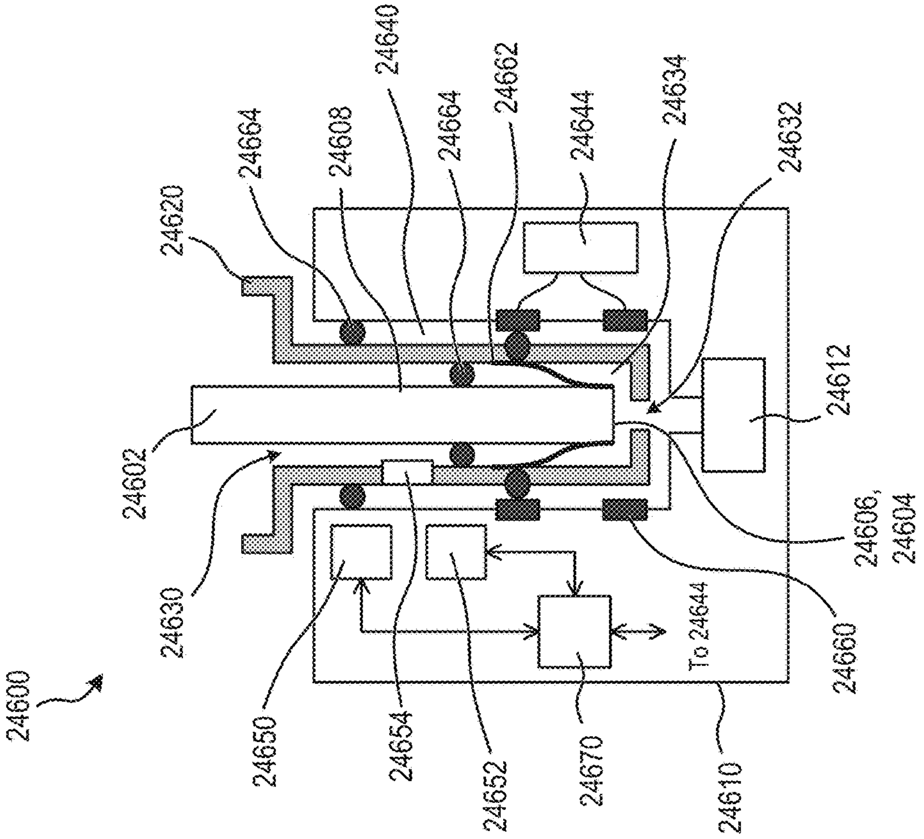
FIG. 24 depicts an apparatus, including an operational unit and an adapter, for plasma treatment of a medical device, consistent with some disclosed embodiments.

FIG. 24 schematically depicts an embodiment of an apparatus 24600 for plasma treatment of a medical device 24602—e.g. endoscope—having an optical element 24604 with an optical surface 24606 at a distal segment 24608 thereof. The optical surface may require treatment as described above prior to using the medical device in a medical procedure. Apparatus 24600 includes an operational unit 24610 and an adapter 24620 detachable from the operational unit. Adapter 24620 contains therein the distal segment 24608 in hollow cylinder 24630. The operational unit includes a slot 24640 configured to receive adapter 24620 therein. It is noted that in some embodiments medical device 24602 may have a non-cylindrical or a non-symmetric shape (at least near the optical element) and the hollow cylinder may have a corresponding non-cylindrical or a non-symmetrical shape, allowing the insertion of the medical device into the hollow cylinder in a single orientation. Yet the external shape of the adapter, as well as the shape of the slot, may be symmetrical, to allow various adapters, corresponding to different types of medical devices, be used with the operational unit. In such cases it may be desired to certify the orientation of the adapter inside the slot.

According to some embodiments hollow cylinder 24630 may be sealed by the medical device 24602 inserted thereto, substantially as described above, thereby being configured to maintain in a distal portion thereof vacuum or an atmosphere that is markedly different in pressure and composition from ambient atmosphere (i.e. air). Hollow cylinder 24630 may be fluidly associated with a vacuum pump or a gas reservoir 24612 of the operational unit via pumping openings 24632 in the adapter, to allow pumping the distal portion 24634 of the hollow cylinder or flush the hollow cylinder with gas as described above. According to some embodiments, hollow cylinder 24630 is not gas-sealed, but only microbially sealed. Apparatus 24600 further includes electrodes 24660, included by the operational unit and electrodes 24662, included by the adapter. Operational unit 24610 further includes a power source 24644 electrically associated with the electrodes 24660 and configured to generate electric power—e.g. power at a high voltage and high frequency—suitable to employ the electrodes 24660 to induce a plasma-generating electric field in hollow cylinder 24630 in the vicinity of optical surface 24606.

Operational unit 24610 further includes a transmitter 24650 configured to transmit a signal towards adapter 24620. According to some embodiments, transmitter 24650 is configured to transmit the signal towards adapter 24620 when adapter 24620 is proximal to slot 24640 or inside slot 24640. Operational unit 24610 further includes a receiver 24652 configured to receive from adapter 24620 a response signal, namely a reflected or transmitted signal respective to the transmitted signal transmitted from transmitter 24650. Adapter 24620 includes a field transponder 24654, configured to reflect or to transmit the response signal, in response to the signal transmitted from transmitter 24650. The signal transmitted towards the adapter and/or from the adapter towards receiver 24652 may be wireless (e.g. an electromagnetic signal such as a RF signal or an optical signal) or may be wired using electrical contacts, as is exemplified herein below.

According to some embodiments transmitter 24650 is a directional transmitter, configured to transmit along a predetermined direction, and field transponder 24654 is localized. In such embodiments only when adapter is suitably positioned in a well-defined position—for example in slot 24640 whereas field transponder 24654 is positioned in the direction of the transmitted signal from transmitter 24650—that transponder 24654 responds with a response signal. According to some embodiments field transponder 24654 is passive, thereby passively reflecting a portion of the transmitted signal. According to some embodiments field transponder 24654 is active thereby actively transmitting a response signal (which may be different in frequency or have a stronger intensity compared to the transmitted signal from transmitter 24650).

According to some embodiments transmitter 24650 is not necessary, and active field transponder 24654 may be configured to actively transmit a certifying signal which certifies the identity of adapter 24620 or the validity thereof or the position thereof when received by receiver 24654. According to some such embodiments, active field transponder 24654 may include a light source, or a directed light source such as a laser or a LED, configured to be directed towards received 24652 in the operational unit when the adapter is suitably positioned in the slot. According to some embodiments active field transponder 24654 may transmit a coded RF signal which may be received by receiver 24652 when the adapter is suitably positioned in the slot. According to some embodiments, active field transponder 24654 may be energized by a portable energy source such as a battery which is included by the adapter. According to some embodiments active field transponder 24654 may be energized—through electric wires and/or wirelessly through induction or otherwise by radiation—by an energy source of the operational unit. According to some embodiments electric contacts on the adapter and on the slot of the operational unit may come into mutual electric contact when the adapter is inserted into the slot, so as to close an electric circuit that allows activation (energizing) active field transponder 24654. According to some embodiments an interaction between transmitter 24650 and transponder 24654 is mutual and not directional, as for example a magnetic force occurring between two magnets.

According to some embodiments operational unit 24610 may further include a controller 24670 functionally associated with receiver 24652 and optionally associated with transmitter 24650. According to some embodiments the controller may receive an output from receiver 24652 indicating receiving a response signal from field transponder 24654. According to some embodiments the controller may be functionally associated with power source 24644, to control power source 24644 to generate power when a valid response signal is received in receiver 24652, and not to generate power when a response signal is not received in receiver 24652.

According to some embodiments, transmitter 24650, receiver 24652 and field transponder 24654 may be shielded, e.g., by an electromagnetic shield (not shown here), to prevent interference of the plasma excitation field with their operation. Each of the transmitter, the receiver and the field transponder may be shielded or not According specifics of the embodiment involved. Such shielding may be required or not depending on several considerations including whether or not interference from the plasma excitation field impairs the operation of the transmitter, the receiver or the field transponder.

Figure 25B:
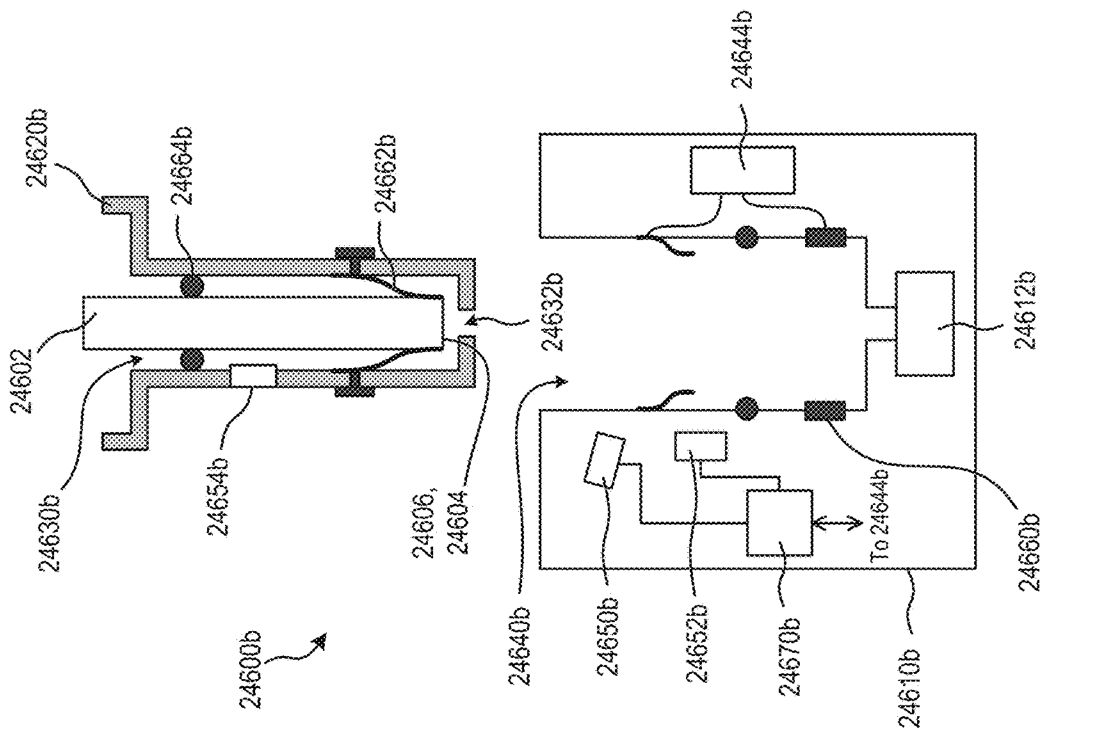
FIG. 25B depicts the apparatus of FIG. 24 in which the adapter includes a transponder with a mirror, consistent with some disclosed embodiments.
Figure 25A:
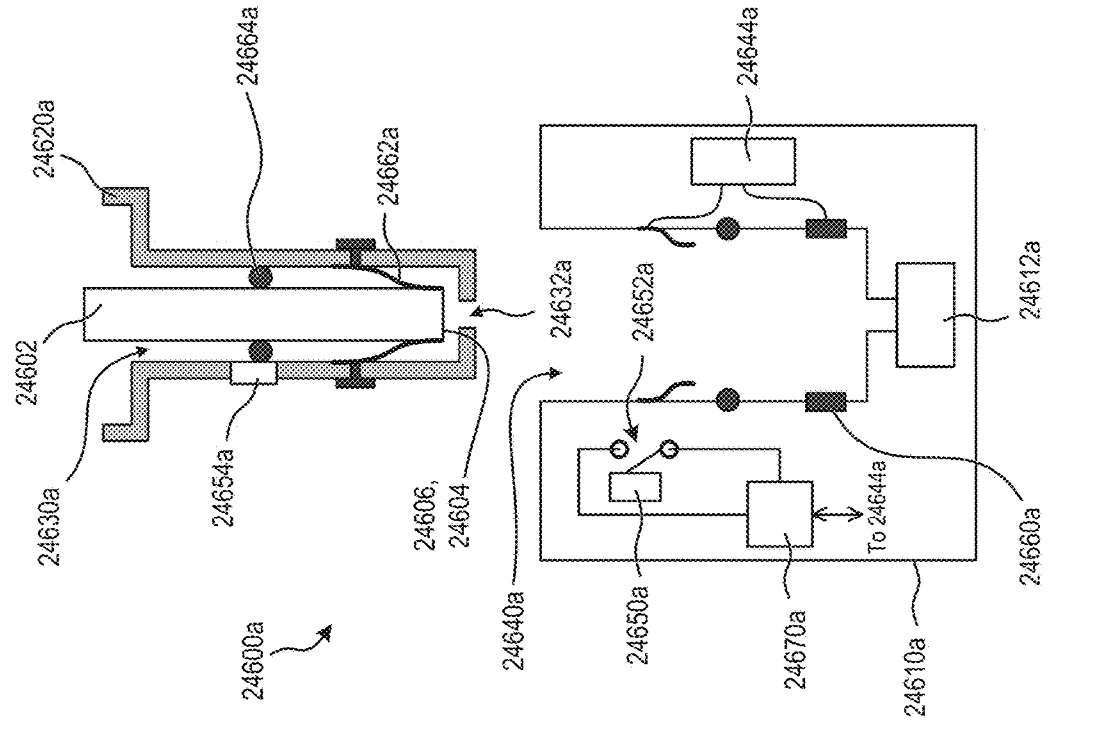
FIG. 25A depicts the apparatus of FIG. 24 in which the adapter includes a transponder with a magnet, consistent with some disclosed embodiments.

FIGS. 25A-25E schematically exemplify some embodiments of corresponding apparatuses configured for certifying an adapter having a field transponder according to the teachings herein. FIG. 25A schematically depicts an embodiment of an apparatus 24600*a* including an operational unit 24610*a* and an adapter 24620*a*. Apparatus 24600*a* exemplifies certifying a correct positioning and/or orientation of the adapter in a slot 24640*a* of the operational unit, employing wireless interaction between a transmitter and a transponder, wherein any one, or both, may be passive, embodied by two magnets. Operational unit 24610*a* includes a ferromagnet 24650*a* positioned near slot 24640*a* and mechanically associated with a switch 24652*a*. Ferromagnet 24650*a* may be a magnetic slab or an electromagnet being energized constantly or towards a validity test of the adapter. Adapter 24620*a* includes a ferromagnetic slab 24654*a* (e.g. a slab of iron or a magnet). When adapter 24620*a* is inserted into slot 24640*a*, a magnetic source between ferromagnet 24650*a* and ferromagnetic slab 24654*a* may displace ferromagnet 24650*a* or otherwise cause switch 24652*a* to close a circuit thereby certifying that adapter 24620*a* is suitably positioned in slot 24640*a*. Switch 24652*a* may be functionally associated with a controller 24670*a*, the controller being configured to control the activation of power source 24644*a* (or otherwise control the application of a plasma-generating EM field in the adapter) as described above, according the state (open or close) of switch 24652*a*. According to various embodiments, both ferromagnet 24650*a* and ferromagnetic slab 24654*a* are magnets; or ferromagnet 24650*a* is a magnet whereas ferromagnetic slab 24654*a* is not a magnet; or ferromagnetic slab 24654*a* is a magnet whereas ferromagnet 24650*a* is not a magnet.

FIG. 25B schematically depicts an embodiment of an apparatus 24600*b* including an operational unit 24610*b* and an adapter 24620*b*, exemplifying certifying a correct positioning and/or orientation of the adapter in a slot 24640*b* of the operational unit, employing wireless interaction between a directional transmitter, a passive transponder and a receiver. Operational unit 24610*b* includes a light source 24650*b* such as a LED or a focused beam source such as a laser. Light produced by light source 24650*b* is directed towards adapter 24620*b*, possibly through a window or an opening (not shown here) in slot 24640*b*. When adapter 24620*b* is suitably positioned inside slot 24640*b*, the light beam produced by the light source is reflected from a reflector 24654*b* (such as a mirror) accommodated on adapter 24620*b*, towards a light detector 24652*b* in operational unit 24610*b*. A detection signal from the light detector may then certify the position of adapter 24620*b* and/or the orientation thereof, inside slot 24640*b*. The detection signal may thereby be used to allow (e.g. by a controller 24670*b*) activation of plasma in the adapter. According to some embodiments, the operational unit does not include a light source whereas the adapter includes a light source (not shown here), for example a directional light source, energized by a battery (not shown here). The light source on the adapter may be configured to direct light towards a light detector of the operational unit, thereby certifying that the adapter is properly positioned in the slot of the operational unit.

Figure 25D:
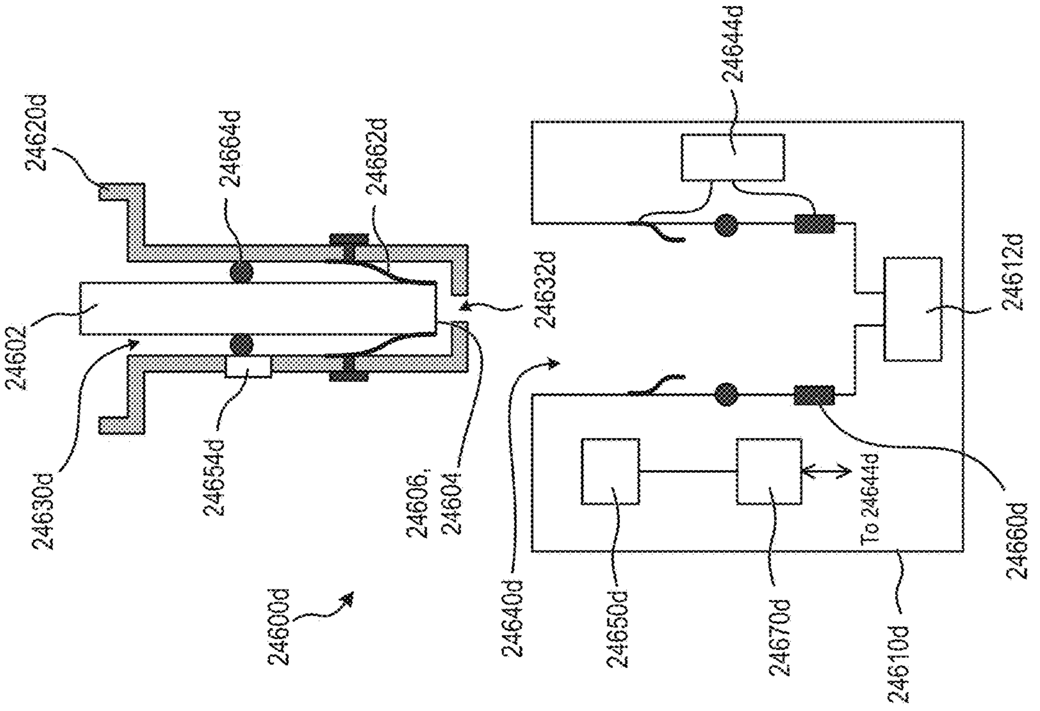
FIG. 25D depicts the apparatus of FIG. 24 in which the adapter includes a transponder with an RFID chip, consistent with some disclosed embodiments.
Figure 25C:
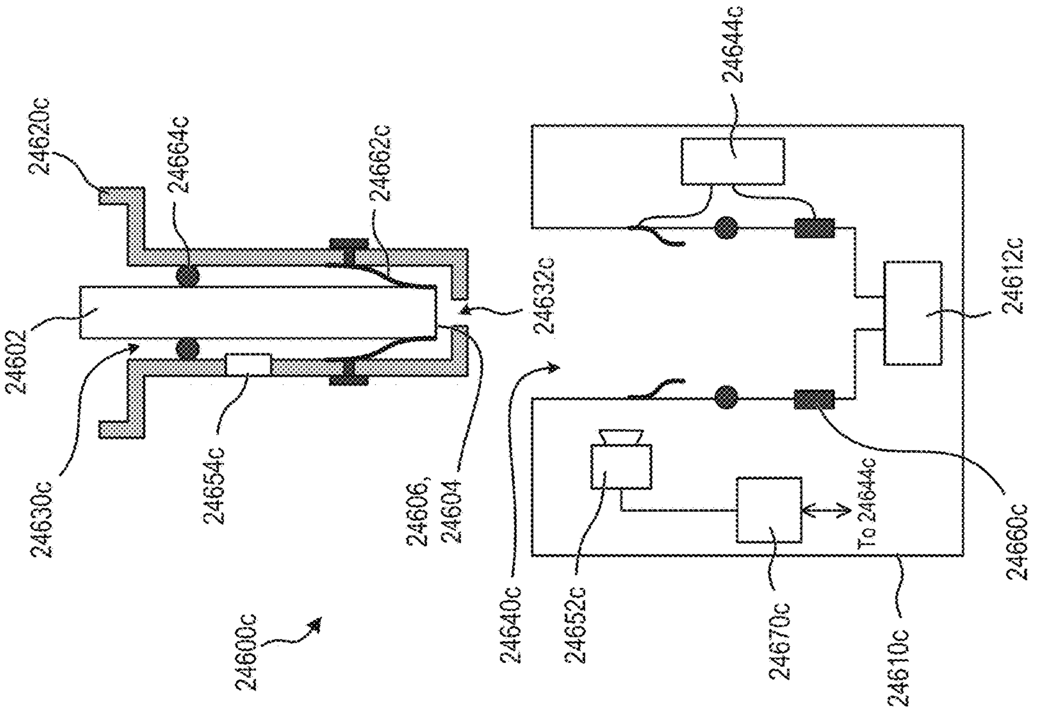
FIG. 25C depicts the apparatus of FIG. 24 in which the adapter includes a transponder with a code sticker, consistent with some disclosed embodiments.

FIG. 25C schematically depicts an embodiment of an apparatus 24600*c* allowing certifying the validity and/or the positioning and/or orientation of a related adapter 24620*c* or the position thereof in slot 24640*c*, without a transmitter. Adapter 24620*c* includes a code sticker 24654*c* whereas an operational unit 24610*c* includes an optical reader 24652*c* configured to read—possibly through a window or an opening (not shown here) of a slot 24640*c*—a code on the code sticker 24654*c* when adapter 24620*c* is suitably positioned inside the slot. Such reading may be accomplished, in some embodiments, using a laser beam as is known in the art. In some embodiments such reading is accomplished without a dedicated light source using ambient light. The code on the code sticker may be decoded by the code reader and a corresponding validation signal may be sent to a controller 24670*c* of the operational unit 24610*c*. Additionally or alternatively, the code on the code sticker may be decoded by the controller (e.g. by way of receiving an image of the code sticker and employing an image analysis algorithm). The code read from the code sticker may be used to validate an identity of the adapter, for example for the purpose of certifying employment of a correct treatment protocol suitable for the specific medical device in the adapter.

FIG. 25D exemplifies an embodiment of an apparatus 24600*d* allowing certifying the validity of a related adapter 24620*d*. An operational unit 24610*d* includes an RFID reader 24650*d* functionally associated with a controller 24670*d*, whereas adapter 24620*d* includes an RFID chip 24654*d*. In some embodiments RFID chip 24654*d* may be activated by radiation received from the RFID reader 24650*d*, rendering the RFID chip substantially independent of a dedicated energy source and responsive from any location around the RFID reader where the received energy is sufficient to activate the RFID chip. According to some embodiments, RFID chip 24654*d* may be activated by a portable energy source of the adapter such as a battery thereby being independent of an energy source external to the adapter. In some embodiments the RFID chip may be energized by an energy source of the operational unit e.g. via electrical contacts or wirelessly, only when the adapter is properly positioned in the slot. When adapter 24620*d* is in the vicinity of operational unit 24610*d*, RFID reader 24650*d* may identify RFID chip 24654*d*, thereby identifying the type of adapter 24620*d*, and, possibly, certifying the adequacy of a plasma activation protocol to the type of medical device inside the adapter. In some embodiments the RFID chip may be configured to register a mere activation of the RFID chip or a transmission of validation response signal towards the RFID reader, thereby enabling monitoring instances of activation or instances of use of the adapter.

Figure 25E:
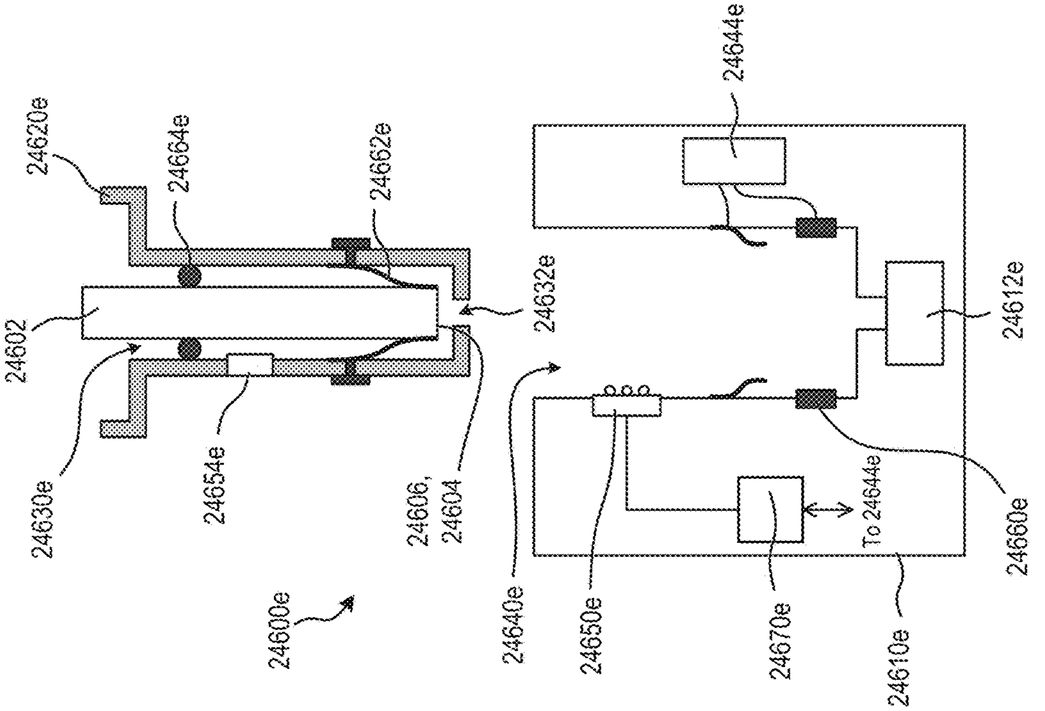
FIG. 25E depicts the apparatus of FIG. 24 in which the adapter includes a transponder with a smart card, consistent with some disclosed embodiments.

FIG. 25E exemplifies an embodiment of an apparatus 24600*e* allowing certifying the validity of a related adapter 24620*e* and the adapter's position in a slot 24640*e* of an operational unit 24610*e*. Adapter 24620*e* includes a smart card 24654*e* (a Universal Integrated Circuit Card (UICC), e.g., a Subscriber Identification Module (SIM)), and operational unit 24610*e* includes a card reader 24650*e* functionally associated with a controller 24670*e*. When adapter 24620*e* is in slot 24640*e*, smart card 24654*e* may be read by a card reader 24650*e* to certify the adequate position of the adapter in the slot and/or to identify the adapter 24620*e* as explained above. To read the smart card, the card reader contacts the smart card, hence accurate positioning of the adapter in the slot is required to validate the adapter and/or the activation of the operational unit. Identification of the adapter may be employed to identify the type of the adapter among several types of adapters, and additionally or alternatively to identify the specific adapter in use. Identification of the adapter may be employed to approve and allow—or to prevent—a plasma treatment protocol according to the type of adapter, and/or to approve and allow—or to prevent—the use of a specific adapter during a specific event of using the apparatus.

There is therefore provided, according to an aspect of the invention, an apparatus (21100, 21100*a*, 23508, 23538, 23568, 24600, 24600*a*, 24600*b*, 24600*c*, 24600*d*, 24600*e*) for preparing a medical device (21200, 22400, 22450, 24602) to a medical procedure. The medical device has a distal segment (21210, 22402, 22452, 24608) intended to be inserted to a patient's body, whereas the distal segment includes an optical member (21220, 22406, 22454, 24604) having an optical surface (21222, 22408, 22456, 24606). It should be understood that, generally, each of the medical devices may be treated by each of the apparatuses, unless explicitly dictated otherwise by the description (for example medical device 22450 may not be treated by adapter 22300 of FIG. 22A, which is explicitly configured to be used with a medical device having a metallic surface at the distal segment thereof).

The apparatus includes an operational unit (21120, 21120*a*, 22420, 23512, 23542, 23572, 24610, 24610*a*, 24610*b*, 24610*c*, 24610*d*, 24610*e*), an adapter (21110, 21110*a*, 22300, 23510, 23540, 23570, 24620, 24620*a*, 24620*b*, 24620*c*, 24620*d*, 24620*e*) detached from the operational unit and at least one electrode (22430, 23516, 23546, 23576, 24660, 24660*a*, 24660*b*, 24660*c*, 24660*d*, 24660*e*) which may be included by the operational unit (anode 22430) or by the adapter (in adapters 23540 and 23570) or by both (in apparatuses 23508, 24600, 24600*a*, 24600*b*, 24600*c*, 24600*d*, 24600*e*). The operational unit may include an EM power source (24644) and a housing including a slot (21122, 21122*a*, 22422, 23530, 23560,590, 24640, 24640*a*, 24640, 24640*b*, 24640*c*, 24640*d*, 24640*e*) configured to receive the adapter in the slot. The operational unit further includes an adapter identifier (24652, 24650*a*, 24652*b*, 24652*c*, 24650*d*, 24650*e*), configured to receive an identification signal from a corresponding transponder (24654, 24654*a*, 24654*b*, 24654*c*, 24654*d*, 24654*e*), and a controller (24670) functionally associated with the adapter identifier.

The adapter includes a hollow cylinder (22312, 23510, 23540, 23570, 24630, 24630*a*, 24630*b*, 24630*c*, 24630*d*, 24630*e*), extending between an opening (21114 in adapter 21110, 21114*a* in adapter 21110*a*, 22314) and a distal end (22316, 23518, 23548, 23578) of the hollow cylinder (the opening is not explicitly shown in FIGS. 23A through 23C, 24, and 25A-25E and the cylinder distal end is not explicitly enumerated in FIGS. 24 and 25A-25E). The opening is dimensioned to allow insertion of the distal segment into the hollow cylinder. The adapter includes a seal (22320, 23520, 23550, 23580, 24664, 24664*a*, 24664*b*, 24664*c*, 24664*d*, 24664*e*) positioned in the hollow cylinder and defining a distal portion (22302, 23524, 23554, 23584, 24634) of the hollow cylinder between the seal and the distal end of the hollow cylinder. The seal is dimensioned to sealingly fit an external circumference of the distal segment when the distal segment is inserted into the hollow cylinder. The adapter further includes the transponder, being configured to transmit the identification signal identifying the adapter or a position thereof relative to the adapter identifier, when the adapter is in the slot. The apparatus is configured, when the distal segment is in the hollow cylinder of the adapter, the adapter is in the slot and the adapter identifier receives the identification signal from the transponder, to apply a plasma-generating EM field in the distal portion of the hollow cylinder by the at least one electrode, the electrode receiving EM power from the power source.

It should be understood that identification systems including an adapter identifier of the operational unit and a transponder of the adapter, which are depicted explicitly and explained in detail in apparatuses 24600 and 24600*a*-24600*e*, may be employed and used in all apparatuses of the invention including apparatuses 21100, 23508, 23538 and 23568.

In some embodiments the transponder includes at least one selected from the group consisting of a magnet (24654*a*), a mirror (24654*b*), a light source, an optical filter, a code sticker (24654*c*), a RFID chip (24654*d*) and a smart card (24654*e*).

In some embodiments the seal is a microbial seal (22320, 23520, 23550, 23580, 24664, 24664*a*, 24664*b*, 24664*c*, 24664*d*, 24664*e*). In some embodiments the seal is a vacuum seal (22320, 23520, 24664, 24664*a*, 24664*b*, 24664*c*, 24664*d*, 24664*e*).

In some embodiments the seal (22320, 24664, 24664*a*, 24664*b*, 24664*c*, 24664*d*, 24664*e*)) is configured to sealingly fit the distal segment along a non-circular circumference. In some embodiments the seal (22320) is configured to sealingly fit distal segments having various circumferences. In some embodiments the seal (22320) is configured to sealingly fit distal segments having circular circumferences in a range between a first circumference L and a second circumference greater than 1.5 L.

In some embodiments the adapter (22312) further includes an external vacuum seal (22380) positioned along an external circumference of the adapter and configured to seal a gap between the adapter and an inner wall of the slot (22422) of the operational unit (22420), when the adapter is inserted into the slot.

In some embodiments the adapter (22300, 23510, 23540, 23570, 24620, 24620*a*, 24620*b*, 24620*c*, 24620*d*, 24620*e*) further includes a pumping opening (22368, 23528, 23558, 23588, 24632, 24632*a*, 24632*b*, 24632*c*, 24632*d*, 24632*e*) on the distal portion of the hollow cylinder, configured for enabling pumping gas from the distal portion of the hollow cylinder or flowing gas thereto (e.g. apparatuses 23538, 23568).

In some embodiments the operational unit (24610, 24610*a*, 24610*b*, 24610*c*, 24610*d*, 24610*e*) further includes a pump (24612, 24612*a*, 24612*b*, 24612*c*, 24612*d*, 24612*e*) configured to pump gas from the distal portion (24634, 24634*a*, 24634*b*, 24634*c*, 24634*d*, 24634*e*) of the hollow cylinder, via the pumping opening, when the adapter is in the slot.

In some embodiments the operational unit further includes a gas port configured to fluidly associate a gas reservoir or a gas pump, external to the operational unit, to the pumping opening of the hollow cylinder, when the adapter is in the slot.

In some embodiments the pumping opening (22368) is equipped with a microbial barrier configured for preventing penetration of contamination into the hollow cylinder through the venting opening during use. In some embodiments the microbial barrier is a sterility filter. In some embodiments wherein the microbial barrier is a unidirectional valve (22370).

In some embodiments the operational unit (21120*a*) further includes a rechargeable battery.

In some embodiments the apparatus (21100*a*) further including a sterility container (21150) detached from the operational unit (21120*a*) and from the adapter (21110*a*), having a container opening (21160) and being dimensioned to house the operational unit there inside when the adapter (21110*a*) is in the slot (21122*a*). In some embodiments the adapter further includes a sterility screen (21152) having a screen opening coinciding with said opening of the hollow cylinder (21114*a*), the sterility screen being dimensioned and configured to fit and close the container opening (21160) when the adapter is in the slot.

In some embodiments the at least one electrode (23544, 23546, 23574, 23576) is included by the adapter (23540, 23570). In some embodiments the at least one electrode (22430) is included by the operational unit (22420).

In some embodiments the adapter (22300) includes an electrical feedthrough (22330*a*, 22330*b*) electrically connecting an external contact (22332*a*, 22332*b*) on the outside of the adapter with an electrical contact (22334*a*, 22334*b*) on the inside (22306) of the hollow cylinder, the electrical contact being configured to contact the distal segment (22402) when the distal segment is received inside the hollow cylinder.

In some embodiments the plasma generating field is applied between the at least one electrode (22430) and a metallic surface (22404) on the distal end (22402), the metallic surface being in contact with the electrical contact (22434*a*, 22434*b*) of the adapter (22300).

There is further provided, according to an aspect of the invention, an adapter (21110, 21110*a*, 22300, 23510, 23540, 23570, 24620, 24620*a*, 24620*b*, 24620*c*, 24620*d*, 24620*e*) for use with an operational unit (21120, 21120*a*, 22420, 23512, 23542, 23572, 24610, 24610*a*, 24610*b*, 24610*c*, 24610*d*, 24610*e*) for preparing a medical device as described above for a medical procedure, the adapter being detachable from the operational unit and from the medical device. The adapter includes a hollow cylinder extending between an opening dimensioned and configured to receive the distal segment of the medical device and a distal end of the hollow cylinder. The adapter further includes a seal (22320, 23520,

23550, 23580, 24664, 24664*a*, 24664*b*, 24664*c*, 24664*d*, 24664*e*) positioned in the hollow cylinder and defining a distal portion (22302, 23524, 23554, 23584, 24634) of the hollow cylinder between the seal and the distal end of the hollow cylinder, the seal dimensioned to sealingly fit an external circumference of the distal segment when the distal segment is inserted into the hollow cylinder. And the adapter further includes a transponder (24654, 24654*a*, 24654*b*, 24654*c*, 24654*d*, 24654*e*) configured to transmit an identification signal identifying the adapter when the adapter is in the slot.

In some embodiments the transponder (24654*c*, 24654*d*, 24654*e*) stores information identifying the adapter. In some embodiments the transponder (24654*d*, 24654*e*) is configured to transmit the identification signal in response to a coded signal, thereby identifying the adapter.

In some embodiments the adapter (22300, 24620, 24620*a*, 24620*b*, 24620*c*, 24620*d*, 24620*e*) further includes an electrical feedthrough (22330) electrically connecting an external contact (22332) on the outside of the adapter to an electrical conductor (22334, 24622*a*, 24622*b*, 24622*c*, 24622*d*, 24622*e*) on the inside of the hollow cylinder.

In some embodiments the electrical conductor (22334) is configured as an electrical contact (22334*a*, 22334*b*) configured to contact an external surface (22404) of the distal segment of the medical device when the distal segment is received in the hollow cylinder. In some embodiments the electrical conductor is configured as an electrode (24622*a*, 24622*b*, 24622*c*, 24622*d*, 24622*e*).

In some embodiments the adapter further includes a stopper (22372) configured to limit advancement of the distal segment of the medical device into the hollow cylinder. In some embodiments the stopper is employed as a dielectric barrier between the first electrode and the second electrode, thereby assisting in focusing plasma towards the optical member of the medical device, during use.

In some embodiments the adapter further includes a hollow stabilizer (22374) positioned near the opening (22314) and configured to receive the distal segment of the medical device there through and adapted to fit an external circumference of the medical device to thereby stabilize the medical device in the hollow cylinder.

In some embodiments the adapter (21110*a*) further includes a rigid sterility screen (21152) having a screen opening coinciding with the opening (21114*a*) of the hollow cylinder.

In some embodiments the seal (22320, 24664, 24664*a*, 24664*b*, 24664*c*, 24664*d*, 24664*e*) is configured to sealingly fit the distal segment along a non-circular circumference. In some embodiments the seal (22320) is configured to sealingly fit distal segments having various circumferences. In some embodiments the seal (22320) is configured to sealingly fit distal segments having circular circumferences in a range between a first circumference L and a second circumference greater than 1.5 L.

In some embodiments the adapter (22300, 23510, 23540, 23570, 24620, 24620*a*, 24620*b*, 24620*c*, 24620*d*, 24620*e*) further includes a pumping opening (22368, 23528, 23558, 23588, 24632, 24632*a*, 24632*b*, 24632*c*, 24632*d*, 24632*e*) at the distal portion of the hollow cylinder enabling pumping gas from—or flowing gas into—the inside of the hollow cylinder through the pumping opening when the distal segment of the medical device is inside the adapter. In some embodiments the adapter (22300) further includes a sterility barrier fluidly associated with said distal opening and configured for preventing penetration of contamination from the outside of the adapter to the inside of the hollow cylinder through the distal opening. In some embodiments the sterility barrier is a unidirectional valve (22370). In some embodiments the sterility barrier is a sterility filter.

In some embodiments the adapter (22300) further includes an external vacuum seal (22380) positioned along an external circumference of the adapter and configured to seal a gap between the adapter and an inner wall of a slot of said apparatus, when the adapter is inserted into the slot.

There is yet further provided, according to an aspect of the invention, an adapter (22300) for use with an operational unit (22420) for preparing a medical device (22400) as described above for a medical procedure, the adapter being detachable from the operational unit and from the medical device. The adapter includes a hollow cylinder (22312) extending between an opening (22314) dimensioned and configured to receive the distal segment of the medical device, and a distal end (22316) of the hollow cylinder. The adapter further includes a seal (22320) positioned in the hollow cylinder and defining a distal portion (22302) of the hollow cylinder between the seal and the distal end of the hollow cylinder. The seal is dimensioned to sealingly fit distal segments having external circumferences in a range between a first circumference L and a second circumference greater than 1.5 L. And the adapter further includes an electrical feedthrough (22330*a*, 22330*b*) electrically connecting an external contact (22332*a*, 22332*b*) outside of the hollow cylinder to an electrical conductor (22334*a*, 22334*b*) inside the hollow cylinder.

There is also provided, according to an aspect of the invention, a method of preparing at least a first medical device and a second medical device for a medical procedure carried out on a single patient. Each of the medical devices has a distal segment including an optical member. The circumference of the distal segment of one of the first and second medical devices is L and the circumference of the distal segment of the other medical device is greater than 1.2 L. The method includes providing a plasma chamber (distal portion 22302 of adapter 22300 when the adapter is in the slot 22422) including at least one electrode (22430) electrically associated with a power source and configured for applying in the plasma chamber a plasma generating EM field. The plasma chamber also has an opening (22314) and a seal (22320) dimensioned and configured to receive the distal segment of each of the first and second medical devices in the opening through the seal. The method further includes inserting the distal segment of the first medical device to the plasma chamber through the opening so that the seal and the distal end together seal the opening. The method further includes supplying EM power from the power source to the at least one electrode, thereby applying a plasma generating EM field and generating plasma in the vicinity of the optical member. And the method further includes repeating said steps of inserting the distal segment and supplying EM power for the second medical device. In some embodiments the medical devices are endoscopes, one having a distal member with a diameter D and the other having a distal member with a diameter 2D.

And there is yet further provided, according to an aspect of the invention, an adaptive seal (22320) made of a flexible material. The seal is shaped as a combined outer tube (22322) and an inner annular ring (22324) extending radially along a wavy curve having at least one crest (22326), between the outer tube and a central opening (22328) of the seal. The adaptive seal is thereby configured to sealingly fit to an external surface of a member positioned in the central opening and having a smooth circumference within a range between a first circumference L and a second circumference 1.5 L. A smooth circumference herein means a convex curve outlining aa convex shape and having no corners or sharp edges.

In some embodiments the outer tube is a circular cylinder. In some embodiments the flexible material is silicone. In some embodiments the flexible material has a hardness of between 25 to 90 Shore. In some embodiments the inner annular ring extends radially along a wavy curve having at least two or at least three crests.

And there is yet further provided, according to an aspect of the invention, a method of sealing a tube using a member inserted into the tube. The method includes providing adaptive seal 22320; disposing the adaptive seal in the tube (e.g. hollow cylinder 22312) to be sealed so that the outer tube (22322) of the seal coincides with the inner wall of the tube; tightening the adaptive seal to the tube using at least one smaller tube (an edge of second middle segment 22344) inserted into the outer tube of the seal, so a gap between the tube and the smaller tube is sealed. The method further includes inserting the member to the central opening of the adaptive seal. In some embodiments the smaller tube is a ring.

Some disclosed embodiments involve the treatment of equipment. As used herein, "equipment" may include any component or device configured to perform a particular function. As a non-limiting example, equipment may include medical devices, or devices configured for examining, diagnosing, and/or treating the body. According to some embodiments, an apparatus is provided for treating equipment. Such an apparatus may include any component or device configured to administer a substance and/or energy to equipment or to otherwise change one or more properties of equipment. For example, non-limiting examples of apparatuses for "treating equipment" may include apparatuses for cleaning or sterilizing equipment, changing a surface quality of equipment (e.g., making equipment more hydrophilic or hydrophobic), altering the appearance of equipment, or depositing material on or removing material from equipment.

Some embodiments may involve treating equipment in a vacuum environment. A "vacuum environment" may include any fully-enclosed or partially-enclosed space with sub-atmospheric pressure. For example, a vacuum environment may have a pressure slightly below atmospheric pressure or at a sub-atmospheric pressure sufficient to enable plasma formation. A "vacuum environment" may additionally or alternatively refer to a sealed volume from which substantially all gas and other materials have been removed (e.g., with a vacuum pump and within the constraints of the vacuum pump employed). In some embodiments, the apparatus disclosed herein may treat equipment while the apparatus and/or equipment is situated in a vacuum environment. Additionally, or alternatively, the apparatus disclosed herein may utilize a vacuum environment in the course of treating the equipment. Some non-limiting examples of locations of formation of a vacuum environment include the inside 322 of sheath 410 (FIGS. 3A-3C), closed space 520 (FIG. 4), plasma generation zone 716 (FIG. 7), distal portion 22302 of hollow cylinder 22312 (FIG. 22C), and/or distal portion 24634 of hollow cylinder 24630 (FIG. 24).

Some embodiments may involve treating equipment of differing dimensions. As used herein, a "dimension" may include any measurable extent of a thing, including and not limited to length, width, breadth, depth, height, diameter, radius, circumference, surface area, cross-sectional area, distance, hypotenuse, and arc length. Thus, the apparatus disclosed herein may be configured to treat multiple pieces of equipment that vary in one or more dimensions. In some embodiments, one or more components of the disclosed apparatus may be adjustable or pliable in order to accommodate equipment of differing dimensions.

Some disclosed embodiments include an enclosure having a channel. Such an enclosure may include any structure, casing, barrier, frame, or cover configured to envelop or surround another device or component, either partially or entirely. For example, an enclosure may be configured to provide an airtight or hermetically-sealed environment within which another device or component may be placed. In some embodiments, a channel may include a "bore," as described herein, as well as any opening or passage from an area outside of the enclosure into an internal space or volume of the enclosure. Some non-limiting examples of an enclosure having a channel include hollow cylinder 312 (which has an interior space or channel), sheath 800 having internal channel 714 (FIGS. 8A-8B), sheath 718 having an internal channel 1104 (FIG. 11), and hollow cylinder 22312 having an internal channel 22313 (FIG. 22A).

In some embodiments, the enclosure is a disposable sheath. As used herein, the term "disposable" may refer to an article intended to be used only once (or for a limited amount of time) and then discarded. For example, a "disposable" article may be intended for use in a single operation or procedure, or inserted one time into a patient's body and subsequently removed and discarded. As discussed elsewhere in the present disclosure, the term "sheath" may refer to a covering or supporting structure that fits closely around an object. For example, a sheath may enclose an optical element of a medical instrument. In one exemplary embodiment, the sheath may be a slender, flexible, disposable tube that retains within the sheath a portion of the medical instrument when the medical instrument is inserted into another device or into the body of a patient. For example, protecting shroud 110 in FIG. 1A, protecting shroud 310 in FIG. 2, and sheath 800 in FIG. 8A are some non-limiting examples of sheaths that may be disposable, in accordance with disclosed embodiments. As another example, protecting shroud 310 may be sized (e.g., dimensioned) to receive distal end 382 of endoscope 380 (FIG. 2), where distal end 382 is provided with viewport 390. Protecting shroud 310 may, accordingly, be another example of a disposable sheath.

In some embodiments, the channel is configured for receiving elongated tools. As used herein, the term "receiving" may refer to a capability for holding, enclosing, supporting, or otherwise containing an object. For example, an object may be inserted into the channel from an area outside of the enclosure (thus, the channel may receive the object) and, optionally, may also be removed from the channel. As also used herein, an elongated tool may include a device or component having a length that is larger than its width. For example, an elongated tool may have a length that is twice as long as its width, three times as large as its width, or any other desired ratio between its length and width. Some non-limiting examples of an elongated tool may include endoscopes, needles, catheters, tubes, syringes, guide wires, and electric wires. In some embodiments, the channel may be sized and configured to receive the entirety of an elongated object. Additionally, or alternatively, the channel may be sized and configured to receive a portion of an elongated tool while another portion of the elongated tool remains outside of the channel.

In some embodiments, the channel is configured for receiving elongated tools of varying diameters. For example, the channel may be configured to receive multiple elongated tools, each tool having a different outer diameter. The multiple elongated tools may be received sequentially within the channel (e.g., a first tool is inserted and removed, then a second tool is inserted, etc.). Additionally, or alternatively, multiple elongated tools may be received within the channel simultaneously (that is, multiple tools may be received within the channel at the same time). As a non-limiting example, FIG. 12 depicts a sheath 800 having an opening 1210 and an internal channel 1212. Channel 1212 may be configured to receive multiple elongated tools 1220 and 1222 (e.g., endoscopes), which may have different outer diameters. For example, tool 1220 may have an outer diameter of "2 d," which is twice as large as outer diameter "d" of tool 1222. Despite having varying diameters, elongated tools 1220 and 1222 may both be passed through opening 1210 into channel 1212.

In some embodiments, the enclosure is divided into a vacuum chamber region and a non-vacuum region. As used herein, a vacuum chamber region may refer to a space within the enclosure having a sub-atmospheric pressure. For example, a vacuum chamber region may refer to a space designed to permit some or all of the gas and other materials to be removed (e.g., with one or more vacuum pumps), thus decreasing the pressure within the vacuum chamber region to a sub-atmospheric pressure. In some embodiments, the vacuum chamber region may have a pressure of between 0.1 atm and 0.01 atm. As also used herein, a non-vacuum region may refer to a space within the enclosure having a higher pressure than the vacuum chamber region. In some embodiments, the non-vacuum region may have a pressure equal to atmospheric pressure (e.g., the non-vacuum region may be open to the external environment). Alternatively, the non-vacuum region may have a sub-atmospheric pressure that is greater than the pressure of the vacuum chamber region. Alternatively, the non-vacuum region may have a pressure greater than atmospheric pressure. In some embodiments, the apparatus may include a mechanism (e.g., one or more vacuum pumps) configured to adjust the pressure in one or both of the vacuum chamber region and the non-vacuum region. In some embodiments, the apparatus may be configured such that the vacuum chamber region and non-vacuum region have equal pressures at certain times (e.g., when an elongated tool is removed from the channel) and different pressures at other times (e.g., when an elongated tool is received within the channel).

As an example, sheath (or shroud) 310 of FIG. 3A includes a sub-atmospheric inside region 322 (i.e., configured to maintain a sub-atmospheric environment) that is separated, via vacuum seal 320, from a proximal region 314 that is configured to be open to an external environment (outside 324). In some embodiments, fluid (e.g., air) may be removed from inside region 322 via hose 364, thus producing a vacuum within inside region 322. As another example, adapter 22300 of FIG. 22C includes a hollow cylinder 22312 that is divided by adaptive vacuum seal 22320 into a distal portion 22302 (an example of a vacuum chamber region) and a proximal portion 22315 (an example of a non-vacuum region). A pressure differential may be established and maintained between the portions, with distal portion 22302 having a lower pressure than proximal portion 22315.

Some disclosed embodiments include an annular seal. As used herein, a "seal" may refer to an element, device, or apparatus configured to prevent the passage or leakage of fluid (e.g., air) from a first area to a second area. For example, a "seal" may refer to a device or apparatus configured to maintain a pressure differential between two areas. In some embodiments, a seal may be provided in a connection or passage between a first, high-pressure area and a second, low-pressure area and may block fluid flow from the first area to the second area. In some embodiments, the seal may be removed or broken (e.g., to allow fluid passage or to receive another device). Additionally, or alternatively, the seal may be adjusted or deformed to allow the passage of materials by or through the seal. As also used herein, the term "annular" may mean "ring-shaped" or may refer to an object having one or more openings extending through it. Thus, an annular seal may refer to a ring-shaped apparatus or device configured to prevent fluid flow or leakage between two areas. Some embodiments may include a single annular seal. Alternative embodiments may include two annular seals, three annular seals, four annular seals, or any other suitable number of annular seals. Some non-limiting examples of an annular seal include a flange gasket, an O-ring, a piston ring, or any other structure configure to form a barrier about a circumference or periphery.

In some embodiments, the annular seal is disposed between the vacuum chamber region and the non-vacuum region. As discussed above, the vacuum chamber region may be configured to maintain a lower pressure than the non-vacuum region. Accordingly, the annular seal may be provided in a fluid passage connecting the vacuum chamber region and non-vacuum region and may block fluid from passing from the non-vacuum region to the vacuum chamber region, thus maintaining the pressure differential between them. As an example, FIG. 12 shows a sheath 800 having a ring-shaped seal 1200 provided in between a distal portion 1214 and a proximal portion 1216. When an elongated device (e.g., tool 1220 or tool 1222) is received within channel 1212, seal 1200 may press against the outer surface of the tool to provide a fluid-tight seal separating distal portion 1214 from proximal portion 1216. As a result, a pressure differential may be maintained between the portions (e.g., distal portion 1214 may have a lower pressure than proximal portion 1216).

In some embodiments, the annular seal is formed of a flexible material. For example, the annular seal may be resilient such that the seal may bend or be compressed by an applied force without breaking. Some non-limiting examples of a flexible material may include rubber, a synthetic rubber (e.g., a EPDM rubber, a fluoroelastomer, a nitrile rubber, or a silicone rubber), a thermoplastic (e.g., PEBA, a thermoplastic polyurethane, or a thermoplastic elastomer), or any other suitable material capable of preventing fluid flow. In some embodiments, the annular seal has a hardness within a range of 25 Shore to 90 Shore based on the General Rockwell A Hardness Values. In some embodiments, the annular seal has a hardness within a range of 35 Shore to 65 Shore based on the General Rockwell A Hardness Values. For example, the annular seal may be sufficiently resistant to plastic deformation so that the seal may return to its original shape after being compressed or otherwise deformed. Thus, the annular seal will not lose its shape (and thus its ability to act as a fluid seal) when a large pressure differential or another force is applied to it.

In some embodiments, and as discussed above, the annular seal includes an opening. The opening may extend from one end of the seal to another, such that an object may be advanced through the opening of the seal. The annular seal may include one opening, two openings, three openings, or any other suitable number of openings. In some embodiments, an opening diameter of the annular seal is less than 4.5 mm. As used herein, an "opening diameter" may refer to the diameter of the opening through the annular seal. In some embodiments, the opening diameter of the seal may be less than 4.5 mm when the opening is in a non-biased position (i.e., in the absence of an applied force that widens or enlarges the opening). As a non-limiting example, annular seal 1200 shown in FIG. 12 includes an opening 1230 that may have a diameter less than 4.5 mm. In some embodiments, a diameter of the opening of the annular seal is configured to change upon tool insertion. For example, and as discussed above, the annular seal may be constructed from a flexible material. As a result, the opening may become larger (that is, may stretch to have a larger diameter) to accommodate a tool having a larger diameter than the diameter of the opening. When the tool is removed from the opening, the opening may return to its original shape and size due to the resilient material from which it is constructed.

In some embodiments, the annular seal includes a flap. As used herein, a "flap" may refer to a component that is connected only at one side to the remainder of the annular seal. As a result, the flap may be hinged or may pivot around the point of connection with the annular seal. In some embodiments, the flap may extend around the opening of the annular seal. For example, the flap may extend around the entire diameter of the opening; thus, the flap may also be annular (i.e., there may be an opening through the flap). Alternatively, the flap may be connected to an outer surface of the annular seal. As a non-limiting example, FIG. 12 shows an annular seal 1200 having an opening 1230 and a flap 1232 that may pivot around the seal's annular side wall 1234. Flap 1232 may also be annular, with the opening 1230 of the seal also being an opening through the flap.

In some embodiments, the annular seal is provided within the channel of the enclosure. For example, the annular seal may be mounted on, or otherwise connected to, an inner wall of the enclosure. As a result, when an elongated tool is advanced into the channel, the annular seal may come into contact with the tool. In some embodiments, the flap of the annular seal is configured to extend inward from a wall of the enclosure into the channel. For example, the annular seal may be seated on a side wall of the enclosure. The flap may extend inward from the inner wall of the enclosure towards the center of the channel, thus providing an opening having a smaller diameter than the channel. As a non-limiting example, FIG. 12 depicts a sheath 800 having an annular seal 1200 situated in channel 1212. Annular seal 1200 may be seated on the side wall of sheath 800 such that flaps 1232 are configured to extend inward from the side wall of sheath 800 towards the center of channel 1212. In alternative embodiments, the annular seal is provided in a different part of the enclosure.

In some embodiments, the annular seal is configured to form a vacuum seal against a wall of a tool inserted through the annular seal. As used herein, a "vacuum seal" may refer to a capacity of the annular seal to press against another object with sufficient force to provide a fluid-tight seal between them (that is, between the annular seal and the other object). For example, due to the resilient material of the annular seal, the opening through the annular seal may stretch to become larger in order to accommodate a passing object (e.g., a tool being advanced through the annular seal's opening). However, due to both the flexibility and the hardness of the material, the material around the opening may press against the object, exerting sufficient force to establish a fluid-tight seal. Thus, when a vacuum is created on one side of the annular seal (such as in the vacuum chamber region), the annular seal may block fluid from leaking between the non-vacuum region and vacuum chamber region and may therefore maintain the pressure differential.

Further, due to its elastic properties, the annular seal may be configured to accommodate, and to form a vacuum seal against, tools with different shapes and dimensions. For example, in some embodiments, the annular seal is configured to form a vacuum seal against a wall of a first tool when the first tool is inserted therein and against a wall of a second tool when the second tool is inserted therein, the first tool having a diameter at least one and a half times greater than a diameter of the second tool. Additionally, or alternatively, the annular seal may be configured to form vacuum seals against tools having other dimensions that differ, such as their respective lengths, widths, surface areas, and cross-sectional areas. As a non-limiting example, FIG. 12 depicts a sheath 800 having an annular seal 1200 configured to receive both a first tool 1220 and a second tool 1222. In the example shown, first tool 1220 may have a diameter 2d that is two-times greater than the diameter d of second tool 1222; however, the tools may have other relative diameters having a ratio of between 1.5 and 4. Annular seal 1200 may be configured to form a vacuum seal against first tool 1220 as first tool 1220 is inserted in opening 1230. Annular seal 1200 may also be configured to form a vacuum seal against second tool 1222 as second tool 1222 is inserted in opening 1230.

In some embodiments, the first tool and the second tool are optical medical scopes of differing sizes. As used herein, an optical medical scope may refer to an instrument configured to be inserted into a body opening (such as a surgical opening or a preexisting opening such as the mouth or anus) in order to visualize an interior body cavity or organ or to assist with a medical procedure. For example, an optical medical scope may include an endoscope, as defined elsewhere in the present disclosure. The optical medical scope may include at least one imaging mechanism (e.g., a small camera) at or near the distal end of the scope. Additionally, or alternatively, an optical medical scope may include a light source at or near its distal end. The first optical medical scope and the second optical medical scope have different sizes, such as at least one of a different diameter, a different length, a different width, a different surface area, and a different cross-sectional area. However, due to its resilient construction and annular shape, the annular seal is configured to adapt to and seal against the differing sizes of the medical scopes.

In some embodiments, the annular seal is configured to adjust to a tool diameter in a first range of 0.5 mm to 8 mm. The first range may, for example, correspond to outer diameter values of the second tool (i.e., the smaller of the first and second tools). Additionally, or alternatively, the annular seal is configured to adjust to a tool diameter in a second range of 2 mm to 12 mm. The second range may, for example, correspond to outer diameter values of the first tool (i.e., the larger of the first and second tools). In some embodiments, the annular seal is configured to form a vacuum seal against a first tool with a diameter of between 2 mm and 12 mm and is also configured to form a vacuum seal against a second, smaller tool with a diameter of between 0.5 mm and 8 mm. As mentioned above, the first tool may have a larger diameter that is at least one and a half times larger than the diameter of the second tool.

In some embodiments, the annular seal is configured to sequentially form a vacuum seal against the first tool and the second tool. For example, the annular seal is sized to enable sealing the vacuum chamber region when the second tool is inserted in the channel after extraction of the first tool from the channel. Said another way, the annular seal is configured to form a vacuum seal against the first tool when the first is inserted therein, such that the pressure differential may be maintained between the vacuum chamber region and the non-vacuum region. The first tool may then be removed, and the second tool inserted in the annular seal. The annular seal may then form a vacuum seal against the second, smaller tool so that the pressure differential may against be established and maintained between the vacuum chamber region and the non-vacuum region.

As discussed above, the first tool and second tool are optical medical scopes in some disclosed embodiments. Such medical scopes (that is, the first tool and the second tool) each have an optical element. As used herein, an optical element of an optical medical scope may include a component or surface positioned on the scope, or connected to the scope, through which light passes and/or is reflected. The optical element may include one or more of a lens, polarizer, diffraction grating, prism, reflector, filter, viewing window, mirror, protective window, or any other component through which light passes or is reflected. By way of example, FIG. 1B shows an object 200 (e.g., an endoscope) including an optical element 220 such as a window or lens of an imaging mechanism, which may be situated at the distal end 210 of the object. As another example, FIG. 7 depicts an optical element 706 of an object 708, such as an endoscope. Optical element 706 may be a lens of an imaging mechanism configured to capture images of a hollow body organ or cavity.

In some embodiments, the vacuum chamber region is configured to contain each optical element therein during treatments that expose each optical element to plasma. As discussed elsewhere in the present disclosure, optical elements such as imaging lenses may be treated with plasma to increase their hydrophilicity, allowing formation of a thin water layer that does not distort passing light and therefore keeps the optical element from fogging. In some embodiments, the vacuum chamber region may correspond to a sub-atmospheric volume in which a plasma cloud may be formed (such as a plasma generation zone, as discussed elsewhere in the present disclosure). Thus, the vacuum chamber region may be configured to contain each optical element while a plasma cloud is formed in the vacuum chamber region for treating the optical element. In some embodiments, the vacuum chamber region is configured to maintain a vacuum of less than about 0.3 atm when the annular seal forms a vacuum seal against at least one of the first tool or the second tool. For example, in some embodiments, the vacuum chamber region is configured to maintain a vacuum of less than about 0.1 atm when the annular seal forms a vacuum seal against at least one of the first tool or the second tool. Since the annular seal is configured to form a vacuum seal against an inserted tool, the vacuum chamber region may be airtight so that the gas and other molecules may be removed from the vacuum chamber region until the desired pressure is achieved (e.g., a vacuum of between 0.1 atm and 0.01 atm). As a non-limiting example, FIG. 7 depicts a tool 708 (e.g., an endoscope) having an optical element 706 contained within plasma generation zone 716 (which may be an example of a vacuum chamber region). Plasma generation zone 716 may be airtight due the vacuum seal formed by the annular seal, so that a desired vacuum pressure may be established within the plasma generation zone (e.g., using a plurality of vacuum pumps connected in series). Although not shown in FIG. 7, apparatus 500 is also configured to perform plasma treatment on other tools of different sizes.

In some embodiments, the enclosure is within a reusable housing. As discussed elsewhere in the present disclosure, a housing may include any structure, casing, frame, enclosure, or support that covers and/or protects components of a plasma generation device. For example, a housing may cover and protect the components of the plasma generation device that are configured to cause the reaction that creates the plasma (e.g., a vacuum chamber, one or more electrode pairs, and a mechanism for supplying reaction gas). As used herein, the term "reusable" may refer to an implement that can be used multiple times or on multiple occasions. For example, a reusable housing may be used in multiple treatment sessions and/or for treatment of multiple patients. For example, a reusable housing may be configured for easy cleaning so that it may safely be used for multiple patients. Housing 710 depicted in FIG. 7 and operational unit 21120 shown in FIG. 21A are examples of a housing that may be reusable in disclosed embodiments.

In some embodiments, the annular seal is configured for reuse. For example, the annular seal may be removed from the enclosure, sterilized, and either returned to the enclosure for reuse or inserted into a different enclosure. Alternatively, the entire enclosure (including the annular seal) may be configured to be sterilized and reused.

In some embodiments, the enclosure is sized to be removably inserted into the housing. For example, the housing may include at least one bore, cavity, or hollow internal chamber that may hold or accommodate at least a portion of the enclosure, either alone or while the enclosure receives an elongated tool therein. The enclosure may be accommodated within the housing (e.g., for plasma treatment of the elongated tool), after which the enclosure (and the elongated tool) can be removed from the housing. In some embodiments, the housing may contain electrical circuitry for inducing a voltage drop to thereby generate plasma within the vacuum chamber region. For example, and as discussed elsewhere in the present disclosure, an electrode pair may be provided between the enclosure and the housing. In some embodiments, a first electrode may be located on the enclosure and a second electrode may be located on the housing. In alternative embodiments, both electrodes may be located on the enclosure or both electrodes may be positioned on the housing. In the latter situation, the enclosure may extend between the electrodes when the enclosure is inserted into the housing. When an enclosure and subsequently a tool is inserted into the housing, a circuit including the electrode pair and associated electrical circuitry (e.g., a power supply) may be closed and may drive current between the electrodes to produce an ionizing field for plasma generation within the vacuum chamber region. Said another way, closing the electrical circuit between the enclosure and the housing causes a voltage drop associated with the ionizing field that induces plasma generation.

In some embodiments, the enclosure is configured to be identifiable by the housing. As used herein, the term "identifiable" may refer to a capacity of the enclosure to send a signal and/or energy to the housing, which may be used by the housing or another device to identify the enclosure. For example, a transponder may be provided on one of the enclosure and the housing, and a receiver may be provided on the other. The transponder may be passive (e.g., a reflector) and/or may be active (e.g., powered by an energy source). When the enclosure is suitably arranged in a well-defined position within the housing, the transponder may transmit a signal and/or energy which is received by the receiver and which may certify the identity of the enclosure or the position thereof relative to the housing. In some embodiments, the transponder may include at least one of a magnet, a mirror, a code sticker, an RFID chip, or a smart card. Non-limiting examples are provided in FIGS. 25A-25E, which depict an adapter 24620 (an example of an enclosure) removably received within a slot 24640 of an operational unit 24610 (an example of a housing). Adapter 24620 may include a transponder 24654 configured, when adapter 24620 is arranged in a particular position relative to operation unit 24610, to transmit a signal and/or energy to a receiver 24652 that identifies the adapter 24620 and/or certifies the adapter's position. In disclosed embodiments, the transponder may include at least one of a magnet (24654*a*), a mirror (24654*b*), a light source, an optical filter, a code sticker (24654*c*), a RFID chip (24654*d*), or a smart card (24654*e*).

Figure 26:
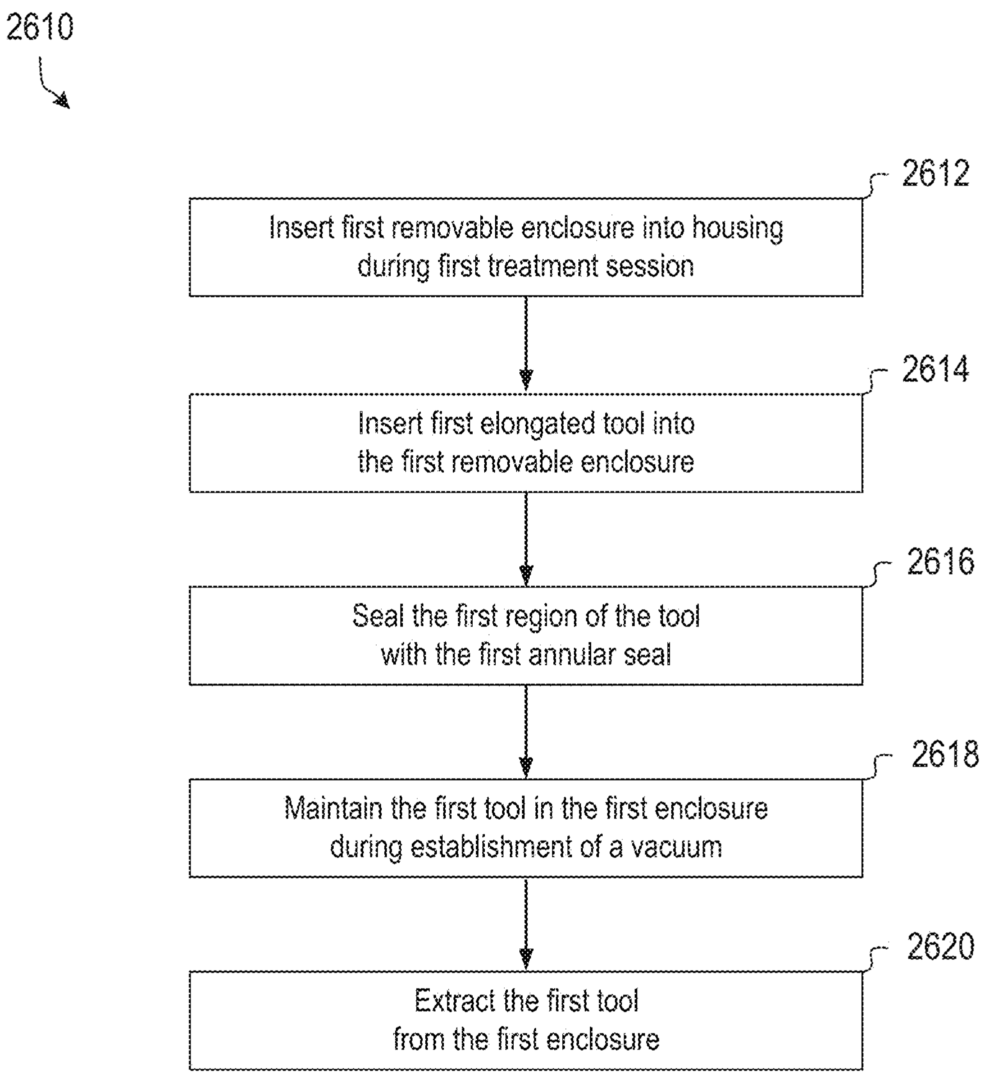
FIG. 26 depicts a flow chart of a method for treating equipment of differing dimensions in a vacuum environment, consistent with some disclosed embodiments.

Some disclosed embodiments include a method for treating equipment of differing dimensions in a vacuum environment. Embodiments include inserting during a first treatment session, a first removable enclosure into a housing, the first removable enclosure being divided into a vacuum chamber region and a non-vacuum region separated by a first annular seal configured to adjust to varying tool sizes. As used herein, a treatment session may refer to a diagnostic, therapeutic, and/or surgical operation performed on a patient. A non-limiting example of a treatment session may include an endoscopic procedure. In some embodiments, and as disclosed elsewhere in the present disclosure, the annular seal is formed of a flexible material and includes an opening diameter of less than 4.5 mm. To illustrate, FIG. 26 depicts a flowchart of an exemplary method 2610 for treating equipment of differing dimensions in a vacuum environment. Method 2610 may include a step 2612 that may include inserting a first removable enclosure into a housing during a first treatment session.

Some disclosed embodiments also include inserting during the first treatment session, a first elongated tool into the first removable enclosure, the first elongated tool having a first region of a first dimension. The first region of the first elongated tool may include a distal portion of the tool and/or another suitable portion of the tool. For example, method 2610 may include a step 2614 that may include inserting a first elongated tool into the first removable enclosure during the first treatment session.

Some disclosed embodiments also include sealing, upon insertion of the first elongated tool, the first region of the first dimension with the first annular seal. For example, sealing may include utilizing the first annular seal to form a vacuum seal against a diameter of the first elongated tool. To illustrate, method 2610 may include a step 2616 including sealing the first region of the first elongated tool having the first dimension with the first annular seal.

Some disclosed embodiments further include maintaining the first elongated tool in the first enclosure during an establishment of at least a partial vacuum in the vacuum chamber region. As used herein, a partial vacuum may refer to an enclosed space having a sub-atmospheric pressure. As discussed elsewhere in the present disclosure, the at least a partial vacuum may be established in the vacuum chamber with a plurality of vacuum pumps connected in series. Some embodiments include generating plasma in the vacuum chamber region during the first treatment session, such as for exposing the first elongated tool to plasma (e.g., as a surface treatment). Plasma may be generated while the first elongated tool is sealed with the first annular seal and the at least partial vacuum is established in the vacuum chamber. To illustrate, method 2610 may include a step 2618 including maintaining the first tool in the first enclosure during establishment of a vacuum in the vacuum chamber region, such as for treating the elongated tool with plasma.

Some disclosed embodiments additionally include extracting the first elongated tool from the first enclosure. To illustrate, method 2610 may include a step 2620 including extracting the first elongated tool from the first enclosure.

Some disclosed embodiments also include inserting a second removable enclosure into the housing during a second treatment session. For example, after extracting the first elongated tool, the first enclosure may be extracted from the housing and a second removable enclosure may be inserted into the housing in a second treatment session. Thus, the housing may be reusable such that it may be used to perform different treatment sessions (e.g., for different patients and/or for different types of treatment). The second removable enclosure may be divided into a second vacuum chamber region and a second non-vacuum region separated by a second annular seal corresponding in configuration to the first annular seal. Embodiments may also include inserting a second elongated tool into the second removable enclosure during the second treatment session. The second elongated tool may have a second region (e.g., a distal portion thereof) having a second dimension differing from the first dimension of the first elongated tool. For example, the second region may differ from the first region in at least one of a length, width, height, diameter, radius, circumference, surface area, cross-sectional area, or arc length. Embodiments may also include sealing, upon insertion of the second elongated tool, the second region of the second dimension with the second annular seal (e.g., using the second annular seal to establish a vacuum seal with the second elongated tool). Embodiments may also include maintaining the second elongated tool in the second enclosure during an establishment of at least a partial vacuum in the second vacuum chamber region. Embodiments may also include extracting the second elongated tool from the second enclosure.

Additionally, or alternatively, some disclosed embodiments include reusing both the housing and the first removable enclosure in a second treatment session. For example, after extracting the first elongated tool, the first enclosure and housing may be sanitized (e.g., by cleaning and/or replacing the annular seal) and then used for a second treatment session (e.g., for a different patient and/or for a different type of treatment). Embodiments include maintaining, during a second treatment session, the first removable enclosure within the housing. Embodiments also include inserting, during the second treatment session, a second elongated tool into the first removable enclosure. The second elongated tool may have a second region (e.g., a distal portion thereof) of a second dimension differing from the first dimension. Embodiments also include sealing, upon insertion of the second elongated tool, the second region of the second dimension with the first annular seal. Some embodiments also include maintaining the second elongated tool in the first enclosure during an establishment of at least a partial vacuum in the vacuum chamber region. Embodiments also include extracting the second elongated tool from the first enclosure.

Some disclosed embodiments include generating plasma in the second vacuum chamber region during the second treatment session. Plasma may be generated while the second removable enclosure is inserted into the housing and the second elongated tool is sealed in the second annular seal to maintain at least a partial vacuum in the second vacuum chamber region. Additionally, or alternatively, plasma may be generated while the first removable enclosure is inserted into the housing and the second elongated tool is sealed in the first annular seal of the first enclosure to maintain at least a partial vacuum in the first vacuum chamber region. Disclosed embodiments include exposing the second elongated tool to plasma, such as for surface treatment of the second elongated tool.

Disclosed embodiments may include any one of the following bullet-pointed features alone or in combination with one or more other bullet-pointed features, whether implemented as a system and/or method, by at least one processor, and/or stored as executable instructions on non-transitory computer readable media.

a plasma generation device for treating objects;

a housing;

a plasma-generation zone within the housing configured to enable accommodation of an object;

circuitry for supplying energy to carry out a plasma treatment for increasing hydrophilicity of the object to a desired level;

at least one sensor configured to measure at least one plasma-activation parameter during the plasma treatment;

at least one processor configured to determine, based on at least one plasma-activation parameter, that the plasma treatment is below a threshold for increasing the hydrophilicity of the object to the desired level;

outputting a notification indicating of plasma treatment failure;

at least one sensor configured to measure at least one plasma-activation parameter by detecting a pressure in a plasma-generating zone during a plasma treatment;

determining that a plasma treatment fails to meet the threshold when a pressure is outside a pressure range;

at least one sensor configured to measure at least one plasma-activation parameter by detecting a voltage at an electrode generating the plasma during a plasma treatment;

determining that a plasma treatment fails to meet the threshold when a detected voltage is outside a voltage range;

at least one sensor configured to measure at least one plasma-activation parameter by detecting a plasma frequency during a plasma treatment;

determining that a plasma treatment fails to meet a threshold when a detected plasma frequency is outside a plasma frequency range a gas reservoir configured to stream a gas into a plasma-generation zone for carrying out a plasma treatment;

determining that a plasma treatment fails to meet a threshold based on a characteristic of a gas;

at least one sensor including at least one of a pressure sensor, a voltage sensor, or a plasma frequency sensor;

an object including an optical element;

an object that is an endoscope;

a plasma generation device including a detachable sheath dimensioned to receive a distal end of an endoscope;

a plasma-generation zone configured to apply a plasma treatment to a distal end of an endoscope within a sheath;

an object that is at least a portion of a medical instrument;

outputting a notification indicating of plasma treatment failure prior to using a medical instrument in a medical procedure;

maintaining a plasma treatment for a predefined time duration;

a predefined time duration based on a characteristic of plasma generated for a plasma treatment;

a predefined time duration based on a physical characteristic of an object;

a predefined time duration based on a desired level of hydrophilicity of an object;

increasing a time duration for a subsequent plasma treatment in response to determining that that a plasma treatment is below a threshold;

a plasma-generation zone associated with a cavity configured to retain an object in a manner exposing at least a portion of an object to a plasma activation zone;

a plasma-generation zone configured to contain a plasma cloud on a first side of a dielectric barrier while an object is located on a second side of the dielectric barrier;

a plasma generator configured to be activated to cause formation of a plasma cloud in a plasma activation zone;

activating a plasma generator for a time period sufficient to increase a hydrophilicity of an object to a desired level;

a desired level of hydrophilicity of an object such that at least one hour after a plasma treatment, droplets hitting a surface of an object have contact angles of less than 10 degrees;

a method for generating plasma to treat an object;

identifying entry of an object into a plasma-generation zone;

activating circuitry for supplying energy to generate plasma in a plasma-generation zone to carry out a plasma treatment for increasing hydrophilicity of an object to a desired level;

measuring at least one plasma-activation parameter during a plasma treatment;

determining, based on at least one plasma-activation parameter, that a plasma treatment is below a threshold for increasing hydrophilicity of an object to a desired level;

outputting a notification indicating of plasma treatment failure;

a non-transitory computer readable medium containing instructions that when executed by at least one processor cause the at least one processor to perform operations for generating plasma to treat an object;

identifying entry of an object into a plasma-generation zone;

activating circuitry for supplying energy to generate plasma in a plasma-generation zone to carry out a plasma treatment for increasing hydrophilicity of an object to a desired level;

measuring at least one plasma-activation parameter during a plasma treatment;

determining, based on at least one plasma-activation parameter, that a plasma treatment is below a threshold for increasing hydrophilicity of an object to a desired level;

outputting a notification indicating of plasma treatment failure;

a device for treating an elongated tool with plasma;

a housing;

a bore within a housing;

a bore having an open end on a surface of a housing for insertion of an elongated tool therein;

at least one vacuum pump for causing a vacuum in at least a portion of a bore;

an insertion detector for determining when an elongated tool is inserted within a bore;

a vacuum sensor associated with a housing for determining an extent of negative pressure in at least a portion of a bore;

a plasma generator for generating plasma within a bore;
at least one processor;
receiving an insertion signal from an insertion detector indicating that an elongated tool is within a bore;
in response to an insertion signal, activating at least one vacuum pump to generate a negative pressure in at least a portion of a bore;
receiving a signal from a vacuum sensor and determining therefrom that a negative pressure in at least a portion of a bore is sufficient for plasma generation;
activating a plasma generator after determination is made that negative pressure in at least a portion of bore is sufficient for plasma generation, thereby exposing a distal end region of an elongated tool to plasma;
a bore configured to receive a sheath therein, the sheath being sized to receive an elongated tool;
causing plasma generation within a sheath;
an insertion detector configured to sense insertion of an elongated tool within a sheath in a bore and to automatically initiate a plasma generation process upon sensed insertion of the elongated tool within the sheath;
an elongated tool that is a scope having an optical element located in a distal end region;
maintaining activation of a plasma generator for a period sufficient to cause an external surface of an optical element to become hydrophilic;
a display;
outputting a signal to a display indicating a status of a plasma generator treatment;
a sheath including a vacuum port and a vacuum seal therein;
a vacuum port being flow-connectable to at least one vacuum pump to enable causation of a negative pressure within a sheath when located within a bore;
a vacuum seal configured to engage with an elongated tool upon insertion of the elongated tool into a sheath to maintain a negative pressure on a distal side of the elongated tool;
a bore including an electrical contact therein configured to engage a contact on a sheath, to thereby enable plasma generation within the sheath;
calculating a number of plasma treatments remaining before required maintenance;
detecting a malfunction of at least one of a plasma generator or at least one vacuum pump and outputting a malfunction indicator;
outputting a warning signal when an optical element is insufficiently treated to achieve a predetermined level of hydrophilicity;
an elongated tool including a lens;
activating a plasma generator for a period sufficient to cause a lens to become super-hydrophilic;
a plasma generator configured for causing a dielectric barrier discharge;
at least one processor is configured to control a plasma generator in a manner causing a voltage drop of at least 1000 volts;
a method for treating an elongated tool with plasma;
detecting that an elongated tool is within a bore of a housing;
an elongated tool including an optical element on a distal end thereof;
upon detecting, generating a negative pressure in at least a portion of a bore in a region of an optical element;
activating a plasma generator during a period of negative pressure to thereby expose an optical element to plasma for a time period sufficient to cause a surface of an optical element to become hydrophilic;
generating a negative pressure and activating a plasma generator automatically in response to detecting that an elongated tool is within a bore;
a time period sufficient to cause a surface of an optical element to become hydrophilic;
a time period sufficient to cause a surface of an optical element to become super-hydrophilic;
a bore configured to receive a sheath therein;
a sheath being sized to receive an elongated tool;
exposing a distal end region of an elongated tool to plasma within a sheath;
outputting a warning signal if an optical element is insufficiently treated to achieve sufficient hydrophilicity;
activating a plasma generator to result in a dielectric barrier discharge;
a device for inhibiting condensation distortion on an optical element of a medical instrument configured for insertion into a body cavity;
a housing;
a cavity within the housing, the cavity being sized to removably retain at least a portion of the medical instrument therein, wherein the portion includes the optical element;
a plasma activation zone within the cavity and arranged such that when the at least a portion of the medical instrument is retained within the cavity, the optical element is located within the plasma activation zone;
a plasma generator configured to be activated to cause formation of a plasma cloud in the plasma activation zone in a vicinity of the optical element;
a controller configured to activate the plasma generator for a time period sufficient to cause the optical element to become hydrophilic prior to insertion into the body cavity;
the medical instrument includes a scope having an elongated shaft, the cavity includes an elongated channel for receiving the elongated shaft, and the plasma activation zone is located proximate a distal end of the elongated channel;
the scope includes a laparoscope or an endoscope;
the optical element includes a lens element on a distal end of the elongated shaft;
the elongated channel is sized to receive a sheath surrounding a portion of the elongated shaft including the optical element;
the sheath is formed of a dielectric material;
the housing is configured such that the sheath surrounds the optical element when the optical element is in the plasma activation zone;
the device is configured to cause the plasma cloud to occur within the sheath;
the cavity is configured to receive a sheath having a sheath electrode therein and having an external electrical contact, and wherein the cavity includes an internal contact configured to form an electrical connection with the external contact when the sheath is located within the cavity, to thereby enable a supply of energy to the sheath electrode;
at least one pump configured to establish at least a partial vacuum within the sheath in an area of the sheath electrode;
the housing includes a housing electrode therein;

the housing electrode is configured to form an electrical circuit with the sheath electrode when the sheath is inserted in the elongated channel;

a circuit for electrically transferring power to the sheath electrode;

the at least one pump includes a plurality of interconnected pumps;

the controller is configured to activate the plasma generator for a time period sufficient to cause the optical element to become super-hydrophilic prior to insertion into the body cavity;

the plasma generator is configured cause formation of the plasma cloud through Dielectric Barrier Discharge;

a method of inhibiting condensation distortion on an optical element of a medical instrument configured for insertion into a body cavity;

removably inserting, within a cavity, at least a portion of the medical instrument, wherein the portion includes an optical element;

locating the optical element within a plasma activation zone inside the cavity, when the at least a portion of the medical instrument is retained within the cavity;

generating plasma to cause formation of a plasma cloud in the plasma activation zone in a vicinity of the optical element;

maintaining the plasma cloud for a time period sufficient to cause the optical element to become hydrophilic;

inserting the hydrophilic optical element in a body cavity;

establishing at least a partial vacuum in a region containing the plasma activation zone maintaining the plasma cloud for a time period sufficient to cause the optical element to become super-hydrophilic prior to insertion into the body cavity;

causing the formation of the plasma cloud is achieved through Dielectric Barrier Discharge;

a device for inhibiting condensation distortion on an optical element;

a housing;

a chamber within a housing;

electrical circuitry in a housing;

a plasma activation region associated with a chamber and configured to retain an optical element in a manner exposing an optical surface of the optical element thereof to a plasma activation region;

a plasma-activation region configured to contain gas on a first side of a dielectric barrier;

an electrical circuitry configured to form an electrical connection with a first electrode located on a first side of a dielectric barrier;

a second electrode connected to an electrical circuitry and being located on a second side of a dielectric barrier, opposite a plasma activation region;

at least one processor;

controlling electricity flow through circuitry to cause an electric field associated with a voltage drop between a first electrode and a second electrode to thereby generate plasma within a plasma-activation region;

maintaining generated plasma in a plasma-generating region for a time period sufficient to cause an optical surface to become hydrophilic;

an optical element including a lens;

an optical surface that is a surface of a lens;

a chamber configured to receive an elongated tool with an optical element proximate to a distal end of an elongated tool;

a dielectric barrier and a first electrode that are removable from a housing;

a dielectric barrier configured to isolate a second electrode from gas in a chamber;

a thickness of a dielectric barrier between about 0.3 mm to about 3 mm;

electrical circuitry in a housing including a plasma generating field applicator configured to cause a voltage drop to be at least 800 V;

electrical circuitry in a housing including a plasma generating field applicator configured to cause a voltage drop to be at least 1000 V;

a plasma-activation region configured to contain a gas that is air;

a plasma-activation region configured to contain a gas that is inert;

at least one pump for causing at least a partial vacuum in a plasma activation region;

a gas pressure associated with a partial vacuum below 0.1 atm;

a stopper for maintaining a gap between an optical element and a second electrode;

a stopper acting as a dielectric barrier between a first electrode and a second electrode;

a method for inhibiting condensation distortion on an optical element;

detecting an optical element inserted into a plasma-generation region within a housing;

a plasma-activation region configured to contain gas on a first side of a dielectric barrier;

electricity connecting a first electrode located on a first side of the dielectric barrier with a second electrode located on a second side of the dielectric barrier, opposite a plasma activation region;

applying an electric field associated with a potential drop of greater than 1000 V between a first electrode and a second electrode to thereby generate plasma within a plasma-activation region;

maintaining a generated plasma in a plasma-generating region for a time period sufficient to cause an optical surface to become hydrophilic;

an optical element that is part of a medical instrument having an elongated shaft;

an optical element including a lens on a distal end of an elongated shaft;

a medical instrument that is a laparoscope or an endoscope;

a time period sufficient to cause an optical surface to become hydrophilic that is less than 1 minute of activated electric field;

a time period sufficient to cause an optical surface to become hydrophilic that is less than 10 seconds of activated electric field;

a time period sufficient to cause an optical surface to become hydrophilic that is less than 5 seconds of activated electric field;

an apparatus for treating equipment of differing dimensions in a vacuum environment;

an enclosure having a channel for receiving elongated tools of varying diameters;

an enclosure being divided into a vacuum chamber region and a non-vacuum region;

an annular seal disposed between a vacuum chamber region and a non-vacuum region;

an annular seal being formed of a flexible material and configured to form a vacuum seal against a wall of a first tool when the first tool is inserted therein and against a wall of a second tool when the second tool is inserted therein, wherein the first tool has a diameter at least one and a half times greater than a diameter of the second tool;

optical medical scopes of differing sizes;

an annular seal configured to adapt to and seal against differing sizes of medical scopes;

medical scopes each having an optical element;

a vacuum chamber region configured to contain optical elements therein during treatments that expose each optical element to plasma;

an annular seal sized to enable sealing a vacuum chamber region when a second tool is inserted in a channel after extraction of a first tool from the channel;

an annular seal configured to adjust to a tool diameter in a range of 0.5 mm to 8 mm;

an annular seal configured to adjust to a tool diameter in a range of 2 mm to 12 mm;

an opening diameter of an annular seal that is less than 4.5 mm;

an annular seal having a hardness within a range of 25 Shore to 90 Shore;

an annular seal including an opening and a diameter of the opening that is configured to change upon tool insertion;

an enclosure that is a disposable sheath;

an enclosure within a reusable housing;

an annular seal configured for reuse;

an annular seal including a flap;

a flap of an annular seal configured to extend inward from a wall of an enclosure into a channel;

a vacuum chamber region configured to maintain a vacuum of less than about 0.3 atm when an annular seal forms a vacuum seal against at least one of a first tool or a second tool;

an enclosure sized to be removably inserted into a housing containing electrical circuitry for inducing a voltage drop to thereby generate plasma within a vacuum chamber region;

an enclosure configured to be identifiable by a housing;

a method for treating equipment of differing dimensions in a vacuum environment;

inserting during a first treatment session, a first removable enclosure into a housing;

a first removable enclosure being divided into a vacuum chamber region and a non-vacuum region separated by a first annular seal configured to adjust to varying tool sizes;

inserting during a first treatment session, a first elongated tool into a first removable enclosure;

a first elongated tool having a first region of a first dimension;

sealing, upon insertion of a first elongated tool, a first region of a first dimension with a first annular seal;

maintaining a first elongated tool in a first enclosure during an establishment of at least a partial vacuum in a vacuum chamber region;

extracting a first elongated tool from a first enclosure;

inserting during a second treatment session, a second removable enclosure into a housing;

a second removable enclosure being divided into a second vacuum chamber region and a second non-vacuum region separated by a second annular seal corresponding in configuration to a first annular seal;

inserting during a second treatment session, a second elongated tool into a second removable enclosure;

a second elongated tool having a second region of a second dimension differing from a first dimension;

sealing, upon insertion of a second elongated tool, a second region of a second dimension with a second annular seal;

maintaining a second elongated tool in a second enclosure during an establishment of at least a partial vacuum in a second vacuum chamber region;

extracting a second elongated tool from a second enclosure;

maintaining during a second treatment session, a first removable enclosure within a housing;

inserting during a second treatment session, a second elongated tool into a first removable enclosure;

a second elongated tool having a second region of a second dimension differing from a first dimension;

sealing, upon insertion of a second elongated tool, a second region of a second dimension with a first annular seal;

maintaining a second elongated tool in a first enclosure during an establishment of at least a partial vacuum in a vacuum chamber region;

extracting a second elongated tool from a first enclosure;

generating plasma in a vacuum chamber region during a first treatment session;

generating plasma in a second vacuum chamber region during a second treatment session;

exposing a first elongated tool to plasma;

exposing a second elongated tool to plasma;

an annular seal formed of a flexible material and including an opening diameter of less than 4.5 mm;

a plasma generation device for treating objects;

a housing;

a plasma generation zone within a housing configured to enable accommodation of an object;

a plasma generator for enabling formation of plasma within a plasma generation zone;

a plurality of vacuum pumps within a housing, each pump having a vacuum inlet;

a plurality of conduits within a housing connecting a plurality of vacuum pumps in series, such that when activated, the series of pumps cause a vacuum within a plasma generation zone;

at least one processor configured to simultaneously operate a plurality of vacuum pumps while an object is in a region of a plasma generation zone;

a series of pumps configured to cause a vacuum of between 0.1 atm and 0.01 atm;

at least one processor configured to activate a plasma generator after a vacuum is caused by a series of pumps;

at least one processor configured to cause plasma to be generated for a period of time sufficient to cause a portion of an object to become hydrophilic;

a plurality of pumps including at least three pumps;

a plurality of pumps including at least four pumps;

a plurality of pumps including at least five pumps;

an object including an optical surface of an endoscope;

a plasma generation zone configured to enable accommodation of an optical surface surrounded by a dielectric barrier;

at least one filter configured to filter air pumped from a plasma generation zone;

a plasma generation zone configured to enable accommodation of an object surrounded by a dielectric casing;

a dielectric casing including a one-way valve for enabling vacuum formation within the casing;

a plasma generator configured to enable formation of plasma within a plasma generation zone to treat an object when the object and a dielectric casing are inserted into a housing;

a series of pumps configured to cause at least a partial vacuum within a portion of a dielectric casing;

receiving an insertion signal indicating that an object is within a region of a plasma generation zone;

in response to an insertion signal, activating a series of pumps to cause a vacuum within a plasma generation zone;

determining that a vacuum in a plasma generation zone is sufficient for plasma generation;

activating a plasma generator after a determination is made that a vacuum in a plasma generation zone is sufficient for plasma generation, thereby exposing at least a portion of an object to plasma;

a method for generating plasma for treating an object;

inserting an object into a plasma generation zone within a housing;

while an object is in a region of a plasma generation zone, simultaneously operating a plurality of vacuum pumps to cause a vacuum within the plasma generation zone;

vacuum pumps connected in series within a housing;

activating a plasma generator while a vacuum is caused within a plasma generation zone, thereby exposing an object to plasma;

a vacuum having a pressure of between 0.1 atm and 0.01 atm;

causing plasma to be generated for a period of time sufficient to cause a portion of an object to become hydrophilic;

a plurality of vacuum pumps including at least three pumps;

a method of inhibiting condensation distortion on an optical element of a medical instrument configured for insertion into a body cavity:

treating the optical element of the medical instrument to cause at least one surface of the optical element to become super-hydrophilic;

inserting the medical instrument, with the super-hydrophilic optical element, into the body cavity;

exposing the super-hydrophilic optical element to moisture, such that the moisture forms a film barrier on the at least one surface of the optical element to thereby inhibit condensation distortion;

treating the optical element includes maintaining a liquid in contact with the optical element for a period sufficient to cause the at least one surface of the optical element to become super-hydrophilic;

the medical instrument is a scope and the optical element is located on a distal end of the scope;

the scope is at least one of an endoscope, duodenoscope or a laparoscope;

the body cavity is a surgical cavity or natural orifice;

treating the optical element occurs in a vacuum chamber;

applying a liquid to the optical element prior to inserting the medical instrument into the body cavity;

treating the optical element includes exposing the optical surface to plasma;

treating the optical element includes coating the optical surface with a liquid solution;

causing the at least one surface of the optical element to become super-hydrophilic includes enabling, for at least one hour after treating the optical element, droplets hitting the at least one surface of the optical element to have contact angles of less than 10 degrees;

the contact angles are less than 8.5 degrees;

the contact angles are less than 7.5 degrees;

causing the at least one surface of the optical element to become super-hydrophilic includes treating the optical element for less than 30 seconds;

treating the optical element includes causing a super-hydrophilic state of the at least one surface of the optical element that deteriorates over time;

the deterioration of the super-hydrophilic state of the at least one surface of the optical element occurs within 24 hours;

after inserting the medical instrument into the body cavity, re-treating the optical element to cause the at least one surface of the optical element to become super-hydrophilic;

re-treating the optical element to cause the at least one surface of the optical element to become super-hydrophilic at least one additional time within 24 hours of treating the optical element;

the at least one additional re-treatment of the optical element includes executing the at least one additional re-treatment by a battery-powered plasma generator;

the at least one additional re-treatment of the optical element includes using the battery-powered plasma generator without charging the battery-powered plasma generator between the treatment and the at least one additional re-treatment; and estimating a number of remaining treatments of the optical element that can be performed before maintenance is required.

Systems and methods disclosed herein involve unconventional improvements over conventional approaches. Descriptions of the disclosed embodiments are not exhaustive and are not limited to the precise forms or embodiments disclosed. Modifications and adaptations of the embodiments will be apparent from consideration of the specification and practice of the disclosed embodiments. Additionally, the disclosed embodiments are not limited to the examples discussed herein.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware and software, but systems and methods consistent with the present disclosure may be implemented as hardware alone.

The features and advantages of the disclosure are apparent from the detailed specification, and thus, it is intended that the appended claims cover all systems and methods falling within the true spirit and scope of the disclosure. As used herein, the indefinite articles “a” and “an” mean “one or more.” Similarly, the use of a plural term does not necessarily denote a plurality unless it is unambiguous in the given context. Words such as “and” or “or” mean “and/or” unless specifically directed otherwise. Further, since numerous modifications and variations will readily occur from studying the present disclosure, it is not desired to limit the disclosure to the exact construction and operation illustrated and described, and, accordingly, all suitable modifications and equivalents may be resorted to, falling within the scope of the disclosure.

Computer programs based on the written description and methods of this specification are within the skill of a software developer. The various functions, scripts, programs, or modules may be created using a variety of programming techniques. For example, programs, scripts, functions, program sections or program modules may be designed in or by means of languages, including JAVASCRIPT, C, C++, JAVA, PHP, PYTHON, RUBY, PERL, BASH, or other programming or scripting languages. One or more of such software sections or modules may be integrated into a computer system, non-transitory computer readable media, or existing communications software. The programs, modules, or code may also be implemented or replicated as firmware or circuit logic.

Moreover, while illustrative embodiments have been described herein, the scope may include any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods may be modified in any manner, including by reordering steps or inserting or deleting steps. It is intended, therefore, that the specification and examples be considered as exemplary only, with a true scope and spirit being indicated by the following claims and their full scope of equivalents.

What is claimed is:

1. A plasma generation device for treating objects, the device comprising:

a housing;

a plasma-generation zone within the housing configured to enable accommodation of an object;

circuitry for supplying energy to carry out a plasma treatment for increasing hydrophilicity of the object to a desired level;

at least one sensor configured to measure at least one plasma-activation parameter during the plasma treatment; and at least one processor configured to:

determine, based on the at least one plasma-activation parameter, that the plasma treatment is below a threshold for increasing the hydrophilicity of the object to the desired level; and output a notification indicating plasma treatment failure.

2. The plasma generation device of claim 1, wherein the at least one sensor is configured to measure the at least one plasma-activation parameter by detecting a pressure in the plasma-generating zone during the plasma treatment, and wherein the at least one processor is further configured to determine that the plasma treatment fails to meet the threshold when the pressure is outside a pressure range.

3. The plasma generation device of claim 1, wherein the at least one sensor is configured to measure the at least one plasma-activation parameter by detecting a voltage at an electrode generating the plasma during the plasma treatment, and wherein the at least one processor is further configured to determine that the plasma treatment fails to meet the threshold when the detected voltage is outside a voltage range.

4. The plasma generation device of claim 1, wherein the at least one sensor is configured to measure the at least one plasma-activation parameter by detecting a plasma frequency during the plasma treatment, and wherein the at least one processor is configured to determine that the plasma treatment fails to meet the threshold when the detected plasma frequency is outside a plasma frequency range.

5. The plasma generation device of claim 1, further comprising a gas reservoir configured to stream a gas into the plasma-generation zone for carrying out the plasma treatment, wherein the at least one processor is further configured to determine that the plasma treatment fails to meet the threshold based on a characteristic of the gas.

6. The plasma generation device of claim 1, wherein the at least one sensor includes at least one of a pressure sensor, a voltage sensor, or a plasma frequency sensor.

7. The plasma generation device of claim 1, wherein the object includes an optical element.

8. The plasma generation device of claim 1, wherein the object is an endoscope, wherein the plasma generation device further comprises a detachable sheath dimensioned to receive a distal end of the endoscope, and wherein the plasma-generation zone is configured to apply the plasma treatment to the distal end of the endoscope within the sheath.

9. The plasma generation device of claim 1, wherein the object is at least a portion of a medical instrument and wherein the at least one processor is further configured to output the notification indicating plasma treatment failure prior to using the medical instrument in a medical procedure.

10. The plasma generation device of claim 1, wherein the at least one processor is further configured to maintain the plasma treatment for a predefined time duration.

11. The plasma generation device of claim 10, wherein the predefined time duration is based on a characteristic of plasma generated for the plasma treatment.

12. The plasma generation device of claim 10, wherein the predefined time duration is based on a physical characteristic of the object.

13. The plasma generation device of claim 10, wherein the predefined time duration is based on the desired level of hydrophilicity of the object.

14. The plasma generation device of claim 10, wherein the at least one processor is further configured to increase a time duration for a subsequent plasma treatment in response to determining that that the plasma treatment is below the threshold.

15. The plasma generation device of claim 1, wherein the plasma-generation zone is associated with a cavity configured to retain the object in a manner exposing at least a portion of the object to the plasma-generation zone.

16. The plasma generation device of claim 1, wherein the plasma-generation zone is configured to contain a plasma cloud on a first side of a dielectric barrier while the object is located on a second side of the dielectric barrier.

17. The plasma generation device of claim 1, further comprising a plasma generator configured to be activated to cause formation of a plasma cloud in the plasma-generation zone, and wherein the at least one processor is further configured to activate the plasma generator for a time period sufficient to increase the hydrophilicity of the object to the desired level.

18. The plasma generation device of claim 1, wherein the desired level of hydrophilicity of the object is such that at least one hour after the plasma treatment, droplets hitting a surface of the object have contact angles of less than 10 degrees.

19. A method for generating plasma to treat an object, the method comprising:

identifying entry of an object into a plasma-generation zone;

activating circuitry for supplying energy to generate plasma in the plasma-generation zone to carry out a plasma treatment for increasing hydrophilicity of the object to a desired level;

measuring at least one plasma-activation parameter during the plasma treatment;

determining, based on the at least one plasma-activation parameter, that the plasma treatment is below a threshold for increasing the hydrophilicity of the object to the desired level; and outputting a notification indicating plasma treatment failure.

20. A non-transitory computer readable medium containing instructions that when executed by at least one processor cause the at least one processor to perform operations for generating plasma to treat an object, the operations comprising:

identifying entry of an object into a plasma-generation zone;

activating circuitry for supplying energy to generate plasma in the plasma-generation zone to carry out a plasma treatment for increasing hydrophilicity of the object to a desired level;

measuring at least one plasma-activation parameter during the plasma treatment;

determining, based on the at least one plasma-activation parameter, that the plasma treatment is below a threshold for increasing the hydrophilicity of the object to the desired level; and outputting a notification indicating plasma treatment failure.

* * * * *